US012660499B2

(12) United States Patent
Takeda et al.

(10) Patent No.: US 12,660,499 B2
(45) Date of Patent: Jun. 16, 2026

(54) ORGANIC COMPOUND, LIGHT-EMITTING DEVICE, LIGHT-EMITTING APPARATUS, ELECTRONIC DEVICE, DISPLAY DEVICE, LIGHTING DEVICE

(71) Applicant: SEMICONDUCTOR ENERGY LABORATORY CO., LTD., Atsugi (JP)

(72) Inventors: Kyoko Takeda, Atsugi (JP); Kunihiko Suzuki, Isehara (JP); Harue Osaka, Atsugi (JP); Satoshi Seo, Sagamihara (JP); Tsunenori Suzuki, Yokohama (JP); Takuya Ishimoto, Isehara (JP); Naoaki Hashimoto, Sagamihara (JP)

(73) Assignee: SEMICONDUCTOR ENERGY LABORATORY CO., LTD., Kanagawa-ken (JP)

( * ) Notice: Subject to any disclaimer, the term of this patent is extended or adjusted under 35 U.S.C. 154(b) by 793 days.

(21) Appl. No.: 17/923,834

(22) PCT Filed: May 6, 2021

(86) PCT No.: PCT/IB2021/053821

§ 371 (c)(1),
(2) Date: Nov. 7, 2022

(87) PCT Pub. No.: WO2021/234491

PCT Pub. Date: Nov. 25, 2021

(65) Prior Publication Data

US 2023/0309385 A1 Sep. 28, 2023

(30) Foreign Application Priority Data

May 20, 2020 (JP) ................................ 2020-088022

(51) Int. Cl.

| | |
|---|---|
| ***C07D 493/14*** | (2006.01) |
| ***C07D 495/14*** | (2006.01) |
| ***C07D 497/14*** | (2006.01) |
| ***C09K 11/06*** | (2006.01) |
| ***H05B 33/02*** | (2006.01) |
| ***H05B 33/12*** | (2006.01) |
| ***H10K 50/11*** | (2023.01) |
| ***H10K 50/14*** | (2023.01) |
| ***H10K 85/60*** | (2023.01) |

(52) U.S. Cl.

CPC ......... *H10K 85/636* (2023.02); *C07D 493/14* (2013.01); *C09K 11/06* (2013.01); *C09K 2211/1018* (2013.01); *H10K 50/11* (2023.02); *H10K 85/6572* (2023.02); *H10K 85/6574* (2023.02)

(58) Field of Classification Search

CPC .. C07D 493/14; C07D 495/14; C07D 497/14; H10K 85/636; H10K 50/11; H10K 85/6572; H10K 85/6574; H10K 50/14; H10K 85/6576; C09K 11/06; C09K 2211/1018; H05B 33/12; H05B 33/02; Y02E 10/549

See application file for complete search history.

(56) References Cited

U.S. PATENT DOCUMENTS

| | | | |
|---|---|---|---|
| 9,586,972 | B2 | 3/2017 | Kitamura et al. |
| 9,997,725 | B2 | 6/2018 | Kawakami et al. |
| 11,225,488 | B2 | 1/2022 | Takeda et al. |
| 11,239,426 | B2 | 2/2022 | Skulason et al. |
| 2019/0152985 | A1 | 5/2019 | Suh et al. |
| 2019/0378992 | A1 | 12/2019 | Skulason et al. |
| 2019/0393420 | A1 | 12/2019 | Takeda et al. |
| 2021/0139496 | A1 | 5/2021 | Takeda et al. |

(Continued)

FOREIGN PATENT DOCUMENTS

| | | | |
|---|---|---|---|
| CN | 109153685 | A | 1/2019 |
| CN | 109641916 | A | 4/2019 |

(Continued)

OTHER PUBLICATIONS

International Search Report (Application No. PCT/IB2021/053821) Dated Jul. 20, 2021.

(Continued)

*Primary Examiner* — Kamal A Saeed
*Assistant Examiner* — Sagar Patel
(74) *Attorney, Agent, or Firm* — NIXON PEABODY LLP; Jeffrey L. Costellia

(57) ABSTRACT

A novel organic compound is provided. Alternatively, an organic compound that emits light with favorable chromaticity is provided. Alternatively, an organic compound that emits blue light with favorable chromaticity is provided. Alternatively, a light-emitting element with favorable emission efficiency is provided. Alternatively, an organic compound with an excellent carrier-transport property is provided. The organic compound includes any of a substituted or unsubstituted dibenzofurobisbenzofuran skeleton, a substituted or unsubstituted dibenzothienobisbenzothiophene skeleton, a substituted or unsubstituted benzobisbenzothienobenzofuran skeleton, and a substituted or unsubstituted dibenzothienobisbenzofuran skeleton and one or two amino groups. In the organic compound, the amino group includes a substituted or unsubstituted heteroaryl group and any of a substituted or unsubstituted aromatic hydrocarbon group having 6 to 25 carbon atoms and a substituted or unsubstituted heteroaryl group having 5 to 25 carbon atoms.

11 Claims, 45 Drawing Sheets

(56) References Cited

U.S. PATENT DOCUMENTS

| | | | |
|---|---|---|---|
| 2021/0193930 | A1 | 6/2021 | Takeda et al. |
| 2022/0093872 | A1 | 3/2022 | Skulason et al. |
| 2022/0194954 | A1 | 6/2022 | Takeda et al. |

FOREIGN PATENT DOCUMENTS

| | | | |
|---|---|---|---|
| CN | 110023319 | A | 7/2019 |
| JP | 2014-045099 | A | 3/2014 |
| JP | 2020-512277 | | 4/2020 |
| KR | 2017-0056425 | A | 5/2017 |
| KR | 2017-0082459 | A | 7/2017 |
| KR | 2018-0068889 | A | 6/2018 |
| KR | 2019-0059998 | A | 5/2019 |
| KR | 2019-0075009 | A | 6/2019 |
| WO | WO-2018/097937 | | 5/2018 |
| WO | WO-2018/110989 | | 6/2018 |
| WO | WO-2018/185571 | | 10/2018 |

OTHER PUBLICATIONS

Written Opinion (Application No. PCT/IB2021/053821) Dated Jul. 20, 2021.

ORGANIC COMPOUND, LIGHT-EMITTING DEVICE, LIGHT-EMITTING APPARATUS, ELECTRONIC DEVICE, DISPLAY DEVICE, LIGHTING DEVICE

TECHNICAL FIELD

One embodiment of the present invention relates to an organic compound, a light-emitting device, a light-emitting apparatus, an electronic device, a display device, a lighting device, or a semiconductor device.

Note that one embodiment of the present invention is not limited to the above technical field. The technical field of one embodiment of the invention disclosed in this specification and the like relates to an object, a method, or a manufacturing method. Alternatively, one embodiment of the present invention relates to a process, a machine, manufacture, or a composition of matter. Thus, more specifically, examples of the technical field of one embodiment of the present invention disclosed in this specification include a semiconductor device, a display device, a light-emitting apparatus, a power storage device, a memory device, a driving method thereof, and a manufacturing method thereof.

BACKGROUND ART

Display devices and light-emitting apparatuses including organic EL elements, some of which have been practically used, are finding wider applications. In recent years, liquid crystal displays have greatly progressed; thus, high quality is naturally required for organic EL displays that are regarded as next-generation displays.

Although a variety of substances have been developed as materials for organic EL displays, not so many of them have sufficient properties to withstand practical use. In consideration of diversity, affinity, and the like of combinations, it is obvious that, the larger the number of options is, the more convenient it is.

Organic EL elements have a function-separated structure in which a plurality of functions are given to different substances. Demands for light-emitting materials among these substances, especially demands for their emission efficiency affecting power consumption and their emission colors for improving display quality, are high.

For example, a known organic compound has at least one amino group in which any one of a substituted or unsubstituted dibenzofuranyl group, a substituted or unsubstituted dibenzothiophenyl group, and a substituted or unsubstituted carbazolyl group is bonded to any one of substituted or unsubstituted naphthobisbenzofuran, a substituted or unsubstituted naphthobisbenzothiophene skeleton, and a substituted or unsubstituted naphthobenzofuranobenzothiophene skeleton (Patent Document 1).

REFERENCE

Patent Document

[Patent Document 1] International Publication No. WO 2018/185571 Pamphlet (WO, A1)

SUMMARY OF THE INVENTION

Problems to be Solved by the Invention

An object of one embodiment of the present invention is to provide a novel organic compound that is highly convenient, useful, or reliable. Another object is to provide a novel light-emitting device that is highly convenient, useful, or reliable. Another object is to provide a novel photoelectric conversion device that is highly convenient, useful, or reliable. Another object is to provide a novel electronic device that is highly convenient, useful, or reliable. Another object is to provide a novel display device that is highly convenient, useful, or reliable. Another object is to provide a novel lighting device that is highly convenient, useful, or reliable. Another object is to provide a novel organic compound, a novel light-emitting device, a novel light-emitting apparatus, a novel electronic device, a novel display device, a novel lighting device, or a novel semiconductor device.

Note that the description of these objects does not preclude the existence of other objects. One embodiment of the present invention does not have to achieve all of these objects. Other objects are apparent from the description of the specification, the drawings, the claims, and the like, and other objects can be derived from the description of the specification, the drawings, the claims, and the like.

Means for Solving the Problems (1) One embodiment of the present invention is an organic compound represented by General Formula (G0) below.

[Chemical Formula 1]

(G0)

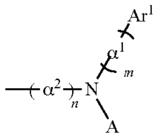

(R0)

In General Formula (G0) above, B represents any one of a substituted or unsubstituted dibenzofurobisbenzofuran skeleton, a substituted or unsubstituted dibenzothienobisbenzothiophene skeleton, a substituted or unsubstituted benzobisbenzothienobenzofuran skeleton, and a substituted or unsubstituted dibenzothienobisbenzofuran skeleton.

Furthermore, q represents an integer of 1 or 2. When q is 2, a pair of HA's may be the same or different from each other.

HA is an amino group or an aryl group including an amino group, the amino group or the aryl group being represented by General Formula (R0) above. In General Formula (R0) above, $\alpha^1$ and $\alpha^2$ each independently represent a substituted or unsubstituted divalent aromatic hydrocarbon group having 6 to 25 carbon atoms.

Furthermore, A represents a substituted or unsubstituted heteroaryl group, $Ar^1$ represents any of a substituted or unsubstituted aromatic hydrocarbon group having 6 to 25 carbon atoms and a substituted or unsubstituted heteroaryl group having 5 to 25 carbon atoms, and m and n each independently represent an integer of 0 or 1.

(2) Another embodiment of the present invention is an organic compound represented by General Formula (G1) below.

[Chemical Formula 2]

(G1)

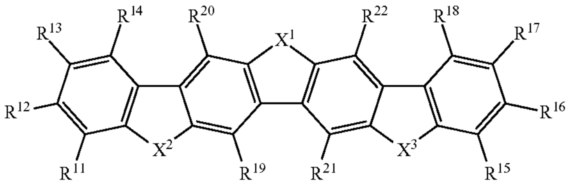

(R0)

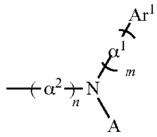

In General Formula (G1) above, $X^1$ to $X^3$ each represent oxygen or sulfur, and $X^1$ to $X^3$ may be the same or different from each other.

One or two of $R^{11}$ to $R^{22}$ are an amino group or an aryl group including an amino group, the amino group or the aryl group being represented by General Formula (R0) above, and $R^{11}$ to $R^{22}$ other than the one or two are each independently any of hydrogen, an alkyl group having 1 to 6 carbon atoms, an alicyclic hydrocarbon group having 3 to 6 carbon atoms, and a substituted or unsubstituted aromatic hydrocarbon group having 6 to 13 carbon atoms. When two of $R^{11}$ to $R^{22}$ are each the amino group or the aryl group including the amino group represented by General Formula (R0) above, a pair of the amino groups or a pair of the aryl groups including the amino groups represented by General Formula (R0) above may be the same or different from each other.

In General Formula (R0) above, $\alpha^1$ and $\alpha^2$ each independently represent a substituted or unsubstituted divalent aromatic hydrocarbon group having 6 to 25 carbon atoms.

Furthermore, A represents a substituted or unsubstituted heteroaryl group, and $Ar^1$ represents any of a substituted or unsubstituted aromatic hydrocarbon group having 6 to 25 carbon atoms and a substituted or unsubstituted heteroaryl group having 5 to 25 carbon atoms. Note that m and n each independently represent an integer of 0 or 1.

(3) Another embodiment of the present invention is the organic compound in which, in General Formula (G1) above, $R^{12}$ and $R^{16}$ are each the amino group or the aryl group including the amino group represented by General Formula (R0) above. Note that the pair of the amino groups or the pair of the aryl groups including the amino groups represented by General Formula (R0) above may be the same or different from each other.

(4) Another embodiment of the present invention is the organic compound in which, in General Formula (R0) above, A includes a five-membered ring and the five-membered ring includes a heteroatom.

(5) Another embodiment of the present invention is the organic compound in which, in General Formula (R0) above, A represents a heteroaryl group including a carbazole skeleton, a dibenzofuran skeleton, or a dibenzothiophene skeleton.

Furthermore, $Ar^1$ represents a phenyl group, a biphenyl group, a naphthyl group, a phenanthryl group, a fluorenyl group, or a substituent including a carbazole skeleton, a dibenzofuran skeleton, or a dibenzothiophene skeleton.

(6) Another embodiment of the present invention is the organic compound in which the amino group or the aryl group including the amino group represented by General Formula (R0) above is General Formula (R1) below.

[Chemical Formula 3]

(R1)

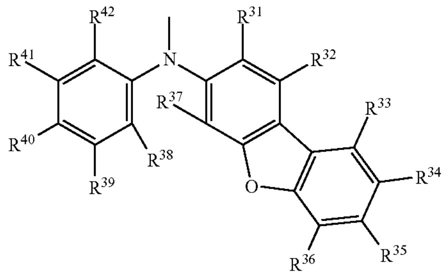

In General Formula (R1) above, $R^{31}$ to $R^{42}$ each independently represent any of hydrogen, an alkyl group having 1 to 6 carbon atoms, an alicyclic hydrocarbon group having 3 to 6 carbon atoms, and a substituted or unsubstituted aromatic hydrocarbon group having 6 to 13 carbon atoms.

(7) Another embodiment of the present invention is the organic compound in which the amino group or the aryl group including the amino group represented by General Formula (R0) is General Formula (R2) below.

[Chemical Formula 4]

(R2)

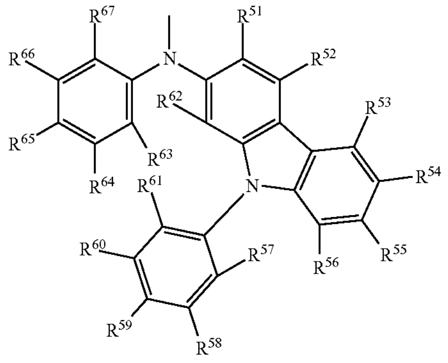

In General Formula (R2) above, $R^{51}$ to $R^{67}$ each independently represent any of hydrogen, an alkyl group having 1 to 6 carbon atoms, an alicyclic hydrocarbon group having 3 to 6 carbon atoms, and a substituted or unsubstituted aromatic hydrocarbon group having 6 to 13 carbon atoms.

Thus, a novel light-emitting material with a high emission quantum yield can be provided. Alternatively, a novel light-emitting material with a high molar absorption coefficient can be provided. Further alternatively, a novel light-emitting material exhibiting a blue color with a sharp emission spectrum can be provided.

(8) Another embodiment of the present invention is a light-emitting device including a first electrode, a second electrode, and a unit. The second electrode includes a region overlapping with the first electrode. The unit includes a region positioned between the first electrode and the second electrode, and the unit includes the above compound.

Thus, a blue-light-emitting element with high color purity can be provided. Alternatively, a light-emitting element with high external quantum efficiency can be provided. Further alternatively, a light-emitting element with a favorable emission lifetime can be provided. Further alternatively, a light-emitting element whose efficiency is less dependent on dopant concentration can be provided. As a result, a novel light-emitting device with favorable characteristics and high industrial productivity can be provided.

(9) Another embodiment of the present invention is a light-emitting apparatus including the above light-emitting device and a transistor or a substrate.

(10) Another embodiment of the present invention is a display device including the above light-emitting device and a transistor or a substrate.

(11) Another embodiment of the present invention is a lighting device including the above light-emitting apparatus and a housing.

(12) Another embodiment of the present invention is an electronic device including the above display device and a sensor, an operation button, a speaker, or a microphone.

Although a block diagram in which components are classified by their functions and shown as independent blocks is shown in the drawing attached to this specification, it is difficult to completely separate actual components according to their functions and one component can relate to a plurality of functions.

Note that the light-emitting apparatus in this specification includes an image display device using a light-emitting element. Moreover, the light-emitting apparatus may also include a module in which a connector such as an anisotropic conductive film or a TCP (Tape Carrier Package) is connected to a light-emitting element, a module in which a printed wiring board is provided on the tip of a TCP, or a module in which an IC (integrated circuit) is directly mounted on a light-emitting element by a COG (Chip On Glass) method. Furthermore, in some cases, lighting equipment or the like includes the light-emitting apparatus.

Effect of the Invention

According to one embodiment of the present invention, a novel organic compound that is highly convenient, useful, or reliable can be provided. Alternatively, a novel light-emitting device that is highly convenient, useful, or reliable can be provided. Alternatively, an object is to provide a novel photoelectric conversion device that is highly convenient, useful, or reliable. Alternatively, a novel light-emitting apparatus that is highly convenient, useful, or reliable can be provided. Alternatively, a novel electronic device that is highly convenient, useful, or reliable can be provided. Alternatively, a novel display device that is highly convenient, useful, or reliable can be provided. Alternatively, a novel lighting device that is highly convenient, useful, or reliable can be provided. Alternatively, a novel organic compound, a novel light-emitting device, a novel light-emitting apparatus, a novel electronic device, a novel display device, a novel lighting device, or a novel semiconductor device can be provided.

Note that the description of these effects does not preclude the existence of other effects. One embodiment of the present invention does not have to have all of these effects. Other effects will be apparent from the description of the specification, the drawings, the claims, and the like, and other effects can be derived from the description of the specification, the drawings, the claims, and the like.

BRIEF DESCRIPTION OF THE DRAWINGS

FIG. 9A, FIG. 9B1, FIG. 9B2, and FIG. 9C are diagrams showing electronic devices.

MODE FOR CARRYING OUT THE INVENTION

Figure 1A:
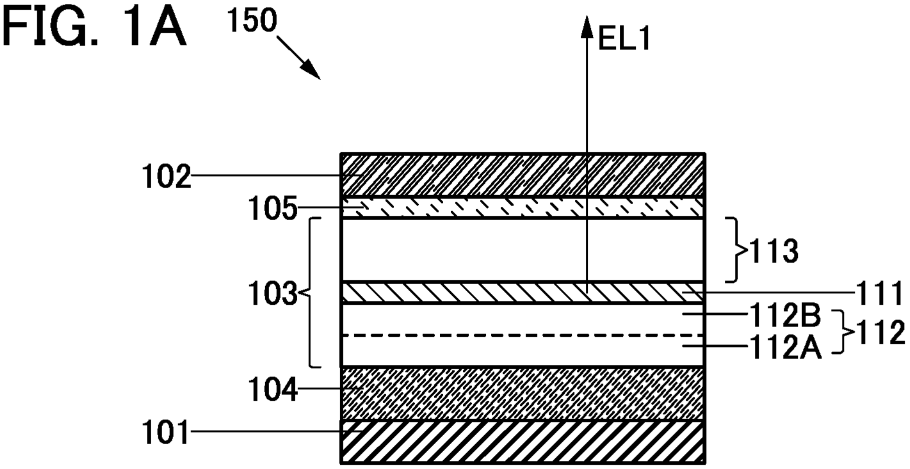
FIG. 1A and FIG. 1B are diagrams illustrating a structure of a light-emitting device of an embodiment.

An organic compound of one embodiment of the present invention includes any of a substituted or unsubstituted dibenzofurobisbenzofuran skeleton, a substituted or unsubstituted dibenzothienobisbenzothiophene skeleton, a substituted or unsubstituted benzobisbenzothienobenzofuran skeleton, and a substituted or unsubstituted dibenzothienobisbenzofuran skeleton and one or two amino groups or one or two aryl groups including amino groups. The amino group includes a substituted or unsubstituted heteroaryl group and any of a substituted or unsubstituted aromatic hydrocarbon group having 6 to 25 carbon atoms and a substituted or unsubstituted heteroaryl group having 5 to 25 carbon atoms.

Thus, a novel light-emitting material with a high emission quantum yield can be provided. Alternatively, a novel light-emitting material with a high molar absorption coefficient can be provided. Further alternatively, a novel light-emitting material exhibiting a blue color with a sharp emission spectrum can be provided. As a result, a novel organic compound that is highly convenient, useful, or reliable can be provided.

Embodiments will be described in detail with reference to the drawings. However, the present invention is not limited to the following description, and it is readily appreciated by those skilled in the art that modes and details can be modified in various ways without departing from the spirit and the scope of the present invention. Thus, the present invention should not be construed as being limited to the description in the following embodiments. Note that in structures of the invention described below, the same portions or portions having similar functions are denoted by the same reference numerals in different drawings, and a description thereof is not repeated.

Embodiment 1

In this embodiment, an organic compound of one embodiment of the present invention will be described.

Example 1 of Organic Compound

An organic compound described in this embodiment is an organic compound represented by General Formula (G0) below.

[Chemical Formula 5]

$$B \!-\!\!(HA)_q \qquad (G0)$$

<<Examples of B>>

In General Formula (G0) above, B represents any one of a substituted or unsubstituted dibenzofurobisbenzofuran skeleton, a substituted or unsubstituted dibenzothienobisbenzothiophene skeleton, a substituted or unsubstituted benzobisbenzothienobenzofuran skeleton, and a substituted or unsubstituted dibenzothienobisbenzofuran skeleton.

Note that the substituted or unsubstituted dibenzofurobisbenzofuran skeleton can be represented by, for example, General Formula (B11) below or General Formula (B12) below.

[Chemical Formula 6]

(B11)

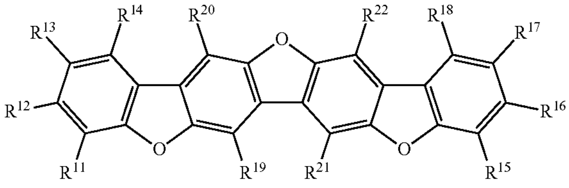

(B12)

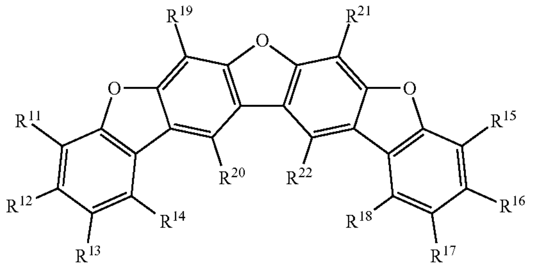

Furthermore, the substituted or unsubstituted dibenzothienobisbenzothiophene skeleton can be represented by, for example, General Formula (B21) below or General Formula (B22) below. The dibenzothienobisbenzothiophene skeleton that can be represented by General Formula (B21) below is particularly preferable because of its relative ease of synthesis.

[Chemical Formula 7]

(B21)

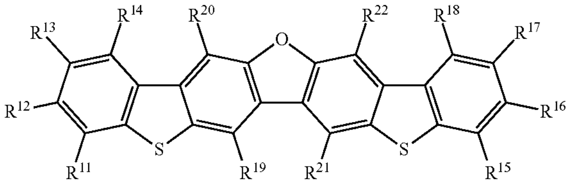

(B22)

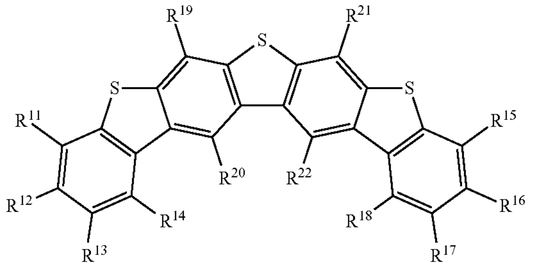

Furthermore, the substituted or unsubstituted benzobisbenzothienobenzofuran skeleton can be represented by, for example, General Formula (B31) below or General Formula (B32) below.

[Chemical Formula 8]

(B31)

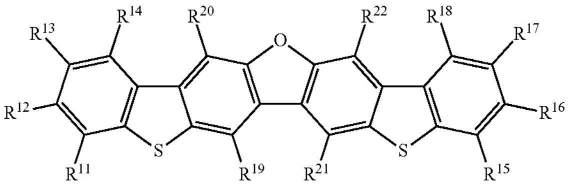

(B32)

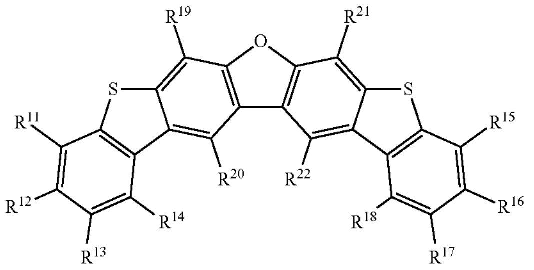

Furthermore, the substituted or unsubstituted dibenzothienobisbenzofuran skeleton can be represented by, for example, General Formula (B41) below or General Formula (B42) below.

[Chemical Formula 9]

(B41)

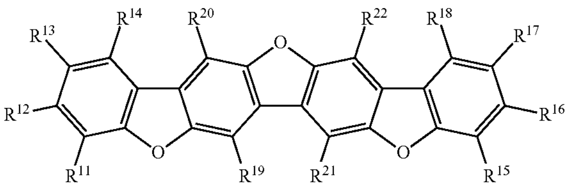

(B42)

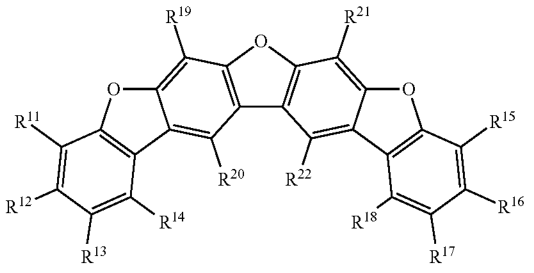

<<Examples of q>>

Furthermore, q represents an integer of 1 or 2, and a pair of HA's of the case where q is 2 may be the same or different from each other. In the case where the pair of HA's are the same, the synthesis can be facilitated. Alternatively, the costs of the synthesis can be reduced.

<<Examples of HA>>

HA is an amino group or an aryl group including an amino group, the amino group or the aryl group being represented by General Formula (R0) below.

[Chemical Formula 10]

(R0)

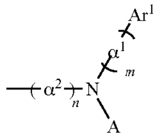

<<Examples of $\alpha^1$ and $\alpha^2$>>

In General Formula (R0) above, $\alpha^1$ and $\alpha^2$ each independently represent a substituted or unsubstituted divalent aromatic hydrocarbon group having 6 to 25 carbon atoms. Note that m and n each independently represent an integer of 0 or 1, General Formula (R0) above is a secondary amino group when n is 0, and General Formula (R0) above is an aryl group including an amino group when n is 1. The organic compound represented by General Formula (G0) above is a tertiary amine.

For example, it is possible to use a structure in which m or n is 0 in General Formula (R0) above. In this case, the molecular weight can be small and the sublimation temperature can be lowered. Alternatively, it is possible to inhibit decomposition due to heat in a sublimation purification step or an evaporation step.

[Examples of Divalent Aromatic Hydrocarbon Group]

As $\alpha^1$ and $\alpha^2$, a phenylene group, a biphenylene group, a terphenylene group, a naphthylene group, a fluorenylene group, a dimethylfluorenyl group, and the like can be used, for example. Specifically, a structure including a phenylene group can lead to a small molecular weight, so that the sublimation temperature can be lowered. Alternatively, it is possible to inhibit decomposition due to heat in a sublimation purification step or an evaporation step.

Specifically, groups represented by Structural Formulae (Ar-1) to (Ar-27) below can be used. Note that these may further have a substituent such as a hydrocarbon group having 1 to 10 carbon atoms, an alicyclic hydrocarbon group having 3 to 10 carbon atoms, or a substituted or unsubstituted aromatic hydrocarbon group having 6 to 14 carbon atoms.

For example, it is possible to use a phenylene group and a group in which a plurality of phenylene groups are connected (see (Ar-1) to (Ar-11)). In this case, extension of conjugation can be inhibited and the singlet excitation level can be kept high. These effects are remarkable in a structure containing a metaphenylene group and thus, the structure is particularly preferable. A structure with a paraphenylene group can improve the reliability of the light-emitting material.

[Chemical Formula 11]

(Ar-1)

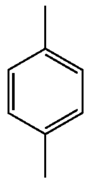

(Ar-2)

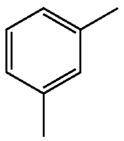

-continued (Ar-3)

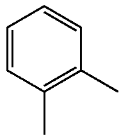

(Ar-4)

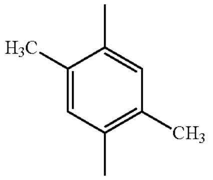

(Ar-5)

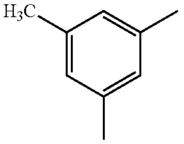

(Ar-6)

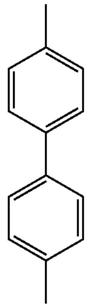

(Ar-7)

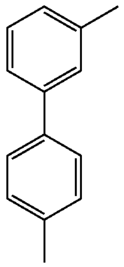

(Ar-8)

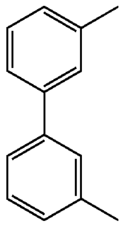

(Ar-9)

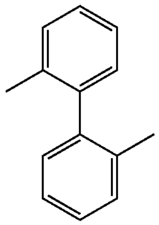

-continued (Ar-10)

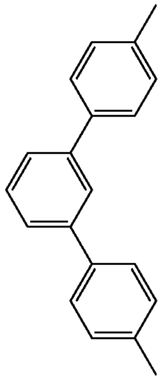

(Ar-11)

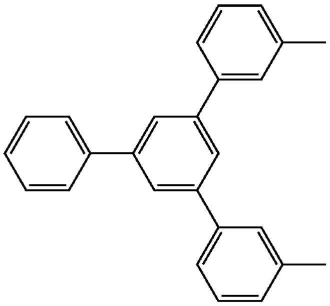

It is possible to use a group in which a substituent is connected at carbon having a sigma bond at the 9-position of fluorene or the like (see (Ar-24) to (Ar-27)). In this case, extension of conjugation can be inhibited and the singlet excitation level can be kept high. Alternatively, the emission wavelength can be further shortened.

[Chemical Formula 12]

(Ar-12)

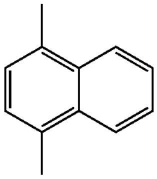

(Ar-13)

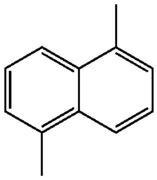

(Ar-14)

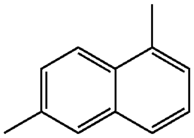

(Ar-15)

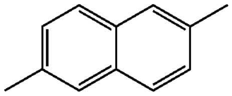

-continued (Ar-16)

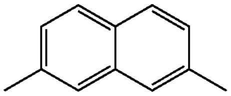

(Ar-17)

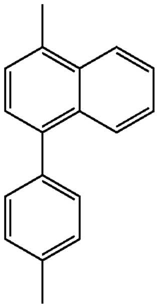

(Ar-18)

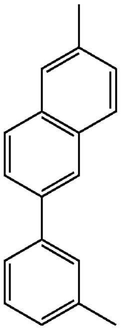

(Ar-19)

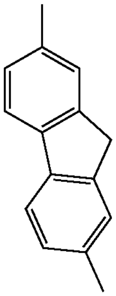

(Ar-20)

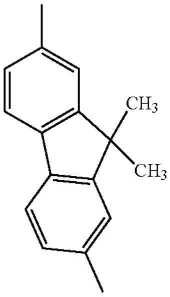

(Ar-21)

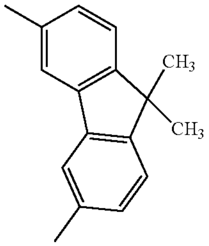

-continued (Ar-22)

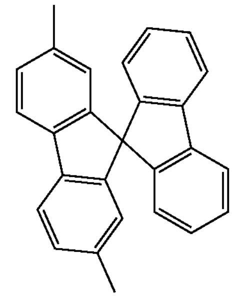

(Ar-23)

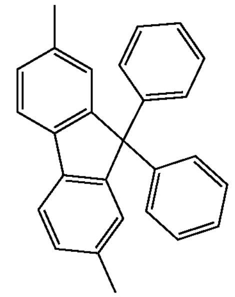

(Ar-24)

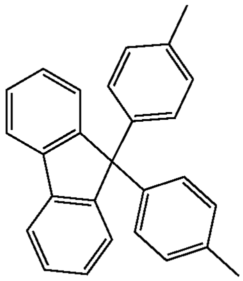

(Ar-25)

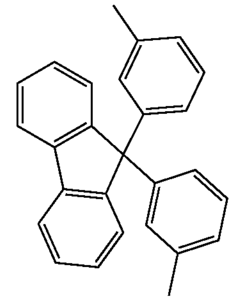

(Ar-26)

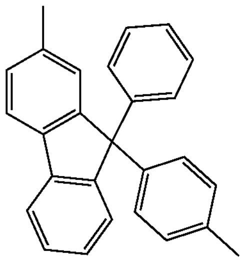

-continued (Ar-27)

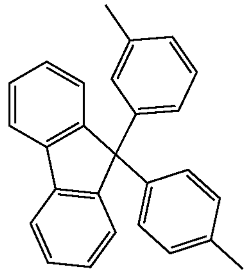

[Examples of Hydrocarbon Group]

Examples of the hydrocarbon group having 1 to 10 carbon atoms include a methyl group, an ethyl group, a propyl group, an isopropyl group, a butyl group, a tert-butyl group, a pentyl group, a hexyl group, a heptyl group, an octyl group, a nonyl group, and a decyl group.

Examples of the alicyclic hydrocarbon group having 3 to 10 carbon atoms include a cyclopropyl group and a cyclohexyl group.

Examples of the aromatic hydrocarbon group having 6 to 14 carbon atoms include a phenyl group, a biphenyl group, a naphthyl group, a phenanthryl group, an anthryl group, and a fluorenyl group. A phenyl group is particularly preferable in consideration of reduction in the synthesis cost and sublimation temperature and shortening of the emission wavelength.

<<Examples of A>>

Furthermore, A represents a substituted or unsubstituted heteroaryl group. For example, a pyridyl group, a furanyl group, or a group having a pyrrole skeleton, a furanyl skeleton, a thienyl skeleton, a pyrazole skeleton, an imidazole skeleton, or an oxazole skeleton can be used as A.

[Examples of Heteroaryl Group]

For example, a carbazolyl group or the like can be used as A. Specifically, groups represented by Structural Formulae (Ar-50) to (Ar-69) and (Ar-76) to (Ar-97) below can be used. Note that these may further have a substituent such as a hydrocarbon group having 1 to 10 carbon atoms, an alicyclic hydrocarbon group having 3 to 10 carbon atoms, or a substituted or unsubstituted aromatic hydrocarbon group having 6 to 14 carbon atoms.

For example, a structure which includes a carbazolyl group and in which the 3-position of the carbazolyl group is bonded to the nitrogen (amine) in General Formula (R0) can be used as A (see (Ar-51) and (Ar-55)). Alternatively, a structure which includes a dibenzofuranyl group and in which the 2-position of the dibenzofuranyl group is bonded to the nitrogen (amine) in General Formula (R0) can be used as A (see (Ar-57)). Alternatively, a structure which includes a dibenzothiophenyl group and in which the 2-position of the dibenzothiophenyl group is bonded to the nitrogen (amine) in General Formula (R0) can be used as A (see (Ar-62)). In either case, extension of conjugation can be facilitated. Alternatively, the hole-transport property can be improved. Alternatively, the emission wavelength can be longer. Alternatively, the reliability can be improved. In particular, these effects are prominent in the case of the carbazolyl group.

For example, a structure which includes a carbazolyl group and in which the 2-position of the carbazolyl group is bonded to the nitrogen (amine) in General Formula (R0) can be used as A (see (Ar-52)). A structure which includes a dibenzofuranyl group and in which the 3-position of the dibenzofuranyl group is bonded to the nitrogen (amine) in General Formula (R0) can be used as A (see (Ar-59)). A structure which includes a dibenzothiophenyl group and in which the 3-position of the dibenzothiophenyl group is bonded to the nitrogen (amine) in General Formula (R0) can be used as A (see (Ar-63)). In either case, the carrier-transport property can be improved. Alternatively, an effect of reducing the drive voltage can be expected.

For example, a dibenzofuranyl group, a dibenzothiophenyl group, or the like can be used as A. Specifically, groups represented by Structural Formulae (Ar-57) to (Ar-67) below can be used. Note that these may further have a substituent such as a hydrocarbon group having 1 to 10 carbon atoms, an alicyclic hydrocarbon group having 3 to 10 carbon atoms, or a substituted or unsubstituted aromatic hydrocarbon group having 6 to 14 carbon atoms.

For example, a structure which includes a dibenzofuranyl group or a dibenzothiophenyl group and in which the 4-position of the dibenzofuranyl group or the dibenzothiophenyl group is bonded to the nitrogen (amine) in General Formula (R0) can be used as A. Specifically, groups represented by Structural Formulae (Ar-58), (Ar-62), and (Ar-64) to (Ar-67) below can be used. In this case, extension of conjugation can be inhibited. Alternatively, the emission wavelength can be further shortened. Alternatively, the reliability can be improved.

For example, a structure which includes a carbazolyl group and in which an aryl group is bonded at the 9-position of the carbazolyl group can be used as A. Specifically, groups represented by Structural Formulae (Ar-50) to (Ar-55) below can be used. In this case, the reliability can be improved.

[Chemical Formula 13]

(Ar-50)

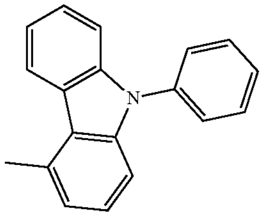

(Ar-51)

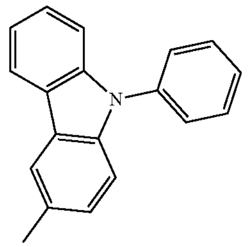

(Ar-52)

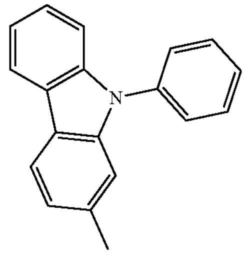

-continued (Ar-53)

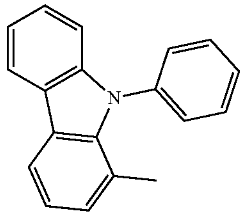

(Ar-54)

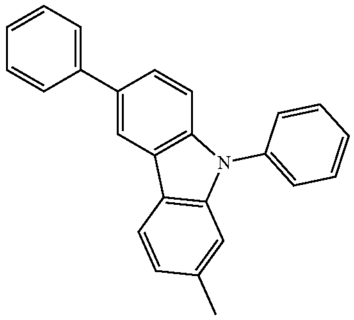

(Ar-55)

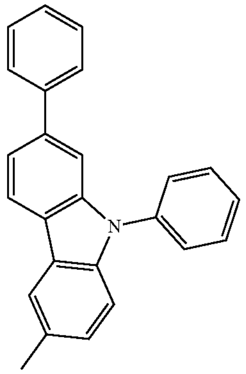

[Chemical Formula 14]

(Ar-56)

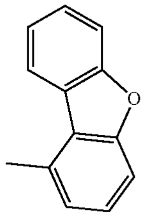

(Ar-57)

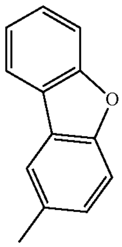

-continued (Ar-58)

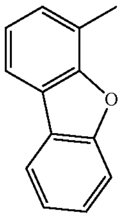

(Ar-59)

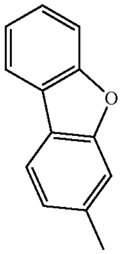

(Ar-60)

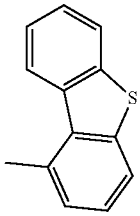

(Ar-61)

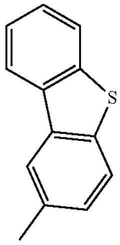

(Ar-62)

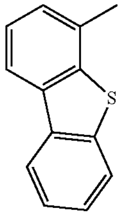

(Ar-63)

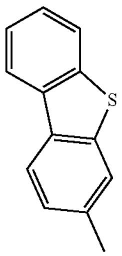

-continued (Ar-64)

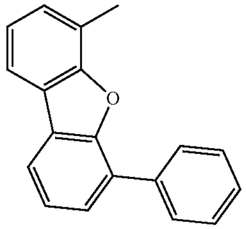

(Ar-65)

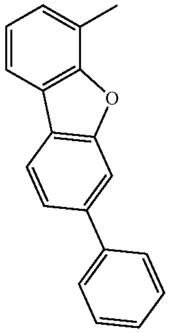

(Ar-66)

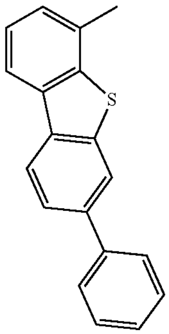

(Ar-67)

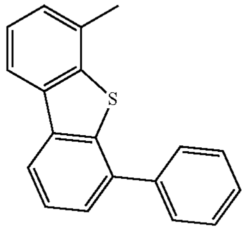

<<Examples of $Ar^1$>>

$Ar^1$ represents any of a substituted or unsubstituted aromatic hydrocarbon group having 6 to 25 carbon atoms and a substituted or unsubstituted heteroaryl group having 5 to 25 carbon atoms, and m and n each independently represent an integer of 0 or 1.

[Examples of Aromatic Hydrocarbon Group]

For example, a phenyl group, a biphenyl group, a terphenyl group, a naphthyl group, a fluorenyl group, a dimethylfluorenyl group, a spirofluorenyl group, a diphenylfluorenyl group, a phenanthryl group, an anthryl group, a dihydroanthryl group, a triphenylenyl group, or a pyrenyl group can be used as $Ar^1$. Specifically, groups represented by Structural Formulae (Ar-100) to (Ar-120) and (Ar-130) to (Ar-140) below can be used. Note that these may further have a substituent such as a hydrocarbon group having 1 to 10 carbon atoms, an alicyclic hydrocarbon group having 3 to 10 carbon atoms, or a substituted or unsubstituted aromatic hydrocarbon group having 6 to 14 carbon atoms.

For example, a structure including a phenyl group can be used as Ar[1] (see (Ar-100) to (Ar-108)). In this case, the reliability can be improved. Alternatively, extension of conjugation can be inhibited. Alternatively, the emission wavelength can be further shortened. Alternatively, the synthesis can be inexpensive; thus, the structure is preferable. Alternatively, the molecular weight can be small and the sublimation temperature can be lowered. Alternatively, it is possible to inhibit decomposition due to heat in a sublimation purification step or an evaporation step.

Furthermore, like (Ar-100) to (Ar-120), the one in which the number of fused six-membered rings is two or less such as a benzene ring, a naphthalene ring, or a fluorene ring, or the one in which the number of fused six-membered rings is three or more and to a six-membered ring, other six-membered rings are fused at the a-face and only one of the c-face and the e-face and which is composed of hydrocarbons, such as a phenanthrene ring, can inhibit extension of conjugation and shorten the wavelength of emitted light.

For example, it is possible to use a structure including an alkyl group or a cycloalkyl group (see (Ar-101) to (Ar-104)). In this case, a bulky molecule can be obtained. Alternatively, the sublimation temperature can be lowered. Alternatively, it is possible to inhibit decomposition due to heat in a sublimation purification step or an evaporation step.

[Chemical Formula 15]

(Ar-100)

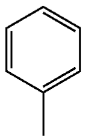

(Ar-101)

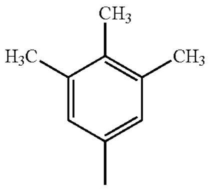

(Ar-102)

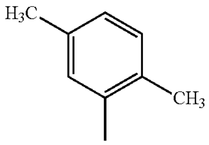

(Ar-103)

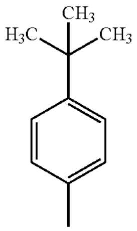

(Ar-104)

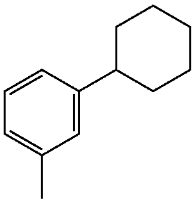

-continued (Ar-105)

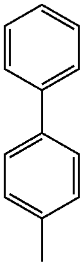

(Ar-106)

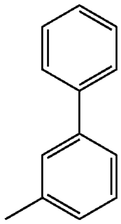

(Ar-107)

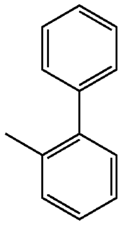

(Ar-108)

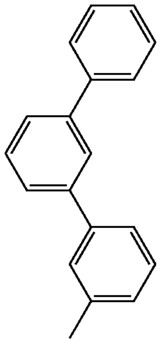

(Ar-109)

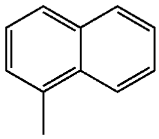

(Ar-110)

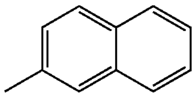

(Ar-111)

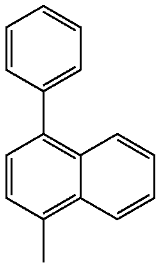

-continued
(Ar-112)
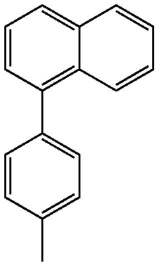
(Ar-113)
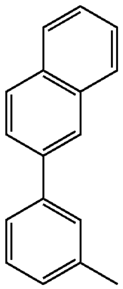
(Ar-114)
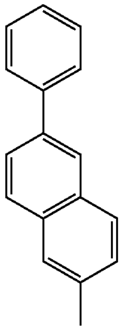
(Ar-115)
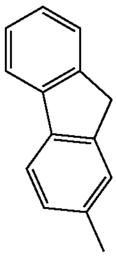
(Ar-116)
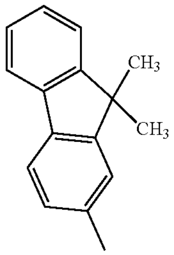
-continued
(Ar-117)
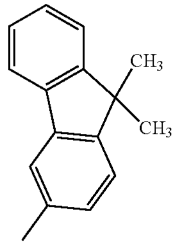
(Ar-118)
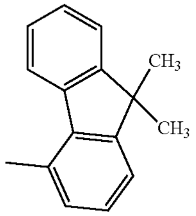
(Ar-119)
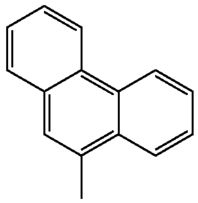
(Ar-120)
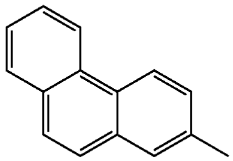
[Chemical Formula 16]
(Ar-130)
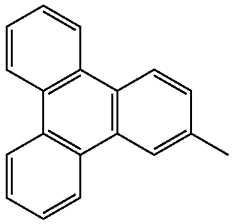
(Ar-131)
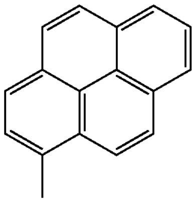
(Ar-132)
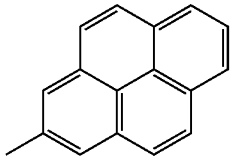

-continued (Ar-133)

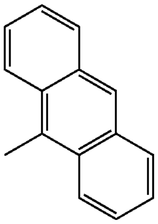

(Ar-134)

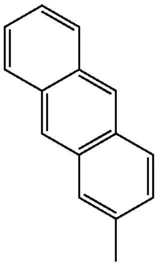

(Ar-135)

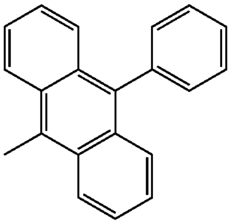

(Ar-136)

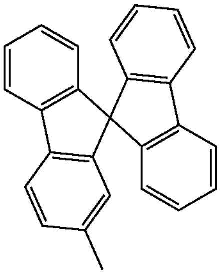

(Ar-137)

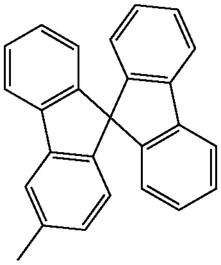

(Ar-138)

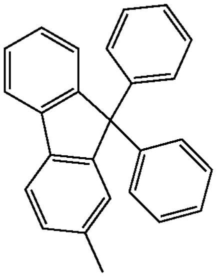

-continued (Ar-139)

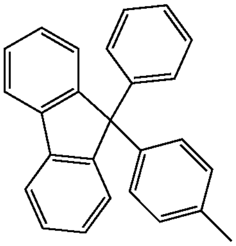

(Ar-140)

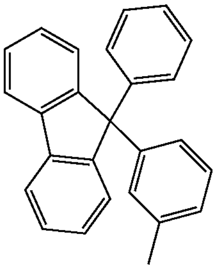

[Examples of Heteroaryl Group]

For example, a carbazolyl group, a dibenzofuranyl group, a dibenzothiophenyl group, or the like can be used as $Ar^1$. Specifically, groups represented by Structural Formulae (Ar-50) to (Ar-67) above and Structural Formulae (Ar-68), (Ar-69), and (Ar-76) to (Ar-97) below can be used. Note that these may further have a substituent such as a hydrocarbon group having 1 to 10 carbon atoms, an alicyclic hydrocarbon group having 3 to 10 carbon atoms, or a substituted or unsubstituted aromatic hydrocarbon group having 6 to 14 carbon atoms.

[Chemical Formula 17]

(Ar-68)

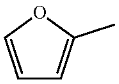

(Ar-69)

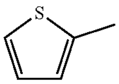

(Ar-76)

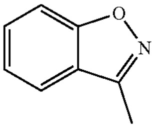

(Ar-77)

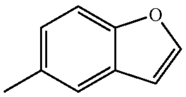

(Ar-78)

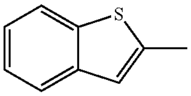

-continued
(Ar-79)
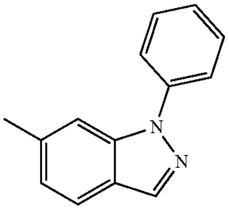
(Ar-80)
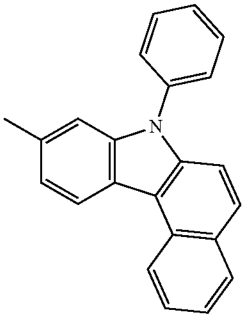
(Ar-81)
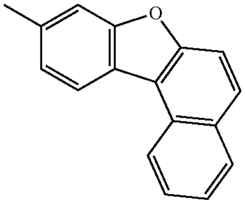
(Ar-82)
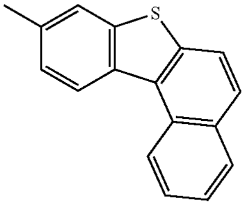
(Ar-83)
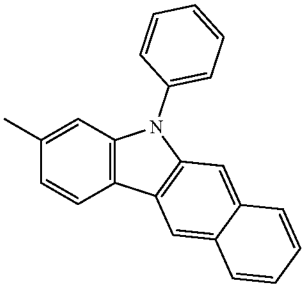
(Ar-84)
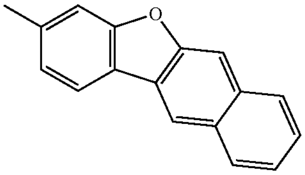
(Ar-85)
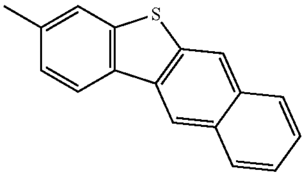
-continued
(Ar-86)
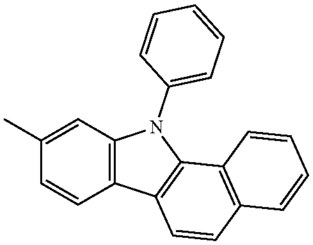
(Ar-87)
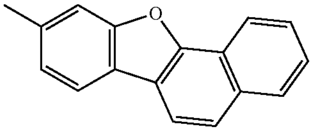
(Ar-88)
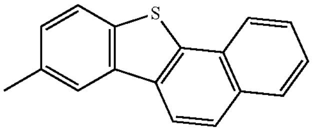
(Ar-89)
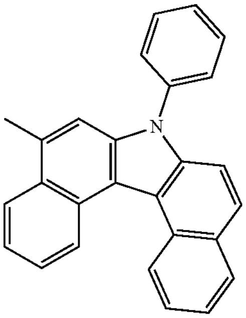
(Ar-90)
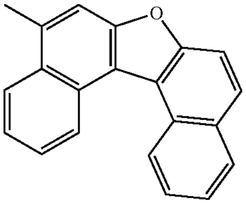
[Chemical Formula 18]
(Ar-91)
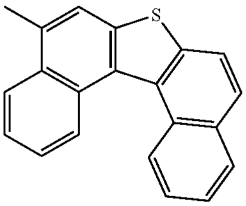

-continued (Ar-92)

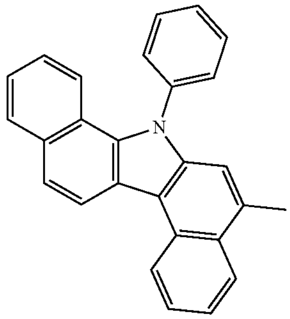

(Ar-93)

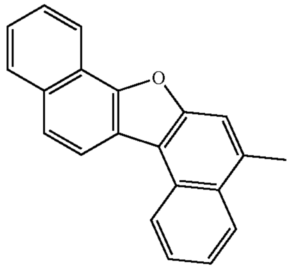

(Ar-94)

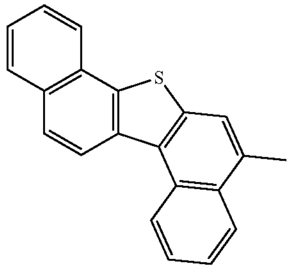

(Ar-95)

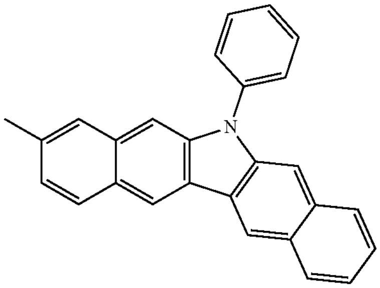

(Ar-96)

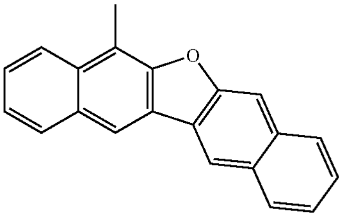

(Ar-97)

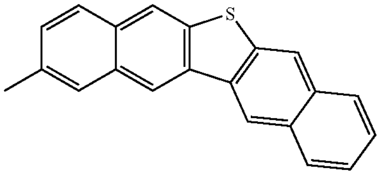

Example 2 of Organic Compound

An organic compound described in this embodiment is an organic compound represented by General Formula (G1) below.

[Chemical Formula 19]

(G1)

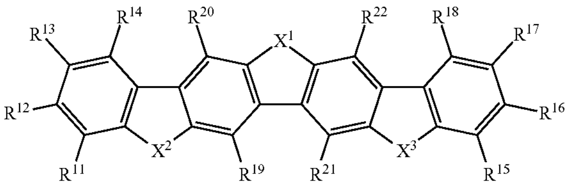

(R0)

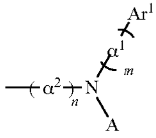

In General Formula (G1) above, $X^1$ to $X^3$ each represent oxygen or sulfur, and $X^1$ to $X^3$ may be the same or different from each other.

One or two of $R^{11}$ to $R^{22}$ are an amino group or an aryl group including an amino group, the amino group or the aryl group being represented by General Formula (R0) above, and $R^{11}$ to $R^{22}$ other than the one or two are each independently any of hydrogen, an alkyl group having 1 to 6 carbon atoms, an alicyclic hydrocarbon group having 3 to 6 carbon atoms, and a substituted or unsubstituted aromatic hydrocarbon group having 6 to 13 carbon atoms. When two of $R^{11}$ to $R^{22}$ are each the amino group or the aryl group including the amino group represented by General Formula (R0) above, a pair of the amino groups or a pair of the aryl groups including the amino groups represented by General Formula (R0) above may be the same or different from each other. In the case where two of $R^{11}$ to $R^{22}$ are each the amino group or the aryl group including the amino group represented by General Formula (R0) above, the emission efficiency can be improved.

In General Formula (R0) above, $\alpha^1$ and $\alpha^2$ each independently represent a substituted or unsubstituted divalent aromatic hydrocarbon group having 6 to 25 carbon atoms.

Furthermore, A represents a substituted or unsubstituted heteroaryl group, and $Ar^1$ represents any of a substituted or unsubstituted aromatic hydrocarbon group having 6 to 25 carbon atoms and a substituted or unsubstituted heteroaryl group having 5 to 25 carbon atoms. Note that m and n each independently represent an integer of 0 or 1.

Example 3 of Organic Compound

An organic compound described in this embodiment is the organic compound in which, in General Formula (G1) above, $R^{12}$ and $R^{16}$ are each the amino group or the aryl group including the amino group represented by General Formula (R0) above. Note that the pair of the amino groups or the pair of the aryl groups including the amino groups represented by General Formula (R0) above may be the same or different from each other. For example, the organic compound described in this embodiment can be represented by General Formula (G2) below. In this case, improvement of the light emission efficiency can be expected.

[Chemical Formula 20]

(G2)

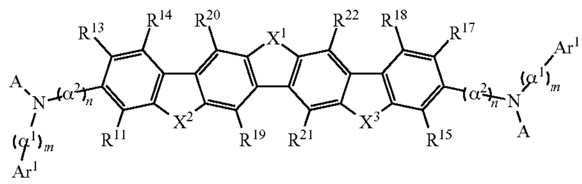

Example 4 of Organic Compound

An organic compound described in this embodiment is the organic compound in which, in General Formula (R0) above, A includes a five-membered ring and the five-membered ring includes a heteroatom.

For example, a group having a pyrrole skeleton, a furanyl skeleton, a thienyl skeleton, a pyrazole skeleton, an imidazole skeleton, or an oxazole skeleton can be used as A. Specifically, a carbazolyl group, a furanyl group, a thienyl group, an indazolyl group, a benzoisoxazolyl group, a benzofuranyl group, a benzocarbazolyl group, a benzonaphthofuranyl group, a benzothiophenyl group, a benzimidazolyl group, a benzonaphthothiophenyl group, a dibenzocarbazolyl group, a dibenzofuranyl group, a dibenzothiophenyl group, or the like can be used as A. Specifically, groups represented by Structural Formulae (Ar-50) to (Ar-69) and (Ar-76) to (Ar-97) above can be used. Note that these may further have a substituent such as a hydrocarbon group having 1 to 10 carbon atoms, an alicyclic hydrocarbon group having 3 to 10 carbon atoms, or a substituted or unsubstituted aromatic hydrocarbon group having 6 to 14 carbon atoms.

For example, a structure in which benzene or naphthalene is fused to a five-membered ring at two or more positions of the five-membered ring can be used (see (Ar-50) to (Ar-67) and (Ar-80) to (Ar-97)). In this case, a photochemical reaction can be inhibited. Alternatively, the reliability of the material can be improved.

For example, a structure in which benzene is fused to a five-membered ring at two or more positions of the five-membered ring can be used (see (Ar-50) to (Ar-67)). In this case, the emission wavelength can be made short. Alternatively, the temperature required in the evaporation step can be lowered.

Example 5 of Organic Compound

An organic compound described in this embodiment is the organic compound in which, in General Formula (R0) above, A represents a heteroaryl group including a carbazole skeleton, a dibenzofuran skeleton, or a dibenzothiophene skeleton. Specifically, groups represented by Structural Formulae (Ar-50) to (Ar-67) and (Ar-80) to (Ar-97) above can be used. Note that these may further have a substituent such as a hydrocarbon group having 1 to 10 carbon atoms, an alicyclic hydrocarbon group having 3 to 10 carbon atoms, or a substituted or unsubstituted aromatic hydrocarbon group having 6 to 14 carbon atoms.

Furthermore, $Ar^1$ represents a phenyl group, a biphenyl group, a naphthyl group, a phenanthryl group, a fluorenyl group, or a substituent including a carbazole skeleton, a dibenzofuran skeleton, or a dibenzothiophene skeleton. For example, a terphenyl group, a dimethylfluorenyl group, a spirofluorenyl group, a diphenylfluorenyl group, an anthryl group, a dihydroanthryl group, a triphenylenyl group, or a pyrenyl group can be used as $Ar^1$. Specifically, groups represented by Structural Formulae (Ar-100) to (Ar-120) and (Ar-130) to (Ar-140) above can be used. Note that these may further have a substituent such as a hydrocarbon group having 1 to 10 carbon atoms, an alicyclic hydrocarbon group having 3 to 10 carbon atoms, or a substituted or unsubstituted aromatic hydrocarbon group having 6 to 14 carbon atoms. For example, a carbazolyl group, a dibenzofuranyl group, a dibenzothiophenyl group, or the like can be used as $Ar^1$. Specifically, groups represented by Structural Formulae (Ar-50) to (Ar-67) above can be used. Note that these may further have a substituent such as a hydrocarbon group having 1 to 10 carbon atoms, an alicyclic hydrocarbon group having 3 to 10 carbon atoms, or a substituted or unsubstituted aromatic hydrocarbon group having 6 to 14 carbon atoms.

Example 6 of Organic Compound

An organic compound described in this embodiment is the organic compound in which the amino group or the aryl group including the amino group represented by General Formula (R0) above is General Formula (R1) below.

[Chemical Formula 21]

(R1)

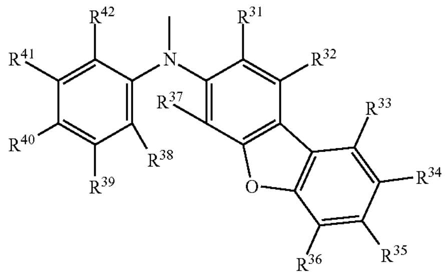

In General Formula (R1) above, $R^{31}$ to $R^{42}$ each independently represent any of hydrogen, an alkyl group having 1 to 6 carbon atoms, an alicyclic hydrocarbon group having 3 to 6 carbon atoms, and a substituted or unsubstituted aromatic hydrocarbon group having 6 to 13 carbon atoms.

Example 7 of Organic Compound

An organic compound described in this embodiment is the organic compound in which the amino group or the aryl group including the amino group represented by General Formula (R0) above is General Formula (R2) below.

[Chemical Formula 22]

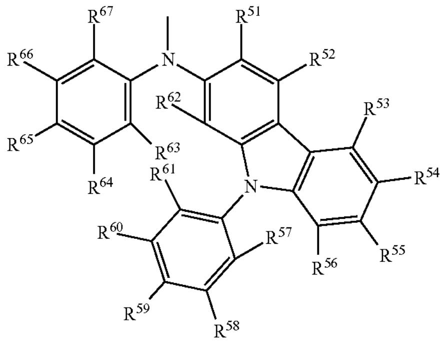

(R2)

In General Formula (R2) above, $R^{11}$ to $R^{67}$ each independently represent any of hydrogen, an alkyl group having 1 to 6 carbon atoms, an alicyclic hydrocarbon group having 3 to 6 carbon atoms, and a substituted or unsubstituted aromatic hydrocarbon group having 6 to 13 carbon atoms.

Note that in terms of heat resistance, the molecular weight is preferably greater than or equal to 850; in terms of a sublimation property, the molecular weight is preferably less than or equal to 1700, further preferably less than or equal to 1500.

Thus, a novel light-emitting material with a high emission quantum yield can be provided. Alternatively, a novel light-emitting material with a high molar absorption coefficient can be provided. Further alternatively, a novel light-emitting material exhibiting a blue color with a sharp emission spectrum can be provided.

Specific examples of the organic compounds with the above structures are shown below.

[Chemical Formula 23]

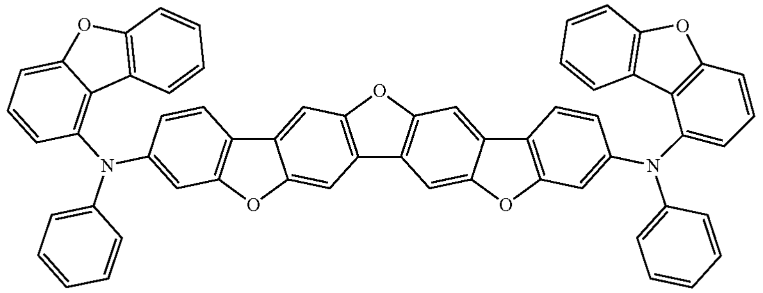

(101)

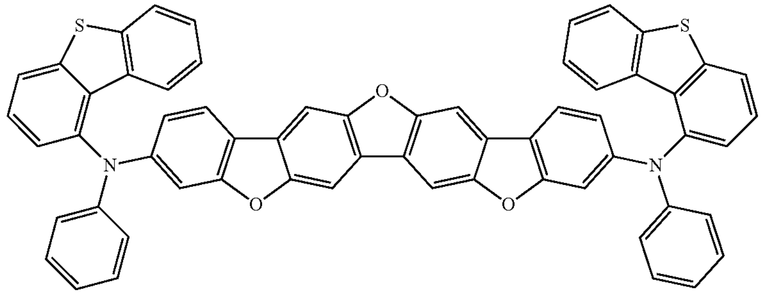

(102)

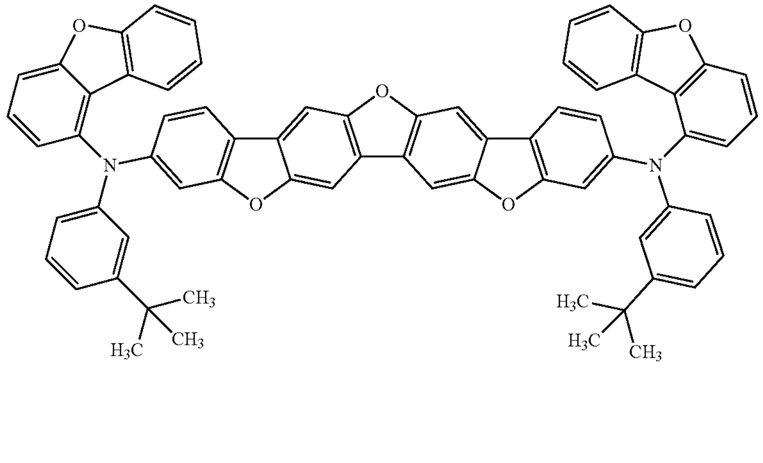

(103)

-continued
(104)
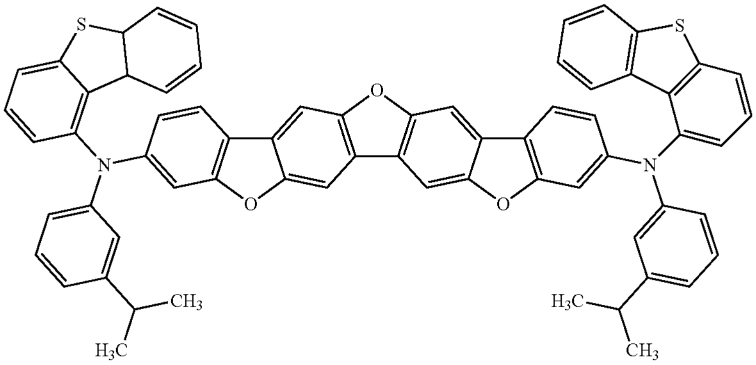
(105)
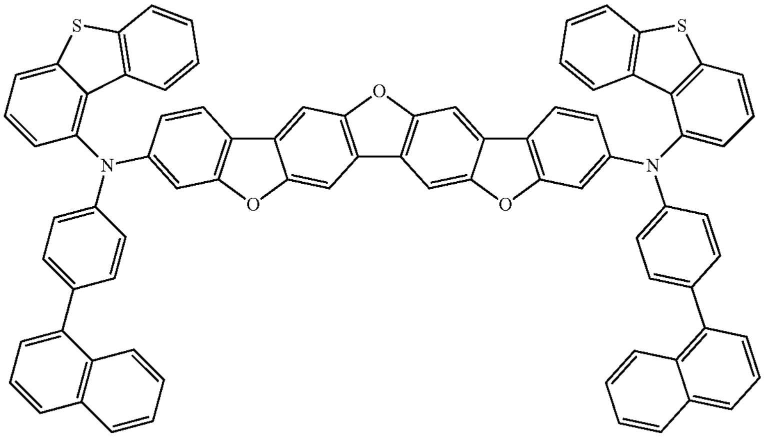
(106)
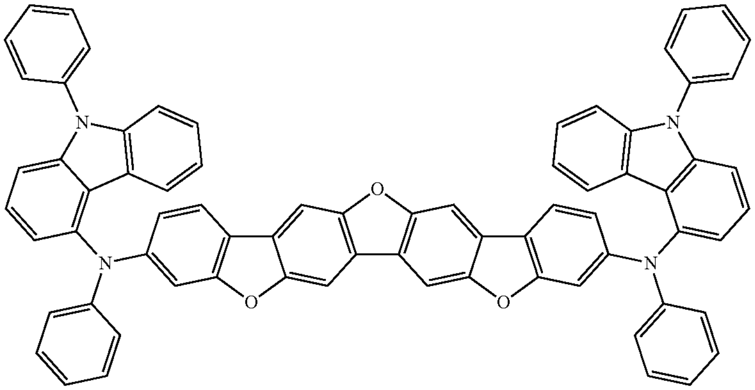
(107)
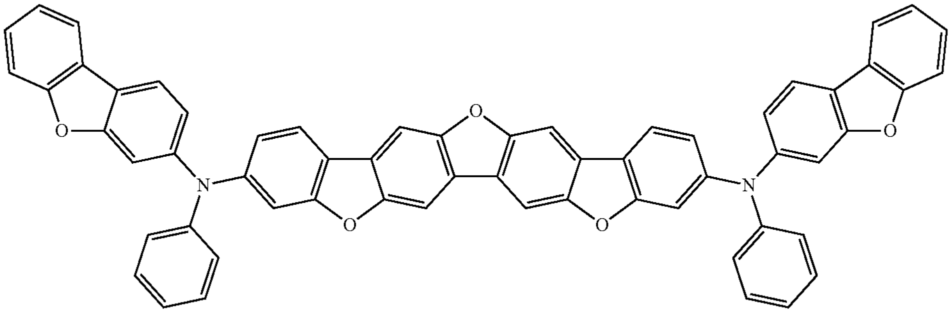

-continued
(108)
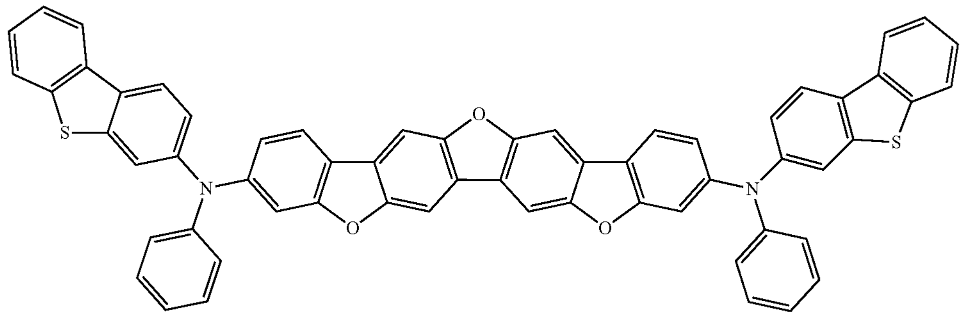
(109)
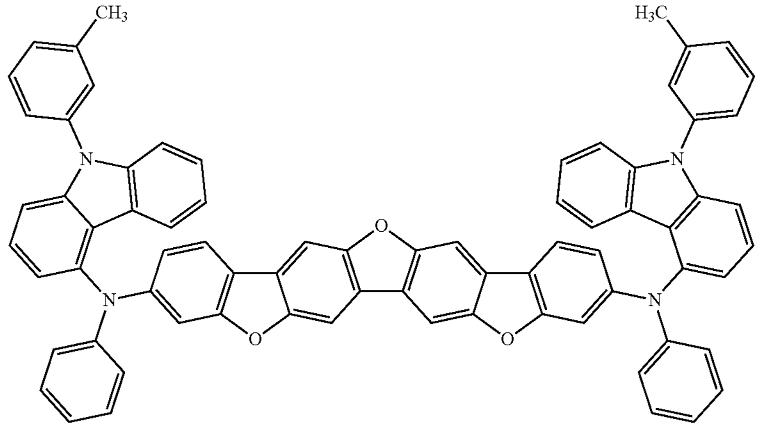
(110)
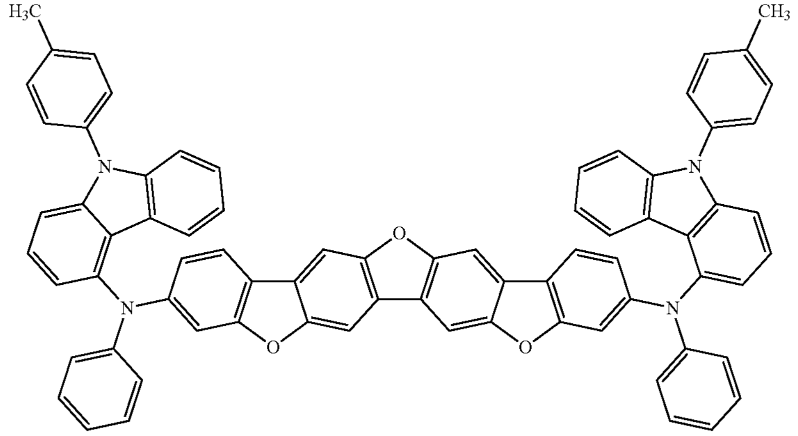
[Chemical Formula 24]
(111)
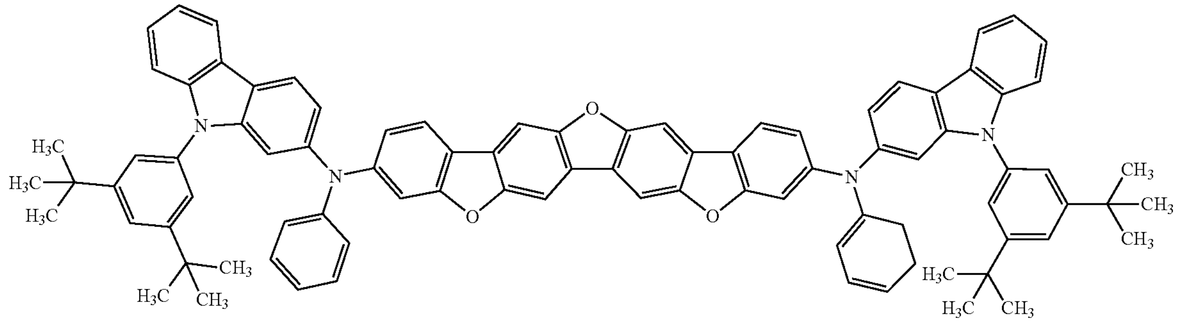

-continued
(112)
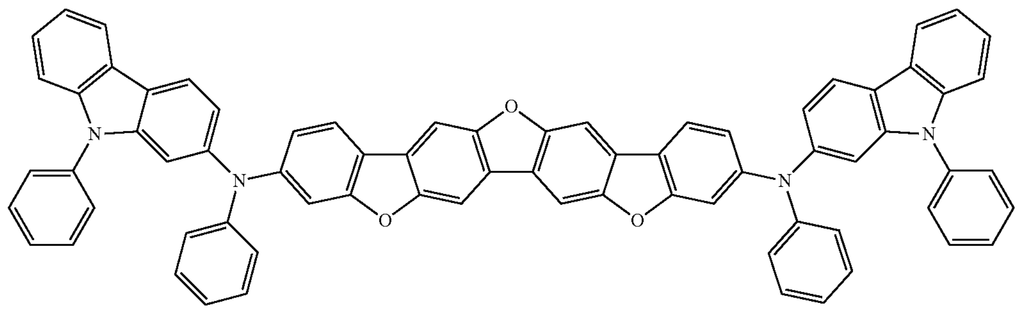
(113)
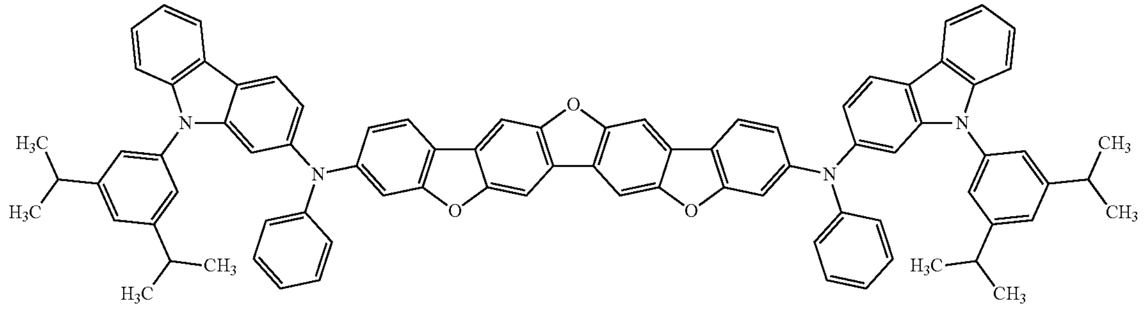
(114)
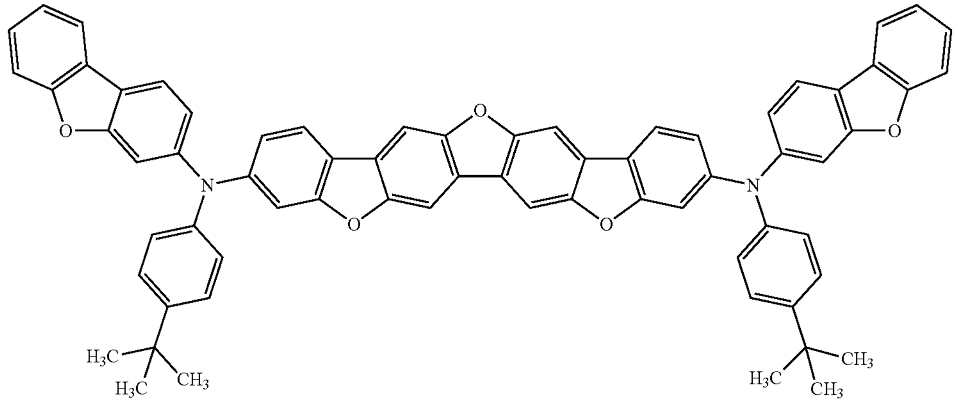
(115)
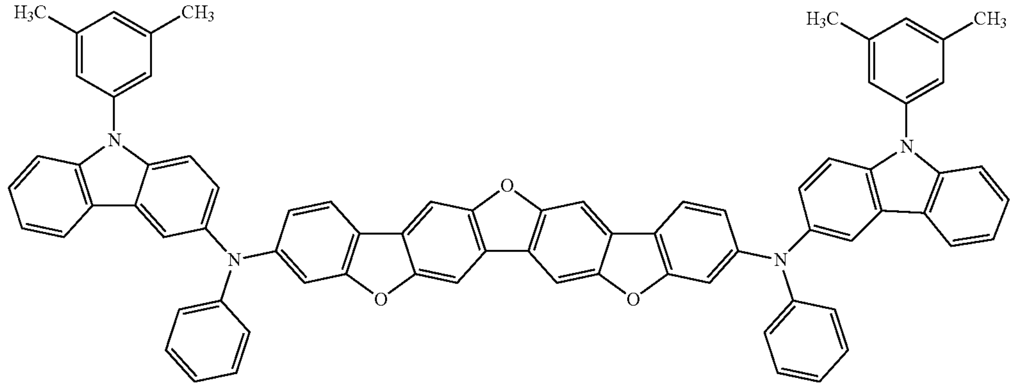

-continued
(116)
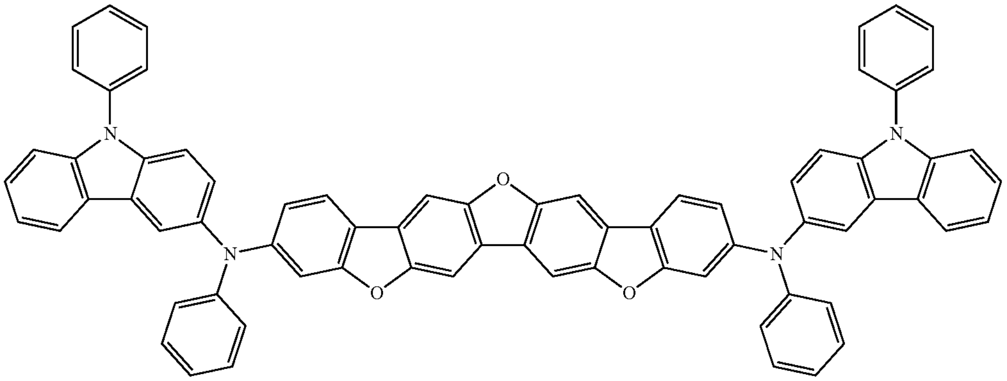
(117)
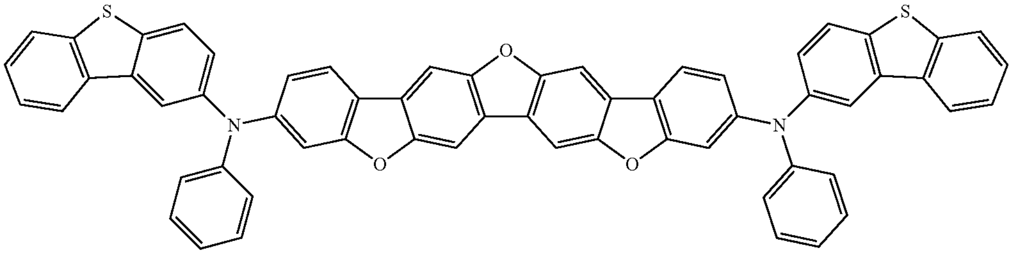
(118)
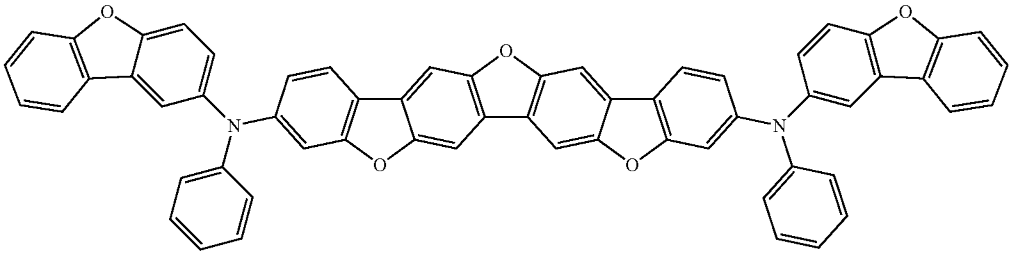
[Chemical Formula 25]
(121)
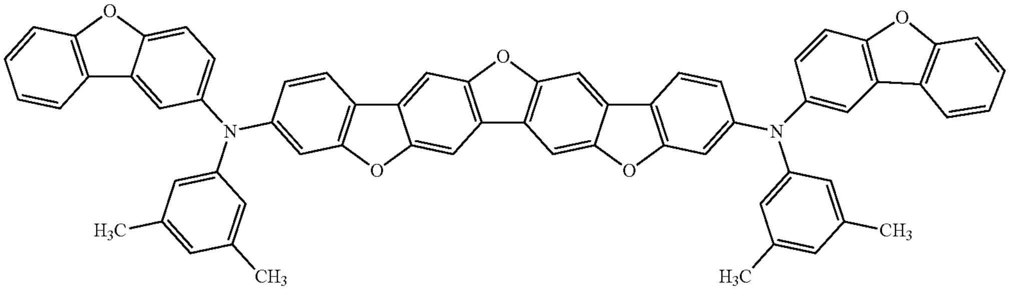
(122)
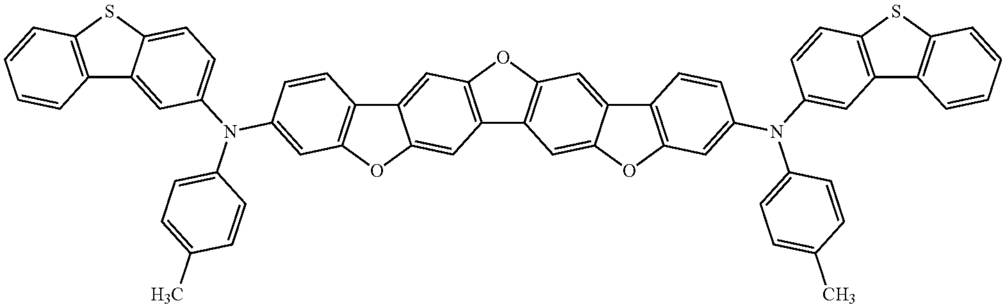

-continued
(123)
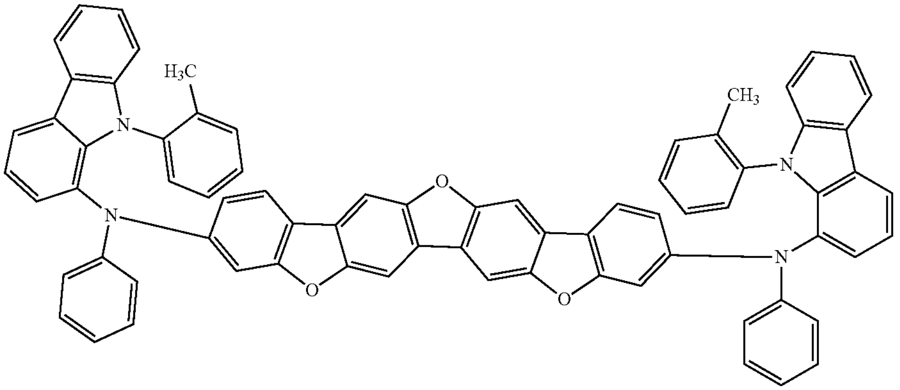
(124)
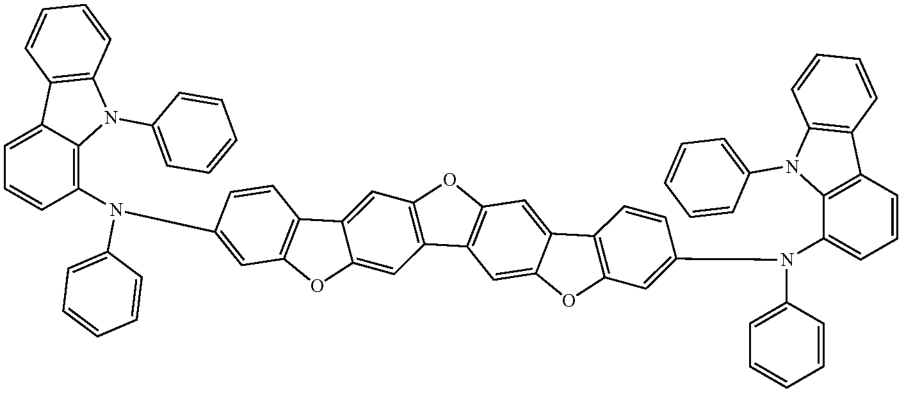
(125)
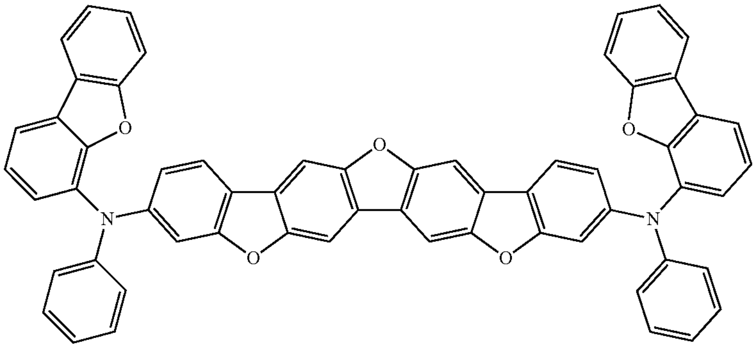
(126)
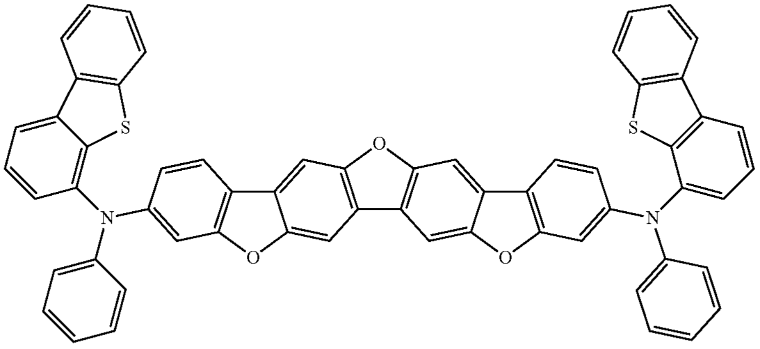

-continued
(127)
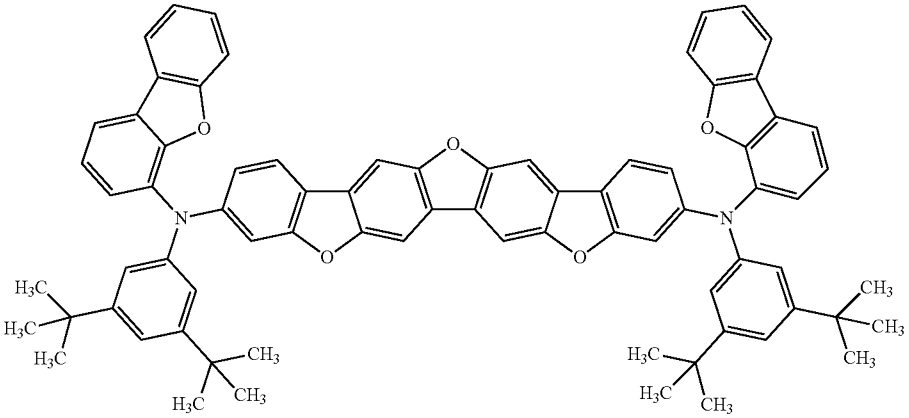
(128)
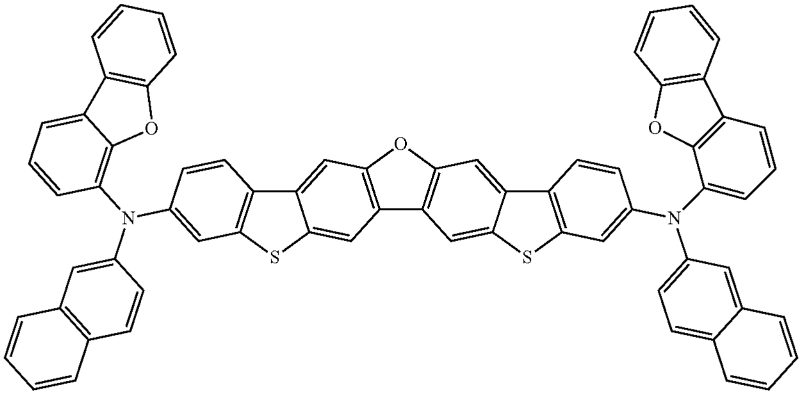
(129)
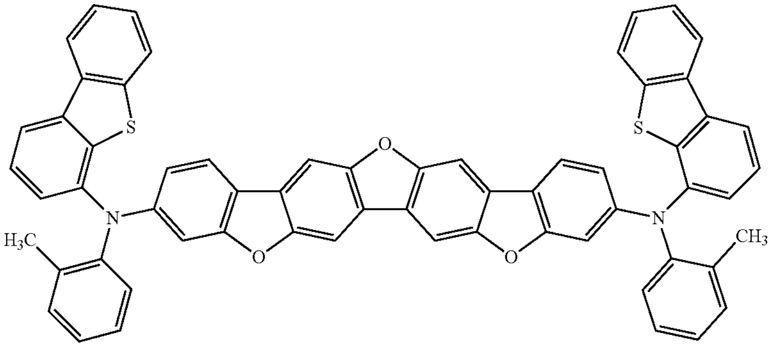
[Chemical Formula 26]
(131)
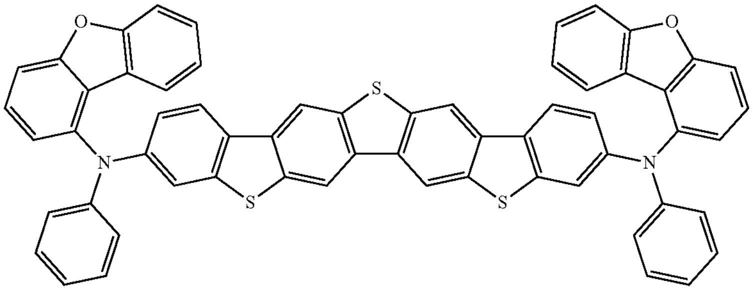

-continued
(132)
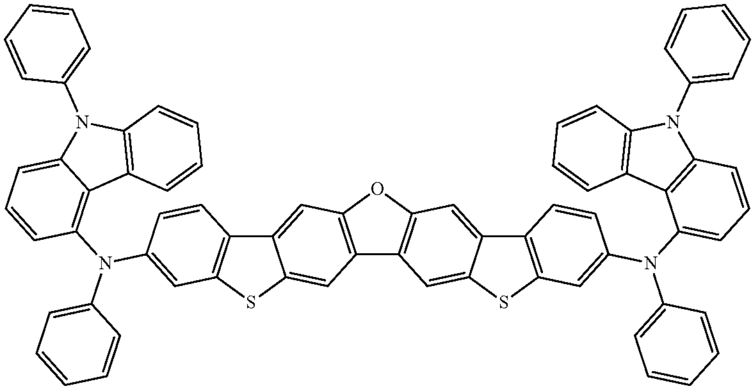
(133)
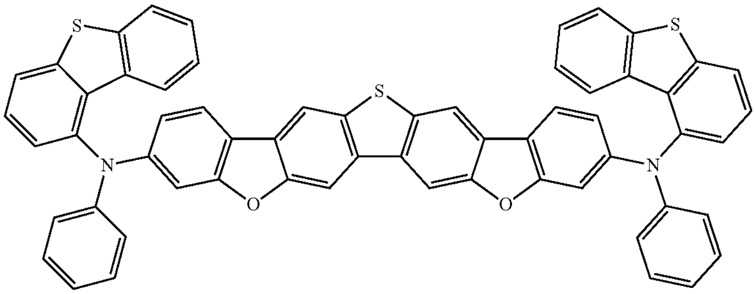
(134)
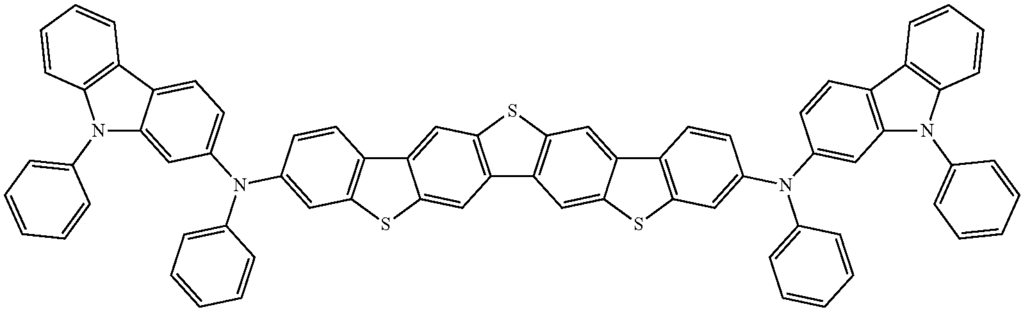
(135)
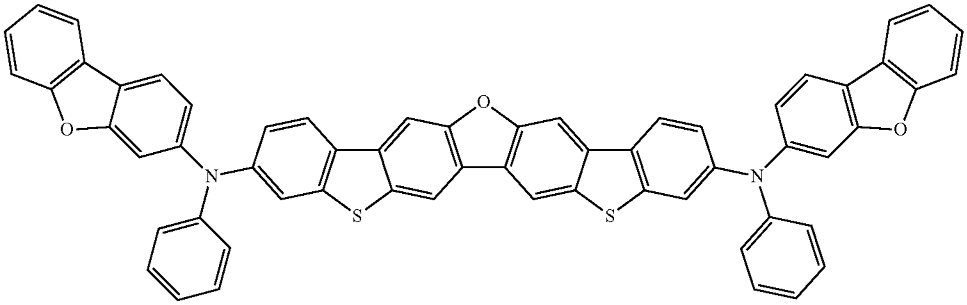
(136)
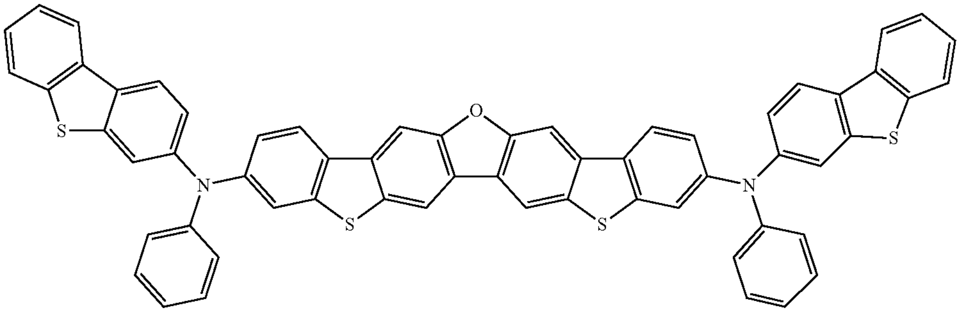

-continued
(137)
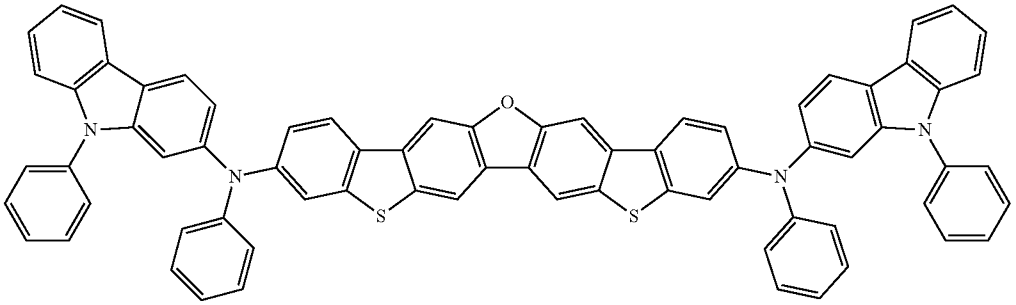
(138)
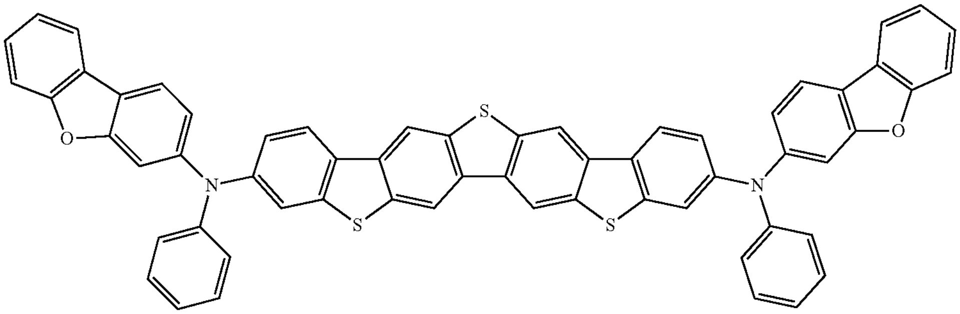
(139)
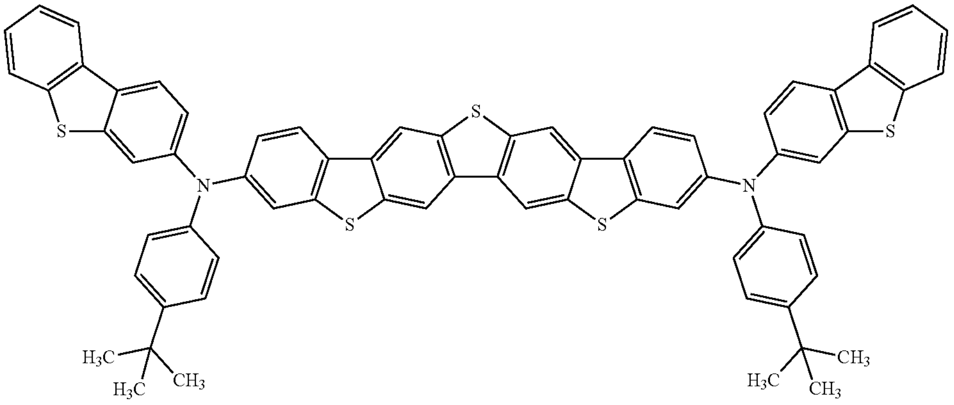
[Chemical Formula 27]
(141)
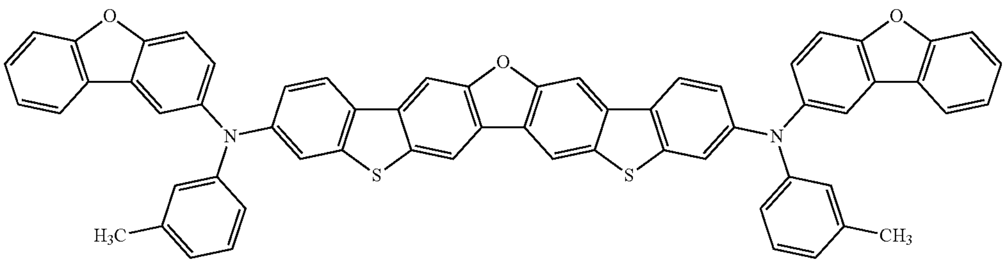

-continued
(142)
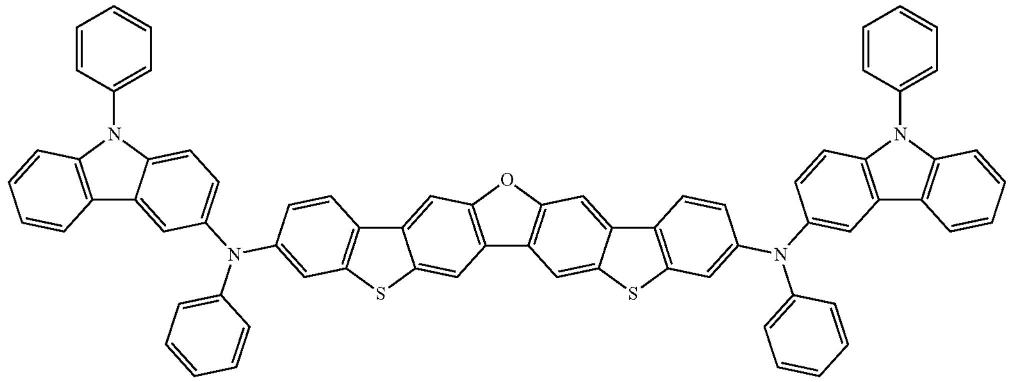
(143)
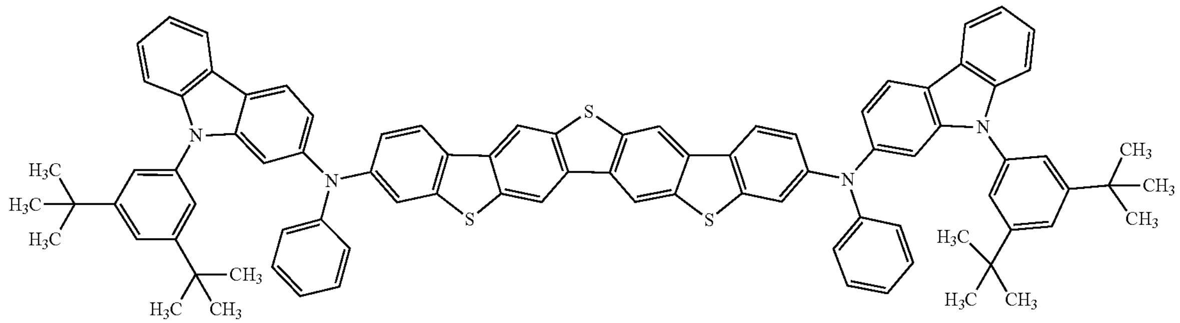
(144)
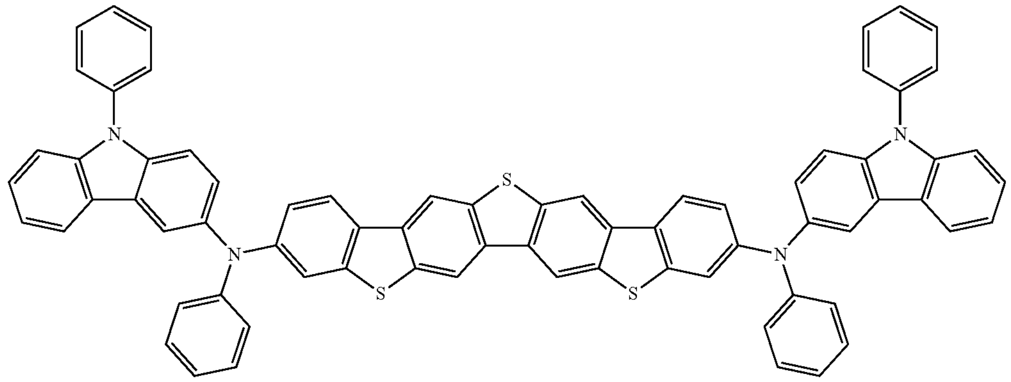
(145)
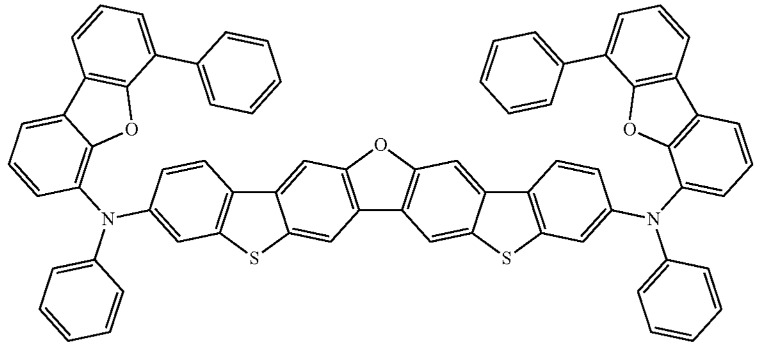

-continued
(146)
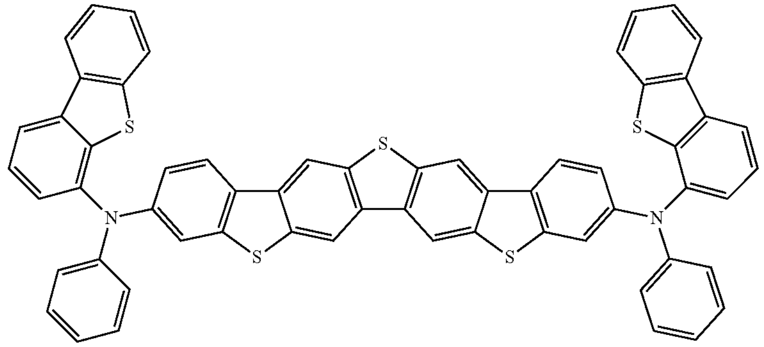
(147)
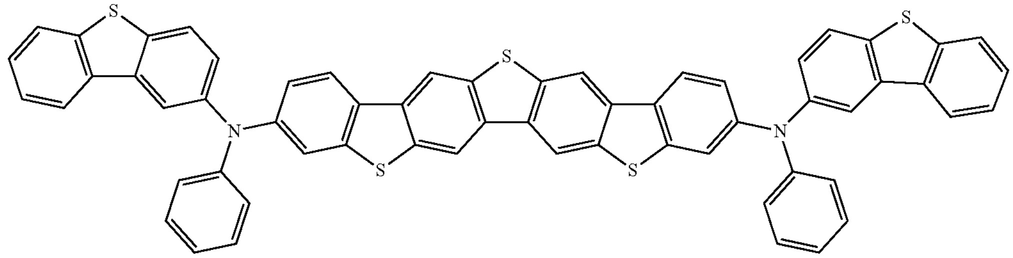
(148)
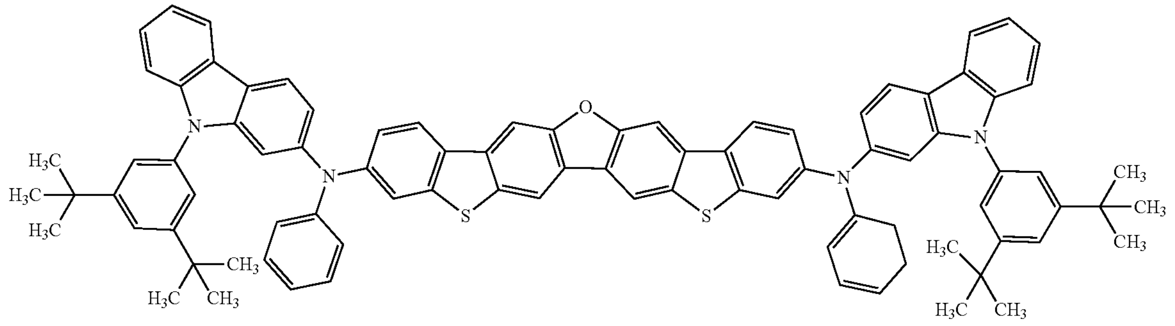
(149)
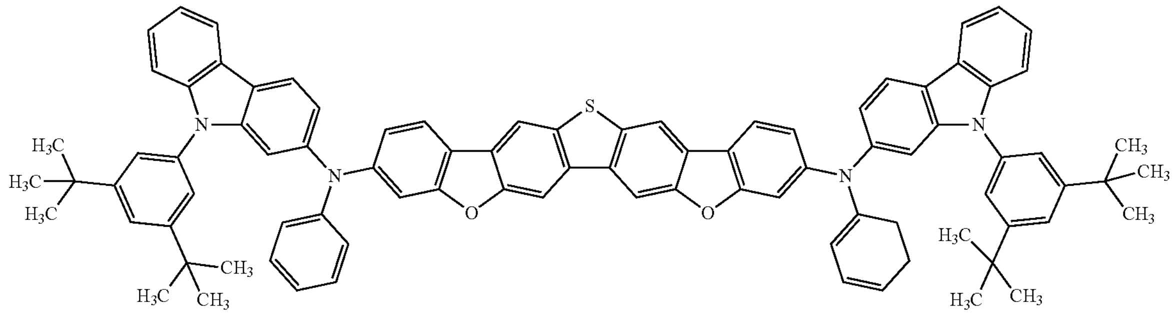

[Chemical Formula 28]
(151)
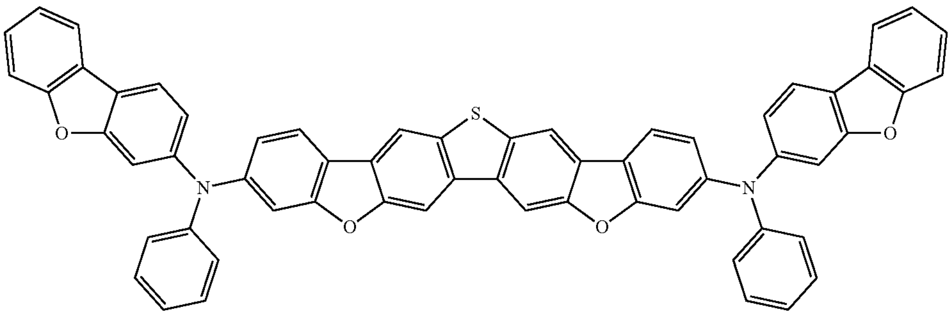
(152)
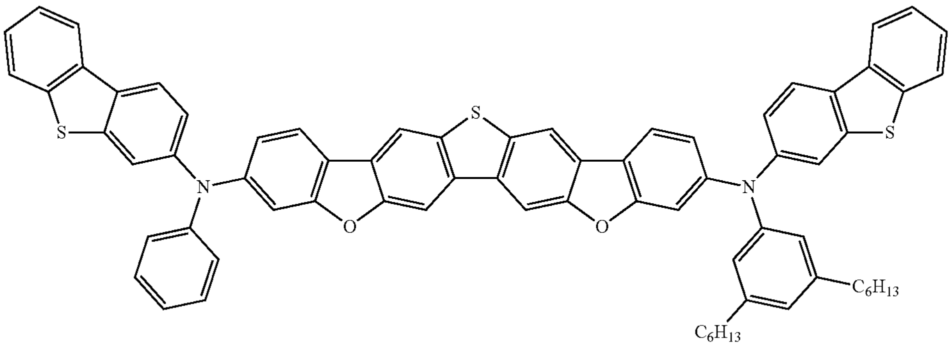
(153)
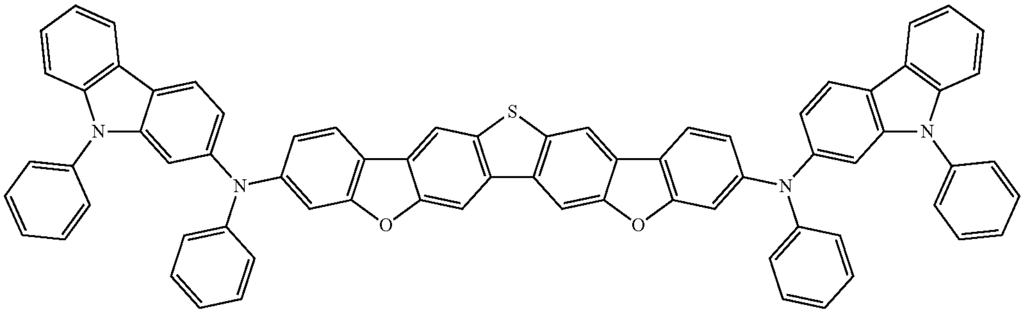
(154)
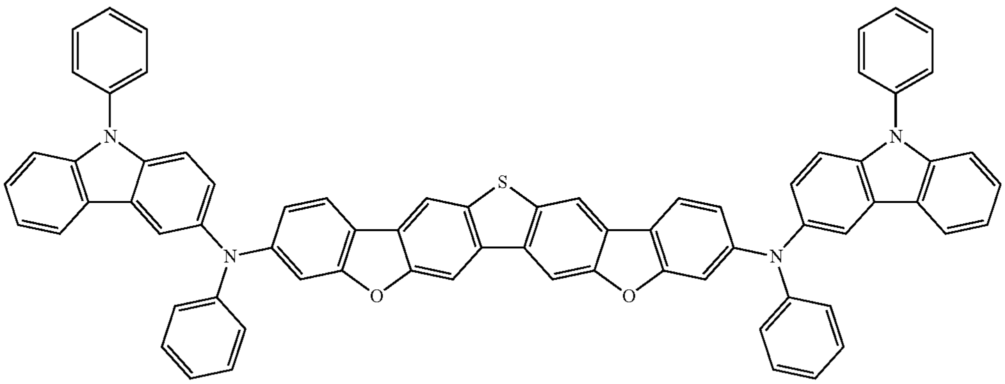

-continued
(155)
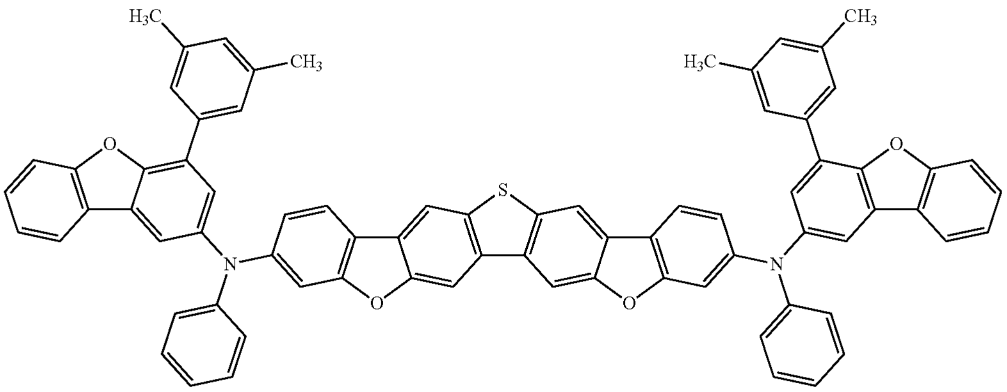
(156)
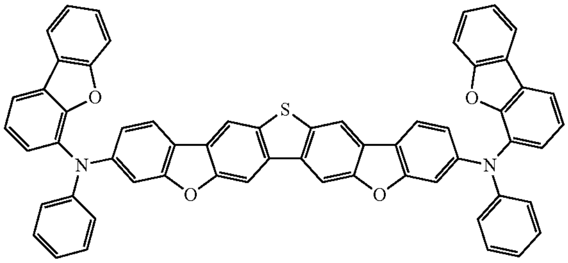
[Chemical Formula 29]
(161)
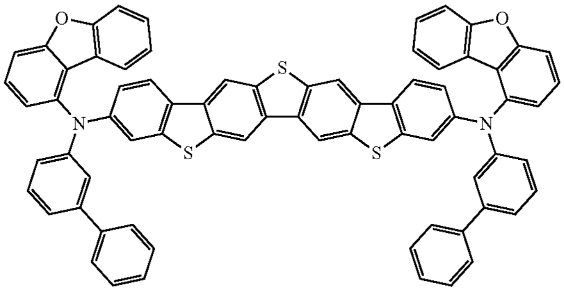
(162)
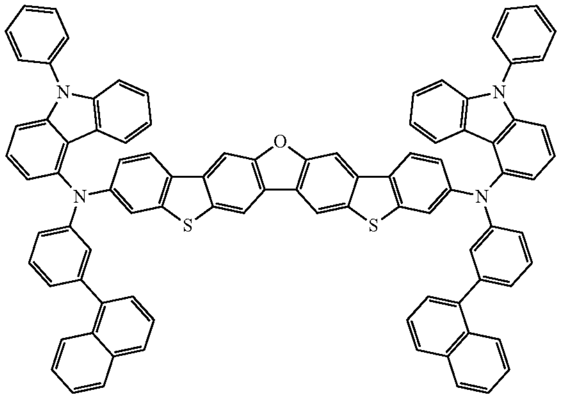
(163)
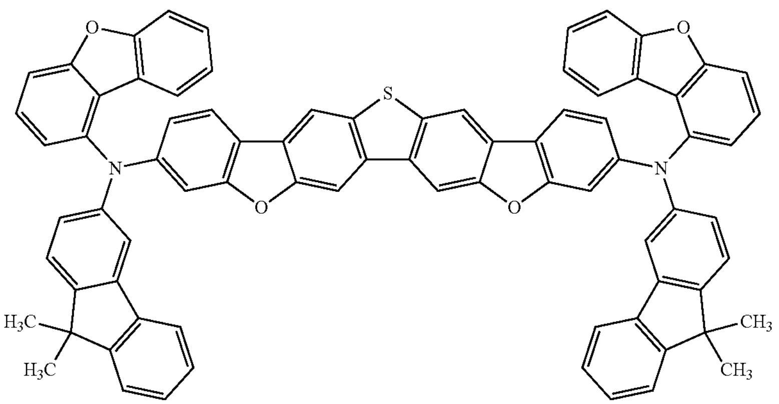

-continued
(164)
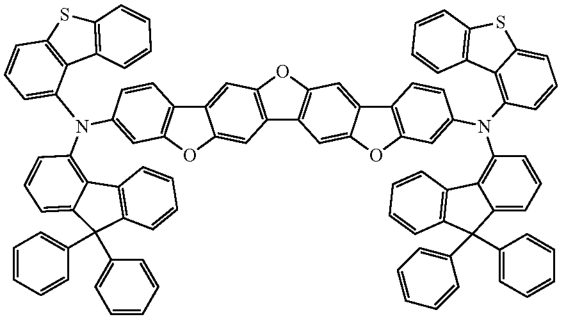
(165)
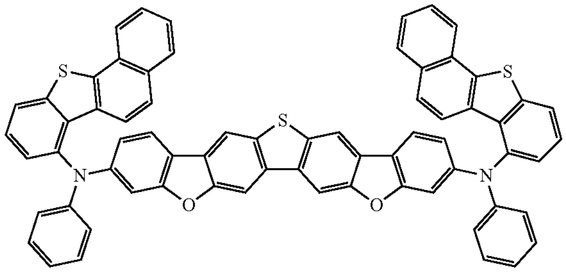
(166)
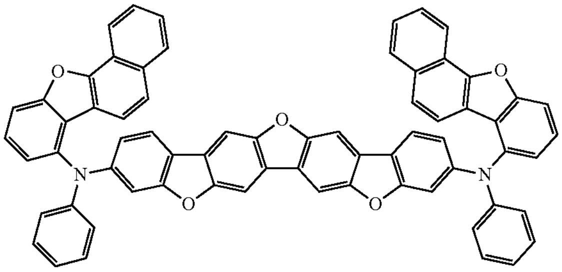
(167)
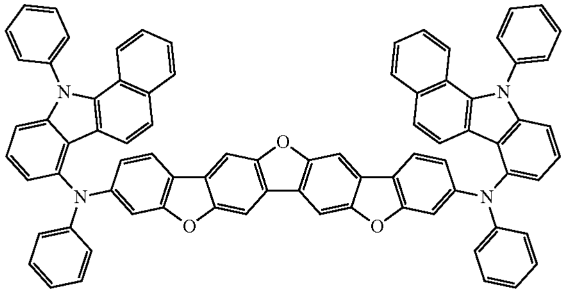
(168)
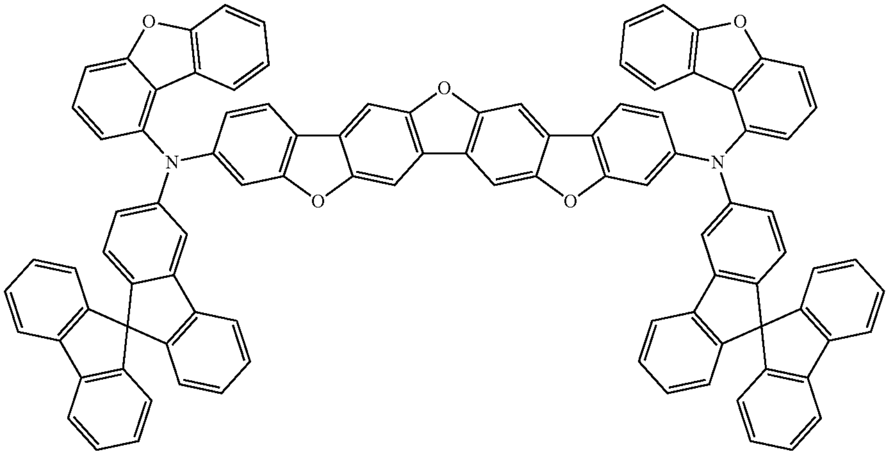
[Chemical Formula 30]
(171)
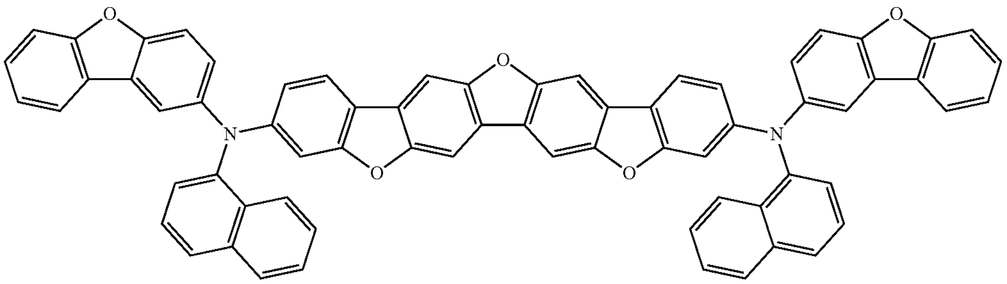

-continued
(172)
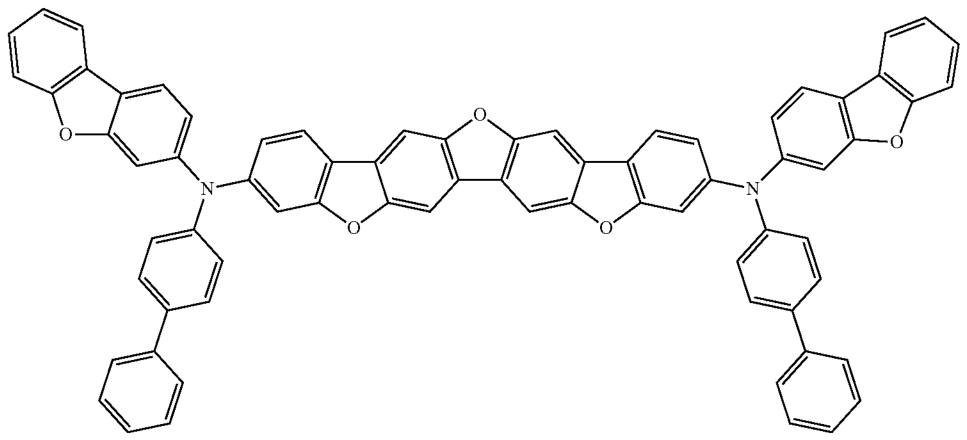
(173)
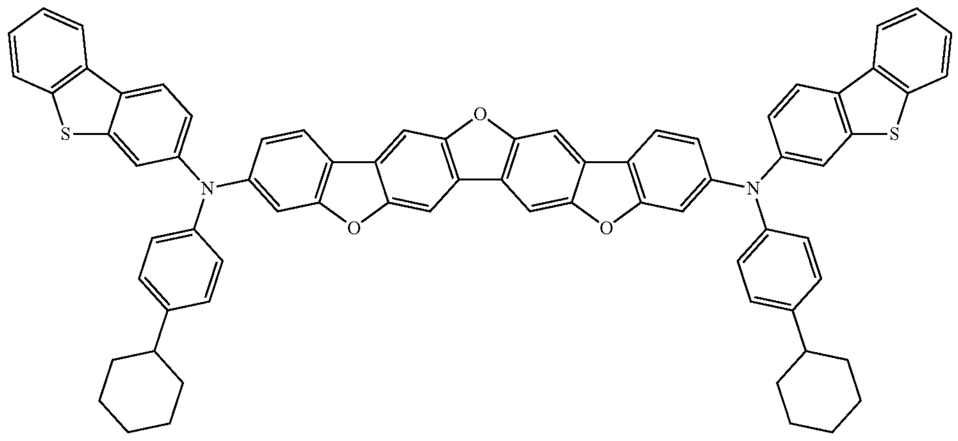
(174)
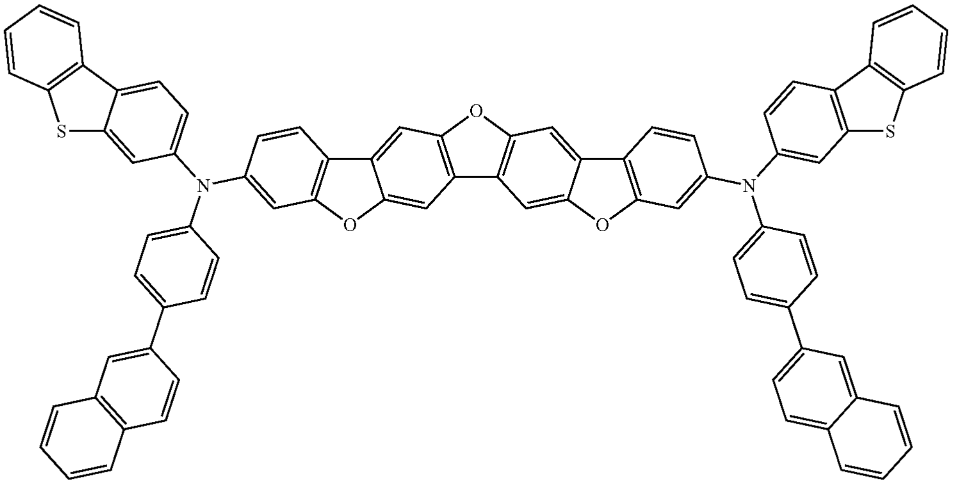

-continued
(175)
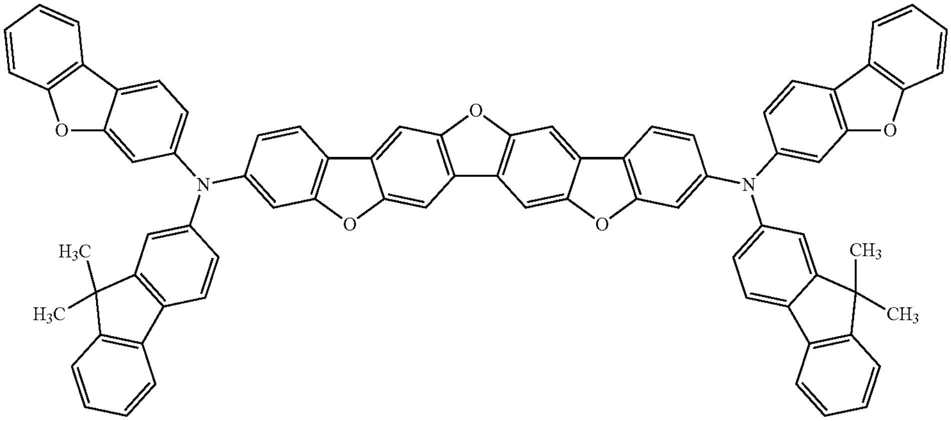
(176)
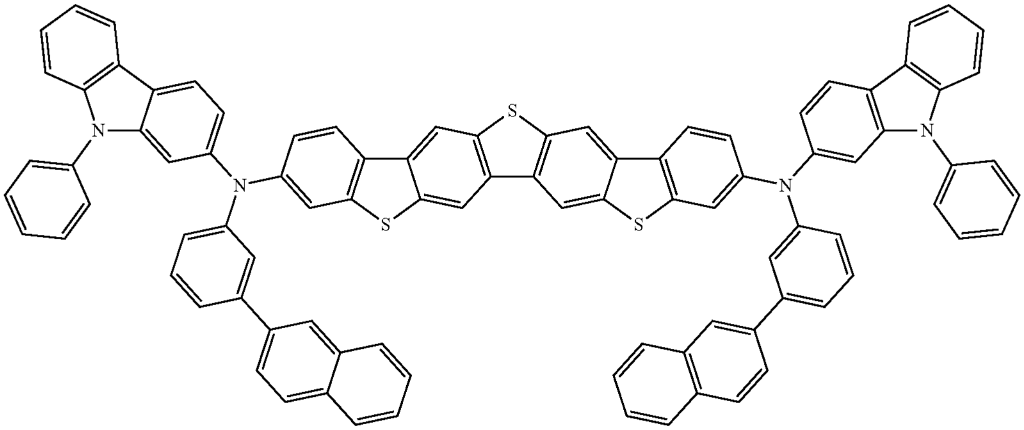
(177)
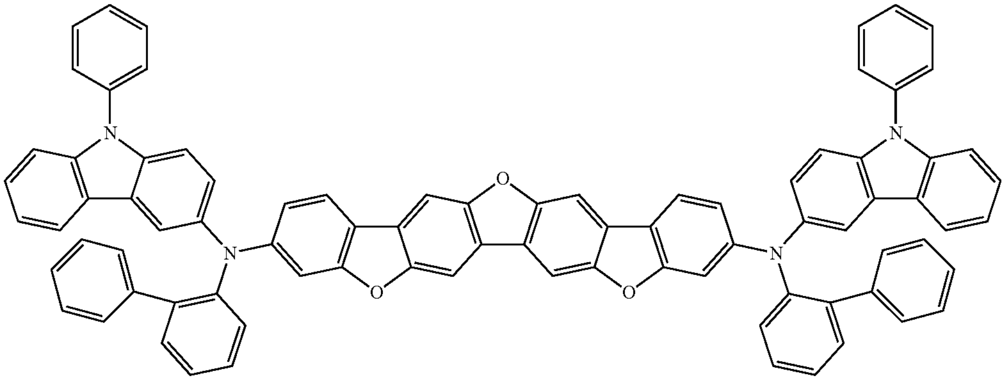
[Chemical Formula 31]
(181)
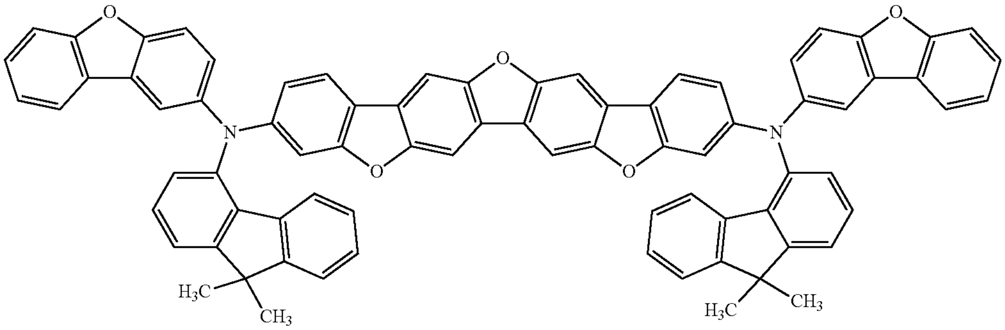

-continued
(182)
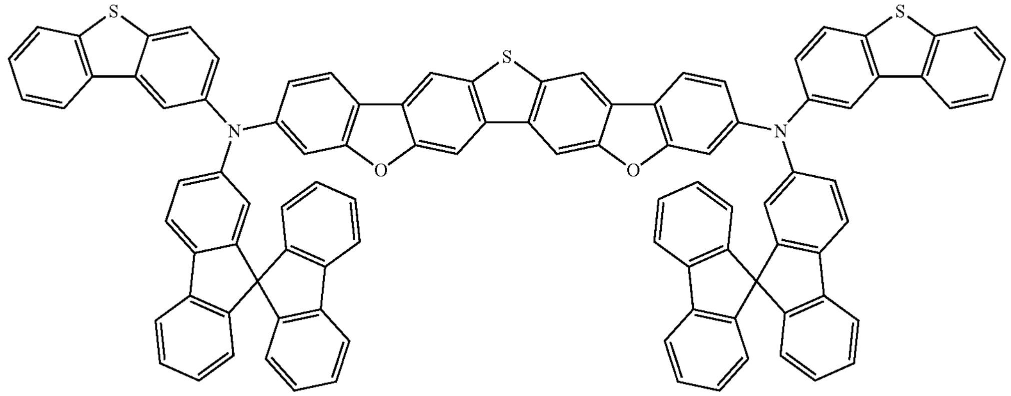
(183)
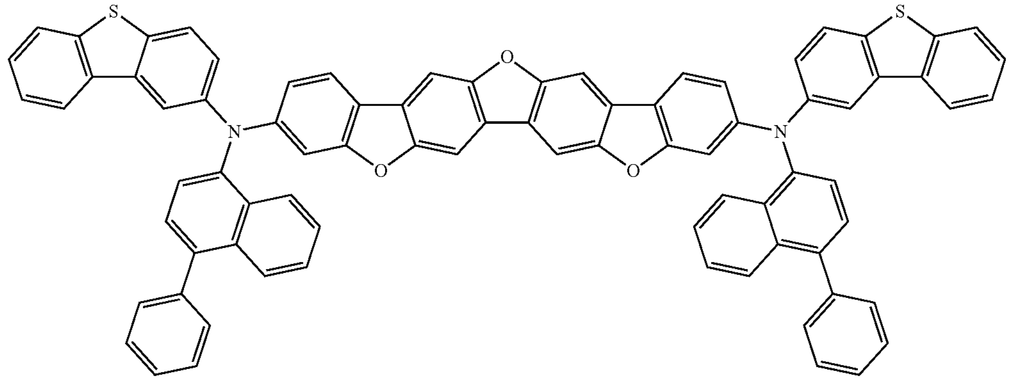
(184)
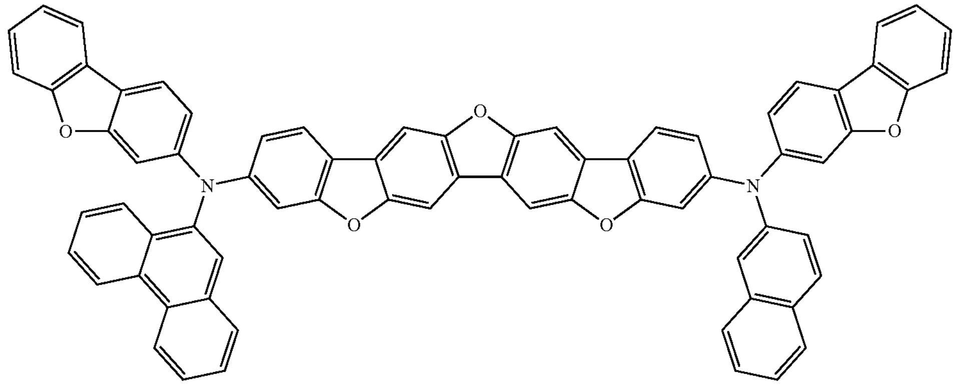
(185)
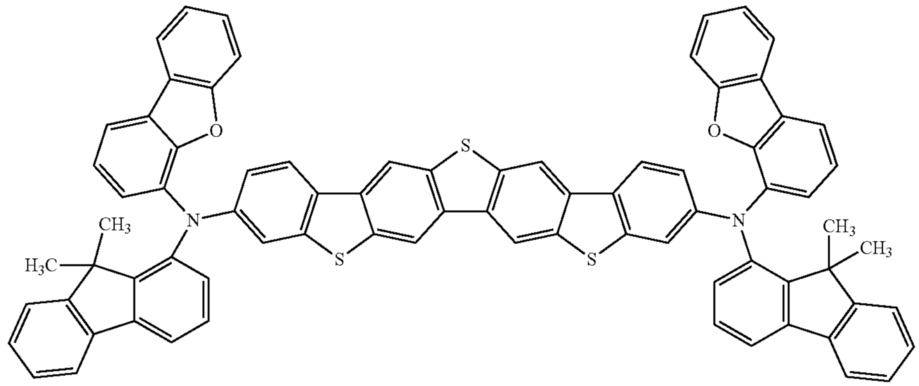

-continued
(186)
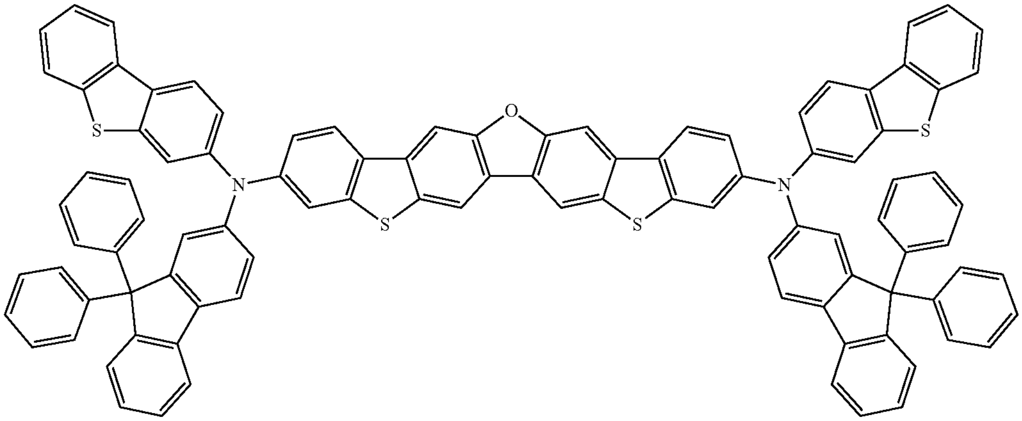
(187)
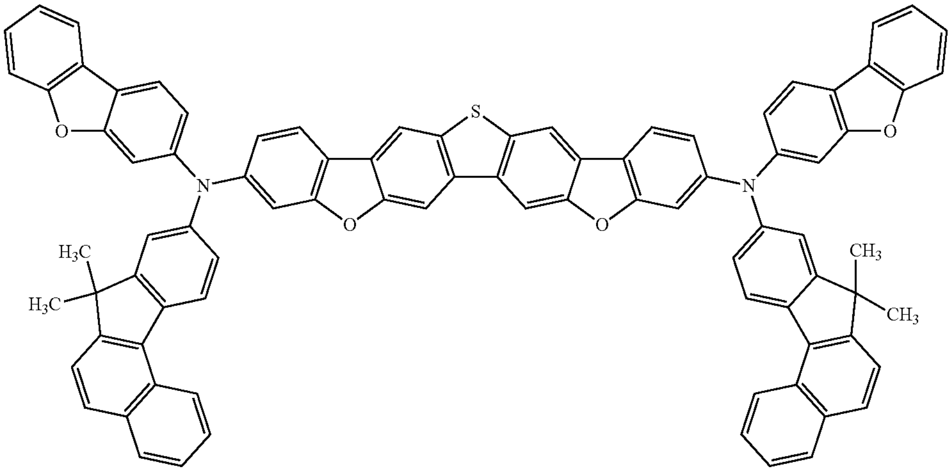
[Chemical Formula 32]
(191)
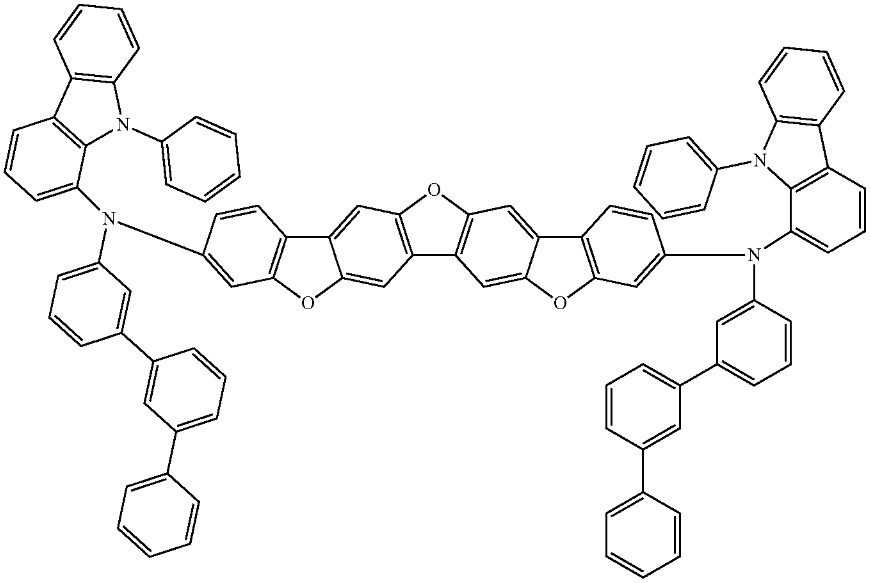

-continued
(192)
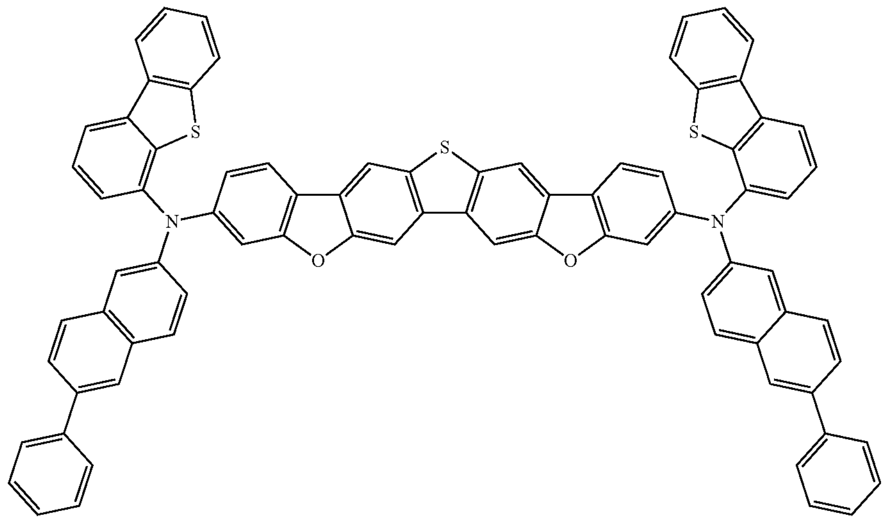
(193)
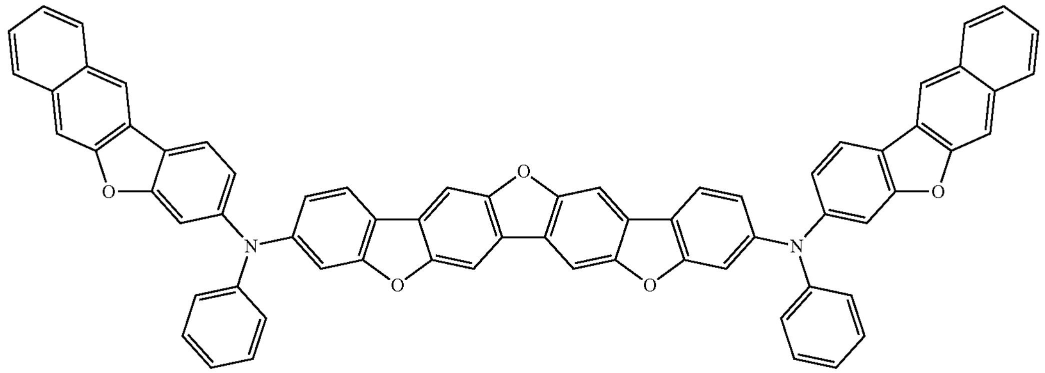
(194)
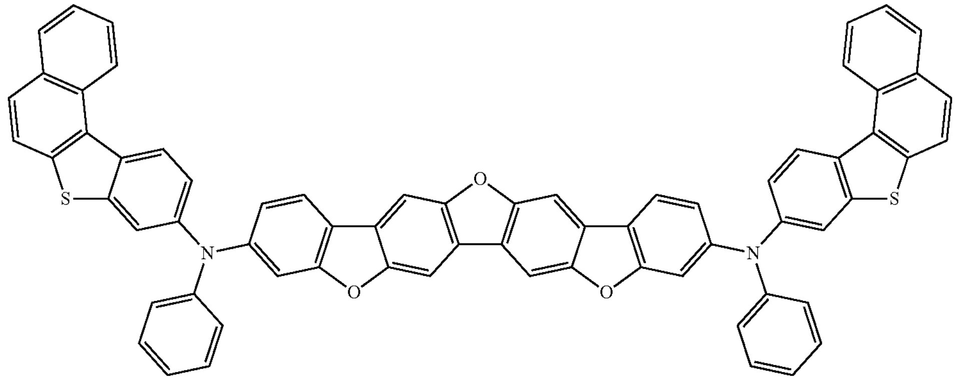

-continued
(195)
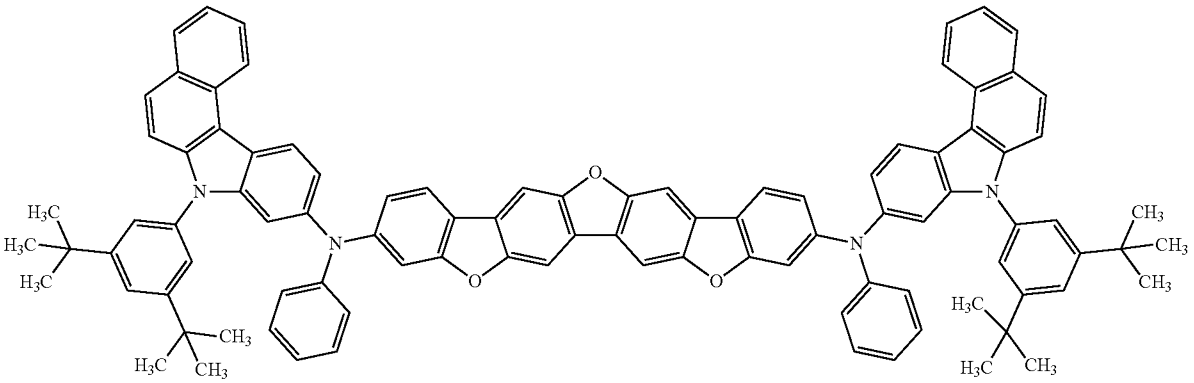
(196)
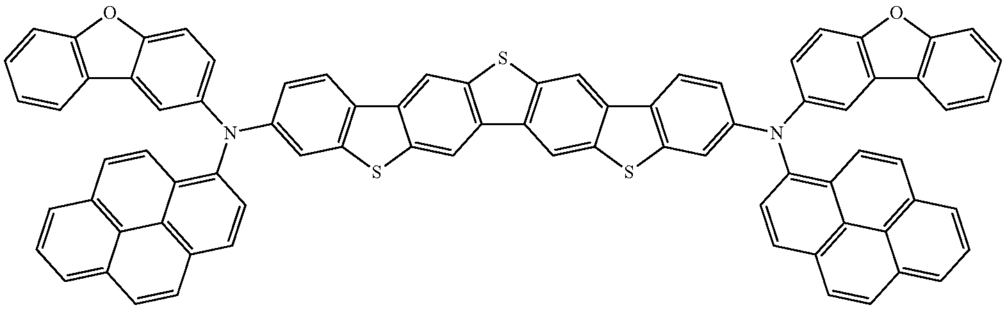
[Chemical Formula 33]
(197)
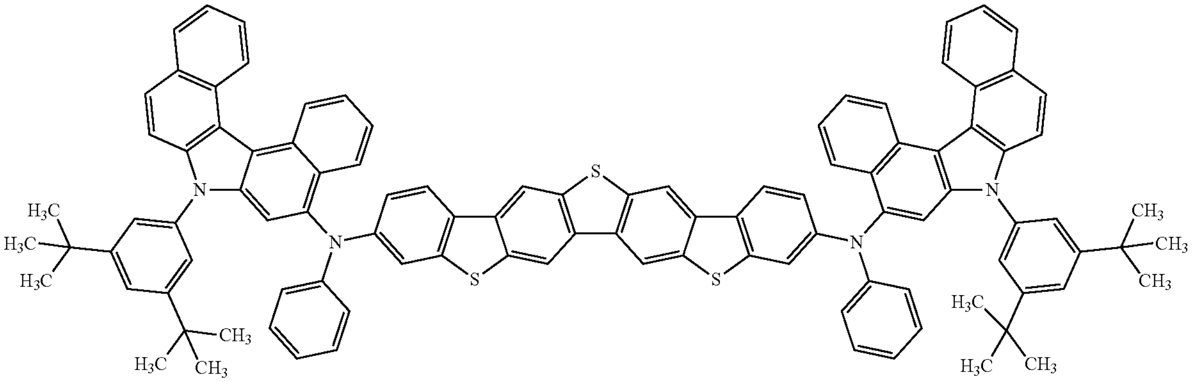
(198)
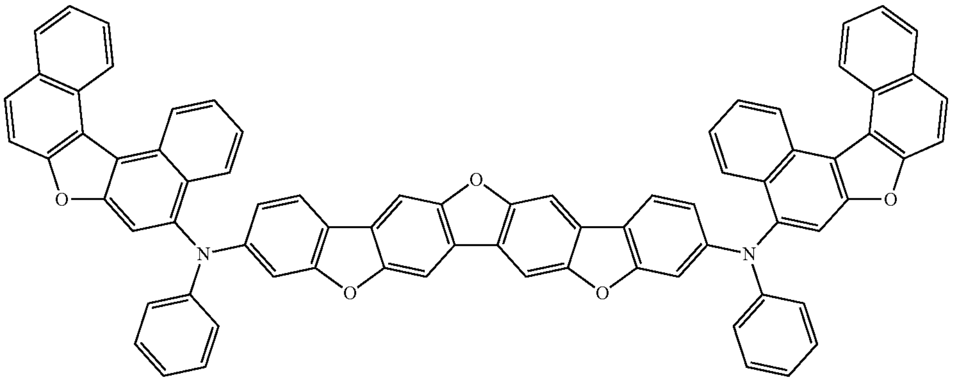

-continued
(201)
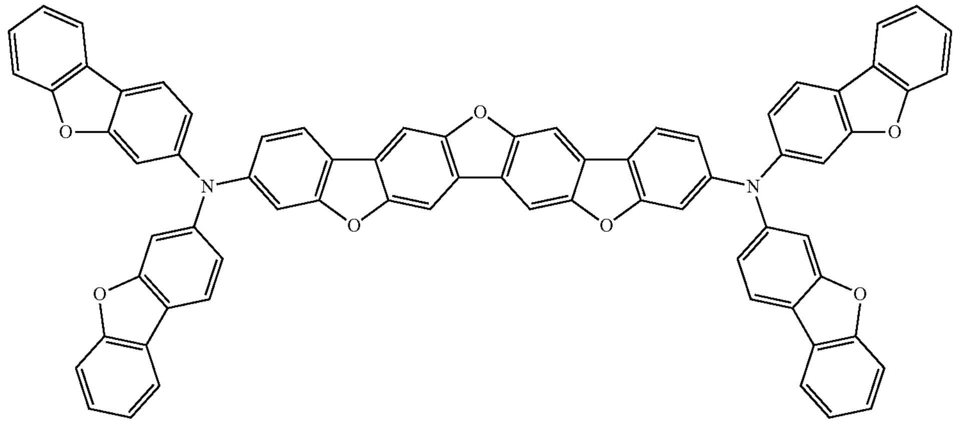
(202)
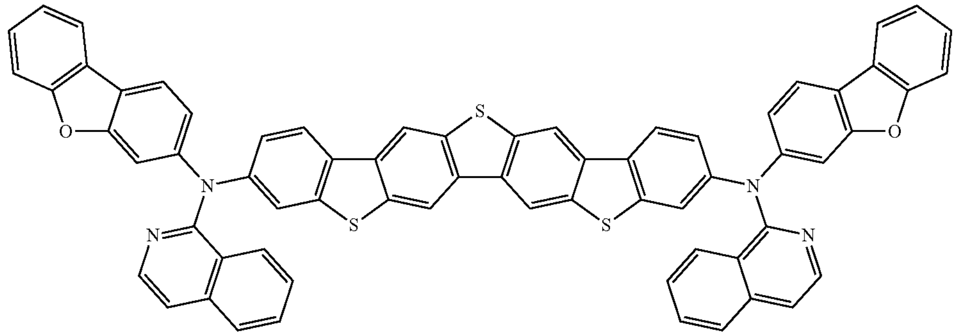
(203)
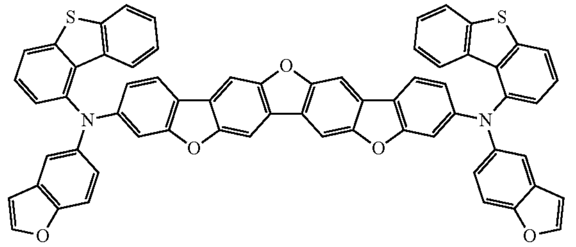
(204)
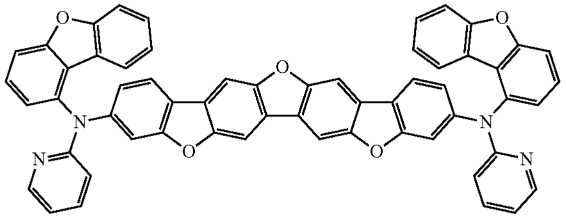
(205)
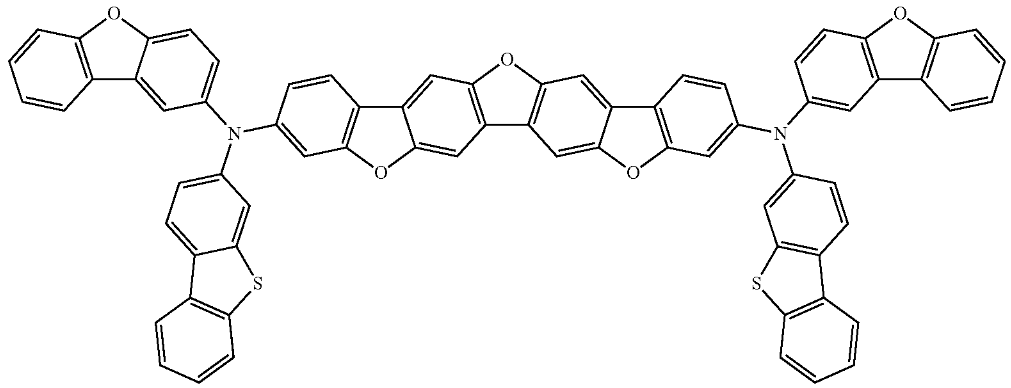

[Chemical Formula 34]
(206)
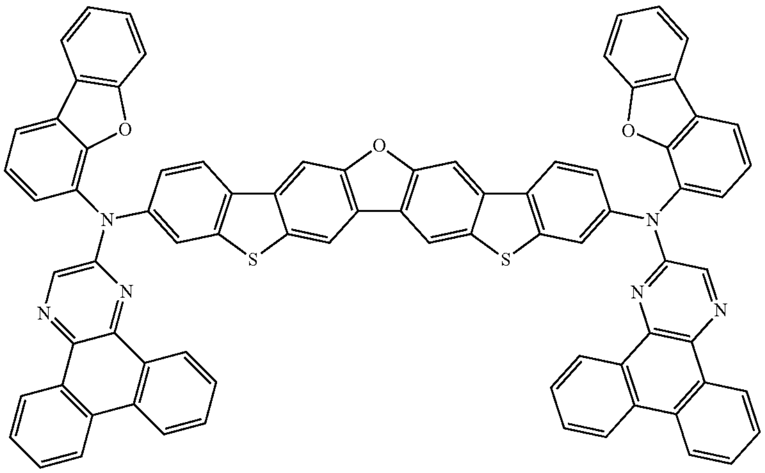
(207)
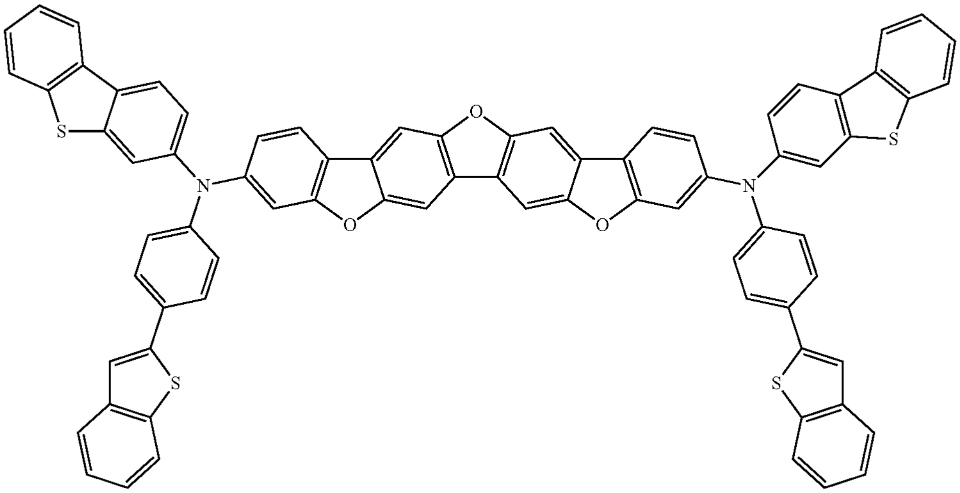
(208)
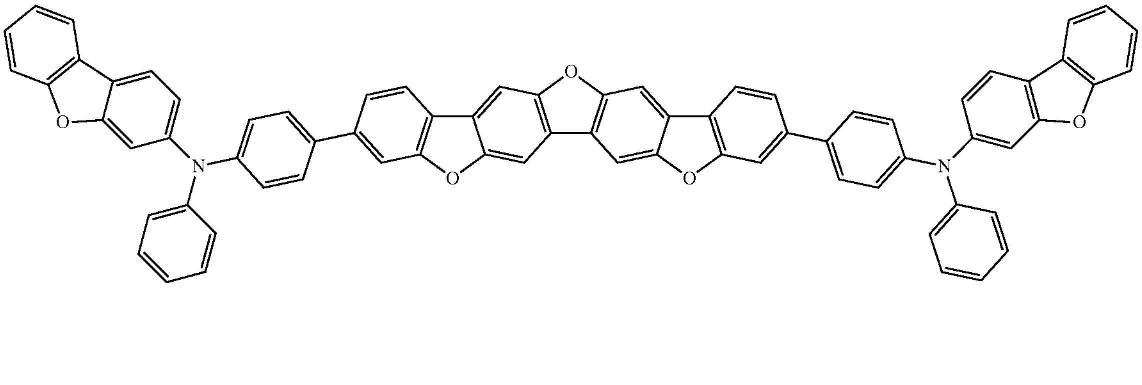

-continued
(211)
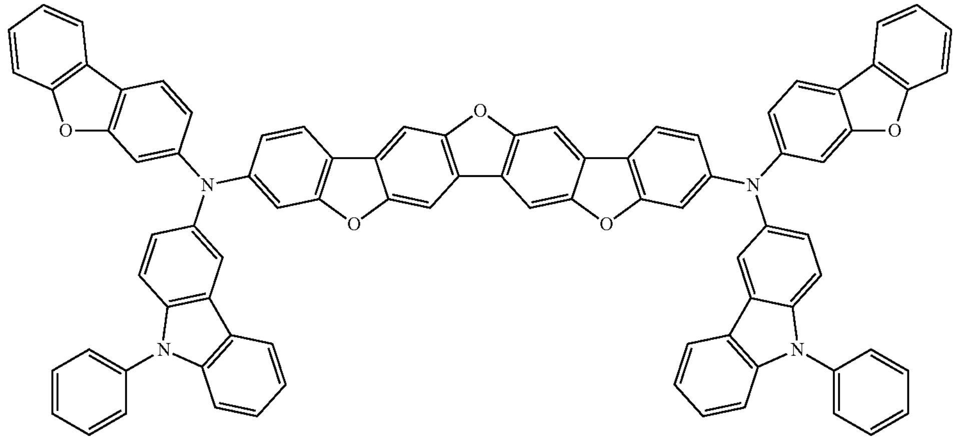
(212)
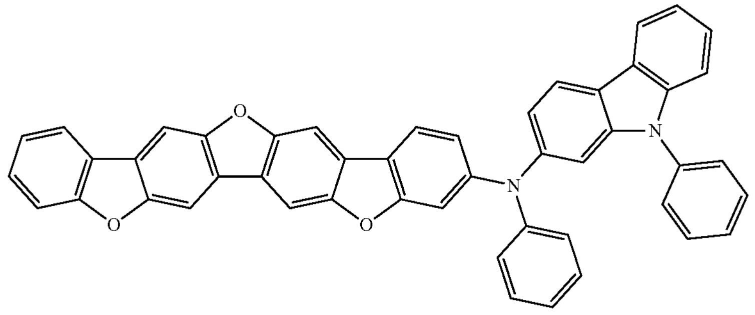
(213)
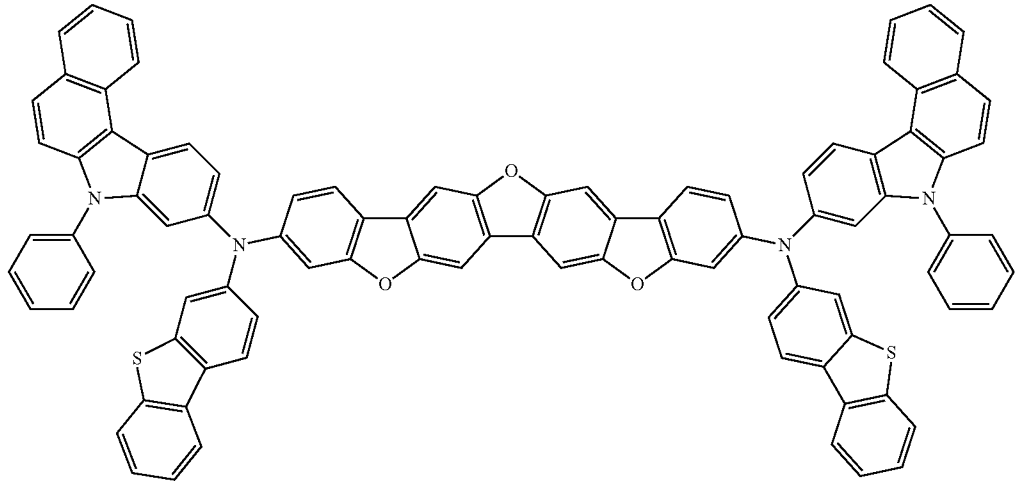

-continued
[Chemical Formula 35]
(214)
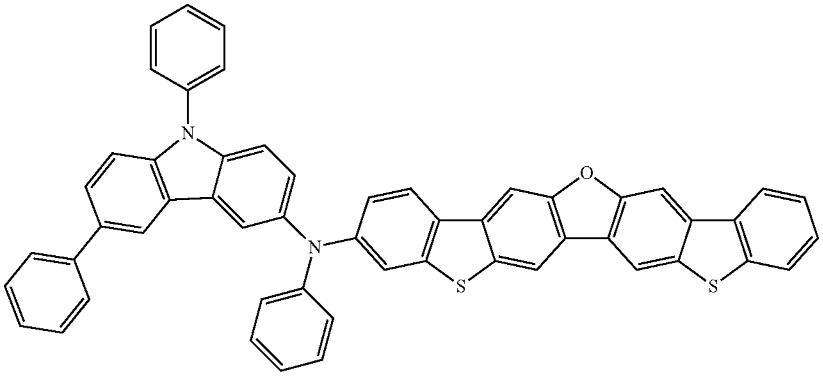
(215)
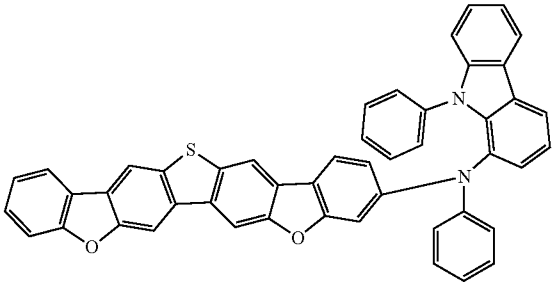
(216)
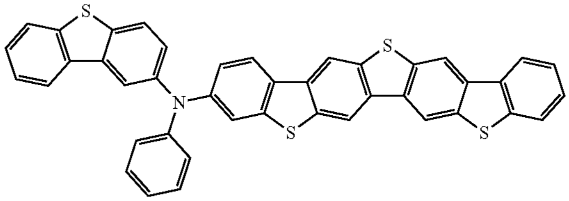
(217)
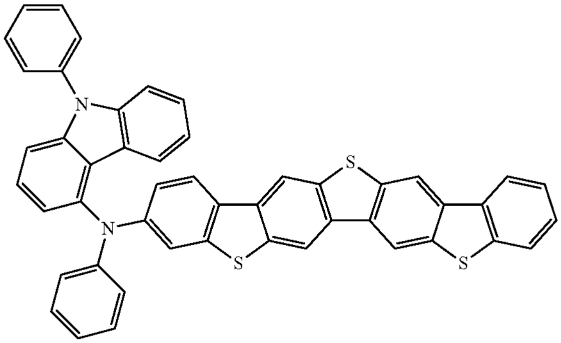
(218)
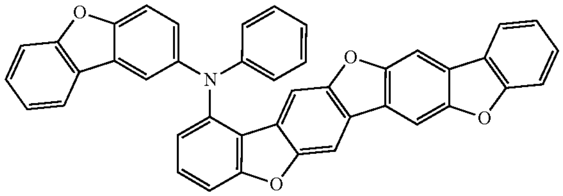
(219)
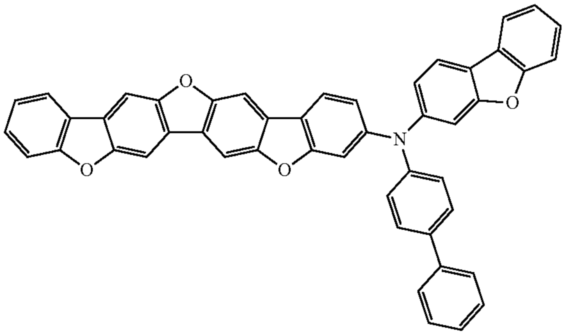
(221)
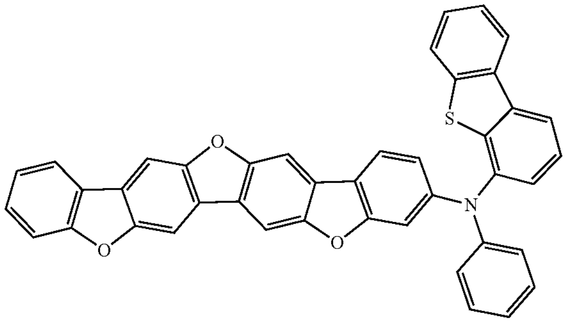

-continued
(222)
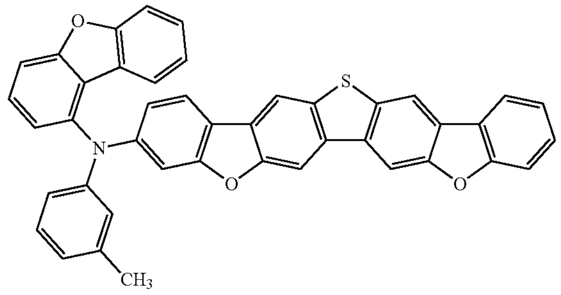
(223)
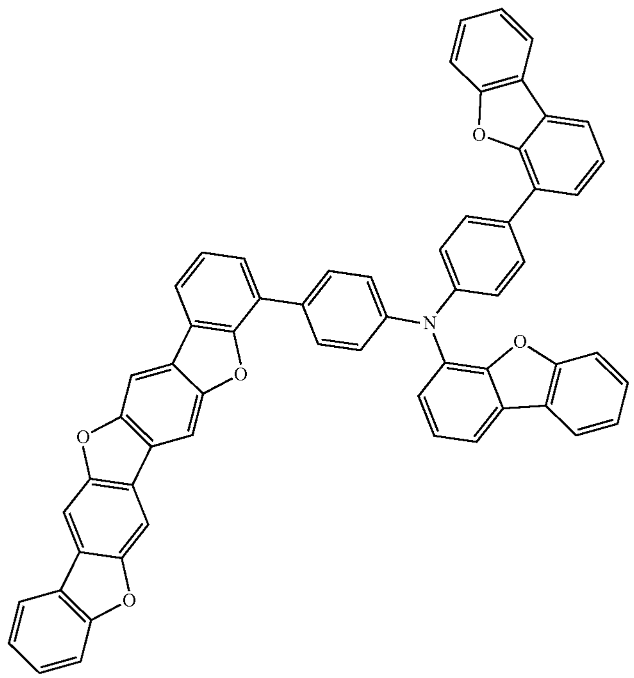
(224)
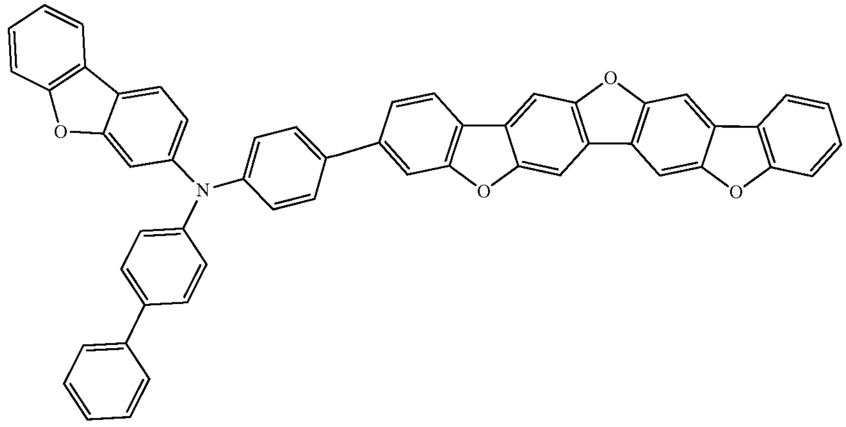

-continued
(225)
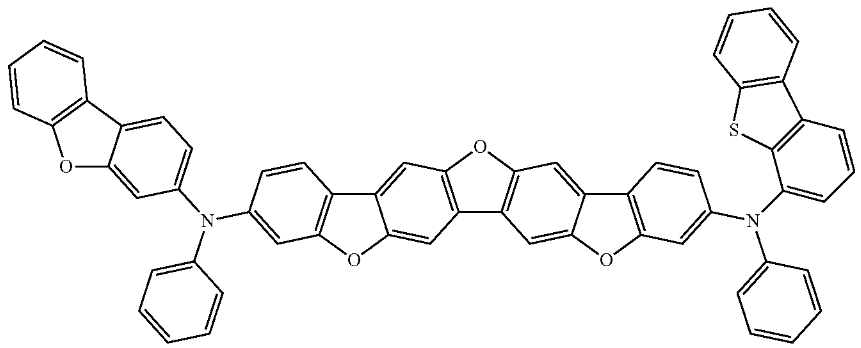
(226)
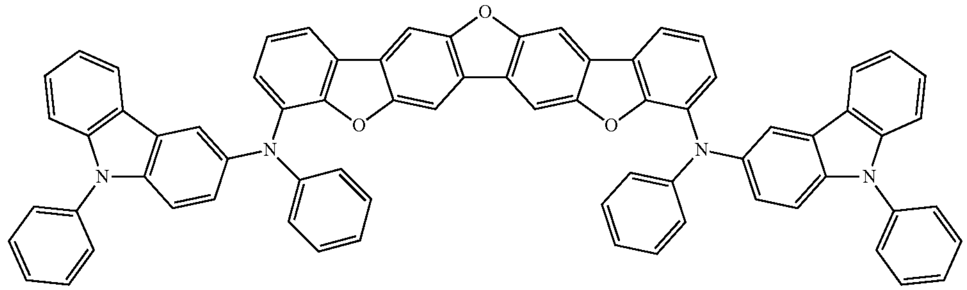
[Chemical Formula 36]
(227)
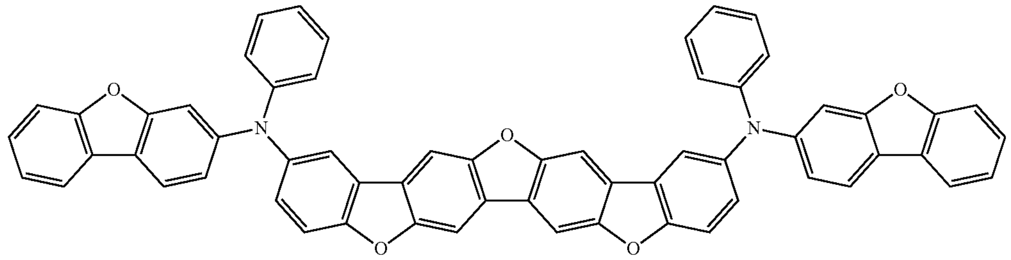
(228)
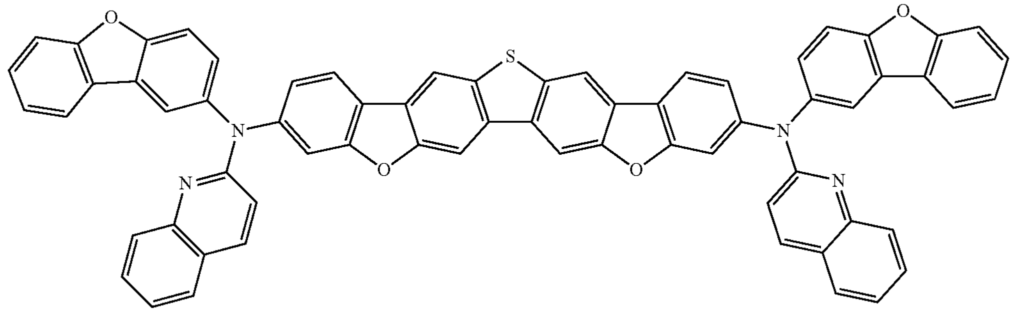
(229)
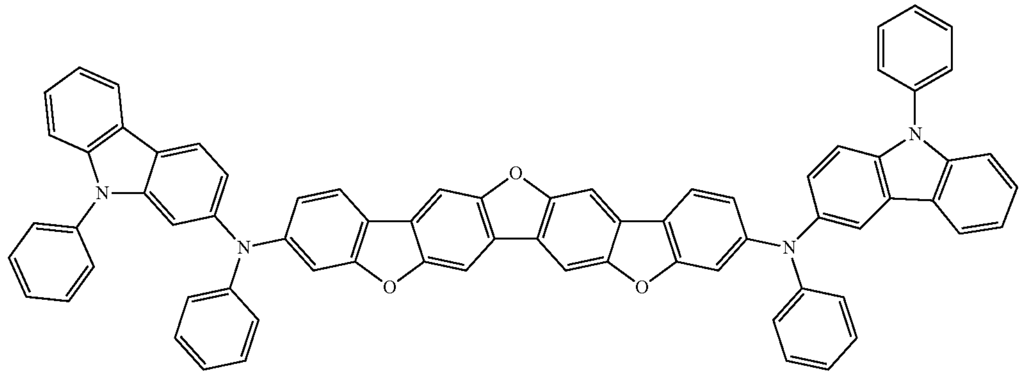

-continued
(231)
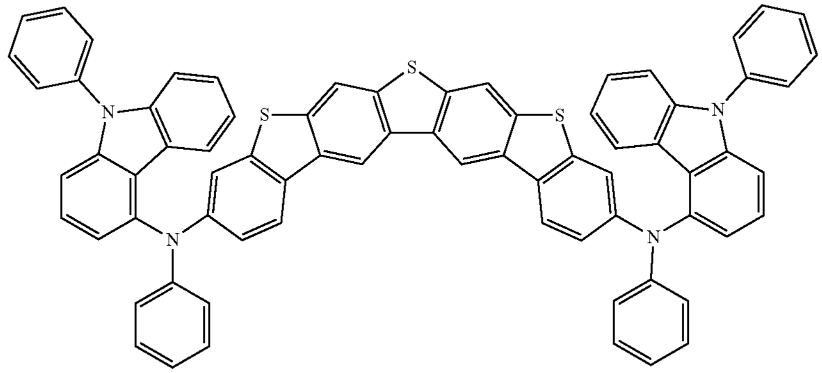
(232)
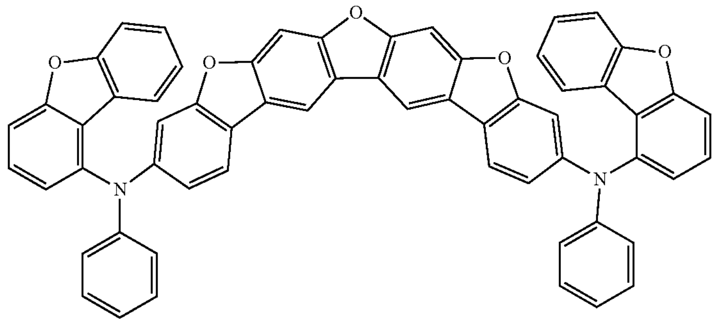
(233)
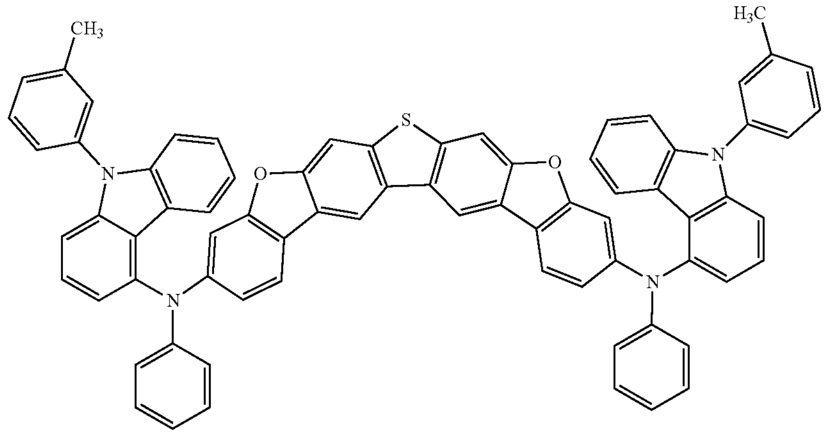
(234)
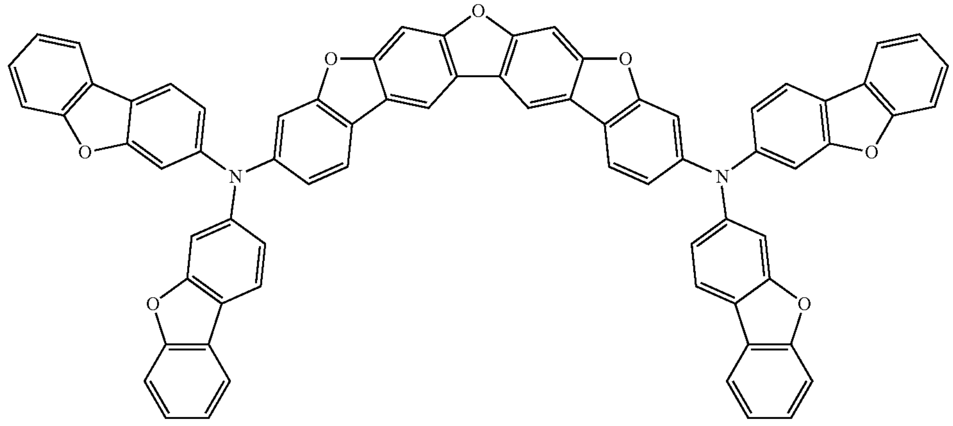

-continued
(235)
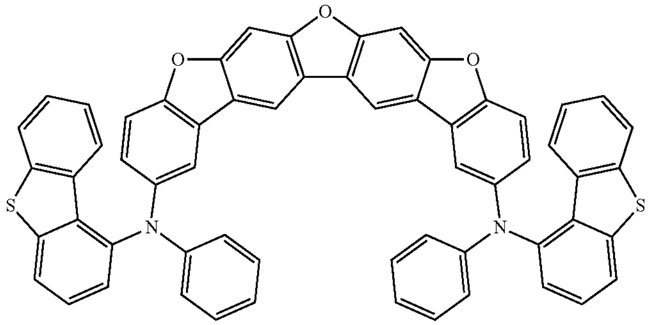
[Chemical Formula 37]
(236)
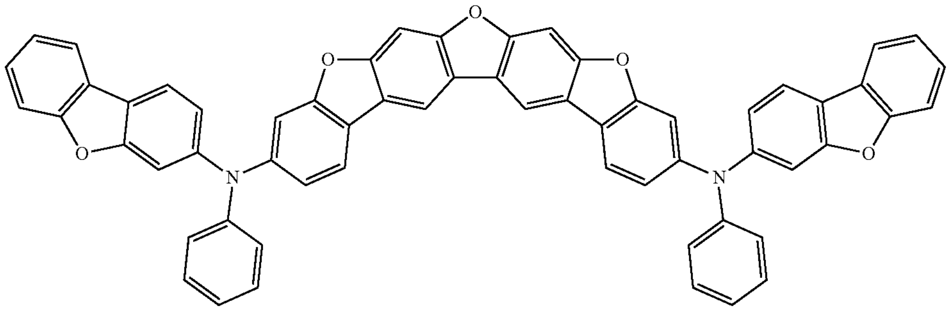
(237)
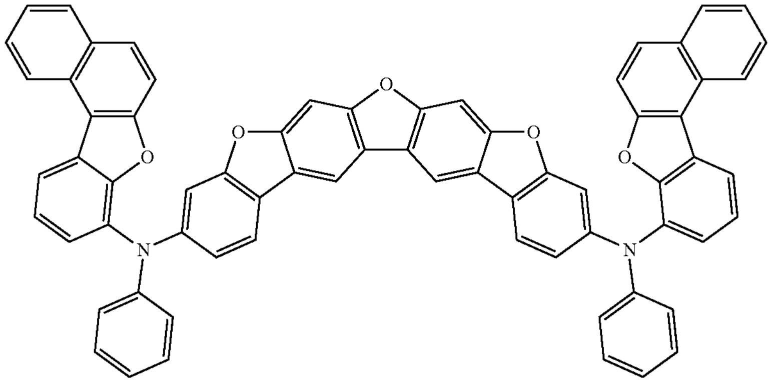
(238)
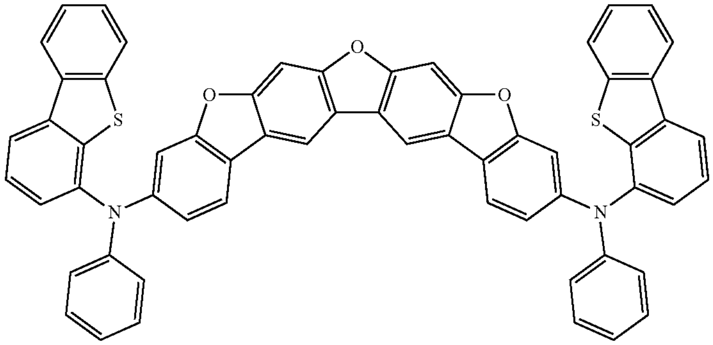

-continued
(239)
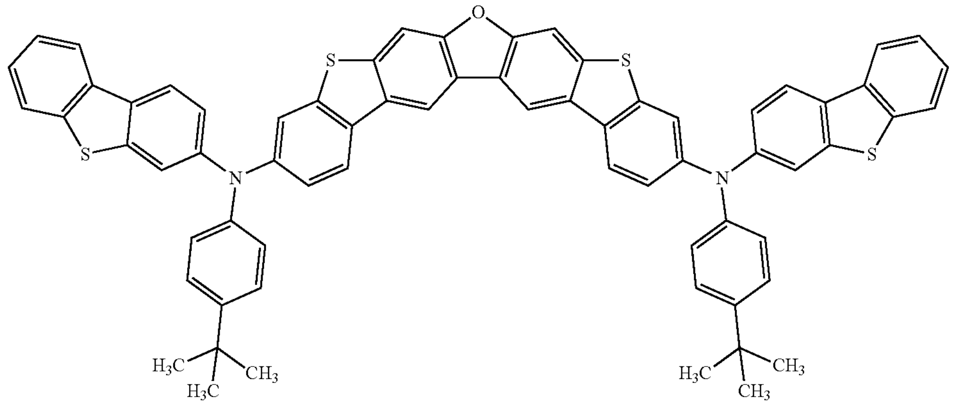
(241)
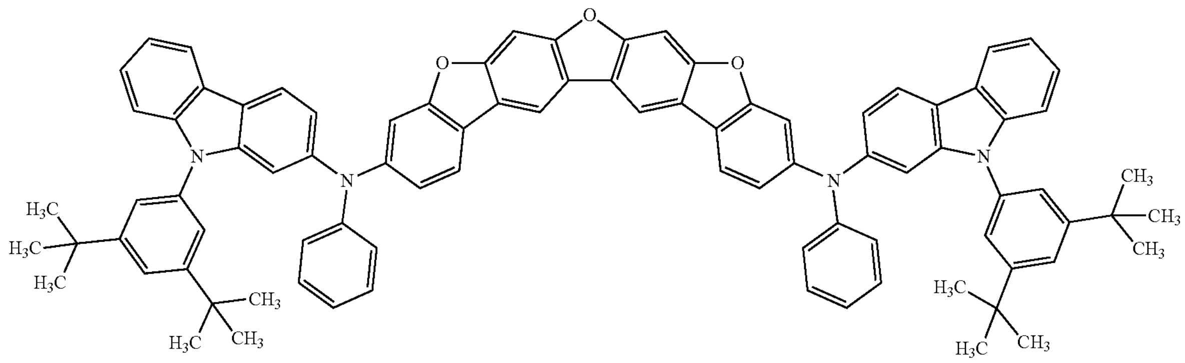
(242)
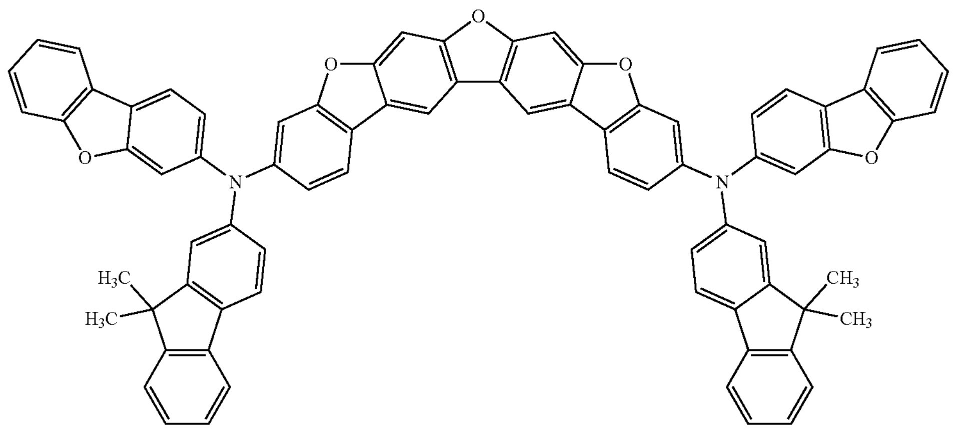

-continued
[Chemical Formula 38]
(243)
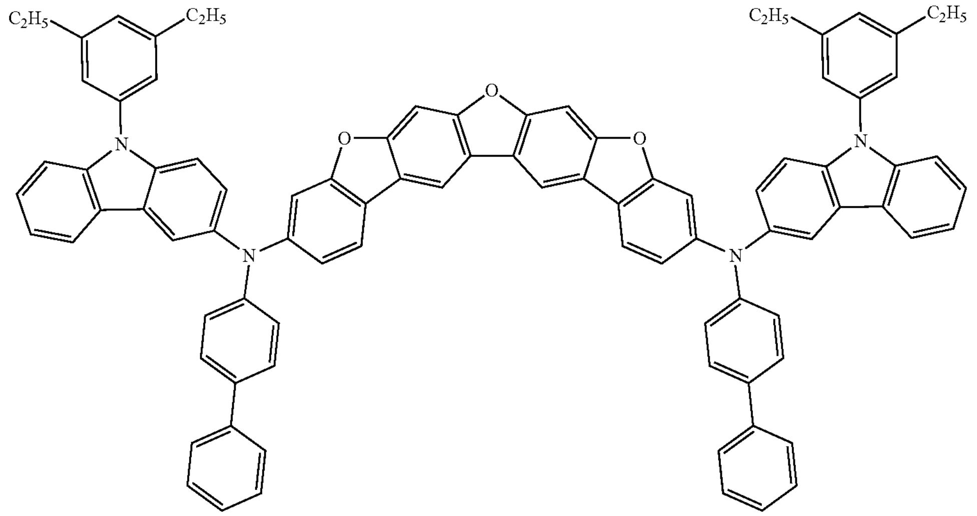
(244)
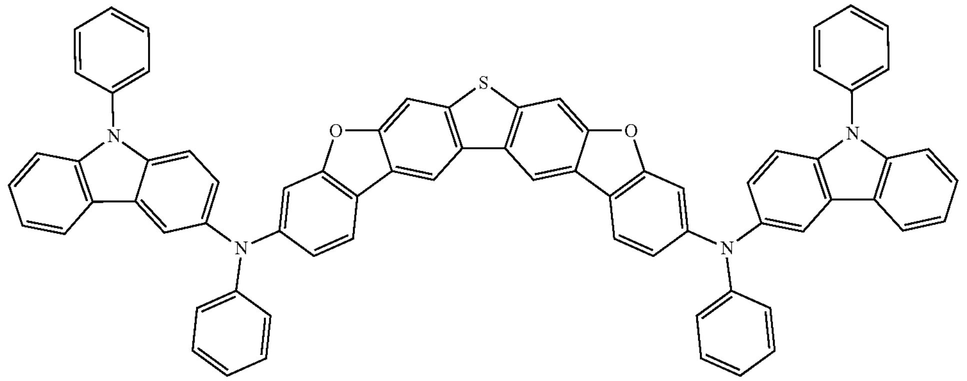
(245)
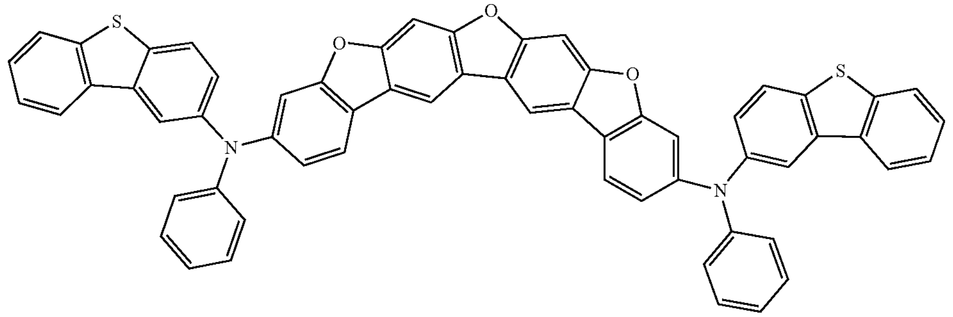
(246)
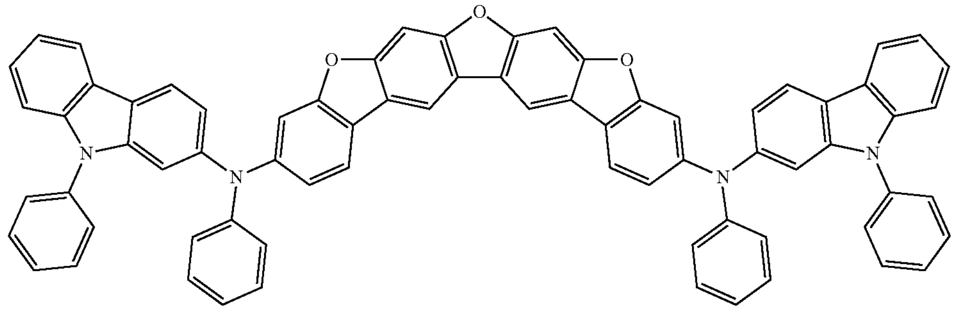

-continued
(251)
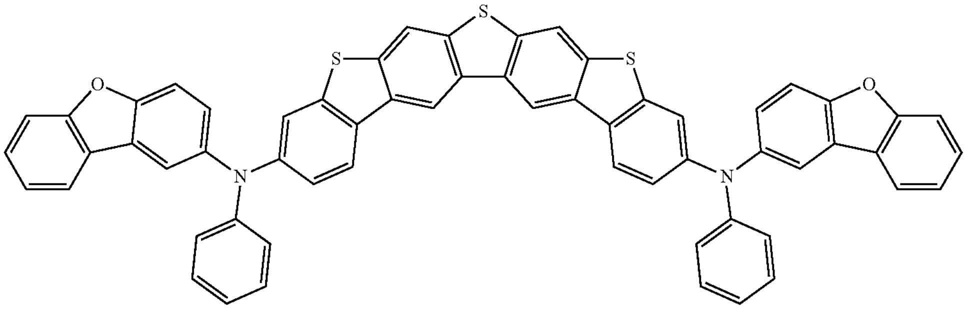
(252)
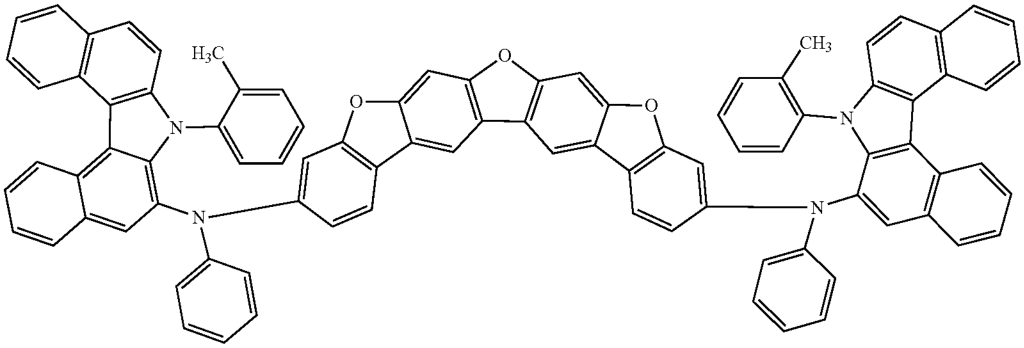
[Chemical Formula 39]
(253)
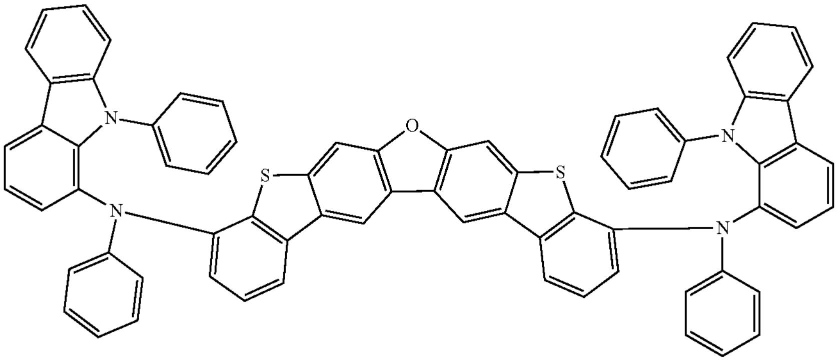
(254)
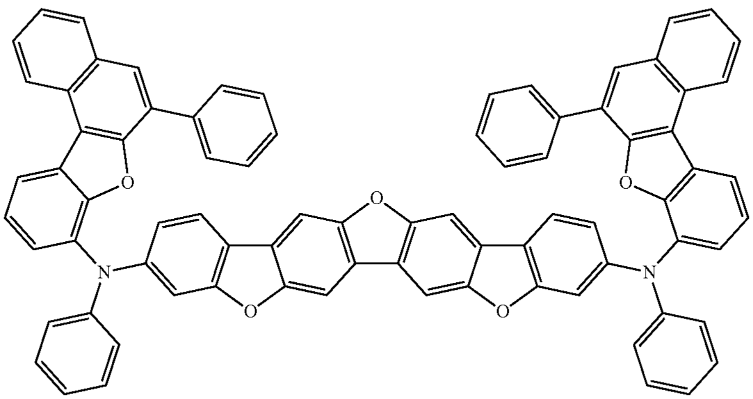

-continued
(255)
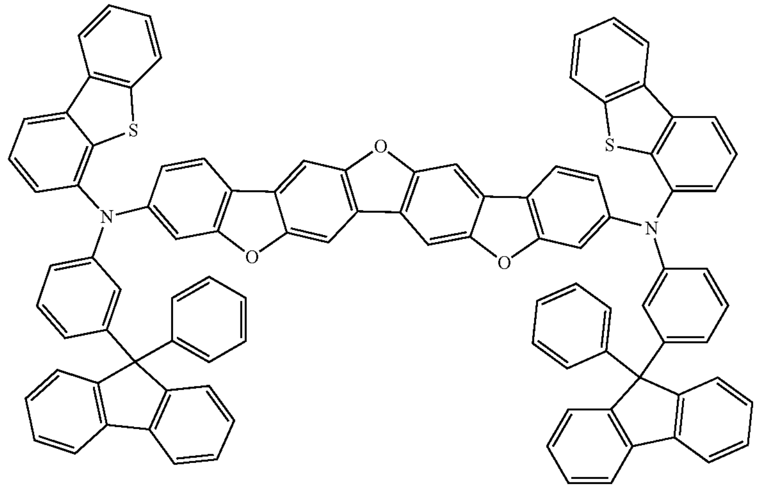
(256)
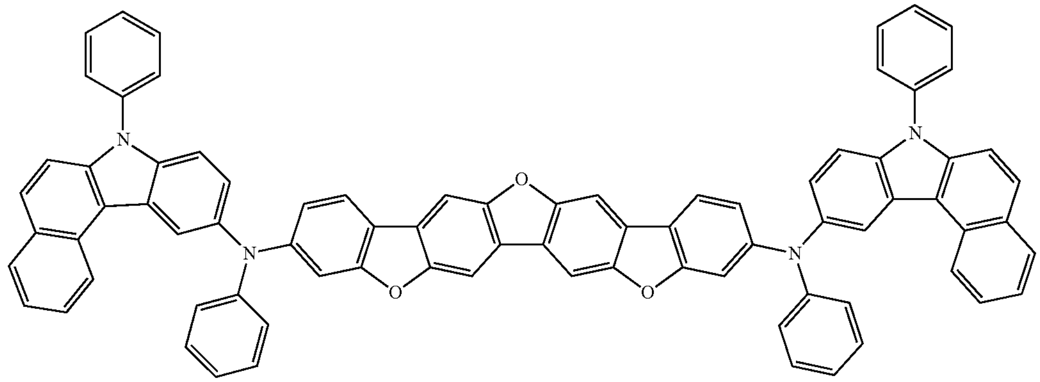
(257)
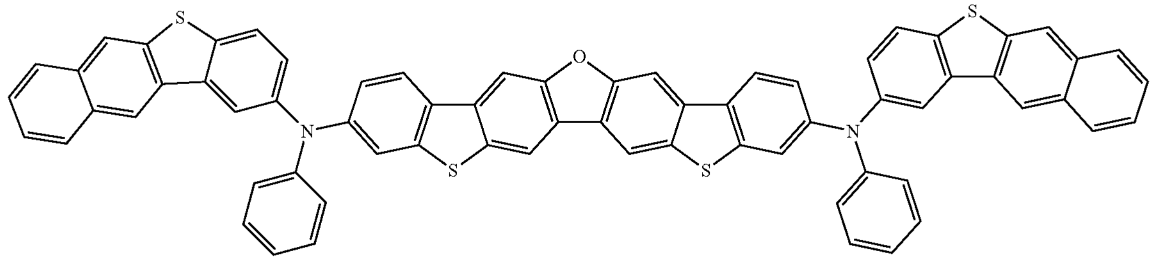
(258)
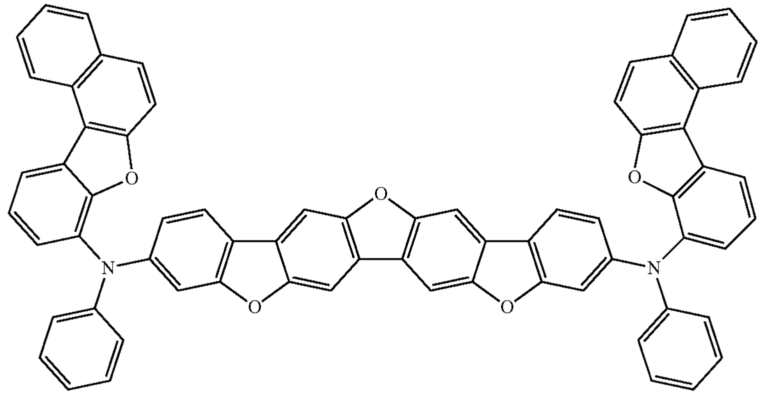

-continued (259)

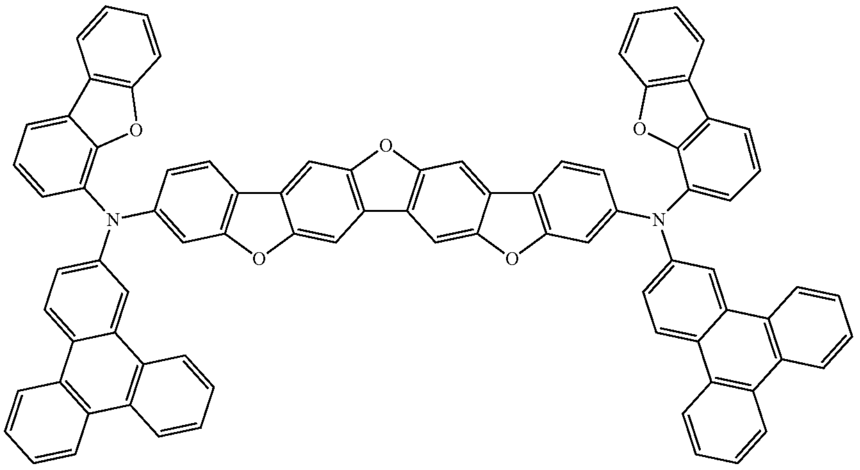

<Synthesis Method of Organic Compound>

A method for synthesizing an organic compound of one embodiment of the present invention is described. Specifically, a method for synthesizing the organic compound represented by General Formula (G0) above is described.

The organic compound represented by General Formula (G0) can be obtained by Synthesis Scheme (SC1) below. Specifically, the organic compound can be obtained through a cross coupling reaction caused between Compound (a1) and q equivalents of Compound (a2) with respect to Compound (a1).

Note that Compound (a1) includes Substituent $X^1$, which can be a halogen such as chlorine, bromine, or iodine, a triflate group, or the like. Compound (a2) includes Substituent $Y^1$, which can be hydrogen, an organotin group, a boronic acid, a dialkoxyboronic acid, or the like.

[Chemical Formula 40]

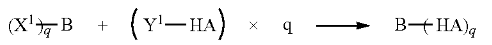

(a1) (a2) (G0)

This reaction can proceed under various conditions. For example, a synthesis method in which a metal catalyst is used under the presence of a base can be employed. Specifically, the Ullmann coupling, the Hartwig-Buchwald reaction, the Suzuki-Miyaura reaction, or the like can be used.

In the case where q is 2 and a pair of HA's are different from each other in General Formula (G0) above, a cross coupling reaction may be caused between Compound (a1) and one selected from two kinds of Compounds (a2), and a cross coupling reaction between the resultant compound and the other selected from the two kinds of Compounds (a2) may be further caused.

In the case where q is 1 in General Formula (G0) above, the organic compound can be obtained by Synthesis Scheme (SC2) below. Specifically, the organic compound can be obtained through a cross coupling reaction between Compound (a3) and Compound (a4).

[Chemical Formula 41]

(SC2)

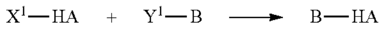

(a3) (a4) (G0)

Note that this embodiment can be combined with any of the other embodiments in this specification as appropriate.

Embodiment 2

In this embodiment, a structure of a light-emitting device 150 of one embodiment of the present invention is described with reference to FIG. 1A and FIG. 1B.

Figure 1B:
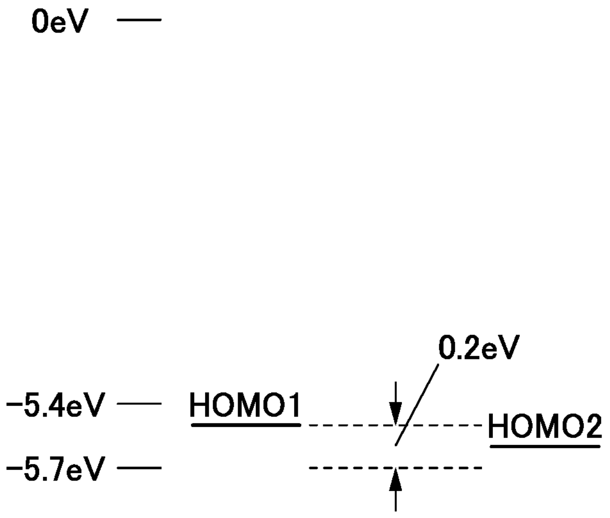

FIG. 1A is a diagram illustrating the structure of the light-emitting device, and FIG. 1B is a diagram illustrating part of the structure of the light-emitting device.

<Structure Example 1 of Light-Emitting Device 150>

The light-emitting device 150 described in this embodiment includes an electrode 101, an electrode 102, and a unit 103 (see FIG. 1A). The electrode 102 includes a region overlapping with the electrode 101. For example, the electrode 101 can be used as an anode and the electrode 102 can be used as a cathode.

<<Structure Example 1 of unit 103>>

The unit 103 includes a region positioned between the electrode 101 and the electrode 102, and the unit 103 contains a light-emitting material and a host material. For example, the compound described in Embodiment 1 can be used as the light-emitting material.

Since the organic compound of one embodiment of the present invention has a high molar absorption coefficient, the efficiency of the energy transfer from a host to the organic compound is high. Accordingly, the organic compound makes it possible to obtain a light-emitting element with high emission efficiency and a favorable lifetime. Specifically, the organic compound is preferred because its molar absorption coefficient with respect to the light corresponding to the transition energy from the S0 level to the S1 level, which is specifically the light with a wavelength of around 400 nm to 500 nm is higher than or equal to $10^5$ ($M^{-1}$ $cm^{-1}$). The emission spectrum has a narrow half width and is sharp; this is preferable because the color purity and the efficiency are resultantly high. In addition, combination with a micro-cavity (micro-optical resonator) structure can make the emission spectrum sharper. Furthermore, the organic compound is preferred because of its glass transition point higher than or equal to 100° C. and high heat resistance.

<<Host Material>>

A material having a carrier-transport property can be used as the host material. For example, a material having a hole-transport property, a material having an electron-transport property, a TADF material, a material having an anthracene skeleton, or a mixed material can be used as the host material.

[Material Having Hole-Transport Property]

The material having a hole-transport property preferably has a hole mobility of $1\times10^{-6}$ $cm^2/Vs$ or more. For example, a compound having an aromatic amine skeleton, a compound having a carbazole skeleton, a compound having a thiophene skeleton, a compound having a furan skeleton, or the like can be used.

The material having a hole-transport property is preferably an amine compound or an organic compound having a π-electron rich heteroaromatic ring skeleton. For example, a compound having an aromatic amine skeleton, a compound having a carbazole skeleton, a compound having a thiophene skeleton, a compound having a furan skeleton, or the like can be used. The organic compound of one embodiment of the present invention can be used, for example.

As the compound having an aromatic amine skeleton, for example, 4,4'-bis[N-(1-naphthyl)-N-phenylamino]biphenyl (abbreviation: NPB), NN-bis(3-methylphenyl)-N,N-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl) triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl) triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), or the like can be used.

As the compound having a carbazole skeleton, for example, 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), 3,3'-bis(9-phenyl-9H-carbazole) (abbreviation: PCCP), or the like can be used.

As the compound having a thiophene skeleton, for example, 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBT-FLP-III), 4-[4-(9-phenyl-9H-fluoren-9-yl)phenyl]-6-phenyldibenzothiophene (abbreviation: DBTFLP-IV), or the like can be used.

As the compound having a furan skeleton, for example, 4,4',4"-(benzene-1,3,5-triyl)tri(dibenzofuran) (abbreviation: DBF3P-II), 4-{3-[3-(9-phenyl-9H-fluoren-9-yl)phenyl] phenyl}dibenzofuran (abbreviation: mmDBFFLBi-II), or the like can be used.

Among the above, the compound having an aromatic amine skeleton and the compound having a carbazole skeleton are preferable because these have favorable reliability, have high hole-transport properties, and contribute to a reduction in driving voltage.

[Material Having Electron-Transport Property]

An organic compound having an anthracene skeleton can be used as the material having an electron-transport property. In particular, an organic compound having both an anthracene skeleton and a heterocyclic skeleton can be favorably used.

For example, it is possible to use an organic compound having both an anthracene skeleton and a nitrogen-containing five-membered ring skeleton or an organic compound having both an anthracene skeleton and a nitrogen-containing six-membered ring skeleton. Alternatively, it is possible to use an organic compound having both an anthracene skeleton and a nitrogen-containing five-membered ring skeleton where two heteroatoms are included in the ring or an organic compound having a nitrogen-containing six-membered ring skeleton where two heteroatoms are included in the ring. Specifically, it is preferable, as the heterocyclic skeleton, to use a pyrazole ring, an imidazole ring, an oxazole ring, a thiazole ring, a pyrazine ring, a pyrimidine ring, a pyridazine ring, or the like.

The material having an electron-transport property is preferably a metal complex or an organic compound having a π-electron deficient heteroaromatic ring skeleton. As examples of the organic compound having a π-electron deficient heteroaromatic ring skeleton, a heterocyclic compound having a polyazole skeleton, a heterocyclic compound having a diazine skeleton, and a heterocyclic compound having a pyridine skeleton are preferable. In particular, the heterocyclic compound having a diazine skeleton and the heterocyclic compound having a pyridine skeleton have favorable reliability and are thus preferable. Furthermore, the heterocyclic compound having a diazine (pyrimidine or pyrazine) skeleton has a high electron-transport property and contributes to a reduction in driving voltage.

As the metal complex, bis(10-hydroxybenzo[h]quinolinato)beryllium(II) (abbreviation: $BeBq_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), bis[2-(2-benzothiazolyl)phenolato]zinc(II) (abbreviation: ZnBTZ), or the like can be used, for example.

As the heterocyclic compound having a polyazole skeleton, 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis [5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2"-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), or the like can be used, for example.

As the heterocyclic compound having a diazine skeleton, 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl] dibenzo[f,h]quinoxaline (abbreviation: 2mCzBPDBq), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), 4,8-bis[3-(dibenzothiophen-4-yl)phenyl]benzo[h]quinazoline (abbreviation: 4,8mDBtP2Bqn), or the like can be used, for example.

As the heterocyclic compound having a pyridine skeleton, 3,5-bis[3-(9H-carbazol-9-yl)phenyl]pyridine (abbreviation:

35DCzPPy), 1,3,5-tri[3-(3-pyridyl)phenyl]benzene (abbreviation: TmPyPB), or the like can be used, for example.

[TADF Material]

Any of the TADF materials given above can be used as the host material. When the TADF material is used as the host material, triplet excitation energy generated in the TADF material is converted into singlet excitation energy by reverse intersystem crossing and transferred to the light-emitting substance, whereby the emission efficiency of the light-emitting device can be increased. At this time, the TADF material functions as an energy donor, and the light-emitting substance functions as an energy acceptor.

This is very effective in the case where the light-emitting substance is a fluorescent substance. In that case, the S1 level of the TADF material is preferably higher than the S1 level of the fluorescent substance in order to achieve high emission efficiency. Furthermore, the T1 level of the TADF material is preferably higher than the S1 level of the fluorescent substance. Therefore, the T1 level of the TADF material is preferably higher than the T1 level of the fluorescent substance.

It is also preferable to use a TADF material that emits light whose wavelength overlaps with the wavelength on a lowest-energy-side absorption band of the fluorescent substance. This enables smooth transfer of excitation energy from the TADF material to the fluorescent substance and accordingly enables efficient light emission, which is preferable.

In order that singlet excitation energy can be efficiently generated from the triplet excitation energy by reverse intersystem crossing, carrier recombination preferably occurs in the TADF material. It is also preferable that the triplet excitation energy generated in the TADF material not be transferred to the triplet excitation energy of the fluorescent substance. For that reason, the fluorescent substance preferably has a protective group around a luminophore (a skeleton that causes light emission) of the fluorescent substance. As the protective group, a substituent having no $\pi$ bond and a saturated hydrocarbon are preferred. Specific examples include an alkyl group having 3 to 10 carbon atoms, a substituted or unsubstituted cycloalkyl group having 3 to 10 carbon atoms, and a trialkylsilyl group having 3 to 10 carbon atoms. It is further preferable that the fluorescent substance have a plurality of protective groups. The substituent having no $\pi$ bond is poor in carrier-transport performance; thus, the TADF material and the luminophore of the fluorescent substance can be kept away from each other with little influence on carrier transportation or carrier recombination.

Here, the luminophore refers to an atomic group (skeleton) that causes light emission in a fluorescent substance. The luminophore is preferably a skeleton having a $\pi$ bond, further preferably includes an aromatic ring, still further preferably includes a fused aromatic ring or a fused heteroaromatic ring.

Examples of the fused aromatic ring or the fused heteroaromatic ring include a phenanthrene skeleton, a stilbene skeleton, an acridone skeleton, a phenoxazine skeleton, a phenothiazine skeleton, and the like. Specifically, a fluorescent substance having any of a naphthalene skeleton, an anthracene skeleton, a fluorene skeleton, a chrysene skeleton, a triphenylene skeleton, a tetracene skeleton, a pyrene skeleton, a perylene skeleton, a coumarin skeleton, a quinacridone skeleton, and a naphthobisbenzofuran skeleton is preferable because of its high fluorescence quantum yield.

[Material Having Anthracene Skeleton]

In the case where a fluorescent substance is used as the light-emitting substance, a material having an anthracene skeleton is suitable for the host material. The use of a substance having an anthracene skeleton as a host material for a fluorescent substance makes it possible to achieve a light-emitting layer with favorable emission efficiency and durability.

As the substance having an anthracene skeleton that is used as the host material, a substance having a diphenylanthracene skeleton, in particular, a substance having a 9,10-diphenylanthracene skeleton, is preferable because of its chemical stability. The host material preferably has a carbazole skeleton to improve the hole-injection and hole-transport properties; further preferably, the host material has a benzocarbazole skeleton, in which a benzene ring is further fused to carbazole, because the HOMO thereof is shallower than that of carbazole by approximately 0.1 eV and thus holes enter the host material easily.

In particular, the host material having a dibenzocarbazole skeleton is preferable because its HOMO is shallower than that of carbazole by approximately 0.1 eV so that holes enter the host material easily, the hole-transport property is excellent, and the heat resistance is increased. Accordingly, a substance that has both a 9,10-diphenylanthracene skeleton and a carbazole skeleton (or a benzocarbazole skeleton or a dibenzocarbazole skeleton) is further preferable as the host material. Note that in terms of the hole-injection and hole-transport properties described above, instead of a carbazole skeleton, a benzofluorene skeleton or a dibenzofluorene skeleton may be used.

As the substance having an anthracene skeleton, for example, 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), 9-(1-naphthyl)-10-[4-(2-naphthyl)phenyl]anthracene (abbreviation: αN-βNPAnth), or the like can be used.

In particular, CzPA, cgDBCzPA, 2mBnfPPA, and PCzPA have excellent characteristics.

[Structure Example 1 of Mixed Material]

A material in which a plurality of kinds of substances are mixed can be used as the host material. For example, a material in which a material having an electron-transport property and a material having a hole-transport property are mixed can be favorably used as the host material. When the material having an electron-transport property is mixed with the material having a hole-transport property, the carrier-transport property of a layer 111 can be easily adjusted. A recombination region can also be controlled easily. The weight ratio of the material having a hole-transport property to the material having an electron-transport property in the mixed material is greater than or equal to 1:19 and less than or equal to 19:1.

[Structure Example 2 of Mixed Material]

In addition, a material mixed with a phosphorescent substance can be used as the host material. When a fluorescent substance is used as the light-emitting substance, the phosphorescent substance can be used as an energy donor for supplying excitation energy to the fluorescent substance.

A mixed material that contains a material forming an exciplex can be used as the host material. For example, a material forming an exciplex whose emission spectrum overlaps with the wavelength of the absorption band on the lowest energy side of the light-emitting substance can be used as the host material. This enables smooth energy transfer and improves emission efficiency. Alternatively, the driving voltage can be reduced.

Note that at least one of the materials forming an exciplex may be a phosphorescent substance. In this case, triplet excitation energy can be efficiently converted into singlet excitation energy by reverse intersystem crossing.

A combination of a material having an electron-transport property and a material having a hole-transport property whose HOMO level is higher than or equal to the HOMO level of the material having an electron-transport property is preferable for forming an exciplex efficiently. In addition, the LUMO level of the material having a hole-transport property is preferably higher than or equal to the LUMO level of the material having an electron-transport property. Note that the LUMO levels and the HOMO levels of the materials can be derived from the electrochemical characteristics (the reduction potentials and the oxidation potentials) of the materials that are measured by cyclic voltammetry (CV).

Note that the formation of an exciplex can be confirmed by a phenomenon in which the emission spectrum of the mixed film in which the material having a hole-transport property and the material having an electron-transport property are mixed is shifted to the longer wavelength side than the emission spectrum of each of the materials (or has another peak on the longer wavelength side), observed by comparison of the emission spectrum of the material having a hole-transport property, the emission spectrum of the material having an electron-transport property, and the emission spectrum of the mixed film of these materials, for example. Alternatively, the formation of an exciplex can be confirmed by a difference in transient response, such as a phenomenon in which the transient photoluminescence (PL) lifetime of the mixed film has longer lifetime components or has a larger proportion of delayed components than that of each of the materials, observed by comparison of the transient PL of the material having a hole-transport property, the transient PL of the material having an electron-transport property, and the transient PL of the mixed film of these materials. The transient PL can be rephrased as transient electroluminescence (EL). That is, the formation of an exciplex can also be confirmed by a difference in transient response observed by comparison of the transient EL of the material having a hole-transport property, the transient EL of the material having an electron-transport property, and the transient EL of the mixed film of these materials.

<<Structure Example 2 of Unit 103>>

The unit 103 includes the layer 111, a layer 112, and a layer 113. For example, the unit 103 can include a layer selected from functional layers such as a hole-transport layer, an electron-transport layer, a carrier-blocking layer, and an exciton-blocking layer.

<<Structure Example of Layer 111<<

The layer 111 includes a region positioned between the layer 112 and the layer 113, and the layer 111 contains a light-emitting material EM and a host material. For example, the compound described in Embodiment 1 can be used as the light-emitting material EM.

The layer 111 can be referred to as a light-emitting layer. The layer 111 is preferably provided in a region where holes and electrons are recombined. This allows efficient conversion of energy generated by recombination of carriers into light EL1 and emission of the light EL1 (see FIG. 1A). Furthermore, the layer 111 is preferably provided apart from a metal used for the electrode or the like. In that case, a quenching phenomenon caused by the metal used for the electrode or the like can be inhibited.

<<Structure Example 1 of Layer 112>>

The layer 112 includes a region positioned between the electrode 101 and the layer 111. For example, a material having a hole-transport property can be used for the layer 112. The layer 112 can be referred to as a hole-transport layer. A substance having a wider band gap than the light-emitting material contained in the layer 111 is preferably used for the layer 112. In that case, energy transfer from excitons generated in the layer 111 to the layer 112 can be inhibited.

[Material Having Hole-Transport Property]

For example, a material with a hole-transport property that can be used for the layer 111 can be used for the layer 112.

<<Structure example 1 of layer 113>>

The layer 113 includes a region positioned between the layer 111 and the electrode 102. For example, a material having an electron-transport property can be used for the layer 113. The layer 113 can be referred to as an electron-transport layer. A substance having a wider band gap than the light-emitting material contained in the layer 111 is preferably used for the layer 113. In that case, energy transfer from excitons generated in the layer 111 to the layer 113 can be inhibited.

[Material Having Electron-Transport Property]

The material having an electron-transport property preferably has an electron mobility higher than or equal to $1\times10^{-7}$ $cm^2/Vs$ and lower than or equal to $5\times10^{-5}$ $cm^2/Vs$ when the square root of the electric field strength [V/cm] is 600. When the electron-transport property of the electron-transport layer is suppressed, the amount of electrons injected into a light-emitting layer can be controlled. Alternatively, the light-emitting layer can be prevented from having excess electrons.

For example, a material having an electron-transport property usable for the layer 111 can be used for the layer 113. Specifically, a material having an electron-transport property usable as a host material can be used for the layer 113.

<Structure Example 2 of Light-Emitting Device 150>

The light-emitting device 150 described in this embodiment includes a layer 105 and a layer 104 (see FIG. 1A).

<<Structure Example of Layer 105>>

The layer 105 includes a region positioned between the electrode 102 and the unit 103.

A material having an electron-injection property can be used for the layer 105, for example. Specifically, a substance having a donor property can be used for the layer 105. Alternatively, a composite material in which a substance having a donor property is contained in the material having an electron-transport property can be used for the layer 105. This can facilitate injection of electrons from the electrode 102, for example. Alternatively, the driving voltage of the light-emitting device can be reduced. Alternatively, a variety of conductive materials can be used for the electrode 102 regardless of the work function. Specifically, Al, Ag, ITO, indium oxide-tin oxide containing silicon or silicon oxide, or the like can be used for the electrode 102.

[Material Having Electron-Injection Property 1]

For example, an alkali metal, an alkaline earth metal, a rare earth metal, or a compound thereof can be used as the substance having a donor property. Alternatively, an organic compound such as tetrathianaphthacene (abbreviation:

TTN), nickelocene, or decamethylnickelocene can be used as the substance having a donor property.

Specifically, an alkali metal compound (including an oxide, a halide, and a carbonate), an alkaline earth metal compound (including an oxide, a halide, and a carbonate), a rare earth metal compound (including an oxide, a halide, and a carbonate), or the like can be used as the material having an electron-injection property.

Specifically, lithium oxide, lithium fluoride (LiF), cesium fluoride (CsF), calcium fluoride ($CaF_2$), lithium carbonate, cesium carbonate, 8-hydroxyquinolinato-lithium (abbreviation: Liq), or the like can be used as the material having an electron-injection property.

[Material Having Electron-Injection Property 2]

For example, a composite material that contains a substance having an electron-transport property and an alkali metal, an alkaline earth metal, or a compound thereof can be used as the material having an electron-injection property.

For example, a material having an electron-transport property usable for the unit 103 can be used as the material having an electron-injection property.

Furthermore, as the material having an electron-injection property, a material that includes a fluoride of an alkali metal in a microcrystalline state and a substance having an electron-transport property, or a material that includes a fluoride of an alkali earth metal in a microcrystalline state and a substance having an electron-transport property can be used.

In particular, a material including a fluoride of an alkali metal or a fluoride of an alkaline earth metal at 50 wt % or higher can be suitably used. Alternatively, an organic compound having a bipyridine skeleton can be suitably used. Thus, the refractive index of the layer 104 can be reduced. Alternatively, the external quantum efficiency of the light-emitting device can be improved.

[Material Having Electron-Injection Property 3]

Furthermore, electrode can be used as the material having an electron-injection property. For example, a substance obtained by adding electrons at high concentration to an oxide where calcium and aluminum are mixed can be used, for example, as the material having an electron-injection property.

<<Structure Example of Electrode 102>>

A conductive material can be used for the electrode 102, for example. Specifically, a metal, an alloy, an electrically conductive compound, a mixture of these, or the like can be used for the electrode 102. For example, a material having a lower work function than the electrode 101 can be used for the electrode 102. Specifically, a material having a work function lower than or equal to 3.8 eV can be favorably used.

For example, an element belonging to Group 1 of the periodic table, an element belonging to Group 2 of the periodic table, a rare earth metal, or an alloy containing any of these elements can be used for the electrode 102.

Specifically, lithium (Li), cesium (Cs), or the like; magnesium (Mg), calcium (Ca), strontium (Sr), or the like; europium (Eu), ytterbium (Yb), or the like; or an alloy containing any of these (MgAg or AlLi) can be used for the electrode 102.

<<Structure Example 1 of Layer 104>>

The layer 104 includes a region positioned between the electrode 101 and the unit 103. Note that the layer 104 can be referred to as a hole-injection layer. For example, a material having a hole-injection property can be used for the layer 104.

Specifically, a material AM having an acceptor property and a composite material can be used for the layer 104. Note that an organic compound and an inorganic compound can be used as the material AM having an acceptor property. The material AM having an acceptor property can extract electrons from an adjacent hole-transport layer (or hole-transport material) by the application of an electric field.

Example 1 of Material Having Hole-Injection Property

The material AM having an acceptor property can be used as the material having a hole-injection property. This can facilitate injection of holes from the electrode 101, for example. Alternatively, the driving voltage of the light-emitting device can be reduced.

[Material AM Having Acceptor Property]

For example, a compound having an electron-withdrawing group (a halogen group or a cyano group) can be used as the material having an acceptor property. Note that an organic compound having an acceptor property is easily evaporated and deposited. As a result, the productivity of the light-emitting device can be increased.

Specifically, any of the following materials can be used as the material having an acceptor property: 7,7,8,8-tetracyano-2,3,5,6-tetrafluoroquinodimethane (abbreviation: F4-TCNQ), chloranil, 2,3,6,7,10,11-hexacyano-1,4,5,8,9,12-hexaazatriphenylene (abbreviation: HAT-CN), 1,3,4,5,7,8-hexafluorotetracyano-naphthoquinodimethane (abbreviation: F6-TCNNQ), 2-(7-dicyanomethylen-1,3,4,5,6,8,9,10-octafluoro-7H-pyren-2-ylidene)malononitrile, and the like.

A compound in which electron-withdrawing groups are bonded to a fused aromatic ring having a plurality of heteroatoms, such as HAT-CN, is particularly preferable because it is thermally stable.

Alternatively, a [3]radialene derivative including an electron-withdrawing group (in particular, a cyano group or a halogen group such as a fluoro group) is preferable because it has a very high electron-accepting property.

Specifically, α,α',α"-1,2,3-cyclopropanetriylidenetris[4-cyano-2,3,5,6-tetrafluorobenzeneacetonitrile], α,α',α"-1,2,3-cyclopropanetriylidenetris[2,6-dichloro-3,5-difluoro-4-(trifluoromethyl)benzeneacetonitrile], α,α',α"-1,2,3-cyclopropanetriylidenetris[2,3,4,5,6-pentafluorobenzeneacetonitrile], or the like can be used.

As the material AM having an acceptor property, molybdenum oxide, vanadium oxide, ruthenium oxide, tungsten oxide, manganese oxide, or the like can be used.

Alternatively, it is possible to use any of the following compounds: phthalocyanine-based complex compounds such as phthalocyanine (abbreviation: $H_2Pc$) and copper phthalocyanine (CuPc); and compounds having an aromatic amine skeleton such as 4,4'-bis[N-(4-diphenylaminophenyl)-N-phenylamino]biphenyl (abbreviation: DPAB) and N,N'-bis{4-[bis(3-methylphenyl)amino]phenyl}-N,N'-diphenyl-(1,1'-biphenyl)-4,4'-diamine (abbreviation: DNTPD).

In addition, a high molecular compound such as poly(3,4-ethylenedioxythiophene)/poly(styrenesulfonic acid) (PEDOT/PSS), or the like can be used.

Example 2 of Material Having Hole-Injection Property

A composite material can be used as the material having a hole-injection property. For example, a composite material in which a material having a hole-transport property contains the material AM having an acceptor property can be used. Thus, selection of a material used to form an electrode can be carried out in a wide range regardless of the work function. Alternatively, besides a material having a high work function, a material having a low work function can also be used for the electrode 101.

A variety of organic compounds can be used as a material having a hole-transport property in the composite material. As the material having a hole-transport property in the composite material, for example, a compound having an aromatic amine skeleton, a carbazole derivative, an aromatic hydrocarbon, a high molecular compound (such as an oligomer, a dendrimer, or a polymer), or the like can be used. A substance having a hole mobility greater than or equal to $1\times10^{-6}$ $cm^2/Vs$ can be favorably used.

Alternatively, for example, a substance having a relatively deep HOMO level that is higher than or equal to −5.7 eV and lower than or equal to −5.4 eV can be favorably used as the material having a hole-transport property in the composite material. Accordingly, hole injection to the hole-transport layer can be facilitated. Alternatively, reliability of the light-emitting device can be improved.

As the compound having an aromatic amine skeleton, for example, N,N-di(p-tolyl)-N,N-diphenyl-p-phenylenediamine (abbreviation: DTDPPA), 4,4'-bis[N-(4-diphenylaminophenyl)-N-phenylamino]biphenyl (abbreviation: DPAB), N,N-bis{4-[bis(3-methylphenyl)amino]phenyl}-N,N-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), or the like can be used.

As the carbazole derivative, for example, 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)]phenyl-10-phenylanthracene (abbreviation: CzPA), 1,4-bis[4-(N-carbazolyl)phenyl]-2,3,5,6-tetraphenylbenzene, or the like can be used.

As the aromatic hydrocarbon, for example, 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, or the like can be used.

As an aromatic hydrocarbon having a vinyl group, for example, 4,4'-bis(2,2-diphenylvinyl)biphenyl (abbreviation: DPVBi), 9,10-bis[4-(2,2-diphenylvinyl)phenyl]anthracene (abbreviation: DPVPA), or the like can be used.

Other examples include pentacene and coronene.

As the high molecular compound, poly(N-vinylcarbazole) (abbreviation: PVK), poly(4-vinyltriphenylamine) (abbreviation: PVTPA), poly[N-(4-{N-[4-(4-diphenylamino)phenyl]phenyl-N-phenylamino}phenyl)methacrylamide](abbreviation: PTPDMA), poly[N,N-bis(4-butylphenyl)-N,N-bis(phenyl)benzidine](abbreviation: Poly-TPD), or the like can be used.

Furthermore, a substance having any of a carbazole skeleton, a dibenzofuran skeleton, a dibenzothiophene skeleton, and an anthracene skeleton can be favorably used as the material having a hole-transport property in the composite material, for example. Moreover, a substance containing any of the following amines can be used: an aromatic amine having a substituent that includes a dibenzofuran ring or a dibenzothiophene ring, an aromatic monoamine that includes a naphthalene ring, and an aromatic monoamine in which a 9-fluorenyl group is bonded to the nitrogen of the amine through an arylene group. With the use of a substance including a N,N-bis(4-biphenyl)amino group, reliability of the light-emitting device can be improved.

As the material having a hole-transport property in the composite material, for example, N-(4-biphenyl)-6,N-diphenylbenzo[b]naphtho[1,2-d]furan-8-amine (abbreviation: BnfABP), N,N-bis(4-biphenyl)-6-phenylbenzo[b]naphtho[1,2-d]furan-8-amine (abbreviation: BBABnf), 4,4'-bis(6-phenylbenzo[b]naphtho[1,2-d]furan-8-yl)-4"-phenyltriphenylamine (abbreviation: BnfBB1BP), NN-bis(4-biphenyl)benzo[b]naphtho[1,2-d]furan-6-amine (abbreviation: BBABnf(6)), NN-bis(4-biphenyl)benzo[b]naphtho[1,2-d]furan-8-amine (abbreviation: BBABnf(8)), NN-bis(4-biphenyl)benzo[b]naphtho[2,3-d]furan-4-amine (abbreviation: BBABnf(II)(4)), NN-bis[4-(dibenzofuran-4-yl)phenyl]-4-amino-p-terphenyl (abbreviation: DBfBB1TP), N-[4-(dibenzothiophen-4-yl)phenyl]-N-phenyl-4-biphenylamine (abbreviation: ThBA1BP), 4-(2-naphthyl)-4',4"-diphenyltriphenylamine (abbreviation: BBApQNB), 4-[4-(2-naphthyl)phenyl]-4',4"-diphenyltriphenylamine (abbreviation: BBApQNBi), 4,4'-diphenyl-4"-(6;1'-binaphthyl-2-yl)triphenylamine (abbreviation: BBAaNpNB), 4,4'-diphenyl-4"-(7;1'-binaphthyl-2-yl)triphenylamine (abbreviation: BBAaNpiNB-03), 4,4'-diphenyl-4"-(7-phenyl)naphthyl-2-yltriphenylamine (abbreviation: BBAPpiNB-03), 4,4'-diphenyl-4"-(6;2'-binaphthyl-2-yl)triphenylamine (abbreviation: BBA(βN2)B), 4,4'-diphenyl-4"-(7;2'-binaphthyl-2-yl)triphenylamine (abbreviation: BBA(βN2)B-03), 4,4'-diphenyl-4"-(4;2'-binaphthyl-1-yl)triphenylamine (abbreviation: BBApβNaNB), 4,4'-diphenyl-4"-(5;2'-binaphthyl-1-yl)triphenylamine (abbreviation: BBApGβNαNB-02), 4-(4-biphenylyl)-4'-(2-naphthyl)-4"-phenyltriphenylamine (abbreviation: TPBiβNB), 4-(3-biphenylyl)-4'-[4-(2-naphthyl)phenyl]-4"-phenyltriphenylamine (abbreviation: mTPBiAβNBi), 4-(4-biphenylyl)-4'-[4-(2-naphthyl)phenyl]-4"-phenyltriphenylamine (abbreviation: TPBiAβGNBi), 4-phenyl-4'-(1-naphthyl)triphenylamine (abbreviation: αNBA1BP), 4,4'-bis(1-naphthyl)triphenylamine (abbreviation: αNBB1BP), 4,4'-diphenyl-4"-[4'-(carbazol-9-yl)biphenyl-4-yl]triphenylamine (abbreviation: YGTBi1BP), 4'-[4-(3-phenyl-9H-carbazol-9-yl)phenyl]tris(1,1'-biphenyl-4-yl)amine (abbreviation: YGTBi1BP-02), 4-diphenyl-4'-(2-naphthyl)-4"-{9-(4-biphenylyl)carbazole)}triphenylamine (abbreviation: YGTBiβNB), N-[4-(9-phenyl-9Hcarbazol-3-yl)phenyl]-N-[4-(1-naphthyl)phenyl]-9,9'-spirobi(9H-fluoren)-2-amine (abbreviation: PCBNBSF), N,N-bis(4-biphenylyl)-9,9'-spirobi[9H-fluoren]-2-amine (abbreviation: BBASF), N,N-bis(1,1'-biphenyl-4-yl)-9,9'-spirobi[9H-fluoren]-4-amine (abbreviation: BBASF(4)), N-(1,1'-biphenyl-2-yl)-N-(9,9-dimethyl-9H-fluoren-2-yl)-9,9'-spirobi(9H-fluoren)-4-amine (abbreviation: oFBiSF), N-(4-biphenyl)-N-(dibenzofuran-4-yl)-9,9-dimethyl-9H-fluoren-2-amine (abbreviation: FrBiF), N-[4-(1-naphthyl)phenyl]-N-[3-(6-phenyldibenzofuran-4-yl)phenyl]-1-naphthylamine (abbreviation: mPDBfBNBN), 4-phenyl-4'-(9-phenylfluoren-9-yl)triphenylamine (abbreviation: BPAFLP), 4-phenyl-3'-(9- phenylfluoren-9-yl)triphenylamine (abbreviation: mBPAFLP), 4-phenyl-4'-[4-(9-phenylfluoren-9-yl)phenyl] triphenylamine (abbreviation: BPAFLBi), 4-phenyl-4'-(9-phenyl-9H-carbazol-3-yl)triphenylamine (abbreviation: PCBA1BP), 4,4'-diphenyl-4"-(9-phenyl-9H-carbazol-3-yl) triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), N-phenyl-N-[4-(9-phenyl-9H-carbazol-3-yl)phenyl]spiro-9, 9'-bifluoren-2-amine (abbreviation: PCBASF), N-(1,1'-biphenyl-4-yl)-9,9-dimethyl-N-[4-(9-phenyl-9H-carbazol-3-yl)phenyl]-9H-fluoren-2-amine (abbreviation: PCBBiF), N,N-bis(9,9-dimethyl-9H-fluoren-2-yl)-9,9'-spirobi-9H-fluoren-4-amine, N,N-bis(9,9-dimethyl-9H-fluoren-2-yl)-9, 9'-spirobi-9H-fluoren-3-amine, N,N-bis(9,9-dimethyl-9H-fluoren-2-yl)-9,9'-spirobi-9H-fluoren-2-amine, N,N-bis(9,9-dimethyl-9H-fluoren-2-yl)-9,9'-spirobi-9H-fluoren-1-amine, or the like can be used.

Example 3 of Material Having Hole-Injection Property

A composite material containing a material having a hole-transport property, the material AM having an acceptor property, and a fluoride of an alkali metal or an alkaline earth metal can be used as the material having a hole-injection property. In particular, a composite material in which the proportion of fluorine atoms is higher than or equal to 20% can be favorably used. Thus, the refractive index of the layer 104 can be reduced. Alternatively, a layer with a low refractive index can be formed inside the light-emitting device. Alternatively, the external quantum efficiency of the light-emitting device can be improved.

<Structure Example 3 of Light-Emitting Device 150>

In the light-emitting device 150 described in this embodiment, the layer 113 contains a material OMC. As the material OMC, an organometallic complex of an alkali metal or an organometallic complex of an alkaline earth metal can be used, for example.

<<Structure Example 2 of Layer 113>>

A material that contains a substance having an electron-transport property and any of an alkali metal, an alkali metal compound, and an alkali metal complex can be used for the layer 113, for example.

The material OMC preferably includes an 8-hydroxyquinolinato structure, for example. Specific examples include 8-hydroxyquinolinato-lithium (abbreviation: Liq) and 8-hydroxyquinolinato-sodium (abbreviation: Naq).

In particular, a complex of a monovalent metal ion, especially a complex of lithium is preferable, and Liq is further preferable. Note that in the case where the 8-hydroxyquinolinato structure is included, a methyl-substituted product (e.g., a 2-methyl-substituted product or a 5-methyl-substituted product) thereof or the like can also be used. There is preferably a difference in the concentration (including 0) of the alkali metal, the alkali metal itself, the compound thereof, or the complex thereof in the electron-transport layer in the thickness direction.

<<Structure Example 2 of Layer 104>>

The layer 104 contains the material AM having an acceptor property and a material HT1. The material HT1 has a first HOMO level HOMO1, and the first HOMO level HOMO1 is higher than or equal to −5.7 eV and lower than or equal to −5.4 eV (see FIG. 1).

For example, an organic compound having an electron-withdrawing group (a halogen group or a cyano group) can be used as the material AM having an acceptor property. Note that an organic compound having an acceptor property is easily evaporated and deposited. As a result, the productivity of the light-emitting device can be increased.

A material having a hole-transport property can be used as the material HT1. For example, a material that can be used for the layer 112 can be used as the material HT1.

<<Structure Example 2 of Layer 112>>

The layer 112 includes a region 112A and a region 112B, and the region 112B includes a region positioned between the layer 111 and the region 112A (see FIG. 1A).

The region 112B contains a material HT2. The material HT2 has a second HOMO level HOMO2, and the second HOMO level HOMO2 differs by −0.2 eV to 0 eV inclusive from the first HOMO level HOMO1 (see FIG. 1).

Note that this embodiment can be combined with any of the other embodiments in this specification as appropriate.

Embodiment 3

In this embodiment, a structure of the light-emitting device 150 of one embodiment of the present invention is described with reference to FIG. 2A.

Figure 2A:
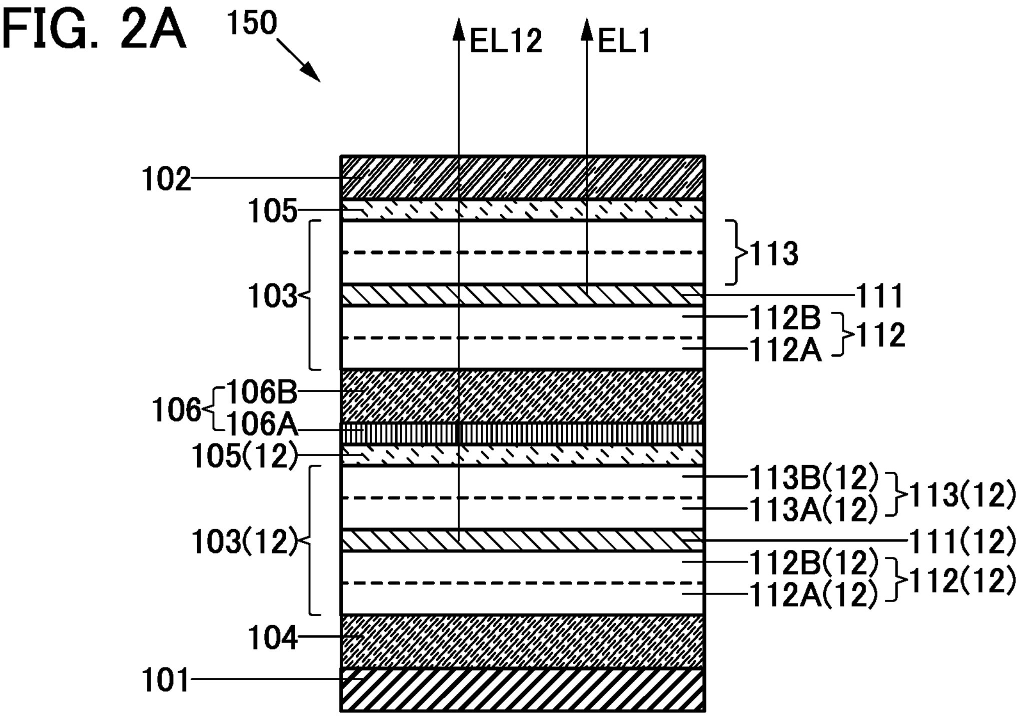
FIG. 2A and FIG. 2B are diagrams illustrating structures of light-emitting devices of embodiments.

FIG. 2A is a cross-sectional view illustrating a structure of a light-emitting device of one embodiment of the present invention, which has a structure different from the structure of the light-emitting device illustrated in FIG. 1A.

<Structure Example of Light-Emitting Device 150>

The light-emitting device 150 described in this embodiment includes the electrode 101, the electrode 102, the unit 103, an intermediate layer 106, and a unit 103(12) (see FIG. 2A). In addition, a layer 105(12) is provided.

The unit 103 includes a region positioned between the electrode 101 and the electrode 102, and the unit 103(12) includes a region positioned between the electrode 101 and the unit 103. The intermediate layer 106 includes a region positioned between the unit 103(12) and the unit 103.

The light-emitting device 150 includes a plurality of units that are stacked. The number of units is not limited to two, and three or more units can be stacked. A light-emitting device that has a structure in which a plurality of units are stacked is referred to as a stacked light-emitting device or a tandem light-emitting device in some cases. This structure enables high luminance emission while the current density is kept low. Alternatively, reliability can be improved. Alternatively, the driving voltage can be reduced in comparison with that of the light-emitting device with the same luminance. Alternatively, power consumption can be reduced.

The layer 105(12) includes a region positioned between the unit 103(12) and the intermediate layer 106. For example, the structure similar to that of the layer 105 described in Embodiment 2 can be employed for the layer 105(12).

<<Structure Example of Unit 103(12)>>

The unit 103(12) has a function of emitting light EL12. The structure that can be used for the unit 103 can be employed for the unit 103(12). For example, the same structure as the unit 103 can be employed for the unit 103(12).

Alternatively, a structure different from the unit 103 can be employed for the unit 103(12). For example, a structure which exhibits an emission color different from the emission color of the unit 103 can be employed for the unit 103(12). Specifically, the unit 103 emitting red light and green light and the unit 103(12) emitting blue light can be employed. With this structure, a light-emitting device emitting light of a desired color can be provided. Alternatively, a light-emitting device emitting white light can be provided, for example.

<<Structure Example of Intermediate Layer 106>>

The intermediate layer 106 includes a layer 106A and a layer 106B. The intermediate layer 106 has a function of supplying electrons to one of the unit 103 and the unit 103(12) and supplying holes to the other.

The layer 106B contains the material AM having an acceptor property and a material having a hole-transport property.

Note that the layer 106B can be referred to as a charge-generation layer. The charge-generation layer has a function of supplying electrons to the anode side and supplying holes to the cathode side when voltage is applied. Specifically, electrons can be supplied to the unit 103(12) that is positioned on the anode side.

The layer 106A includes a region positioned between the layer 106B and the unit 103(12). Note that the layer 106A can be referred to as, for example, an electron-relay layer.

For example, a substance having an electron-transport property can be used for the electron-relay layer. When the electron-relay layer (the layer 106A) is provided, a layer that is on the anode side and in contact with the electron-relay layer can be distanced from a layer that is on the cathode side and in contact with the electron-relay layer. Alternatively, interaction between the layer that is on the anode side and in contact with the electron-relay layer and the layer that is on the cathode side and in contact with the electron-relay layer can be reduced. Alternatively, electrons can be smoothly supplied to the layer that is on the anode side and in contact with the electron-relay layer.

For example, a substance having an electron-transport property can be favorably used for the electron-relay layer. Specifically, a substance having a LUMO level between the LUMO level of the material AM having an acceptor property and used for the layer 106B and the LUMO level of the material having a hole-transport property and used for the layer 106B can be favorably used for the electron-relay layer.

For example, a substance with an electron-transport property having a LUMO level in a range higher than or equal to −5.0 eV, preferably higher than or equal to −5.0 eV and lower than or equal to −3.0 eV, can be used for the electron-relay layer.

Specifically, a phthalocyanine-based material can be used for the electron-relay layer. Alternatively, a metal complex having a metal-oxygen bond and an aromatic ligand can be used for the electron-relay layer.

Note that the layer 106B can be referred to as a charge-generation layer. The charge-generation layer has a function of supplying electrons to the anode side and supplying holes to the cathode side when voltage is applied. Specifically, electrons can be supplied to the unit 103(12) that is positioned on the anode side.

Note that this embodiment can be combined with any of the other embodiments in this specification as appropriate.

Embodiment 4

In this embodiment, a structure of the light-emitting device 150 of one embodiment of the present invention is described with reference to FIG. 2B.

Figure 2B:
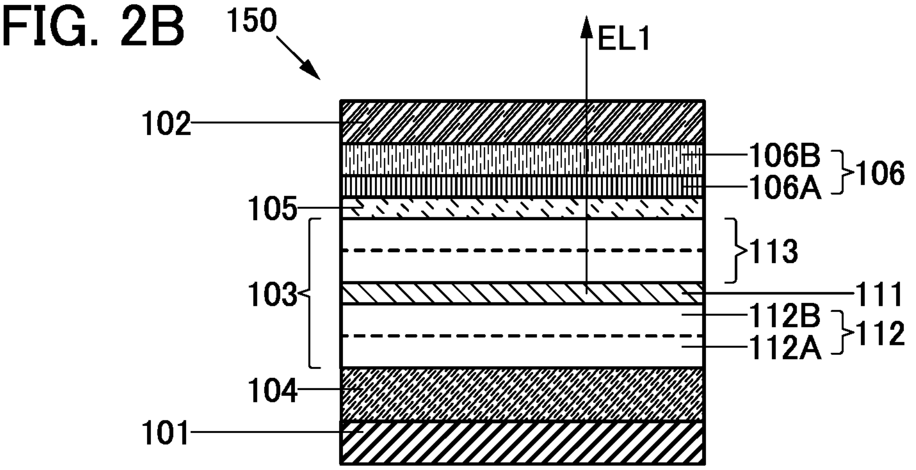

FIG. 2B is a cross-sectional view illustrating a structure of a light-emitting device of one embodiment of the present invention, which has a structure different from the structure of the light-emitting device illustrated in FIG. 1A.

<Structure Example of Light-Emitting Device 150>

The light-emitting device 150 described in this embodiment includes the electrode 101, the electrode 102, the unit 103, the layer 104, and the intermediate layer 106 (see FIG. 2B).

Note that the light-emitting device 150 is different from the structure illustrated in FIG. 1 in that the intermediate layer 106 is included between the layer 105 and the electrode 102. Different portions will be described in detail here, and refer to the above description for portions that can use similar structures.

<<Structure Example of Intermediate Layer 106>>

The intermediate layer 106 includes a region positioned between the unit 103 and the electrode 102, and the intermediate layer 106 includes the layer 106A and the layer 106B.

<<Structure Example of Layer 106A>>

The layer 106A includes a region positioned between the layer 106B and the layer 105. For example, the electron-relay layer described in Embodiment 3 can be used as the layer 106A.

<<Structure Example of Layer 106B>>

The layer 106B can be referred to as, for example, a charge-generation layer. The charge-generation layer has a function of supplying electrons to the anode side and supplying holes to the cathode side when voltage is applied. Specifically, electrons can be supplied to the unit 103 that is positioned on the anode side.

For example, any of the composite materials given as examples of the material having a hole-injection property can be used for the charge-generation layer. In addition, for example, a stacked film in which a film including the composite material and a film including a material having a hole-transport property are stacked can be used as the charge-generation layer.

<Manufacturing Method of Light-Emitting Device 150>

For example, each layer of the electrode 101, the electrode 102, the unit 103, and the intermediate layer 106 can be formed by a dry process, a wet process, an evaporation method, a droplet discharge method, a coating method, a printing method, or the like. Each layer of the unit 103(12) described in Embodiment 3 can also be formed by a similar method. A formation method may differ between the components.

Specifically, the light-emitting device 150 can be manufactured with a vacuum evaporation machine, an ink-jet machine, a coating machine such as a spin coater, a gravure printing machine, an offset printing machine, a screen printing machine, or the like.

For example, the electrode can be formed by a wet process or a sol-gel method using a paste of a metal material. Specifically, an indium oxide-zinc oxide film can be formed by a sputtering method using a target obtained by adding, to indium oxide, zinc oxide at higher than or equal to 1 wt % and lower than or equal to 20 wt %. Furthermore, an indium oxide film containing tungsten oxide and zinc oxide (IWZO) can be formed by a sputtering method using a target containing, with respect to indium oxide, tungsten oxide at higher than or equal to 0.5 wt % and lower than or equal to 5 wt % and zinc oxide at higher than or equal to 0.1 wt % and lower than or equal to 1 wt %.

Note that this embodiment can be combined with any of the other embodiments in this specification as appropriate.

Embodiment 5

In this embodiment, a structure of a light-emitting panel 700 of one embodiment of the present invention is described with reference to FIG. 3A.

<Structure Example of Light-Emitting Panel 700>

Figure 3A:
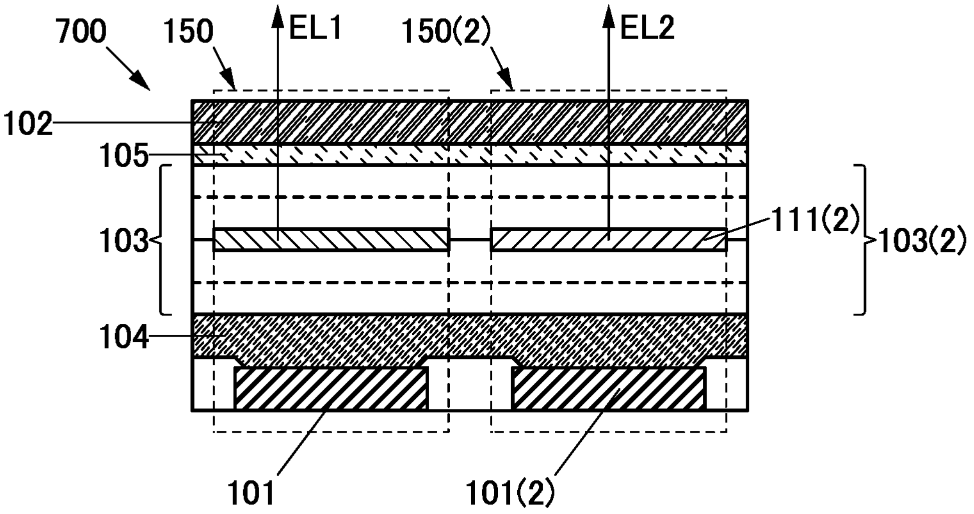
FIG. 3A is a diagram illustrating a structure of a light-emitting panel of an embodiment.

The light-emitting panel 700 described in this embodiment includes the light-emitting device 150 and a light-emitting device 150(2) (see FIG. 3A).

For example, the light-emitting device described in any one of Embodiment 2 to Embodiment 4 can be used as the light-emitting device 150.

<Structure Example of Light-Emitting Device 150(2)>

The light-emitting device 150(2) described in this embodiment includes an electrode 101(2), the electrode 102, and a unit 103(2) (see FIG. 3A). For example, part of the structure of the light-emitting device 150 can be used as part of the structure of the light-emitting device 150(2). Thus, the part of the structure can be used in common. Alternatively, the manufacturing process can be simplified.

<<Structure Example of Unit 103(2)>>

The unit 103(2) includes a region positioned between the electrode 101(2) and the electrode 102.

The unit 103(2) has a single-layer structure or a stacked-layer structure. For example, the unit 103(2) can include a layer selected from functional layers such as a hole-transport layer, an electron-transport layer, a carrier-blocking layer, and an exciton-blocking layer.

The unit 103(2) includes a region where electrons injected from one electrode recombine with holes injected from the other electrode. For example, a region where holes injected from the electrode 101(2) recombine with electrons injected from the electrode 102 is included.

The unit 103(2) includes a layer 111(2). For example, a light-emitting material emitting light of a color different from a color of light from the layer 111 included in the unit 103 can be used for the layer 111(2).

<<Structure Example 1 of Layer 111(2)>>

The layer 111(2) includes a region, and the layer 104 is positioned between the region and the electrode 101. The layer 111(2) contains the light-emitting material EM.

Note that the layer 111(2) contains a host material. The layer 111(2) can be referred to as a light-emitting layer. The layer 111(2) is preferably provided in a region where holes and electrons are recombined. This allows efficient conversion of energy generated by recombination of carriers into light and emission of the light. Furthermore, the layer 111(2) is preferably provided apart from a metal used for the electrode or the like. In that case, a quenching phenomenon caused by the metal used for the electrode or the like can be inhibited.

For example, a fluorescent substance, a phosphorescent substance, or a substance exhibiting thermally activated delayed fluorescence TADF (Thermally Delayed Fluorescence) can be used as the light-emitting material. Thus, energy generated by recombination of carriers can be released as light EL2 from the light-emitting material (see FIG. 3A).

[Fluorescent Substance]

A fluorescent substance can be used for the layer 111(2). For example, the following fluorescent substances can be used for the layer 111(2). Note that without being limited to the following ones, a variety of known fluorescent substances can be used for the layer 111(2).

Specifically, it is possible to use 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N-diphenyl-N,N'-bis[4-(9-phenyl-9H-fluoren-9-yl)phenyl]pyrene-1,6-diamine (abbreviation: 1,6FLPAPrn), N,N-bis(3-methylphenyl)-N,N-bis[3-(9-phenyl-9H-fluoren-9-yl)phenyl]pyrene-1,6-diamine (abbreviation: 1,6mMemFLPAPrn), N,N-bis[4-(9H-carbazol-9-yl)phenyl]-N,N-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N'-(2-tert-butylanthracene-9,10-diyldi-4,1-phenylene)bis[N,N,N-triphenyl-1,4-phenylenediamine](abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N,N-triphenyl-1,4-phenylenediamine (abbreviation: 2DPAPPA), N,N,N,N,N',N',N",N"-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N,N'-triphenyl-1,4-phenylenediamine (abbreviation: 2DPAPA), N-[9,10-bis(1,1'-biphenyl-2-yl)-2-anthryl]-N,N,N-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, NN-diphenylquinacridone, (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N,N-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), N,N-(pyrene-1,6-diyl)bis[(6,N-diphenylbenzo[b]naphtho[1,2-d]furan)-8-amine](abbreviation: 1,6BnfAPrn-03), 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02), 3,10-bis[N-(dibenzofuran-3-yl)-N-phenylamino]naphtho[2,3-b;6,7-b']bisbenzofuran (abbreviation: 3,10FrA2Nbf(IV)-02), or the like.

In particular, a fused aromatic diamine compound typified by a pyrenediamine compound such as 1,6FLPAPrn, 1,6mMemFLPAPrn, or 1,6BnfAPrn-03 is preferable because of its high hole-trapping property, high emission efficiency, or high reliability.

[Phosphorescent Substance 1]

A phosphorescent substance can be used for the layer 111(2). For example, the following phosphorescent substances can be used for the layer 111(2). Note that without being limited to the following ones, a variety of known phosphorescent substances can be used for the layer 111(2).

Specifically, an organometallic iridium complex having a 4H-triazole skeleton, or the like can be used for the layer 111(2). Specifically, tris{2-[5-(2-methylphenyl)-4-(2,6-dimethylphenyl)-4H-1,2,4-triazol-3-yl-κN2]phenyl-κC}iridium (III) (abbreviation: $[Ir(mpptz\text{-}dmp)_3]$), tris(5-methyl-3,4-diphenyl-4H-1,2,4-triazolato)iridium(III) (abbreviation: $[Ir(Mptz)_3]$), tris[4-(3-biphenyl)-5-isopropyl-3-phenyl-4H-1,2,4-triazolato]iridium(III) (abbreviation: $[Ir(iPrptz\text{-}3b)_3]$), or the like can be used.

Alternatively, for example, an organometallic iridium complex having a 1H-triazole skeleton, or the like can be used. Specifically, tris[3-methyl-1-(2-methylphenyl)-5-phenyl-1H-1,2,4-triazolato]iridium(III) (abbreviation: $[Ir(Mptz1\text{-}mp)_3]$), tris(1-methyl-5-phenyl-3-propyl-1H-1,2,4-triazolato]iridium(III) (abbreviation: $[Ir(Prptz1\text{-}Me)_3]$), or the like can be used.

Alternatively, for example, an organometallic iridium complex having an imidazole skeleton, or the like can be used. Specifically, fac-tris[1-(2,6-diisopropylphenyl)-2-phenyl-1H-imidazole]iridium(III) (abbreviation: $[Ir(iPrpmi)_3]$), tris[3-(2,6-dimethylphenyl)-7-methylimidazo[1,2-f] phenanthridinato]iridium(III) (abbreviation: $[Ir(dmpimpt\text{-}Me)_3]$), or the like can be used.

Alternatively, for example, an organometallic iridium complex having a phenylpyridine derivative with an electron-withdrawing group as a ligand, or the like can be used. Specifically, bis[2-(4',6'-difluorophenyl)pyridinato-N,$C^{2'}$] iridium(III) tetrakis(1-pyrazolyl)borate (abbreviation: FIr6), bis[2-(4',6'-difluorophenyl)pyridinato-N,$C^{2'}$]iridium(III) picolinate (abbreviation: FIrpic), bis{2-[3',5'-bis(trifluoromethyl)phenyl]pyridinato-N,$C^{2'}$}iridium(III) picolinate (abbreviation: $[Ir(CF_3ppy)_2(pic)]$), bis[2-(4',6'-difluorophenyl) pyridinato-N,$C^{2'}$]iridium(III) acetylacetonate (abbreviation: FIracac), or the like can be used.

Note that these are compounds exhibiting blue phosphorescence, and are compounds having an emission wavelength peak at 440 nm to 520 nm.

[Fluorescent Substance 2]

For example, an organometallic iridium complex having a pyrimidine skeleton, or the like can be used for the layer 111(2). Specifically, it is possible to use tris(4-methyl-6-phenylpyrimidinato)iridium(III) (abbreviation: $[Ir(mppm)_3]$), tris(4-t-butyl-6-phenylpyrimidinato)iridium(III) (abbreviation: $[Ir(tBuppm)_3]$), (acetylacetonato)bis(6-methyl-4-phenylpyrimidinato)iridium(III) (abbreviation: $[Ir(mppm)_2(acac)]$), (acetylacetonato)bis(6-tert-butyl-4-phenylpyrimidinato)iridium(III) (abbreviation: $[Ir(tBuppm)_2(acac)]$), (acetylacetonato)bis[6-(2-norbornyl)-4-phenylpyrimidinato]iridium(III) (abbreviation: $[Ir(nbppm)_2(acac)]$), (acetylacetonato)bis[5-methyl-6-(2-methylphenyl)-4-phenylpyrimidinato]iridium(III) (abbreviation: $[Ir(mpmppm)_2(acac)]$), (acetylacetonato)bis (4,6-diphenylpyrimidinato)iridium(III) (abbreviation: $[Ir(dppm)_2(acac)]$), or the like.

For example, an organometallic iridium complex having a pyrazine skeleton, or the like can be used. Specifically, (acetylacetonato)bis(3,5-dimethyl-2-phenylpyrazinato) iridium(III) (abbreviation: $[Ir(mppr\text{-}Me)_2(acac)]$), (acetylacetonato)bis(5-isopropyl-3-methyl-2-phenylpyrazinato) iridium(III) (abbreviation: $[Ir(mppr\text{-}iPr)_2(acac)]$), or the like can be used.

For example, an organometallic iridium complex having a pyridine skeleton, or the like can be used. Specifically, it is possible to use tris(2-phenylpyridinato-N,$C^{2'}$)iridium(III) (abbreviation: $[Ir(ppy)_3]$), bis(2-phenylpyridinato-N,$C^{2'}$) iridium(III) acetylacetonate (abbreviation: $[Ir(ppy)_2(acac)]$), bis(benzo[h]quinolinato)iridium(III) acetylacetonate (abbreviation: $[Ir(bzq)_2(acac)]$), tris(benzo[h]quinolinato)iridium (III) (abbreviation: $[Ir(bzq)_3]$), tris(2-phenylquinolinato-N,$C^{2'}$)iridium(III) (abbreviation: $[Ir(pq)_3]$), bis(2-phenylquinolinato-N,$C^{2'}$)iridium(III) acetylacetonate (abbreviation: $[Ir(pq)_2(acac)]$), [2-d3-methyl-(2-pyridinyl-κN)benzofuro[2,3-b]pyridine-κC]bis[2-(5-d3-methyl-2-pyridyl-κN2)phenyl-κ]iridium(III) (abbreviation: $[Ir(5mppy\text{-}d3)_2(mbfpypy\text{-}d3)]$), [2-d3-methyl-(2-pyridinyl-κN)benzofuro[2,3-b]pyridine-κC]bis[2-(2-pyridinyl-κN) phenyl-κC]iridium(III) (abbreviation: $[Ir(ppy)_2(mbfpypy\text{-}d3)]$), or the like.

For example, a rare earth metal complex or the like can be used. Specific examples include tris(acetylacetonato)(monophenanthroline)terbium(III) (abbreviation: $[Tb(acac)_3(Phen)]$).

Note that these are compounds mainly exhibiting green phosphorescence, and have an emission wavelength peak at 500 nm to 600 nm. Note that an organometallic iridium complex having a pyrimidine skeleton is particularly preferable because of its distinctively high reliability or emission efficiency.

[Fluorescent Substance 3]

For example, an organometallic iridium complex having a pyrimidine skeleton, or the like can be used for the layer 111(2). Specifically, (diisobutyrylmethanato)bis[4,6-bis(3-methylphenyl)pyrimidinato]iridium(III) (abbreviation: $[Ir(5mdppm)_2(dibm)]$), bis[4,6-bis(3-methylphenyl)pyrimidinato](dipivaloylmethanato)iridium(III) (abbreviation: $[Ir(5mdppm)_2(dpm)]$), bis[4,6-di(naphthalen-1-yl) pyrimidinato](dipivaloylmethanato)iridium(III) (abbreviation: $[Ir(d1npm)_2(dpm)]$), or the like can be used.

For example, an organometallic iridium complex having a pyrazine skeleton, or the like can be used. Specifically, (acetylacetonato)bis(2,3,5-triphenylpyrazinato)iridium(III) (abbreviation: $[Ir(tppr)_2(acac)]$), bis(2,3,5-triphenylpyrazinato)(dipivaloylmethanato)iridium(III) (abbreviation: $[Ir(tppr)_2(dpm)]$), (acetylacetonato)bis[2,3-bis(4-fluorophenyl)quinoxalinato]iridium(III) (abbreviation: $[Ir(Fdpq)_2(acac)]$), or the like can be used.

For example, an organometallic iridium complex having a pyridine skeleton, or the like can be used. Specifically, tris(1-phenylisoquinolinato-N,$C^{2'}$)iridium(III) (abbreviation: $[Ir(piq)_3]$), bis(1-phenylisoquinolinato-N,$C^{2'}$)iridium (III) acetylacetonate (abbreviation: $[Ir(piq)_2(acac)]$), or the like can be used.

For example, a platinum complex or the like can be used. Specifically, 2,3,7,8,12,13,17,18-octaethyl-21H,23H-porphyrin platinum(II) (abbreviation: PtOEP) or the like can be used.

For example, a rare earth metal complex or the like can be used. Specifically, tris(1,3-diphenyl-1,3-propanedionato) (monophenanthroline)europium(III) (abbreviation: $[Eu(DBM)_3(Phen)]$), tris[1-(2-thenoyl)-3,3,3-trifluoroacetonato](monophenanthroline)europium(III) (abbreviation: $[Eu(TTA)_3(Phen)]$), or the like can be used.

Note that these are compounds exhibiting red phosphorescence, and have an emission peak at 600 nm to 700 nm. Furthermore, from the organometallic iridium complex having a pyrazine skeleton, red light emission with chromaticity favorably used for display devices can be obtained.

[Substance Exhibiting Thermally Activated Delayed Fluorescence (TADF)]

A substance exhibiting thermally activated delayed fluorescence (TADF) (the substance is also referred to as a TADF material) can be used for the layer 111(2). For example, any of the TADF materials given below can be used for the layer 111(2). Note that without being limited thereto, a variety of known TADF materials can be used for the layer 111(2).

For example, a fullerene, a derivative thereof, an acridine, a derivative thereof, an eosin derivative, or the like can be used as the TADF material. Furthermore, porphyrin containing a metal such as magnesium (Mg), zinc (Zn), cadmium (Cd), tin (Sn), platinum (Pt), indium (In), or palladium (Pd) can be used as the TADF material.

Specifically, any of the following materials whose structural formulae are shown below can be used: a protoporphyrin-tin fluoride complex ($SnF_2$(Proto IX)), a mesoporphyrin-tin fluoride complex ($SnF_2$(Meso IX)), a hematoporphyrin-tin fluoride complex ($SnF_2$(Hemato IX)), a coproporphyrin tetramethyl ester-tin fluoride complex ($SnF_2$(Copro III-4Me)), an octaethylporphyrin-tin fluoride complex ($SnF_2$(OEP)), an etioporphyrin-tin fluoride complex ($SnF_2$(Etio I)), an octaethylporphyrin-platinum chloride complex ($PtCl_2OEP$), and the like.

[Chemical Formula 42]

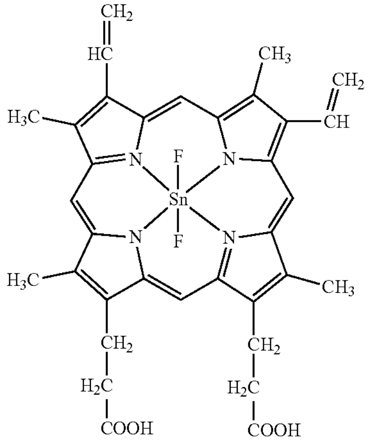

$SnF_2$(Proto IX)

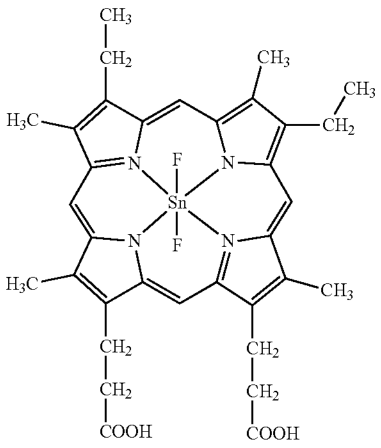

$SnF_2$(Meso IX)

-continued

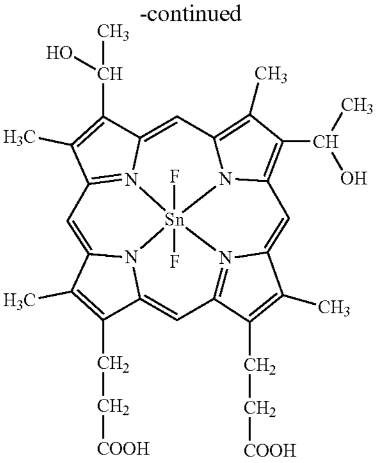

$SnF_2$(Hemato IX)

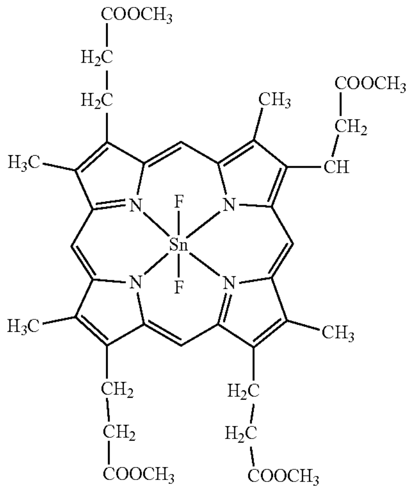

$SnF_2$(Copro III-4Me)

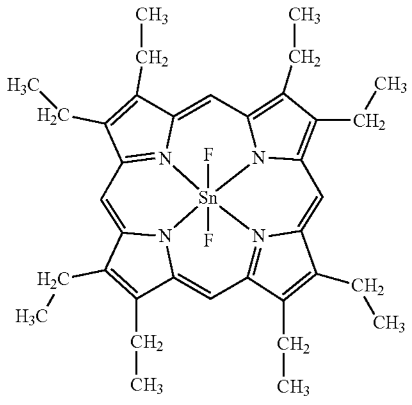

$SnF_2$(OEP)

-continued

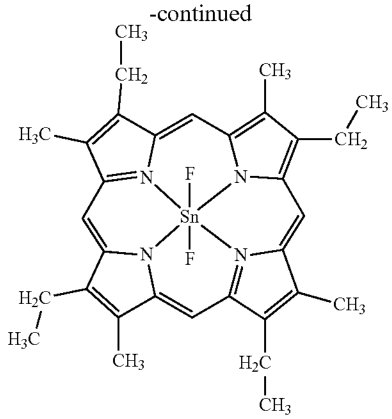

$SnF_2$(Etio I)

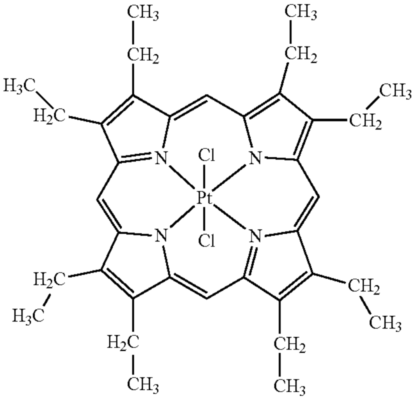

$PtCl_2OEP$

Furthermore, a heterocyclic compound including one or both of a π-electron rich heteroaromatic ring and a π-electron deficient heteroaromatic ring can be used, for example, as the TADF material.

Specifically, any of the following materials whose structural formulae are shown below can be used: 2-(biphenyl-4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-nanthen-9-one (abbreviation: ACRXTN), bis[4-(9,9-dimethyl-9,10-dihydroacridine)phenyl]sulfone (abbreviation: DMAC-DPS), 10-phenyl-10H,10'H-spiro[acridin-9,9'-anthracen]-10'-one (abbreviation: ACRSA), and the like.

[Chemical Formula 43]

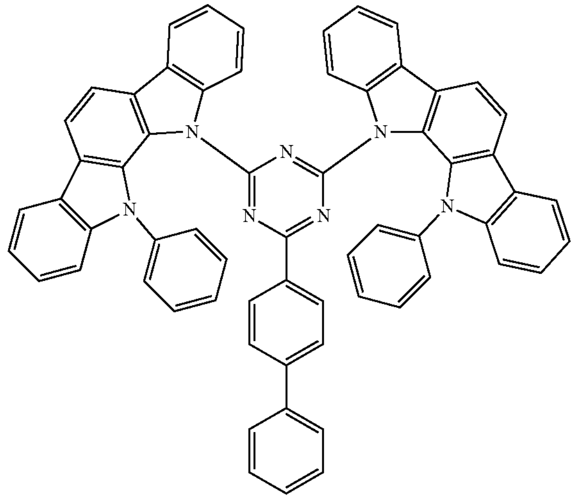

PIC-TRZ

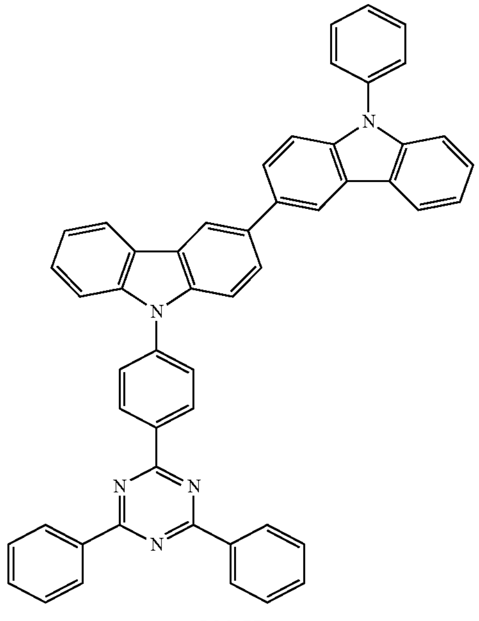

PCCzPTzn

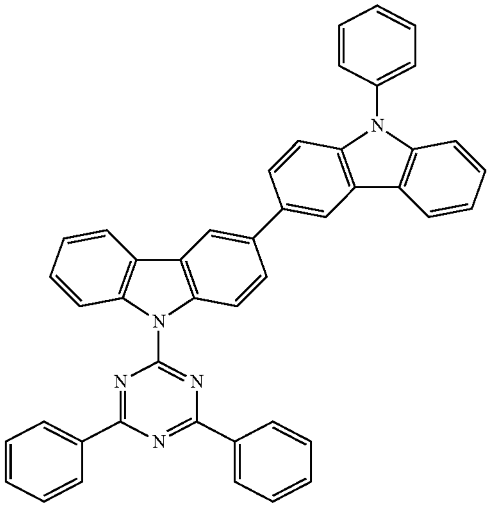

PCCzTzn

-continued

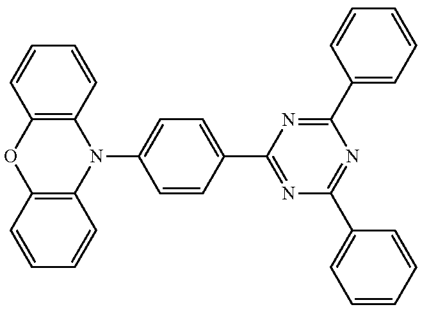

PXZ-TRZ

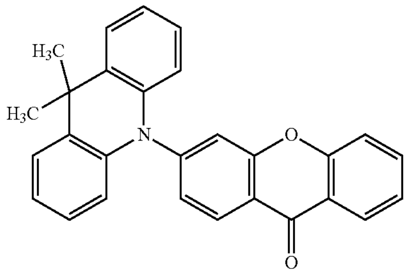

ACRXTN

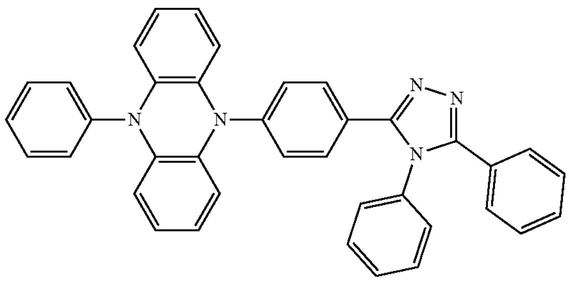

PPZ-3TPT

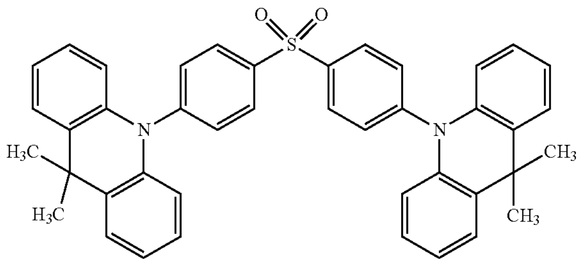

DMAC-DPS

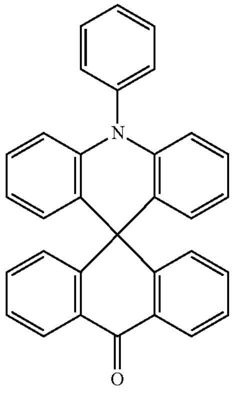

ACRSA

These heterocyclic compounds are preferable because of having both a high electron-transport property and a high hole-transport property owing to the π-electron rich heteroaromatic ring and the π-electron deficient heteroaromatic ring. Among skeletons having a π-electron deficient heteroaromatic ring, a pyridine skeleton, a diazine skeleton (a pyrimidine skeleton, a pyrazine skeleton, and a pyridazine skeleton), and a triazine skeleton are particularly preferable because of their high stability and reliability. In particular, a benzofuropyrimidine skeleton, a benzothienopyrimidine skeleton, a benzofuropyrazine skeleton, and a benzothienopyrazine skeleton are preferable because of their high acceptor properties and reliability.

Among skeletons having a π-electron rich heteroaromatic ring, an acridine skeleton, a phenoxazine skeleton, a phenothiazine skeleton, a furan skeleton, a thiophene skeleton, and a pyrrole skeleton have high stability and reliability; therefore, at least one of these skeletons is preferably included. Note that a dibenzofuran skeleton and a dibenzothiophene skeleton are preferable as the furan skeleton and the thiophene skeleton, respectively. As the pyrrole skeleton, an indole skeleton, a carbazole skeleton, an indolocarbazole skeleton, a bicarbazole skeleton, and a 3-(9-phenyl-9H-carbazol-3-yl)-9H-carbazole skeleton are particularly preferable.

Note that a substance in which a π-electron rich heteroaromatic ring and a π-electron deficient heteroaromatic ring are directly bonded to each other is particularly preferable because the electron-donating property of the π-electron rich heteroaromatic ring and the electron-accepting property of the π-electron deficient heteroaromatic ring are both increased and the energy difference between the S1 level and the T1 level becomes small, and thus thermally activated delayed fluorescence can be obtained efficiently. Note that an aromatic ring to which an electron-withdrawing group such as a cyano group is bonded may be used instead of the π-electron deficient heteroaromatic ring. As a π-electron rich skeleton, an aromatic amine skeleton, a phenazine skeleton, or the like can be used.

As a π-electron deficient skeleton, a xanthene skeleton, a thioxanthene dioxide skeleton, an oxadiazole skeleton, a triazole skeleton, an imidazole skeleton, an anthraquinone skeleton, a boron-containing skeleton such as phenylborane or boranthrene, an aromatic ring or a heteroaromatic ring having a nitrile group or a cyano group, such as benzonitrile or cyanobenzene, a carbonyl skeleton such as benzophenone, a phosphine oxide skeleton, a sulfone skeleton, or the like can be used.

As described above, a π-electron deficient skeleton and a π-electron rich skeleton can be used instead of at least one of the π-electron deficient heteroaromatic ring and the π-electron rich heteroaromatic ring.

Note that the TADF material is a material that has a small difference between the S1 level and the T1 level and has a function of converting triplet excitation energy into singlet excitation energy by reverse intersystem crossing. Thus, it is possible to upconvert triplet excitation energy into singlet excitation energy (reverse intersystem crossing) using a little thermal energy and to efficiently generate a singlet excited state. In addition, the triplet excitation energy can be converted into light emission.

An exciplex whose excited state is formed by two kinds of substances has an extremely small difference between the S1 level and the T1 level and has a function of a TADF material that can convert triplet excitation energy into singlet excitation energy.

Note that a phosphorescent spectrum observed at low temperatures (e.g., 77 K to 10 K) is used for an index of the T1 level. When the level of energy with a wavelength of the line obtained by extrapolating a tangent to the fluorescent spectrum at a tail on the short wavelength side is the S1 level and the level of energy with a wavelength of the line obtained by extrapolating a tangent to the phosphorescent spectrum at a tail on the short wavelength side is the T1 level, the difference between S1 and T1 of the TADF material is preferably less than or equal to 0.3 eV, further preferably less than or equal to 0.2 eV.

When the TADF material is used as a light-emitting substance, the S1 level of the host material is preferably higher than the S1 level of the TADF material. In addition, the T1 level of the host material is preferably higher than the T1 level of the TADF material.

Note that this embodiment can be combined with any of the other embodiments in this specification as appropriate.

Embodiment 6

In this embodiment, a structure of a photoelectric conversion device of one embodiment of the present invention is described with reference to FIG. 3B.

<Structure Example of Photoelectric Conversion Device>

Figure 3B:
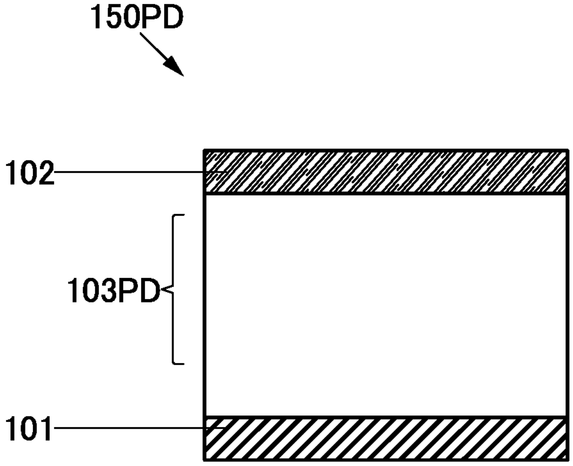
FIG. 3B is a diagram illustrating a structure of a photoelectric conversion device of an embodiment.

A photoelectric conversion device 150PD described in this embodiment includes the electrode 101, the electrode 102, and a unit 103PD (see FIG. 3B). The electrode 102 includes a region overlapping with the electrode 101.

<<Structure example 1 of unit 103PD>>

The unit 103PD includes a region positioned between the electrode 101 and the electrode 102, and the unit 103PD contains a material having a donor property, a material having an acceptor property, and a material having a carrier-transport property. The unit 103PD has a function of converting irradiation light into electric power.

For example, the compound described in Embodiment 1 can be used as the material having a carrier-transport property. Specifically, the compound can be used as a material having a hole-transport property.

Note that this embodiment can be combined with any of the other embodiments in this specification as appropriate.

Embodiment 7

In this embodiment, a light-emitting apparatus including the light-emitting device described in any one of Embodiment 2 to Embodiment 5 is described.

Figure 4A:
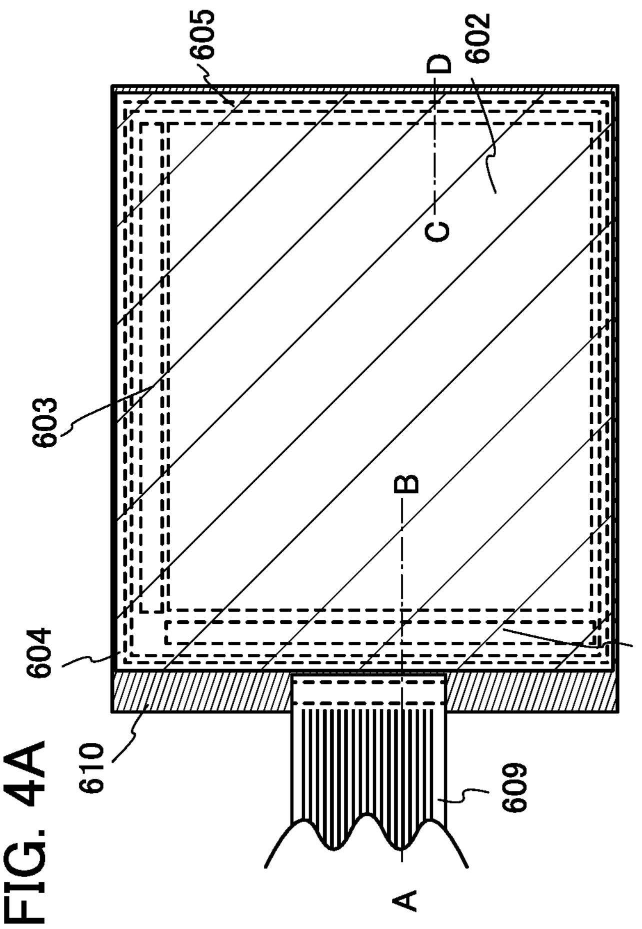
FIG. 4A and FIG. 4B are conceptual diagrams of an active matrix light-emitting apparatus.
Figure 4B:
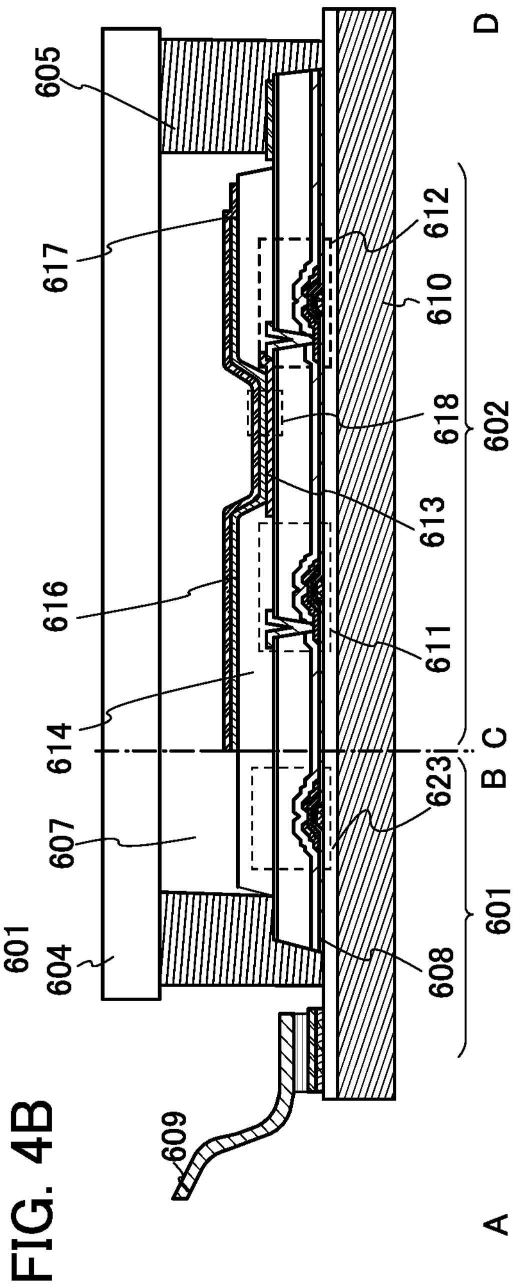

In this embodiment, a light-emitting apparatus fabricated using the light-emitting device described in any one of Embodiment 2 to Embodiment 5 is described with reference to FIG. 4. Note that FIG. 4A is a top view illustrating the light-emitting apparatus, and FIG. 4B is a cross-sectional view taken along A-B and C-D in FIG. 4A. This light-emitting apparatus includes a driver circuit portion (source line driver circuit 601), a pixel portion 602, and a driver circuit portion (gate line driver circuit 603), which are to control light emission of the light-emitting device and are illustrated with dotted lines. Furthermore, 604 denotes a sealing substrate, 605 denotes a sealant, and the inside surrounded by the sealant 605 is a space 607.

Note that a lead wiring 608 is a wiring for transmitting signals to be input to the source line driver circuit 601 and the gate line driver circuit 603 and receiving a video signal, a clock signal, a start signal, a reset signal, and the like from an FPC (flexible printed circuit) 609 serving as an external input terminal. Although only the FPC is illustrated here, a printed wiring board (PWB) may be attached to this FPC. The light-emitting apparatus in this specification includes not only the light-emitting apparatus itself but also the apparatus provided with the FPC or the PWB.

Next, a cross-sectional structure is described with reference to FIG. 4B. The driver circuit portion and the pixel portion are formed over an element substrate 610. Here, the source line driver circuit 601, which is the driver circuit portion, and one pixel of the pixel portion 602 are illustrated.

The element substrate 610 may be fabricated using a substrate containing glass, quartz, an organic resin, a metal, an alloy, a semiconductor, or the like, or a plastic substrate formed of FRP (Fiber Reinforced Plastic), PVF (polyvinyl fluoride), polyester, an acrylic resin, or the like.

There is no particular limitation on the structure of transistors used in pixels or driver circuits. For example, inverted staggered transistors or staggered transistors may be used. Furthermore, top-gate transistors or bottom-gate transistors may be used. There is no particular limitation on a semiconductor material used for the transistors, and for example, silicon, germanium, silicon carbide, gallium nitride, or the like can be used. Alternatively, an oxide semiconductor containing at least one of indium, gallium, and zinc, such as In—Ga—Zn-based metal oxide, may be used.

There is no particular limitation on the crystallinity of a semiconductor material used for the transistors, and either an amorphous semiconductor or a semiconductor having crystallinity (a microcrystalline semiconductor, a polycrystalline semiconductor, a single-crystal semiconductor, and a semiconductor partly including crystal regions) may be used. A semiconductor having crystallinity is preferably used, in which case deterioration of the transistor characteristics can be inhibited.

Here, an oxide semiconductor is preferably used for semiconductor devices such as the transistors provided in the pixels or the driver circuits and transistors used for touch sensors described later, and the like. In particular, an oxide semiconductor having a wider band gap than silicon is preferably used. The use of an oxide semiconductor having a wider band gap than silicon can reduce the off-state current of the transistors.

The oxide semiconductor preferably contains at least indium (In) or zinc (Zn). Further preferably, the oxide semiconductor contains an oxide represented by an In-M-Zn-based oxide (M represents a metal such as Al, Ti, Ga, Ge, Y, Zr, Sn, La, Ce, or Hf).

As a semiconductor layer, it is particularly preferable to use an oxide semiconductor film including a plurality of crystal parts whose c-axes are aligned perpendicular to a surface on which the semiconductor layer is formed or the top surface of the semiconductor layer and in which the adjacent crystal parts have no grain boundary.

The use of such a material for the semiconductor layer makes it possible to achieve a highly reliable transistor in which a change in the electrical characteristics is reduced.

Charge accumulated in a capacitor through a transistor including the above-described semiconductor layer can be retained for a long time because of the low off-state current of the transistor. The use of such a transistor in pixels allows a driver circuit to stop while the gray level of an image displayed on each display region is maintained. As a result, an electronic device with significantly reduced power consumption can be achieved.

For stable characteristics of the transistor or the like, a base film is preferably provided. The base film can be formed to be a single layer or a stacked layer using an inorganic insulating film such as a silicon oxide film, a silicon nitride film, a silicon oxynitride film, or a silicon nitride oxide film. The base film can be formed by a sputtering method, a CVD (Chemical Vapor Deposition) method (e.g., a plasma CVD method, a thermal CVD method, or an MOCVD (Metal Organic CVD) method), an ALD (Atomic Layer Deposition) method, a coating method, a printing method, or the like. Note that the base film is not necessarily provided when not needed.

Note that an FET 623 is illustrated as a transistor formed in the source line driver circuit 601. The driver circuit can be formed using various circuits such as a CMOS circuit, a PMOS circuit, and an NMOS circuit. Although a driver-integrated type in which the driver circuit is formed over the substrate is described in this embodiment, the driver circuit is not necessarily formed over the substrate and can be formed outside.

The pixel portion 602 is formed with a plurality of pixels including a switching FET 611, a current control FET 612, and a first electrode 613 electrically connected to a drain of the current control FET 612; however, without being limited thereto, a pixel portion in which three or more FETs and a capacitor are combined may be employed.

Note that an insulator 614 is formed to cover an end portion of the first electrode 613. The insulator 614 can be formed using a positive photosensitive acrylic resin film here.

In order to improve the coverage with an EL layer or the like to be formed later, the insulator 614 is formed so as to have a curved surface with curvature at its upper end portion or lower end portion. For example, in the case where a positive photosensitive acrylic resin is used as a material for the insulator 614, only the upper end portion of the insulator 614 preferably has a curved surface with a curvature radius (greater than or equal to 0.2 μm and less than or equal to 3 μm). As the insulator 614, either a negative photosensitive resin or a positive photosensitive resin can be used.

An EL layer 616 and a second electrode 617 are formed over the first electrode 613. Here, as a material used for the first electrode 613 functioning as an anode, a material with a high work function is desirably used. For example, a single-layer film of an ITO film, an indium tin oxide film containing silicon, an indium oxide film containing zinc oxide at higher than or equal to 2 wt % and lower than or equal to 20 wt %, a titanium nitride film, a chromium film, a tungsten film, a Zn film, a Pt film, or the like, a stacked layer of a titanium nitride film and a film containing aluminum as its main component, a three-layer structure of a titanium nitride film, a film containing aluminum as its main component, and a titanium nitride film, or the like can be used. Note that the stacked-layer structure achieves low wiring resistance, a favorable ohmic contact, and a function of an anode.

The EL layer 616 is formed by any of a variety of methods such as an evaporation method using an evaporation mask, an inkjet method, and a spin coating method. The EL layer 616 includes the structure described in any one of Embodiment 2 to Embodiment 5. Alternatively, a material included in the EL layer 616 may be a low molecular compound or a high molecular compound (including an oligomer or a dendrimer).

As a material used for the second electrode 617, which is formed over the EL layer 616 and functions as a cathode, a material with a low work function (e.g., Al, Mg, Li, Ca, or an alloy or a compound thereof (e.g., MgAg, MgIn, or AlLi)) is preferably used. Note that in the case where light generated in the EL layer 616 passes through the second electrode 617, it is preferable to use, for the second electrode 617, a stacked layer of a thin metal film and a transparent conductive film (e.g., ITO, indium oxide containing zinc oxide at higher than or equal to 2 wt % and lower than or equal to 20 wt %, indium tin oxide containing silicon, or zinc oxide (ZnO)).

Note that a light-emitting device 618 is formed with the first electrode 613, the EL layer 616, and the second electrode 617. The light-emitting device is the light-emitting device described in any one of Embodiment 2 to Embodiment 5. A plurality of light-emitting devices are formed in the pixel portion, and the light-emitting apparatus of this embodiment may include both the light-emitting device described in any one of Embodiment 2 to Embodiment 5 and a light-emitting device having a different structure.

The sealing substrate 604 and the element substrate 610 are attached to each other using the sealant 605, so that a structure is formed in which the light-emitting device 618 is provided in the space 607 surrounded by the element substrate 610, the sealing substrate 604, and the sealant 605. The space 607 is filled with a filler; it is filled with an inert gas (e.g., nitrogen or argon) in some cases, and filled with the sealant in other cases. The structure of the sealing substrate in which a recessed portion is formed and a desiccant is provided is preferable because deterioration due to the influence of moisture can be inhibited.

Note that an epoxy-based resin or glass frit is preferably used for the sealant 605. Furthermore, these materials are preferably materials that transmit moisture and oxygen as little as possible. As the material used for the sealing substrate 604, in addition to a glass substrate and a quartz substrate, a plastic substrate formed of FRP (Fiber Reinforced Plastics), PVF (polyvinyl fluoride), polyester, an acrylic resin, or the like can be used.

Although not illustrated in FIG. 4, a protective film may be provided over the second electrode. The protective film may be formed using an organic resin film or an inorganic insulating film. The protective film may be formed so as to cover an exposed portion of the sealant 605. The protective film may be provided so as to cover surfaces and side surfaces of the pair of substrates and exposed side surfaces of a sealing layer, an insulating layer, and the like.

For the protective film, a material that is less likely to transmit an impurity such as water can be used. Thus, diffusion of an impurity such as water from the outside into the inside can be effectively inhibited.

As a material included in the protective film, an oxide, a nitride, a fluoride, a sulfide, a ternary compound, a metal, a polymer, or the like can be used; for example, it is possible to use a material containing aluminum oxide, hafnium oxide, hafnium silicate, lanthanum oxide, silicon oxide, strontium titanate, tantalum oxide, titanium oxide, zinc oxide, niobium oxide, zirconium oxide, tin oxide, yttrium oxide, cerium oxide, scandium oxide, erbium oxide, vanadium oxide, indium oxide, or the like; a material containing aluminum nitride, hafnium nitride, silicon nitride, tantalum nitride, titanium nitride, niobium nitride, molybdenum nitride, zirconium nitride, gallium nitride, or the like; or a material containing a nitride containing titanium and aluminum, an oxide containing titanium and aluminum, an oxide containing aluminum and zinc, a sulfide containing manganese and zinc, a sulfide containing cerium and strontium, an oxide containing erbium and aluminum, an oxide containing yttrium and zirconium, or the like.

The protective film is preferably formed using a deposition method that enables favorable step coverage. One such method is an atomic layer deposition (ALD) method. A material that can be formed by an ALD method is preferably used for the protective film. With the use of an ALD method, a dense protective film with reduced defects such as cracks or pinholes or with a uniform thickness can be formed. Furthermore, damage caused to a process member in forming the protective film can be reduced.

By an ALD method, for example, a uniform protective film with few defects can be formed even on a surface with a complex uneven shape or upper, side, and lower surfaces of a touch panel.

As described above, the light-emitting apparatus fabricated using the light-emitting device described in any one of Embodiment 2 to Embodiment 5 can be obtained.

For the light-emitting apparatus in this embodiment, the light-emitting device described in any one of Embodiment 2 to Embodiment 5 is used and thus, a light-emitting apparatus having favorable characteristics can be obtained. Specifically, since the light-emitting device described in any one of Embodiment 2 to Embodiment 5 has favorable emission efficiency, the light-emitting apparatus with low power consumption can be obtained.

Figure 5A:
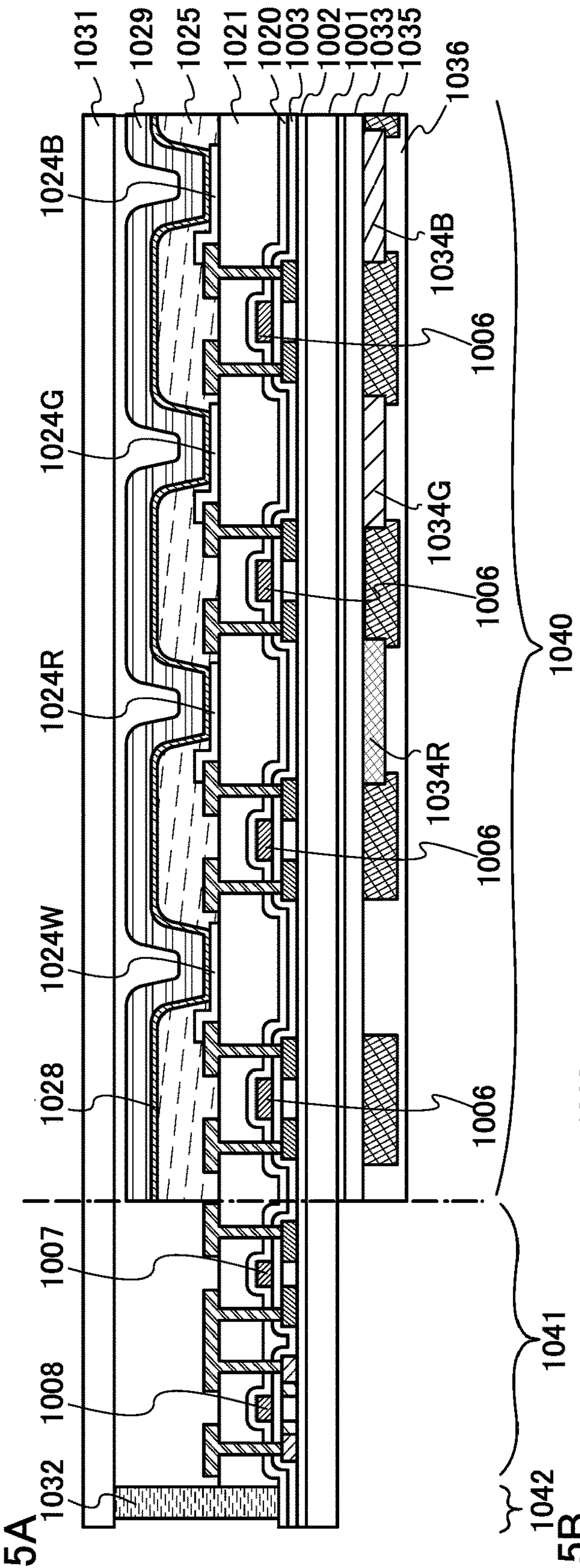
FIG. 5A and FIG. 5B are conceptual diagrams of active matrix light-emitting apparatuses.

FIG. 5 illustrates examples of a light-emitting apparatus in which full color display is achieved by formation of a light-emitting device exhibiting white light emission and provision of coloring layers (color filters) and the like. FIG. 5A illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of the light-emitting devices, a partition 1025, an EL layer 1028, a second electrode 1029 of the light-emitting devices, a sealing substrate 1031, a sealant 1032, and the like.

In FIG. 5A, coloring layers (a red coloring layer 1034R, a green coloring layer 1034G, and a blue coloring layer 1034B) are provided on a transparent base material 1033. A black matrix 1035 may be additionally provided. The transparent base material 1033 provided with the coloring layers and the black matrix is positioned and fixed to the substrate 1001. Note that the coloring layers and the black matrix 1035 are covered with an overcoat layer 1036. In FIG. 5A, a light-emitting layer from which light is emitted to the outside without passing through the coloring layer and light-emitting layers from which light is emitted to the outside, passing through the coloring layers of the respective colors are shown. Since light that does not pass through the coloring layer is white and light that passes through the coloring layer is red, green, or blue, an image can be expressed by pixels of the four colors.

Figure 5B:
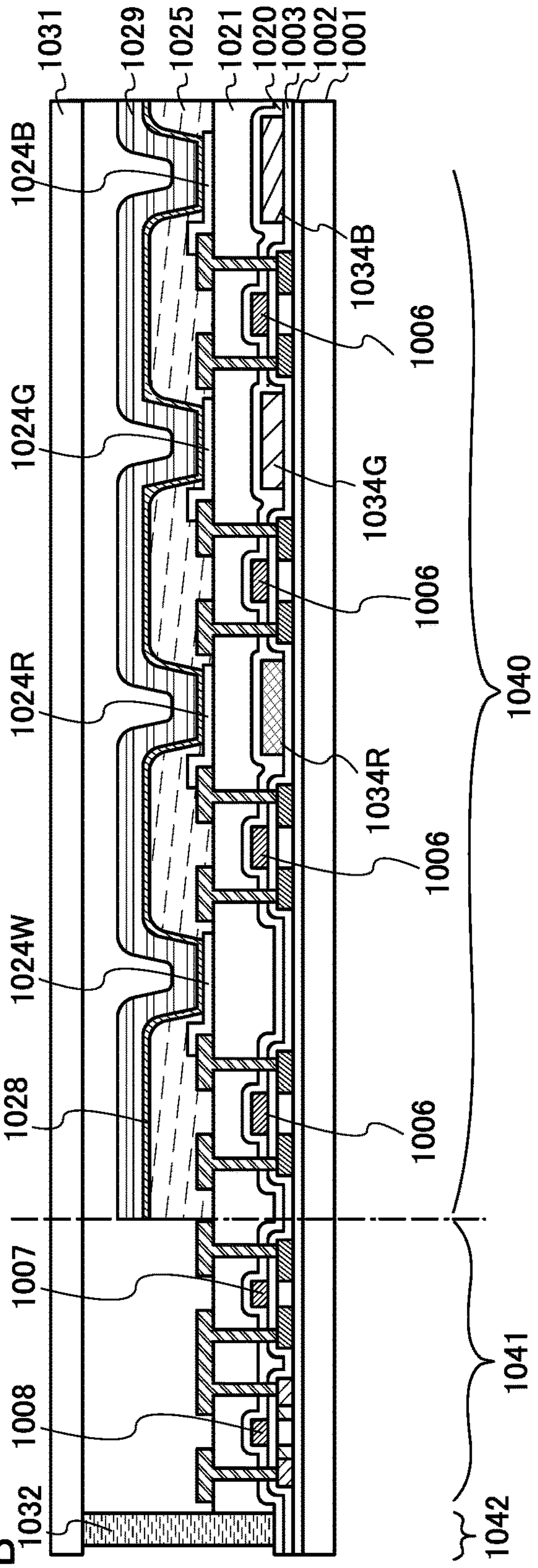

FIG. 5B shows an example in which the coloring layers (the red coloring layer 1034R, the green coloring layer 1034G, and the blue coloring layer 1034B) are formed between the gate insulating film 1003 and the first interlayer insulating film 1020. The coloring layers may be provided between the substrate 1001 and the sealing substrate 1031 in this manner.

Figure 6:
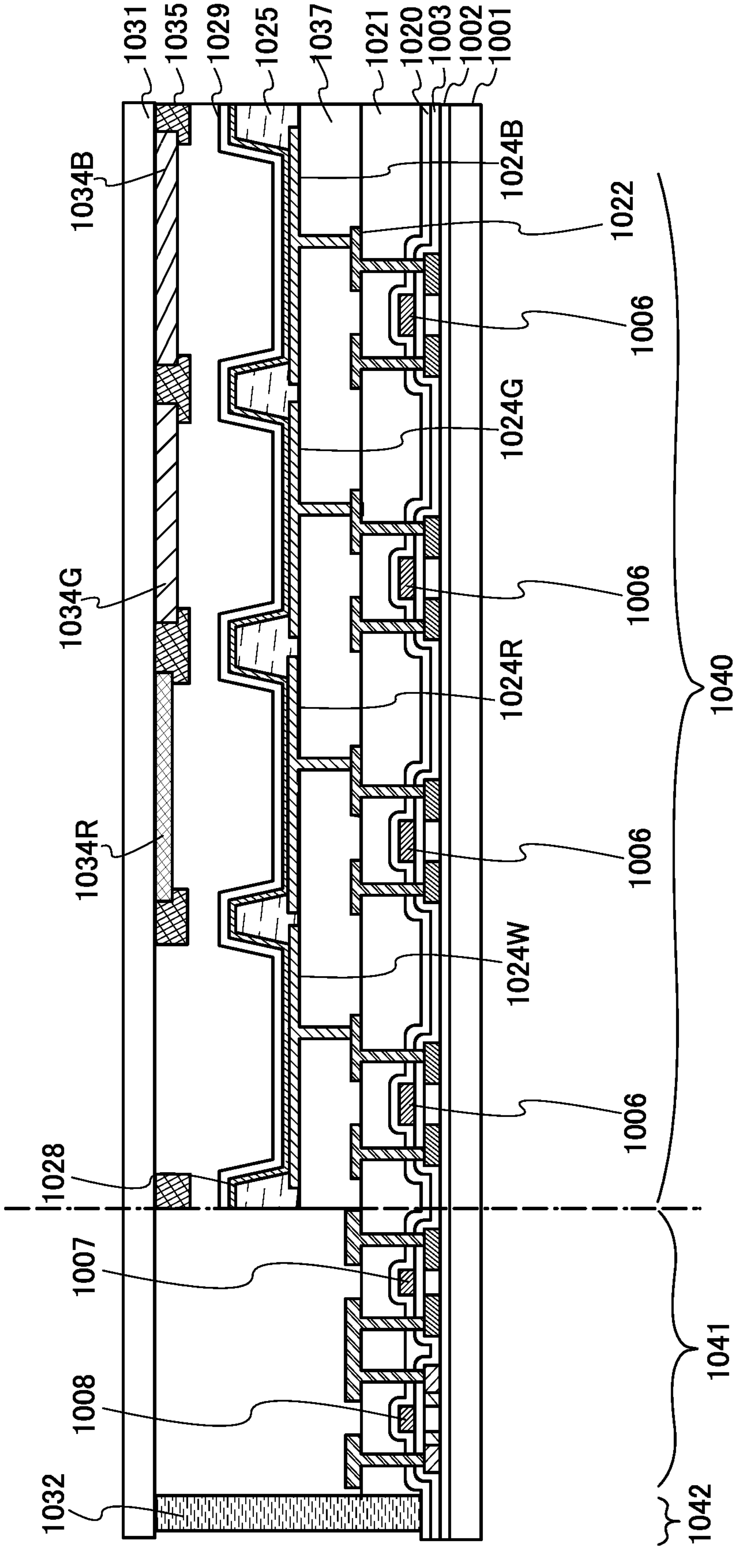
FIG. 6 is a conceptual diagram of an active matrix light-emitting apparatus.

The above-described light-emitting apparatus is a light-emitting apparatus having a structure in which light is extracted to the substrate 1001 side where the FETs are formed (a bottom-emission type), but may be a light-emitting apparatus having a structure in which light emission is extracted to the sealing substrate 1031 side (a top-emission type). FIG. 6 shows a cross-sectional view of atop-emission light-emitting apparatus. In this case, a substrate that does not transmit light can be used as the substrate 1001. The top-emission light-emitting apparatus is formed in a manner similar to that of the bottom-emission light-emitting apparatus until a connection electrode which connects the FET and the anode of the light-emitting device is formed. Then, a third interlayer insulating film 1037 is formed to cover an electrode 1022. This insulating film may have a planarization function. The third interlayer insulating film 1037 can be formed using a material similar to that for the second interlayer insulating film or using any other known materials.

The first electrodes 1024W, 1024R, 1024G, and 1024B of the light-emitting devices are each an anode here, but may each be a cathode. Furthermore, in the case of the top-emission light-emitting apparatus illustrated in FIG. 6, the first electrodes are preferably reflective electrodes. The structure of the EL layer 1028 is such a structure as that of the unit 103 described in any one of Embodiment 2 to Embodiment 5, and an element structure with which white light emission can be obtained.

In the case of such a top-emission structure as in FIG. 6, sealing can be performed with the sealing substrate 1031 on which the coloring layers (the red coloring layer 1034R, the green coloring layer 1034G, and the blue coloring layer 1034B) are provided. The sealing substrate 1031 may be provided with the black matrix 1035 which is positioned between pixels. The coloring layers (the red coloring layer 1034R, the green coloring layer 1034G, and the blue coloring layer 1034B) or the black matrix may be covered with the overcoat layer 1036. Note that a light-transmitting substrate is used as the sealing substrate 1031. Although an example in which full color display is performed using four colors of red, green, blue, and white is shown here, there is no particular limitation and full color display may be performed using four colors of red, yellow, green, and blue or three colors of red, green, and blue.

In the top-emission light-emitting apparatus, a microcavity structure can be favorably employed. A light-emitting device with a microcavity structure can be obtained with the use of a reflective electrode as the first electrode and a semi-transmissive and semi-reflective electrode as the second electrode. The light-emitting device with a microcavity structure includes at least an EL layer between the reflective electrode and the semi-transmissive and semi-reflective electrode, which includes at least a light-emitting layer serving as a light-emitting region.

Note that the reflective electrode is a film having a visible light reflectivity of 40% to 100%, preferably 70% to 100%, and a resistivity of $1\times10^{-2}$ Ωcm or lower. In addition, the semi-transmissive and semi-reflective electrode is a film having a visible light reflectivity of 20% to 80%, preferably 40% to 70%, and a resistivity of $1\times10^{-2}$ Ωcm or lower.

Light emitted from the light-emitting layer included in the EL layer is reflected and resonated by the reflective electrode and the semi-transmissive and semi-reflective electrode.

In the light-emitting device, by changing thicknesses of the transparent conductive film, the above-described composite material, the carrier-transport material, and the like, the optical path length between the reflective electrode and the semi-transmissive and semi-reflective electrode can be changed. Thus, light with a wavelength that is resonated between the reflective electrode and the semi-transmissive and semi-reflective electrode can be intensified while light with a wavelength that is not resonated therebetween can be attenuated.

Note that light that is reflected back by the reflective electrode (first reflected light) considerably interferes with light that directly enters the semi-transmissive and semi-reflective electrode from the light-emitting layer (first incident light); therefore, the optical path length between the reflective electrode and the light-emitting layer is preferably adjusted to (2n−1)λ/4 (n is a natural number of 1 or larger and λ is a wavelength of light emission to be amplified). By adjusting the optical path length, the phases of the first reflected light and the first incident light can be aligned with each other and the light emitted from the light-emitting layer can be further amplified.

Note that in the above structure, the EL layer may include a plurality of light-emitting layers or may include a single light-emitting layer; for example, in combination with the structure of the above-described tandem light-emitting device, a plurality of EL layers each including a single or a plurality of light-emitting layer(s) may be provided in one light-emitting device with a charge-generation layer interposed between the EL layers.

With the microcavity structure, emission intensity with a specific wavelength in the front direction can be increased, whereby power consumption can be reduced. Note that in the case of a light-emitting apparatus which displays images with subpixels of four colors, red, yellow, green, and blue, the light-emitting apparatus can have favorable characteristics because a microcavity structure suitable for the wavelength of the corresponding color is employed in each subpixel, in addition to the effect of an improvement in luminance owing to yellow light emission.

For the light-emitting apparatus in this embodiment, the light-emitting device described in any one of Embodiment 2 to Embodiment 5 is used and thus a light-emitting apparatus having favorable characteristics can be obtained. Specifically, since the light-emitting device described in any one of Embodiment 2 to Embodiment 5 has favorable emission efficiency, the light-emitting apparatus with low power consumption can be obtained.

Figure 7A:
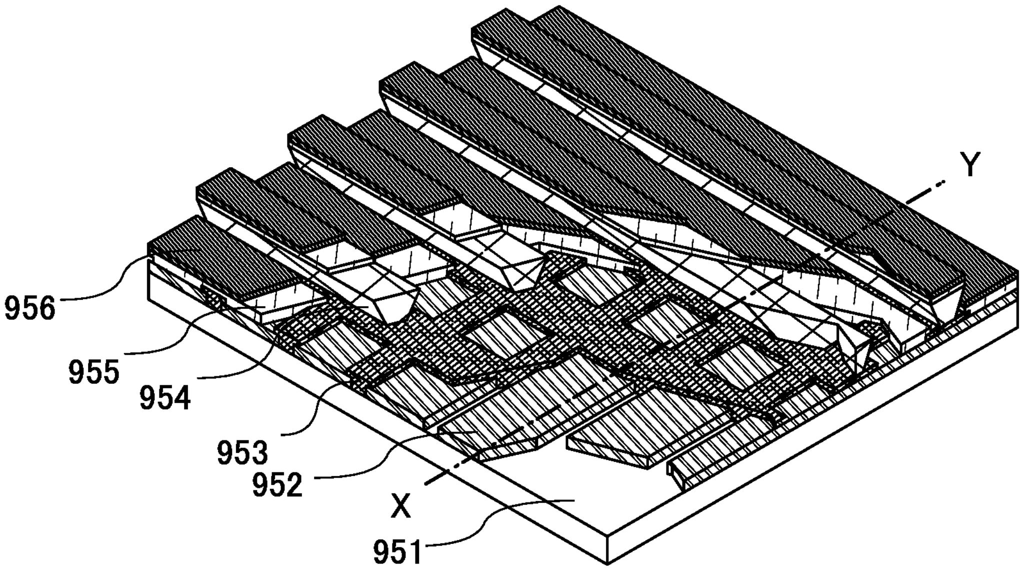
FIG. 7A and FIG. 7B are conceptual diagrams of a passive matrix light-emitting apparatus.
Figure 7B:
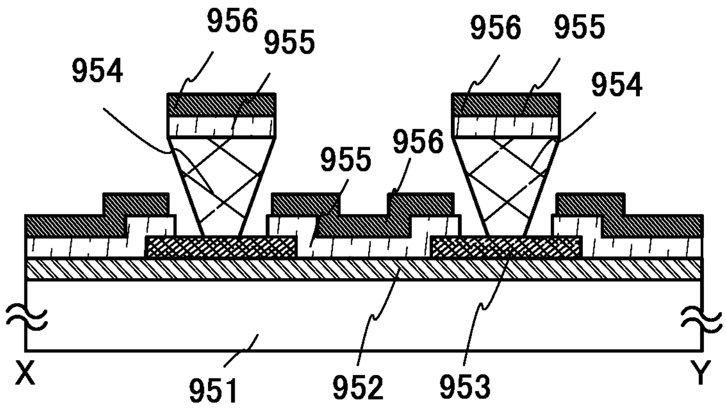

The active matrix light-emitting apparatus is described above, whereas a passive matrix light-emitting apparatus is described below. FIG. 7 illustrates a passive matrix light-emitting apparatus fabricated using the present invention. Note that FIG. 7A is a perspective view illustrating the light-emitting apparatus, and FIG. 7B is a cross-sectional view taken along X-Y in FIG. 7A. In FIG. 7, over a substrate 951, an EL layer 955 is provided between an electrode 952 and an electrode 956. An end portion of the electrode 952 is covered with an insulating layer 953. A partition layer 954 is provided over the insulating layer 953. Sidewalls of the partition layer 954 are aslope such that the distance between one sidewall and the other sidewall is gradually narrowed toward the surface of the substrate. That is, a cross section in the short side direction of the partition layer 954 is a trapezoidal shape, and the lower side (the side facing the same direction as the plane direction of the insulating layer 953 and touching the insulating layer 953) is shorter than the upper side (the side facing the same direction as the plane direction of the insulating layer 953, and not touching the insulating layer 953). By providing the partition layer 954 in this manner, defects of the light-emitting device due to static charge or the like can be prevented. The passive-matrix light-emitting apparatus also uses the light-emitting device described in any one of Embodiment 2 to Embodiment 5; thus, the light-emitting apparatus can have favorable reliability or low power consumption.

Since many minute light-emitting devices arranged in a matrix can each be controlled in the light-emitting apparatus described above, the light-emitting apparatus can be suitably used as a display device for displaying images.

This embodiment can be freely combined with any of the other embodiments.

Embodiment 8

Figure 8A:
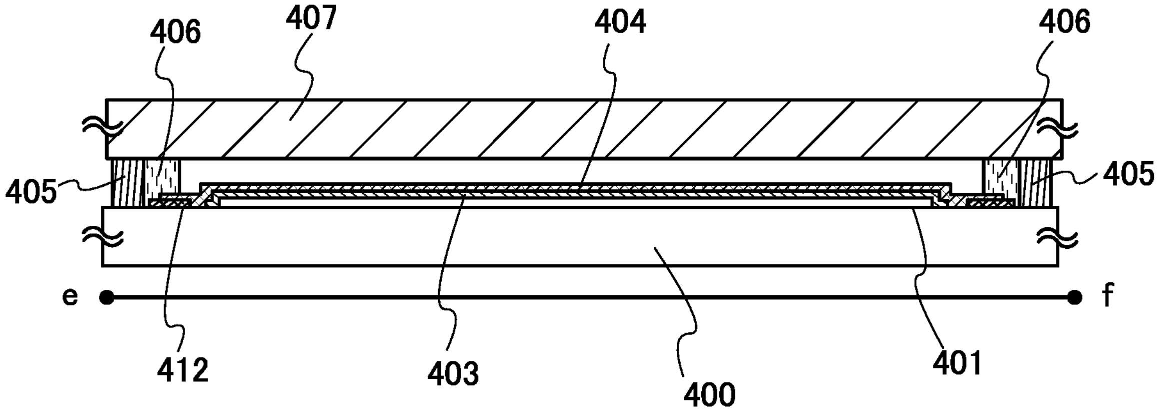
FIG. 8A and FIG. 8B are diagrams showing a lighting device.
Figure 8B:
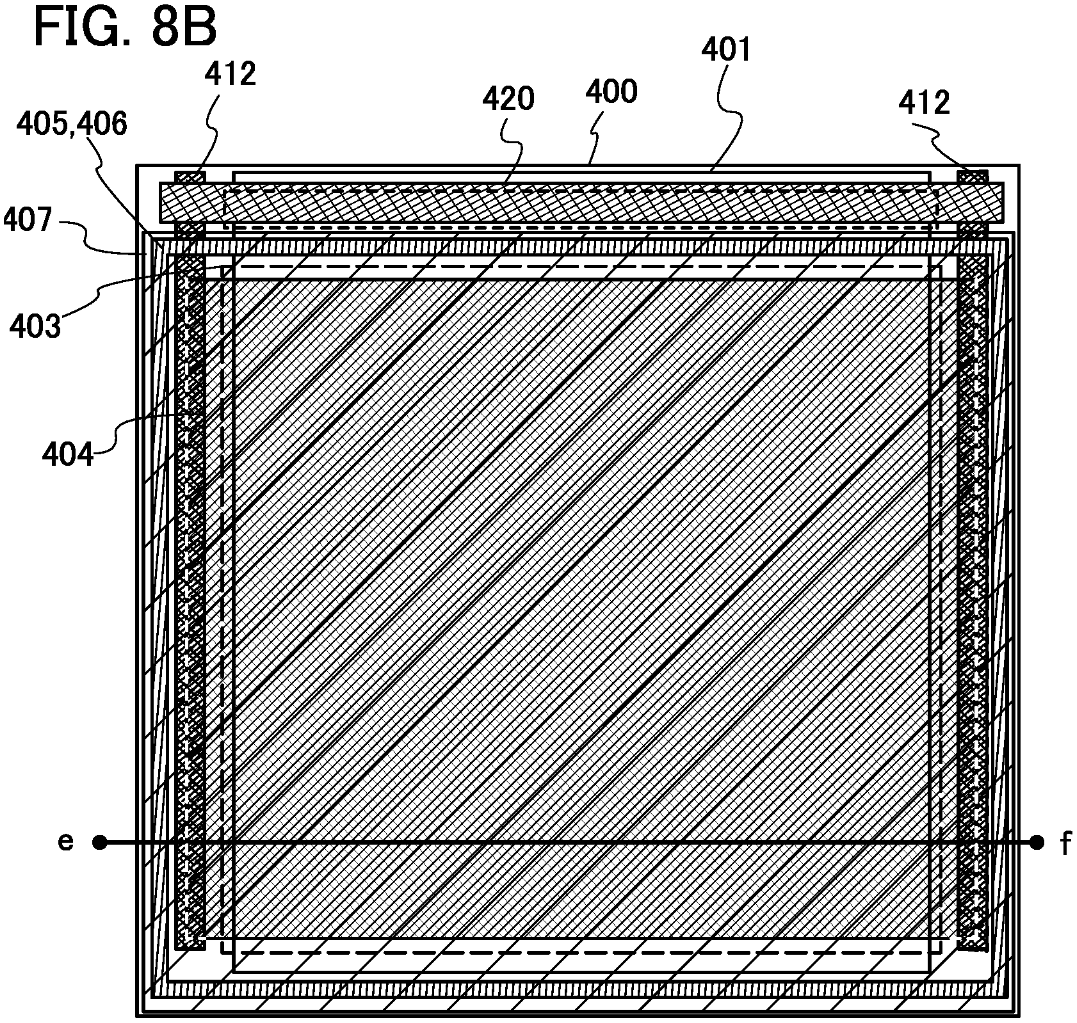

In this embodiment, an example in which the light-emitting device described in any one of Embodiment 2 to Embodiment 5 is used for a lighting device is described with reference to FIG. 8. FIG. 8B is atop view of the lighting device, and FIG. 8A is a cross-sectional view taken along e-f in FIG. 8B.

In the lighting device in this embodiment, a first electrode 401 is formed over a substrate 400 which is a support and has a light-transmitting property. The first electrode 401 corresponds to the first electrode 101 in any one of Embodiment 2 to Embodiment 5. In the case where light emission is extracted from the first electrode 401 side, the first electrode 401 is formed using a material having a light-transmitting property.

A pad 412 for supplying a voltage to a second electrode 404 is formed over the substrate 400.

An EL layer 403 is formed over the first electrode 401. The EL layer 403 includes the structure of the unit 103 in any one of Embodiment 2 to Embodiment 5. Note that for these structures, the corresponding description is to be referred to.

The second electrode 404 is formed to cover the EL layer 403. The second electrode 404 corresponds to the electrode 102 in any one of Embodiment 2 to Embodiment 5. In the case where light emission is extracted from the first electrode 401 side, the second electrode 404 is formed using a material having high reflectivity. The second electrode 404 is supplied with a voltage when connected to the pad 412.

As described above, the lighting device described in this embodiment includes the light-emitting device including the first electrode 401, the EL layer 403, and the second electrode 404. Since the light-emitting device is a light-emitting device with high emission efficiency, the lighting device in this embodiment can be a lighting device with low power consumption.

The substrate 400 over which the light-emitting device having the above structure is formed is fixed to a sealing substrate 407 with sealants 405 and 406 and sealing is performed, so that the lighting device is completed. It is possible to use only either the sealant 405 or 406. In addition, the inner sealant 406 (not shown in FIG. 8B) can be mixed with a desiccant, which enables moisture to be adsorbed, resulting in improved reliability.

When parts of the pad 412 and the first electrode 401 are provided to extend to the outside of the sealants 405 and 406, those can serve as external input terminals. An IC chip 420 or the like mounted with a converter or the like may be provided over the external input terminals.

As described above, the lighting device described in this embodiment includes the light-emitting device described in any one of Embodiment 2 to Embodiment 5 as an EL element; thus, the lighting device can have low power consumption.

Embodiment 9

In this embodiment, examples of electronic devices each partly including the light-emitting device described in any one of Embodiment 2 to Embodiment 5 are described. The light-emitting device described in any one of Embodiment 2 to Embodiment 5 is a light-emitting device with favorable emission efficiency and low power consumption. As a result, the electronic devices described in this embodiment can be electronic devices each including a light-emitting portion with low power consumption.

Examples of electronic devices to which the light-emitting device is applied include television devices (also referred to as TV or television receivers), monitors for computers and the like, digital cameras, digital video cameras, digital photo frames, mobile phones (also referred to as portable telephones or portable telephone devices), portable game machines, portable information terminals, audio playback devices, and large game machines such as pachinko machines. Specific examples of these electronic devices are shown below.

Figure 9A:
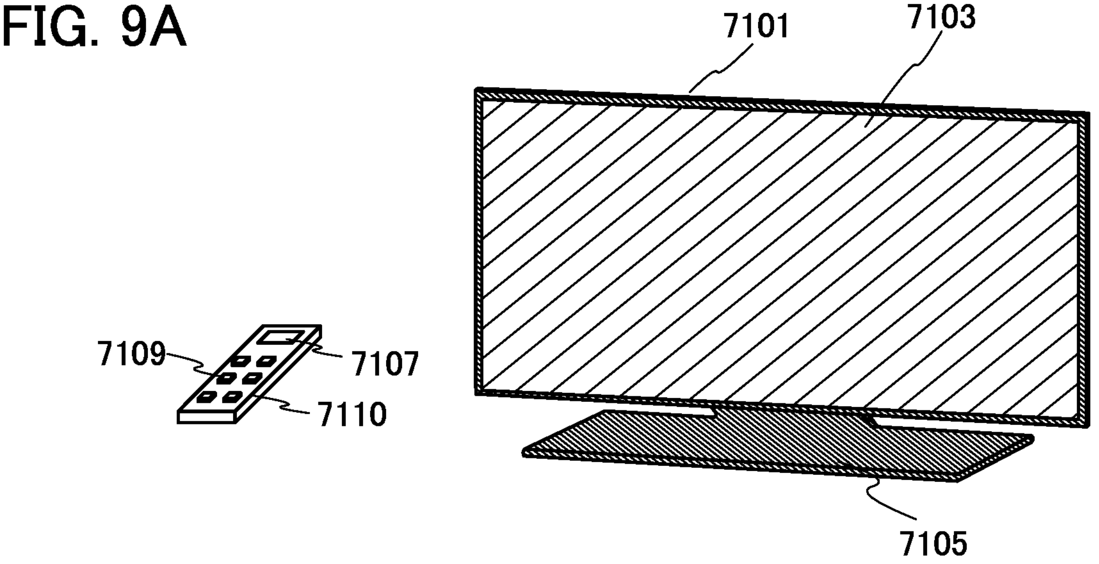
Figure 9A:
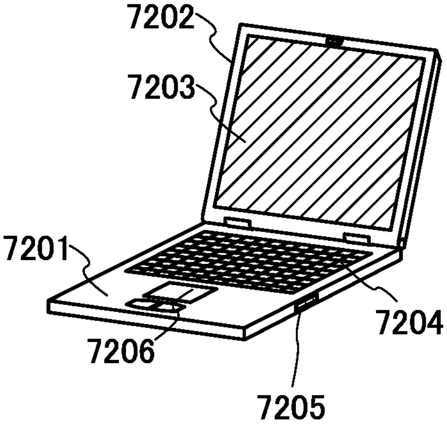
Figure 9A:
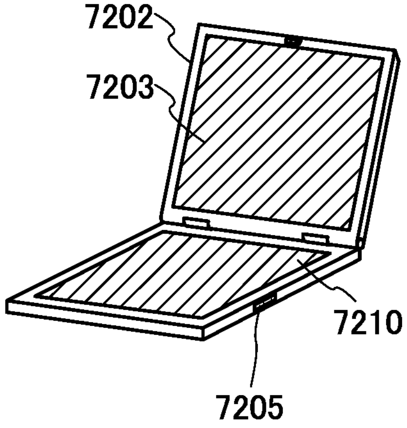

FIG. 9A shows an example of a television device. In the television device, a display portion 7103 is incorporated in a housing 7101. Here, a structure in which the housing 7101 is supported by a stand 7105 is shown. Images can be displayed on the display portion 7103, and the light-emitting devices described in any one of Embodiment 2 to Embodiment 5 are arranged in a matrix in the display portion 7103.

The television device can be operated with an operation switch of the housing 7101 or a separate remote controller 7110. With operation keys 7109 of the remote controller 7110, channels and volume can be operated and images displayed on the display portion 7103 can be operated. Furthermore, a structure may be employed in which the remote controller 7110 is provided with a display portion 7107 for displaying information output from the remote controller 7110.

Note that the television device is provided with a receiver, a modem, or the like. With the use of the receiver, general television broadcast can be received, and moreover, when the television device is connected to a communication network with or without a wire via the modem, one-way (from a sender to a receiver) or two-way (between a sender and a receiver or between receivers) information communication can be performed.

FIG. 9B1 is a computer which includes a main body 7201, a housing 7202, a display portion 7203, a keyboard 7204, an external connection port 7205, a pointing device 7206, and the like. Note that this computer is fabricated using the light-emitting devices described in any one of Embodiment 2 to Embodiment 5 arranged in a matrix in the display portion 7203. The computer in FIG. 9B1 may be such a mode as illustrated in FIG. 9B2. The computer in FIG. 9B2 is provided with a second display portion 7210 instead of the keyboard 7204 and the pointing device 7206. The second display portion 7210 is of a touch-panel type, and input can be performed by operating display for input displayed on the second display portion 7210 with a finger or a dedicated pen. The second display portion 7210 can also display images other than the display for input. The display portion 7203 may also be a touch panel. Connecting the two screens with a hinge can prevent troubles such as a crack in or damage to the screens caused when the computer is stored or carried.

Figure 9C:
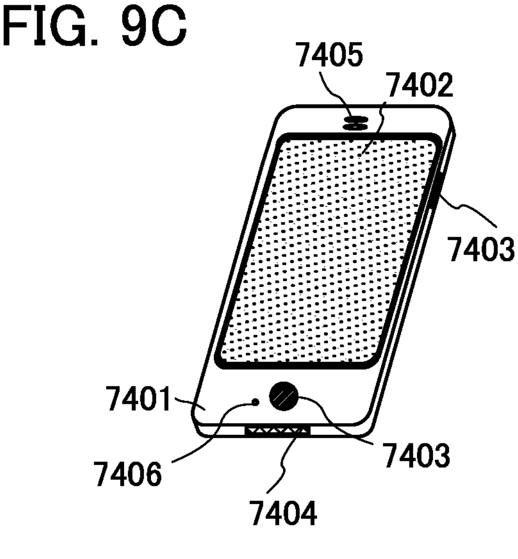

FIG. 9C shows an example of a portable terminal. A mobile phone includes operation buttons 7403, an external connection port 7404, a speaker 7405, a microphone 7406, and the like in addition to a display portion 7402 incorporated in a housing 7401. Note that the mobile phone includes the display portion 7402 which is fabricated by arranging the light-emitting devices described in any one of Embodiment 2 to Embodiment 5 in a matrix.

The portable terminal illustrated in FIG. 9C can have a structure in which information can be input by touching the display portion 7402 with a finger or the like. In this case, operations such as making a call and creating an e-mail can be performed by touching the display portion 7402 with a finger or the like.

The display portion 7402 has mainly three screen modes. The first one is a display mode mainly for displaying images, and the second one is an input mode mainly for inputting information such as text. The third one is a display+input mode in which two modes of the display mode and the input mode are combined.

For example, in the case of making a call or creating an e-mail, a text input mode mainly for inputting text is selected for the display portion 7402 so that an operation of inputting characters displayed on the screen may be performed. In this case, it is preferable to display a keyboard or number buttons on almost the entire screen of the display portion 7402.

When a sensing device including a sensor for sensing inclination, such as a gyroscope sensor or an acceleration sensor, is provided inside the portable terminal, screen display of the display portion 7402 can be automatically changed by determining the orientation of the portable terminal (whether the portable terminal is placed horizontally or vertically).

The screen modes are changed by touching the display portion 7402 or operating the operation buttons 7403 of the housing 7401. Alternatively, the screen modes can be changed depending on the kind of the image displayed on the display portion 7402. For example, when a signal of an image displayed on the display portion is moving image data, the screen mode is changed to the display mode, and when the signal is text data, the screen mode is changed to the input mode.

Moreover, in the input mode, when input by the touch operation of the display portion 7402 is not performed for a certain period while a signal sensed by an optical sensor in the display portion 7402 is sensed, the screen mode may be controlled so as to be changed from the input mode to the display mode.

The display portion 7402 can also function as an image sensor. For example, an image of a palm print, a fingerprint, or the like is taken when the display portion 7402 is touched with the palm or the finger, whereby personal authentication can be performed. Furthermore, by using a backlight which emits near-infrared light or a sensing light source which emits near-infrared light in the display portion, an image of a finger vein, a palm vein, or the like can be taken.

Figure 10A:
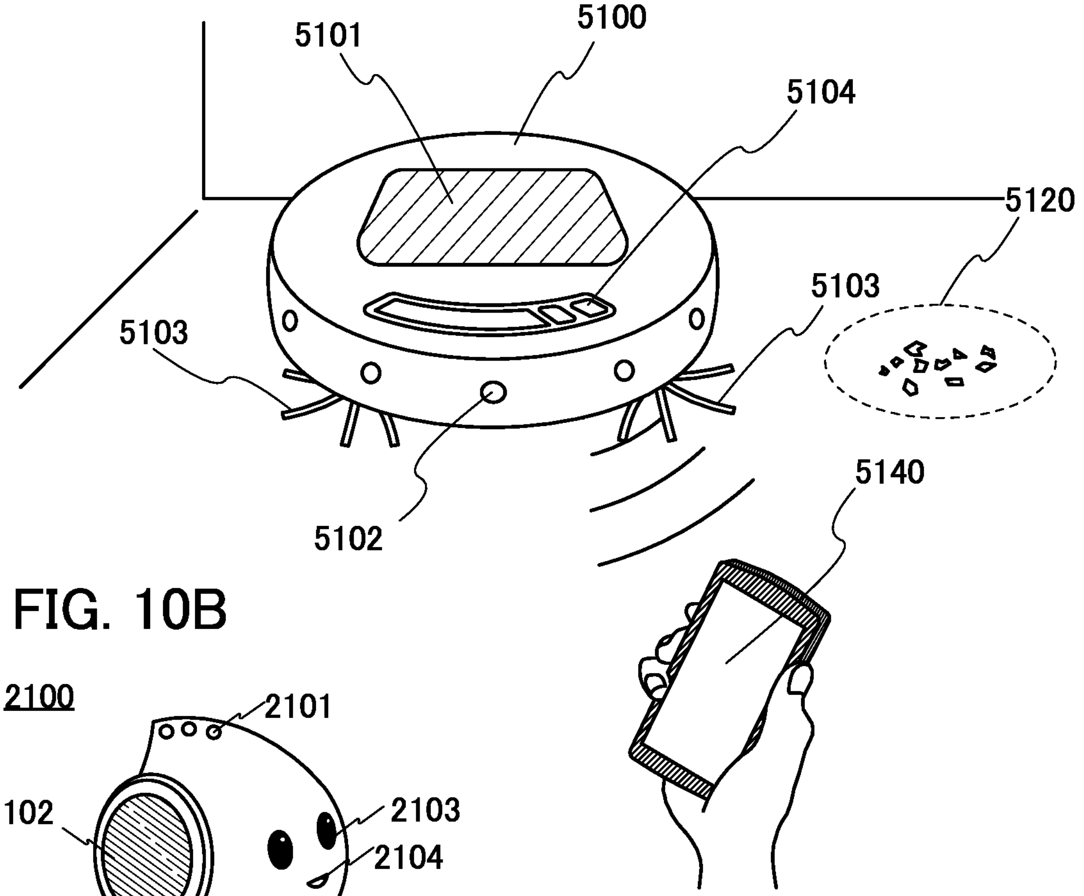
FIG. 10A to FIG. 10C are diagrams showing electronic devices.

FIG. 10A is a schematic view showing an example of a cleaning robot.

A cleaning robot 5100 includes a display 5101 placed on its top surface, a plurality of cameras 5102 placed on its side surface, a brush 5103, and operation buttons 5104. Although not illustrated, the bottom surface of the cleaning robot 5100 is provided with a tire, an inlet, and the like. Furthermore, the cleaning robot 5100 includes various sensors such as an infrared sensor, an ultrasonic sensor, an acceleration sensor, a piezoelectric sensor, an optical sensor, and a gyroscope sensor. In addition, the cleaning robot 5100 has a wireless communication means.

The cleaning robot 5100 is self-propelled, detects dust 5120, and sucks up the dust through the inlet provided on the bottom surface.

The cleaning robot 5100 can judge whether there is an obstacle such as a wall, furniture, or a step by analyzing images taken by the cameras 5102. When an object that is likely to be caught in the brush 5103, such as a wire, is detected by image analysis, the rotation of the brush 5103 can be stopped.

The display 5101 can display the remaining capacity of a battery, the amount of vacuumed dust, or the like. The display 5101 may display a path on which the cleaning robot 5100 has run. The display 5101 may be a touch panel, and the operation buttons 5104 may be provided on the display 5101.

The cleaning robot 5100 can communicate with a portable electronic device 5140 such as a smartphone. The portable electronic device 5140 can display images taken by the cameras 5102. Accordingly, an owner of the cleaning robot 5100 can monitor the room even from the outside. The display on the display 5101 can be checked by the portable electronic device such as a smartphone.

The light-emitting apparatus of one embodiment of the present invention can be used for the display 5101.

Figure 10B:
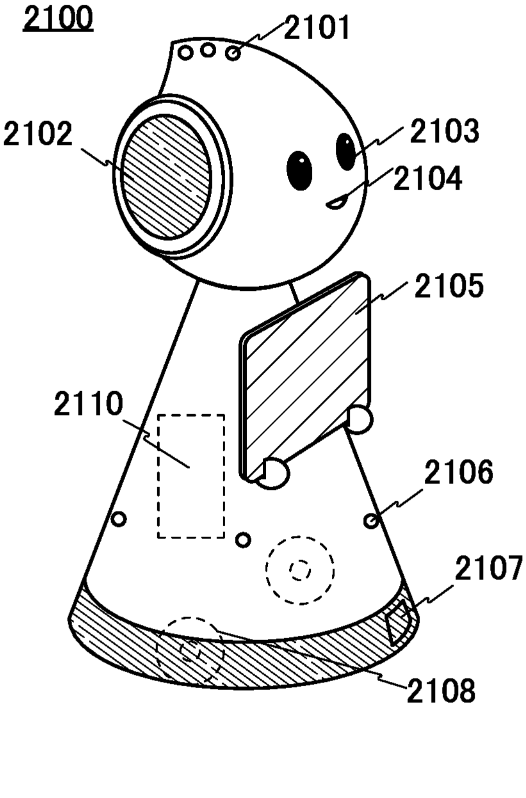

A robot 2100 illustrated in FIG. 10B includes an arithmetic device 2110, an illuminance sensor 2101, a microphone 2102, an upper camera 2103, a speaker 2104, a display 2105, a lower camera 2106, an obstacle sensor 2107, and a moving mechanism 2108.

The microphone 2102 has a function of detecting a speaking voice of a user, an environmental sound, and the like. The speaker 2104 also has a function of outputting sound. The robot 2100 can communicate with a user using the microphone 2102 and the speaker 2104.

The display 2105 has a function of displaying various kinds of information. The robot 2100 can display information desired by a user on the display 2105. The display 2105 may be provided with a touch panel. Moreover, the display 2105 may be a detachable information terminal, in which case charging and data communication can be performed when the display 2105 is set at the home position of the robot 2100.

The upper camera 2103 and the lower camera 2106 each have a function of taking an image of the surroundings of the robot 2100. The obstacle sensor 2107 can detect the presence of an obstacle in the direction where the robot 2100 advances with the moving mechanism 2108. The robot 2100 can move safely by recognizing the surroundings with the upper camera 2103, the lower camera 2106, and the obstacle sensor 2107. The light-emitting apparatus of one embodiment of the present invention can be used for the display 2105.

Figure 10C:
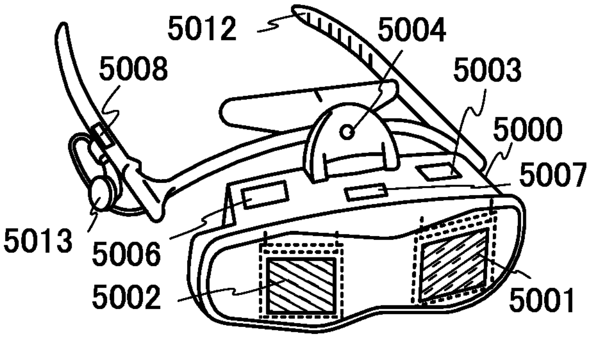

FIG. 10C shows an example of a goggle-type display. The goggle-type display includes, for example, a housing 5000, a display portion 5001, a speaker 5003, an LED lamp 5004, a connection terminal 5006, a sensor 5007 (a sensor having a function of measuring force, displacement, position, speed, acceleration, angular velocity, rotational frequency, distance, light, liquid, magnetism, temperature, a chemical substance, sound, time, hardness, an electric field, a current, a voltage, electric power, radiation, flow rate, humidity, gradient, oscillation, odor, or infrared ray), a microphone 5008, a display portion 5002, a support 5012, and an earphone 5013.

The light-emitting apparatus of one embodiment of the present invention can be used for the display portion 5001 and the display portion 5002.

Figure 11:
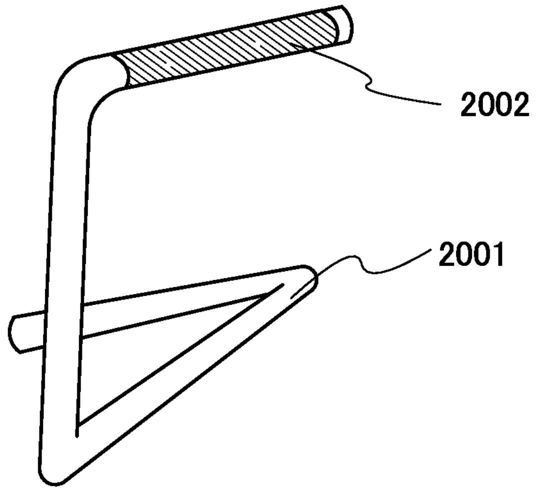
FIG. 11 is a diagram showing a lighting device.

FIG. 11 shows an example in which the light-emitting device described in any one of Embodiment 2 to Embodiment 5 is used for a table lamp which is a lighting device. The table lamp illustrated in FIG. 11 includes a housing 2001 and a light source 2002, and the lighting device described in Embodiment 3 may be used for the light source 2002.

Figure 12:
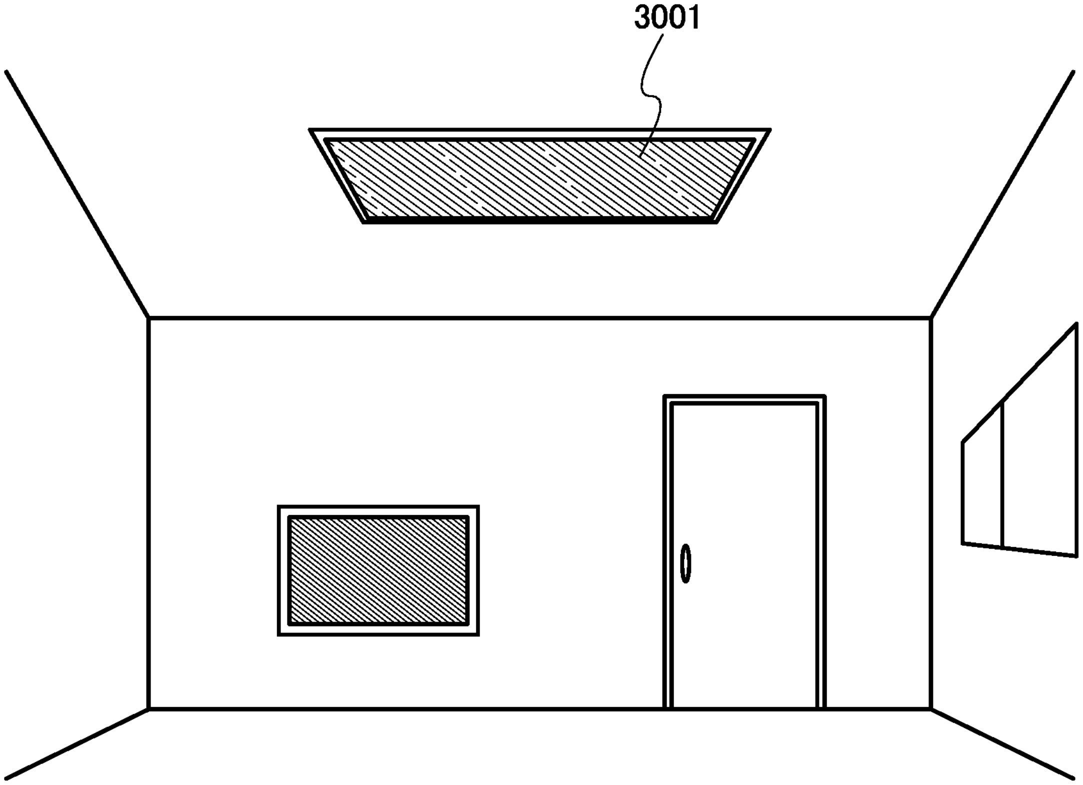
FIG. 12 is a diagram showing a lighting device.

FIG. 12 shows an example in which the light-emitting device described in any one of Embodiment 2 to Embodiment 5 is used for an indoor lighting device 3001. Since the light-emitting device described in any one of Embodiment 2 to Embodiment 5 is a light-emitting device with high emission efficiency, the lighting device can have low power consumption. Furthermore, the light-emitting device described in any one of Embodiment 2 to Embodiment 5 can have a larger area, and thus can be used for a large-area lighting device. Furthermore, the light-emitting device described in any one of Embodiment 2 to Embodiment 5 is thin, and thus can be used for a lighting device having a reduced thickness.

Figure 13:
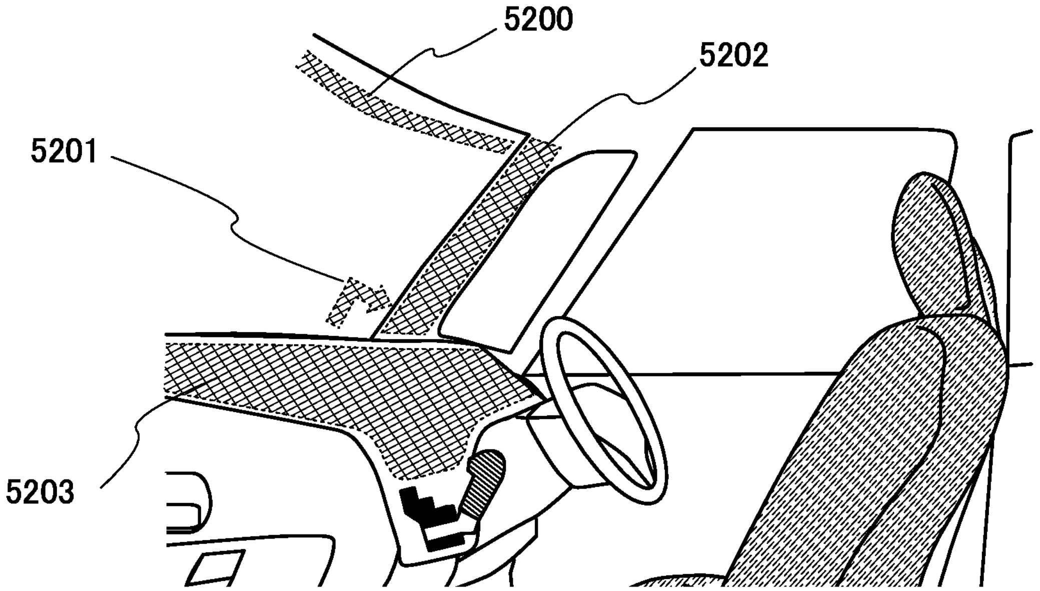
FIG. 13 is a diagram showing in-vehicle display devices and lighting devices.

The light-emitting device described in any one of Embodiment 2 to Embodiment 5 can also be incorporated in an automobile windshield or an automobile dashboard. FIG. 13 illustrates one mode in which the light-emitting device described in any one of Embodiment 2 to Embodiment 5 is used for a windshield or a dashboard of an automobile. A display region 5200 to a display region 5203 are each a display region provided using the light-emitting device described in any one of Embodiment 2 to Embodiment 5.

The display region 5200 and the display region 5201 are display devices provided in the automobile windshield, in which the light-emitting devices described in any one of Embodiment 2 to Embodiment 5 are incorporated. When the light-emitting devices described in any one of Embodiment 2 to Embodiment 5 are fabricated using electrodes having light-transmitting properties as a first electrode and a second electrode, what is called see-through display devices, through which the opposite side can be seen, can be obtained. See-through display can be provided without hindering the vision even when being provided in the automobile windshield. Note that in the case where a driving transistor or the like is provided, a transistor having a light-transmitting property, such as an organic transistor using an organic semiconductor material or a transistor using an oxide semiconductor, is preferably used.

The display region 5202 is a display device provided in a pillar portion, in which the light-emitting devices described in any one of Embodiment 2 to Embodiment 5 are incorporated. The display region 5202 can compensate for the view hindered by the pillar by displaying an image taken by an imaging means provided on the car body. Similarly, the display region 5203 provided in the dashboard portion can compensate for the view hindered by the car body by displaying an image taken by an imaging means provided on the outside of the automobile. Thus, blind areas can be compensated for and the safety can be enhanced. Showing an image so as to compensate for the area that cannot be seen makes it possible to confirm safety more naturally and comfortably.

The display region 5203 can provide a variety of kinds of information by displaying navigation information, a speedometer, a rotation rate, a mileage, a fuel meter, a gearshift state, air-condition setting, and the like. The content or layout of the display can be changed freely in accordance with the preference of a user. Note that such information can also be provided on the display region 5200 to the display region 5202. The display region 5200 to the display region 5203 can also be used as lighting devices.

Figure 14A:
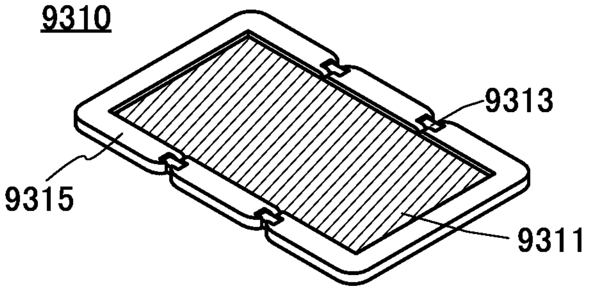
FIG. 14A to FIG. 14C are diagrams showing an electronic device.
Figure 14B:
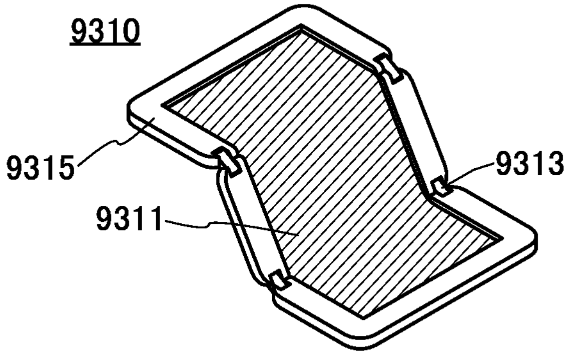
Figure 14C:
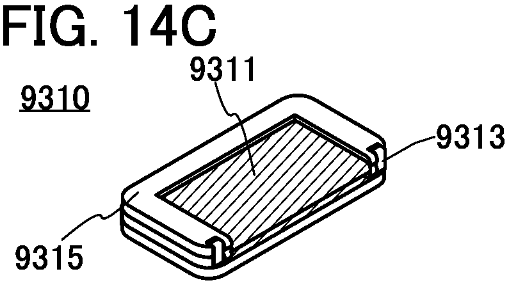

FIG. 14A to FIG. 14C illustrate a foldable portable information terminal 9310. FIG. 14A illustrates the portable information terminal 9310 that is opened. FIG. 14B illustrates the portable information terminal 9310 that is in the state of being changed from one of an opened state and a folded state to the other. FIG. 14C illustrates the portable information terminal 9310 that is folded. The portable information terminal 9310 is excellent in portability when folded, and is excellent in display browsability when opened because of a seamless large display region.

A display panel 9311 is supported by three housings 9315 joined together by hinges 9313. Note that the display panel 9311 may be a touch panel (an input/output device) including a touch sensor (an input device). By folding the display panel 9311 at the hinges 9313 between two housings 9315, the portable information terminal 9310 can be reversibly changed in shape from the opened state to the folded state. The light-emitting apparatus of one embodiment of the present invention can be used for the display panel 9311.

Note that the structures described in this embodiment can be combined with the structures described in any of Embodiment 2 to Embodiment 5 as appropriate.

As described above, the application range of the light-emitting apparatus including the light-emitting device described in any one of Embodiment 2 to Embodiment 5 is wide, so that this light-emitting apparatus can be applied to electronic devices in a variety of fields. With the use of the light-emitting device described in any one of Embodiment 2 to Embodiment 5, an electronic device with low power consumption can be obtained.

Note that this embodiment can be combined with any of the other embodiments in this specification as appropriate.

Example 1

Synthesis Example 1

In this example, the physical properties of the organic compound of one embodiment of the present invention and a method for synthesizing the organic compound will be described with reference to FIG. 15 to FIG. 17. Specifically, the characteristics and synthesis method of N,N-bis(9-phenyl-9H-carbazol-2-yl)-N,N-diphenyldibenzo[b,b']furo[2,3-f;5,4-f]bisbenzofuran-3,10-diamine (abbreviation: PCA2Dfbf-02) represented by Structural Formula (112) in Embodiment 1 are described. The structural formula of PCA2Dfbf-02 is shown below.

[Chemical Formula 44]

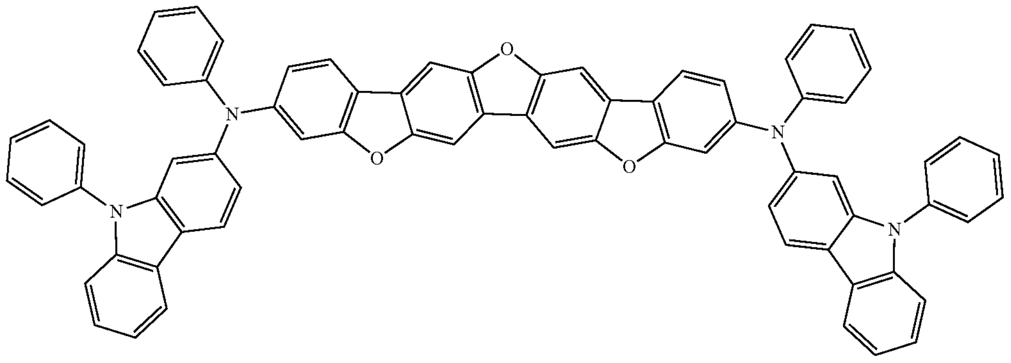

PCA2Dfbf-02

Figure 15:
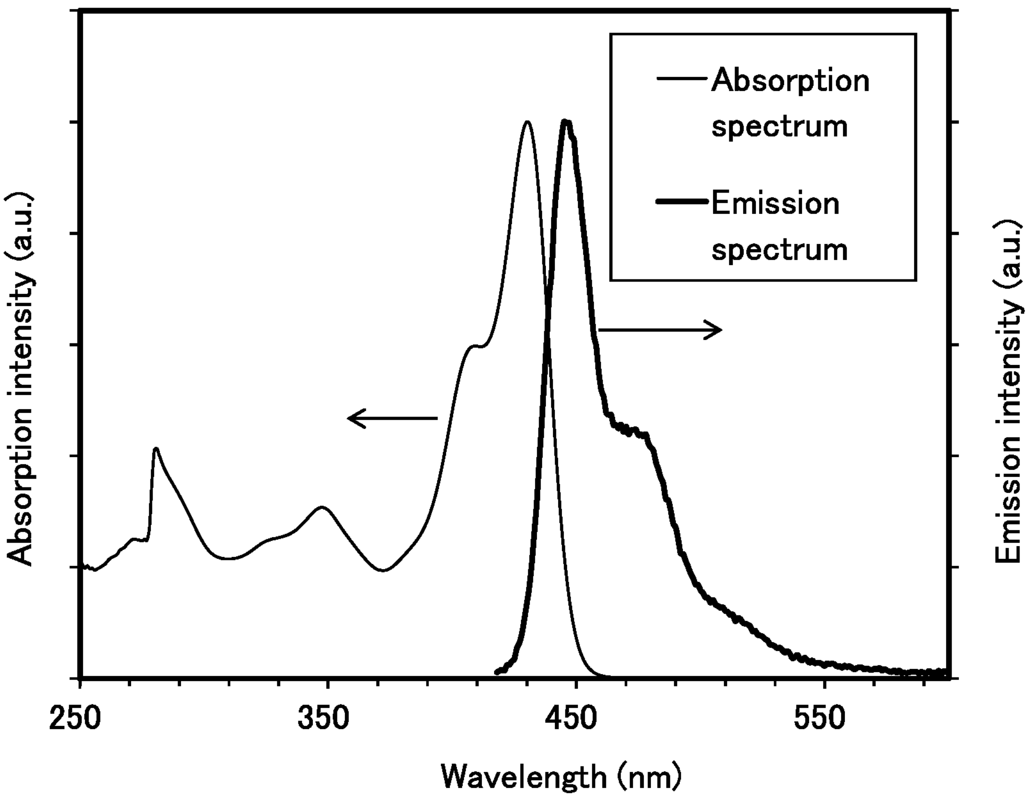
FIG. 15 is a diagram showing an absorption spectrum and an emission spectrum of PCA2Dfbf-02 in a toluene solution.

FIG. 15 is a diagram illustrating an absorption spectrum and an emission spectrum of a toluene solution containing PCA2Dfbf-02.

Figure 16:
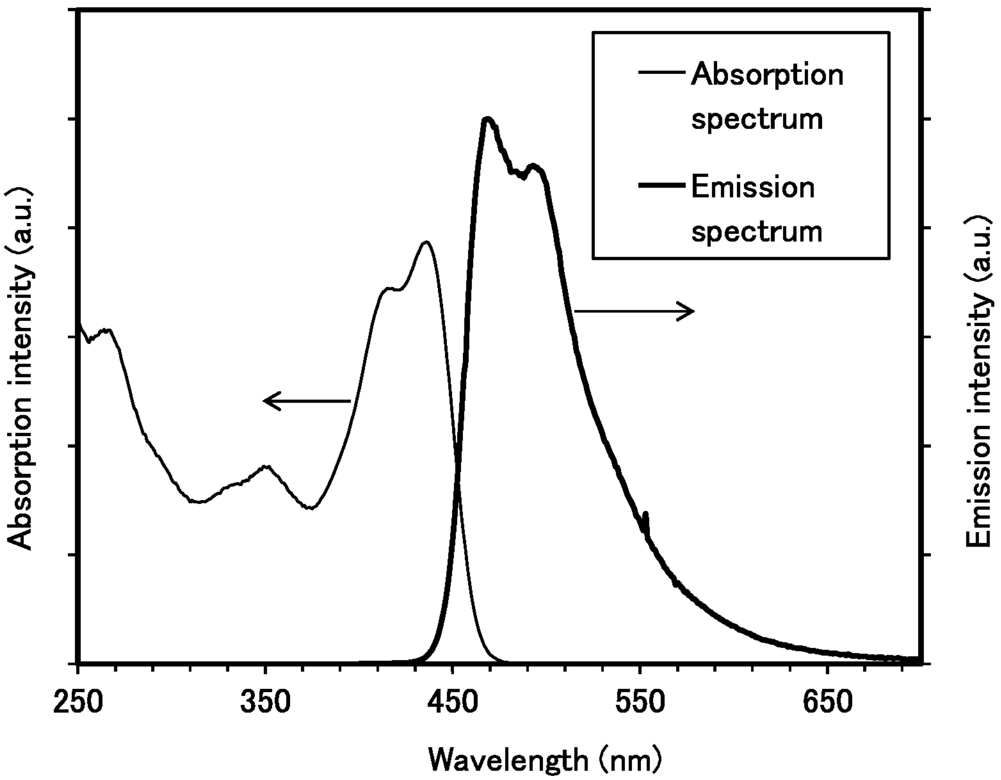
FIG. 16 is a diagram showing an absorption spectrum and an emission spectrum of PCA2Dfbf-02 in a thin film state.

FIG. 16 is a diagram illustrating an absorption spectrum and an emission spectrum of PCA2Dfbf-02 in a solid thin film form.

Figure 17A:
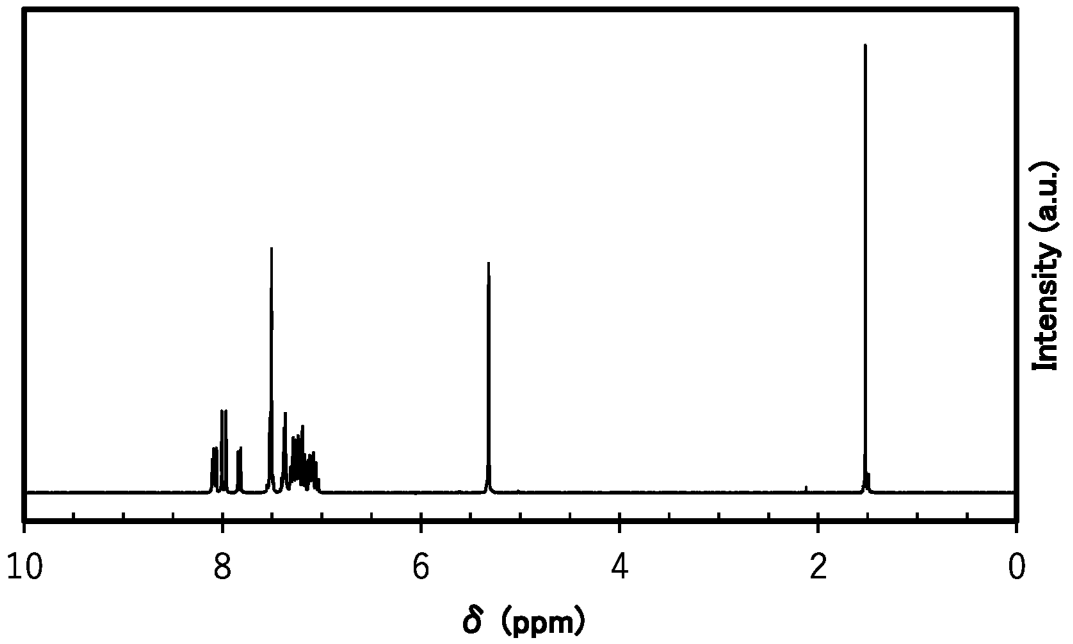
FIG. 17A and FIG. 17B are diagrams showing $^1$H NMR spectra of PCA2Dfbf-02.
Figure 17B:
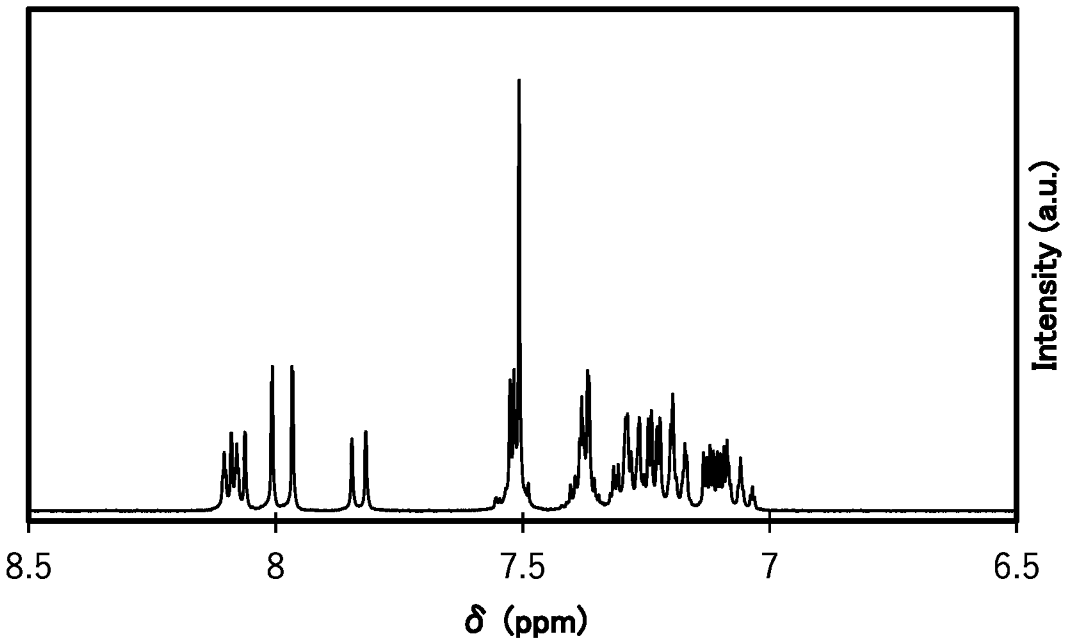

FIG. 17A and FIG. 17B are diagrams illustrating $^1$H NMR spectra of PCA2Dfbf-02.

<Measurement Apparatus and Method for Manufacturing Measurement Sample>

The absorption spectrum of the toluene solution was measured with an ultraviolet and visible spectrophotometer (V550, manufactured by JASCO Corporation), and the absorption spectrum derived from toluene was subtracted.

For the absorption spectrum of the sample in the solid thin film form, a spectrophotometer (U4100 Spectrophotometer, manufactured by Hitachi High-Technologies Corporation) was used.

The emission spectra were measured using a fluorescence spectrophotometer (FS920, manufactured by Hamamatsu Photonics K.K.), and the quantum yield was measured using an absolute PL quantum yields measurement system (Quantaurus-QY, manufactured by Hamamatsu Photonics K.K.).

Note that the solid sample in the thin film form was formed over a quartz substrate by a vacuum evaporation method.

<Physical Properties>

The absorption spectrum of the toluene solution containing PCA2Dfbf-02 had peaks at 430 nm, 409 nm, 347 nm, and 281 nm (see FIG. 15). The emission spectrum thereof had peaks at 446 nm and 477 nm, and the intensity at 477 nm was lower than or equal to half the intensity at 446 nm. The half width was 25 nm. Note that light with a wavelength of 408 nm was used as excitation light. The quantum yield in the toluene solution was 94%.

The molar absorption coefficient of the solution of PCA2Dfbf-02 was $1.3\times10^5$ ($M^{-1}$ $cm^{-1}$) at 430 nm. It was thus found that the organic compound of one embodiment of the present invention exhibits an extremely high molar absorption coefficient.

The absorption spectrum of the solid thin film of PCA2Dfbf-02 had peaks at 436 nm, 416 nm, 352 nm, and 266 nm (see FIG. 16). The emission spectrum thereof had peaks at 469 nm and 493 nm. Note that light with a wavelength of 380 nm was used as excitation light.

It was thus found that PCA2Dfbf-02 emits blue light. Moreover, PCA2Dfbf-02 was found to be usable as a light-emitting material or a host material for a fluorescent material in the visible region. Furthermore, PCA2Dfbf-02 was found to have an extremely high quantum yield and a half width of an emission spectrum of less than or equal to 30 nm and to be suitable as a light-emitting material.

<Synthesis Method>

A method for synthesizing PCA2Dfbf-02 is described. Synthesis Scheme (SC3) is shown below.

[Chemical Formula 45]

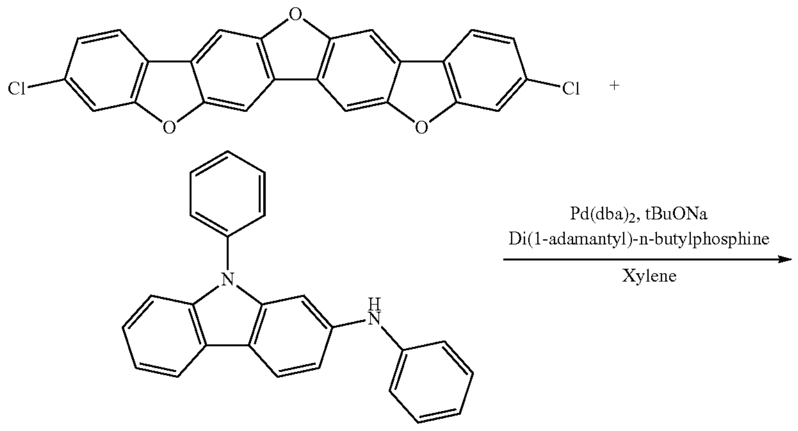

-continued

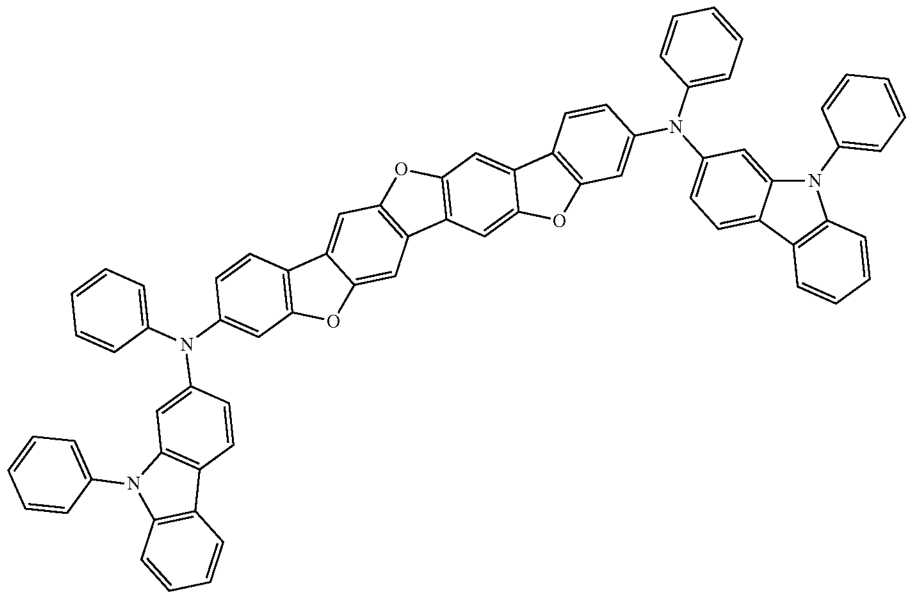

(SC3)

Into a 200-mL three-necked flask were put 1.0 g (2.5 mmol) of 3,10-dichlorodibenzo[b,b']furo[2,3-f;5,4-f]bisbenzofuran, 2.1 g (6.2 mmol) of N,9-diphenyl-9H-carbazol-2-amine, 89 mg (0.25 mmol) of di(1-adamantyl)-n-butylphosphine, and 1.4 g (15 mmol) of sodium tert-butoxide. To this mixture was added 25 mL of xylene. This mixture was degassed by being stirred while the pressure was reduced. To this mixture was added 28 mg (49 μmol) of bis(dibenzylideneacetone)palladium(0), and the mixture was stirred under a nitrogen stream at 150° C. for 14 hours.

After the stirring, toluene was added to this mixture, which was then subjected to suction filtration through Florisil, Celite, and alumina, and the filtrate was concentrated to give a solid.

The obtained solid was purified by silica gel column chromatography (developing solvent: toluene:hexane=2:3), so that a solid was obtained. Furthermore, the obtained solid was reprecipitated with toluene/ethanol, so that 2.0 g of a yellow solid was obtained in a yield of 81%.

By a train sublimation method, 1.1 g of the yellow solid was sublimated and purified. The heating was performed at 400° C. under the conditions where the pressure was $1.8\times10^{-2}$ Pa and the flow rate of argon was 0 mL/min. After the sublimation purification, 0.73 g of a yellow solid was obtained at a collection rate of 68%.

[$^1$H NMR]

FIG. 17A and FIG. 17B show the $^1$H NMR spectra of a dichloromethane solution of the obtained yellow solid. In addition, numerical data is shown below. This indicated that PCA2Dfbf-02 was obtained in this synthesis example.

$^1$H NMR ($CD_2Cl_2$, 300 MHz): δ=7.03-7.13 (m, 6H), 7.16-7.32 (m, 14H), 7.35-7.42 (m, 6H), 7.49-7.55 (m, 8H), 7.83 (d, $J_1$=8.4 Hz, 2H), 7.97 (d, $J_1$=0.6 Hz, 2H), 8.01 (d, $J_1$=0.6 Hz, 2H), 8.06-8.11 (m, 4H).

Synthesis Example 2

In this example, the physical properties of the organic compound of one embodiment of the present invention and a method for synthesizing the organic compound will be described with reference to FIG. 18 to FIG. 20. Specifically, the characteristics and synthesis method of N,N'-bis(dibenzofuran-3-yl)-N,N-diphenyldibenzo[b,b']furo[2,3-f;5,4-f]bisbenzofuran-3,10-diamine (abbreviation: FrA2Dfbf-02) represented by Structural Formula (107) in Embodiment 1 are described. The structural formula of FrA2Dfbf-02 is shown below.

[Chemical Formula 46]

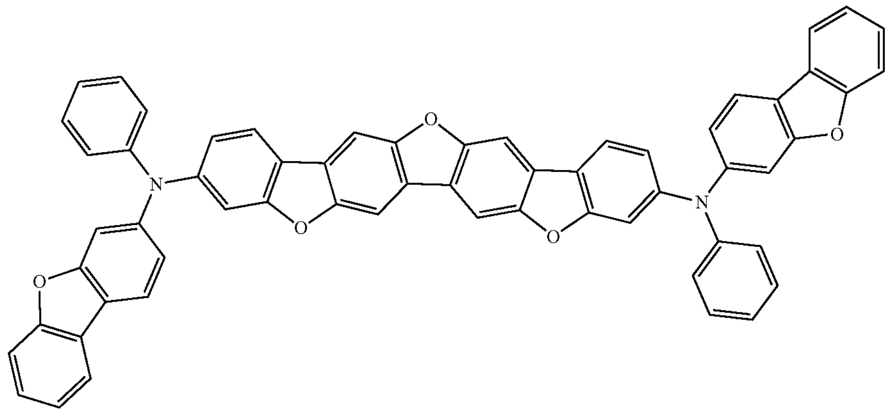

FrA2Dfbf-02

Figure 18:
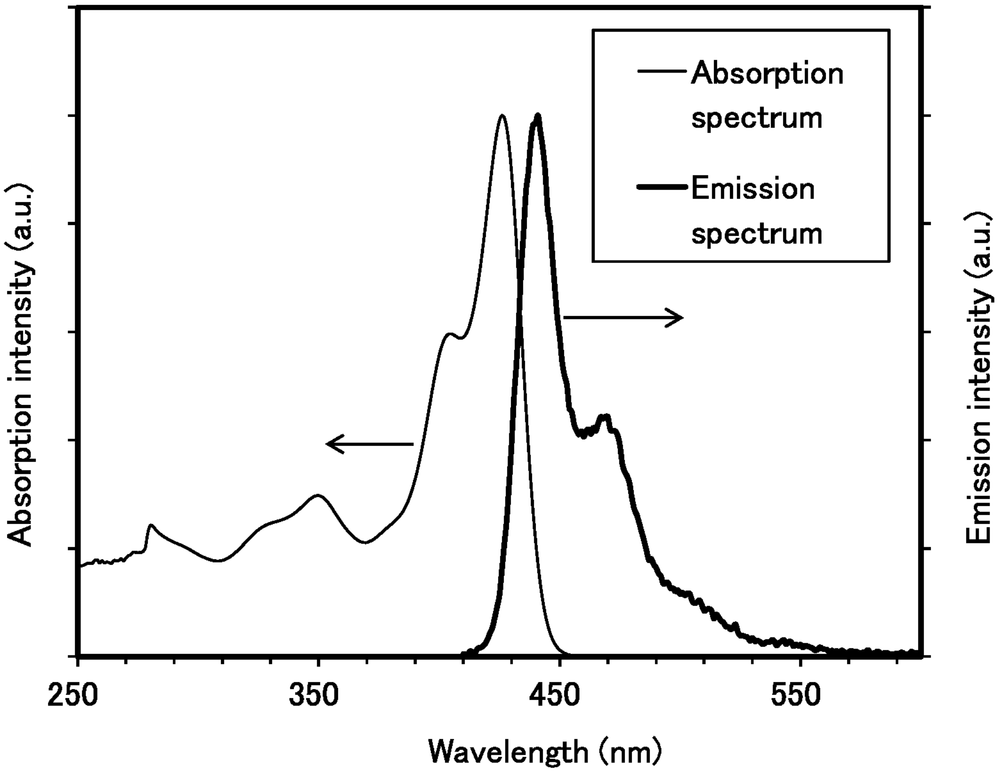
FIG. 18 is a diagram showing an absorption spectrum and an emission spectrum of FrA2Dfbf-02 in a toluene solution.

FIG. 18 is a diagram illustrating an absorption spectrum and an emission spectrum of a toluene solution containing FrA2Dfbf-02.

Figure 19:
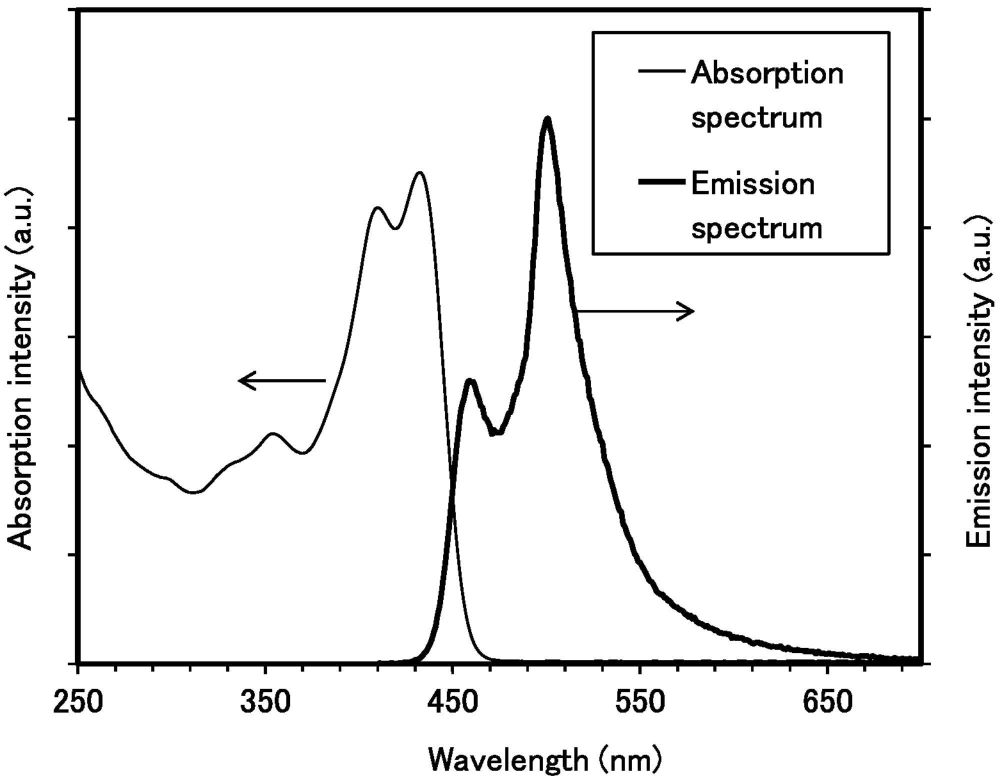
FIG. 19 is a diagram showing an absorption spectrum and an emission spectrum of FrA2Dfbf-02 in a thin film state.

FIG. 19 is a diagram illustrating an absorption spectrum and an emission spectrum of FrA2Dfbf-02 in a solid thin film form.

Figure 20A:
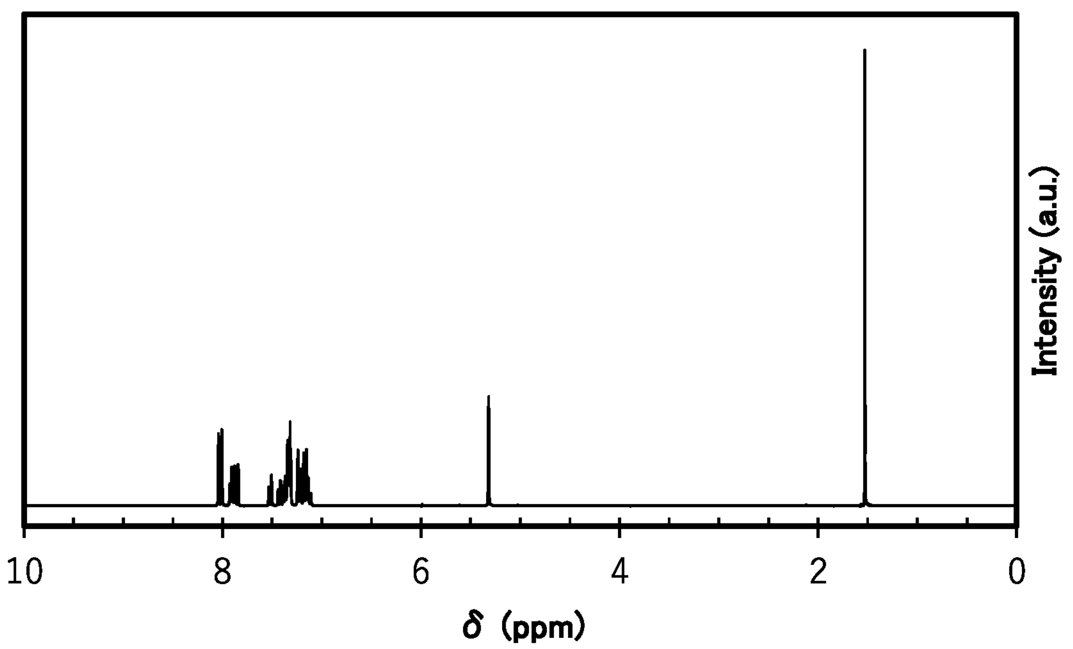
FIG. 20A and FIG. 20B are diagrams showing $^1$H NMR spectra of FrA2Dfbf-02.
Figure 20B:
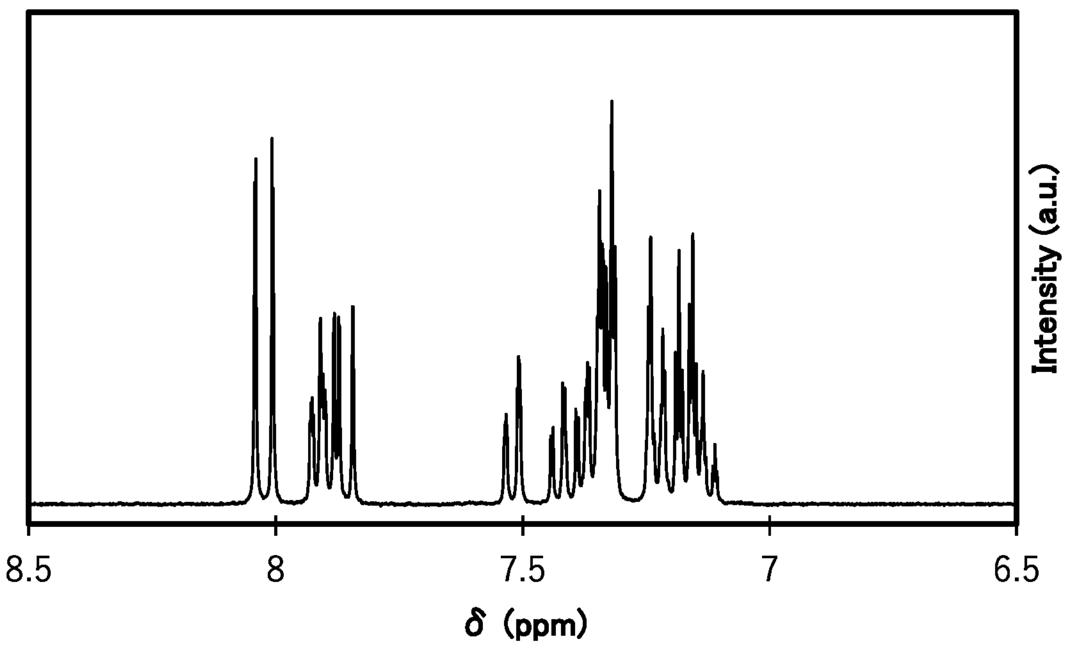

FIG. 20A and FIG. 20B are diagrams illustrating $^1$H NMR spectra of FrA2Dfbf-02.

<Measurement Apparatus and Method for Manufacturing Measurement Sample>

The absorption spectrum of the toluene solution was measured with an ultraviolet and visible spectrophotometer (V550, manufactured by JASCO Corporation), and the absorption spectrum derived from toluene was subtracted.

For the absorption spectrum of the sample in the solid thin film form, a spectrophotometer (U4100 Spectrophotometer, manufactured by Hitachi High-Technologies Corporation) was used.

The emission spectra were measured using a fluorescence spectrophotometer (FS920, manufactured by Hamamatsu Photonics K.K.), and the quantum yield was measured using an absolute PL quantum yields measurement system (Quantaurus-QY, manufactured by Hamamatsu Photonics K.K.).

Note that the solid sample in the thin film form was formed over a quartz substrate by a vacuum evaporation method.

<Physical Properties>

The absorption spectrum of the toluene solution containing FrA2Dfbf-02 had peaks at 426 nm, 405 nm, 350 nm, 327 nm, and 280 nm (see FIG. 18). The emission spectrum thereof had peaks at 440 nm and 468 nm, and the intensity at 468 nm was lower than or equal to half the intensity at 440 nm. The half width was 22 nm. Note that light with a wavelength of 400 nm was used as excitation light. The quantum yield in the toluene solution was 93%.

The absorption spectrum of the solid thin film of FrA2Dfbf-02 had peaks at 431 nm, 410 nm, 356 nm, 332 nm, and 296 nm (see FIG. 19). The emission spectrum thereof had peaks at 460 nm and 501 nm. Note that light with a wavelength of 400 nm was used as excitation light.

It was thus found that FrA2Dfbf-02 emits blue light. Moreover, FrA2Dfbf-02 was found to be usable as a light-emitting material or a host material for a fluorescent material in the visible region. Furthermore, FrA2Dfbf-02 was found to have an extremely high quantum yield and a half width of an emission spectrum of less than or equal to 30 nm and to be suitable as a light-emitting material.

<Synthesis Method>

A method for synthesizing FrA2Dfbf-02 is described. Synthesis Scheme (SC4) is shown below.

[Chemical Formula 47]

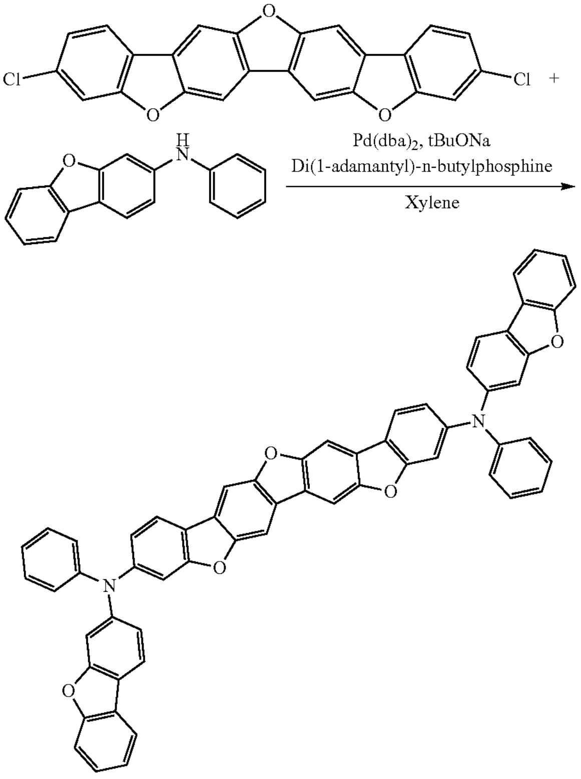

(SC4)

Into a 200-mL three-necked flask were put 0.97 g (2.3 mmol) of 3,10-dichlorodibenzo[b,b']furo[2,3-f;5,4-f]bisbenzofuran, 1.5 g (5.8 mmol) of N-phenyldibenzofuran-3-amine, 83 mg (0.23 mmol) of di(1-adamantyl)-n-butylphosphine, and 1.3 g (14 mmol) of sodium tert-butoxide. To this mixture was added 25 mL of xylene. This mixture was degassed by being stirred while the pressure was reduced. To this mixture was added 27 mg (46 μmol) of bis(dibenzylideneacetone)palladium(0), and the mixture was stirred under a nitrogen stream at 150° C. for 20.5 hours.

After the stirring, toluene was added to this mixture, which was then subjected to suction filtration through Florisil, Celite, and alumina, and the filtrate was concentrated to give a solid.

The obtained solid was purified by silica gel column chromatography (developing solvent: toluene:hexane=2:3), so that a solid was obtained. Furthermore, the obtained solid was recrystallized with toluene, so that 1.2 g of a yellow solid was obtained in a yield of 59%.

By a train sublimation method, 1.2 g of the yellow solid was sublimated and purified. The heating was performed at 385° C. under the conditions where the pressure was 2.6× $10^{-2}$ Pa and the flow rate of argon was 0 mL/min. After the sublimation purification, 0.95 g of a yellow solid was obtained at a collection rate of 83%.

[$^1$H NMR]

FIG. 20A and FIG. 20B show the $^1$H NMR spectra of a dichloromethane solution of the obtained yellow solid. In addition, numerical data is shown below. This indicated that FrA2Dfbf-02 was obtained in this synthesis example.

$^1$H NMR ($CD_2Cl_2$, 300 MHz): δ=7.11-7.19 (m, 6H), 7.21-7.25 (m, 4H), 7.31-7.44 (m, 12H), 7.51-7.54 (m, 2H), 7.84-7.93 (m, 6H), 8.01 (d, $J_1$=0.6 Hz, 2H), 8.04 (d, $J_1$=0.6 Hz, 2H).

Synthesis Example 3

In this example, the physical properties of the organic compound of one embodiment of the present invention and a method for synthesizing the organic compound will be described with reference to FIG. 21 to FIG. 23. Specifically, the characteristics and synthesis method of N,N-bis(dibenzofuran-3-yl)-N,N-di(4-tert-butylphenyl)dibenzo[b,b']furo[2,3-f;5,4-f]bisbenzofuran-3,10-diamine (abbreviation: tBuFrA2Dfbf-02) represented by Structural Formula (114) in Embodiment 1 are described. The structural formula of tBuFrA2Dfbf-02 is shown below.

[Chemical Formula 48]

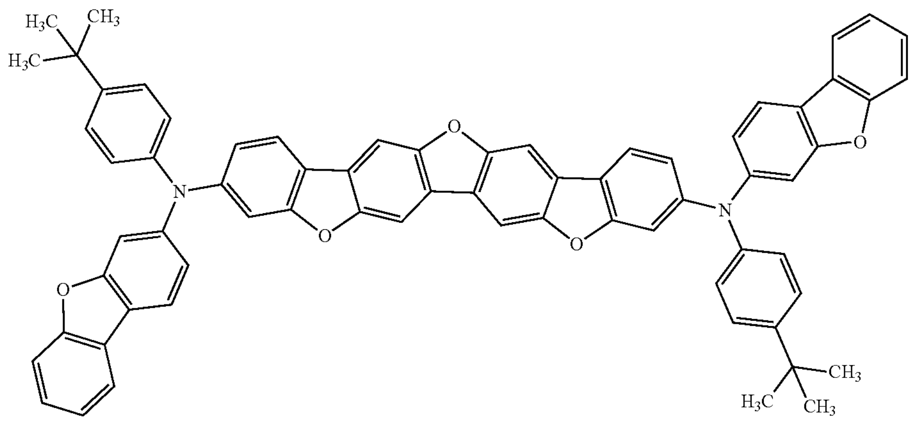

tBuFrA2Dfbf-02

Figure 21:
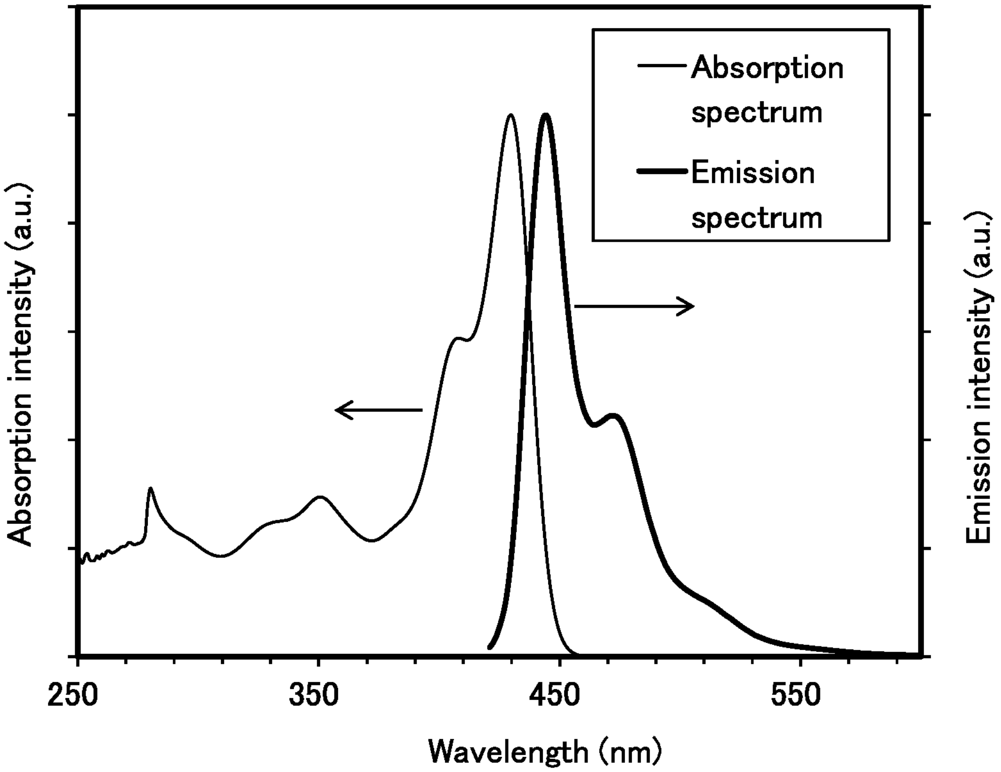
FIG. 21 is a diagram showing an absorption spectrum and an emission spectrum of tBuFrA2Dfbf-02 in a toluene solution.

FIG. 21 is a diagram illustrating an absorption spectrum and an emission spectrum of a toluene solution containing tBuFrA2Dfbf-02.

Figure 22:
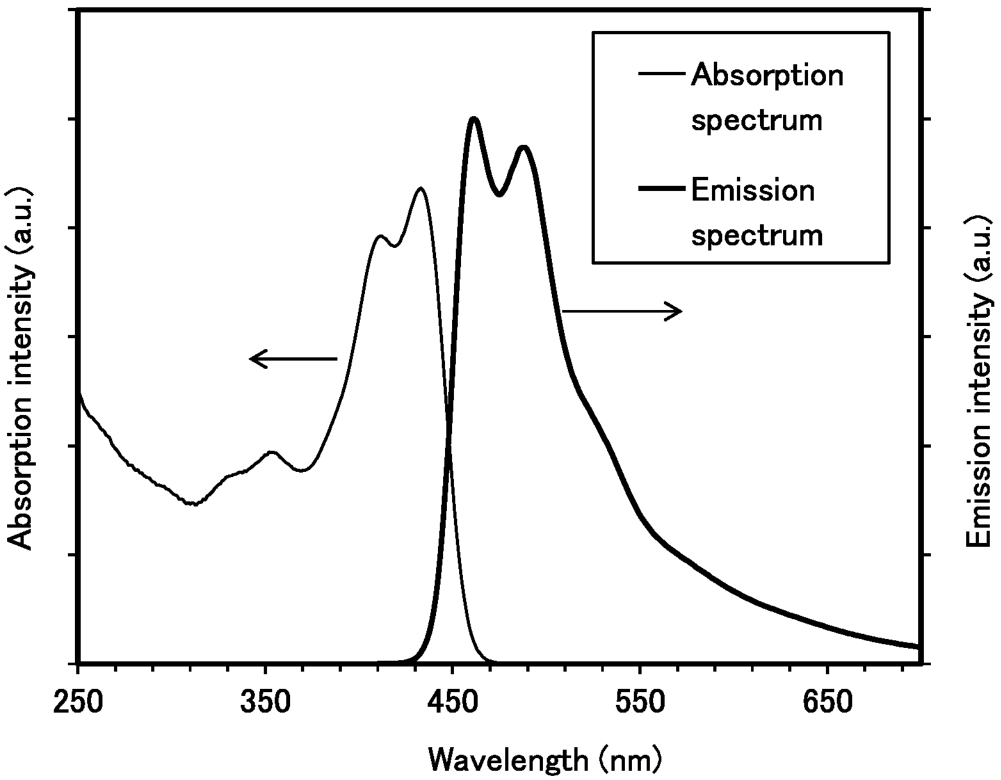
FIG. 22 is a diagram showing an absorption spectrum and an emission spectrum of tBuFrA2Dfbf-02 in a thin film state.

FIG. 22 is a diagram illustrating an absorption spectrum and an emission spectrum of tBuFrA2Dfbf-02 in a solid thin film form.

Figure 23A:
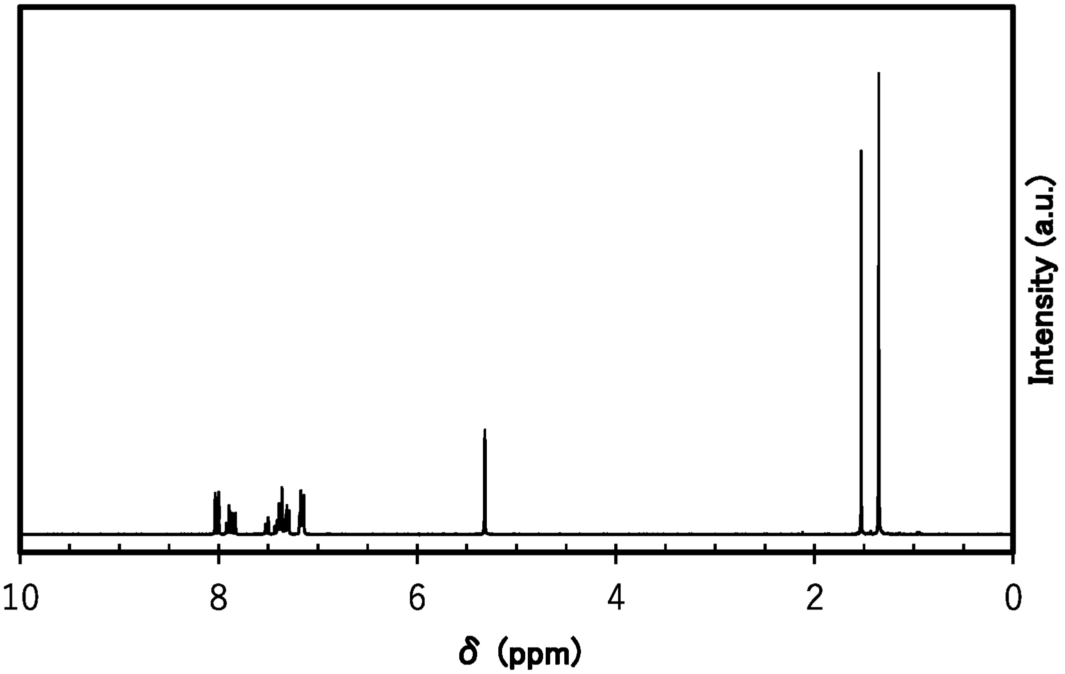
FIG. 23A and FIG. 23B are diagrams showing $^1$H NMR spectra of tBuFrA2Dfbf-02.
Figure 23B:
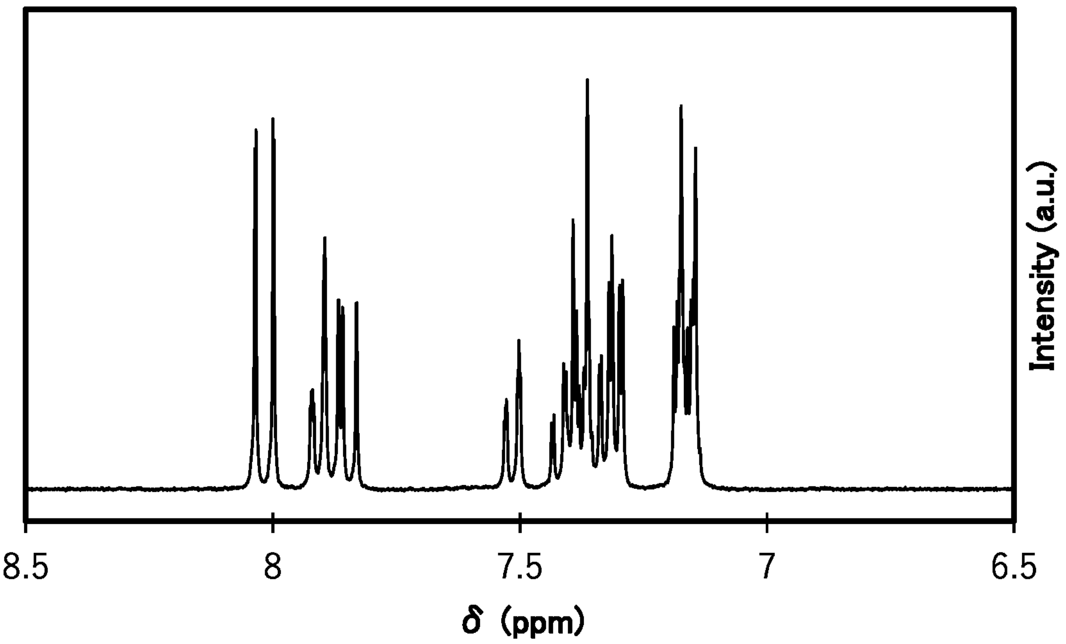

FIG. 23A and FIG. 23B are diagrams illustrating $^1H$ NMR spectra of tBuFrA2Dfbf-02.

<Measurement Apparatus and Method for Manufacturing Measurement Sample>

The absorption spectrum of the toluene solution was measured with an ultraviolet and visible spectrophotometer (V550, manufactured by JASCO Corporation), and the absorption spectrum derived from toluene was subtracted.

For the absorption spectrum of the sample in the solid thin film form, a spectrophotometer (U4100 Spectrophotometer, manufactured by Hitachi High-Technologies Corporation) was used.

The emission spectra were measured using a fluorescence spectrophotometer (FP-8600, manufactured by JASCO Corporation), and the quantum yield was measured using an absolute PL quantum yields measurement system (Quantaurus-QY, manufactured by Hamamatsu Photonics K.K.).

Note that the solid sample in the thin film form was formed over a quartz substrate by a vacuum evaporation method.

<Physical Properties>

The absorption spectrum of the toluene solution containing tBuFrA2Dfbf-02 had peaks at 430 nm, 408 nm, 351 nm, and 329 nm (see FIG. 21). The emission spectrum thereof had peaks at 444 nm and 472 nm, and the intensity at 472 nm was lower than or equal to half the intensity at 444 nm. The half width was 23 nm. Note that light with a wavelength of 406 nm was used as excitation light. The quantum yield in the toluene solution was 92%.

The molar absorption coefficient of the solution of tBuFrA2Dfbf-02 was $1.4\times10^5$ ($M^{-1}$ $cm^{-1}$) at 426 nm. It was thus found that the organic compound of one embodiment of the present invention exhibits an extremely high molar absorption coefficient.

The absorption spectrum of the solid thin film of tBuFrA2Dfbf-02 had peaks at 434 nm, 412 nm, 356 nm, and 333 nm (see FIG. 22). The emission spectrum thereof had peaks at 461 nm, 489 nm, and 530 nm. Note that light with a wavelength of 400 nm was used as excitation light.

It was thus found that tBuFrA2Dfbf-02 emits blue light. Moreover, tBuFrA2Dfbf-02 was found to be usable as a light-emitting material or a host material for a fluorescent material in the visible region. Furthermore, tBuFrA2Dfbf-02 was found to have an extremely high quantum yield and a half width of an emission spectrum of less than or equal to 30 nm and to be suitable as a light-emitting material.

<Synthesis Method>

A method for synthesizing tBuFrA2Dfbf-02 is described. Synthesis Scheme (SC5) is shown below.

[Chemical Formula 49]

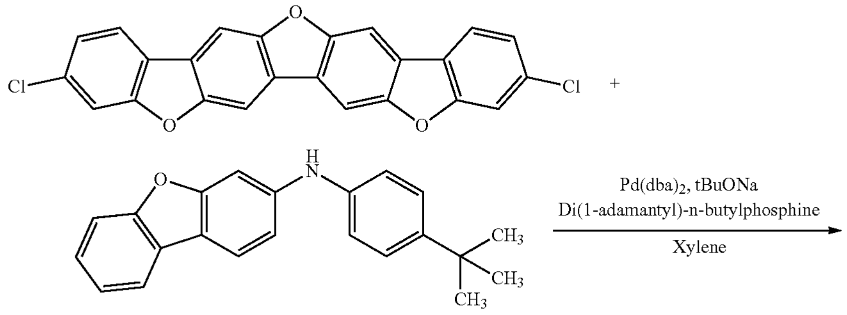

-continued

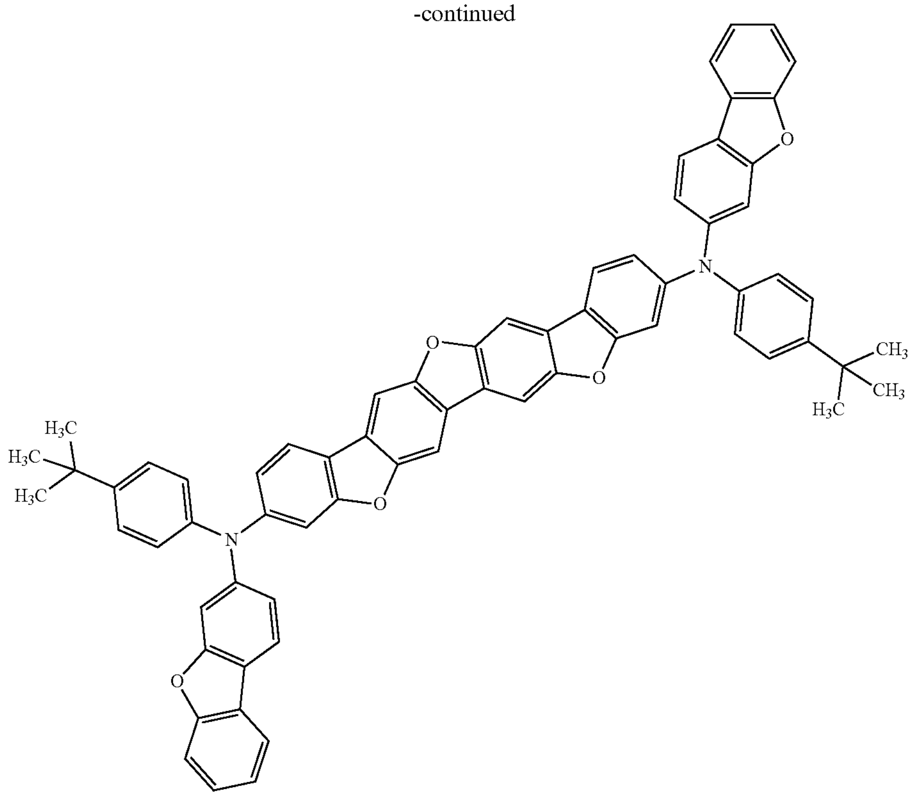

(SC5)

Into a 200-mL three-necked flask were put 0.86 g (2.1 mmol) of 3,10-dichlorodibenzo[b,b']furo[2,3-f;5,4-f]bisbenzofuran, 1.6 g (5.1 mmol) of N-(4-tert-butylphenyl)dibenzofuran-3-amine, 74 mg (0.21 mmol) of di(1-adamantyl)-n-butylphosphine, and 1.2 g (12 mmol) of sodium tert-butoxide. To this mixture was added 20 mL of xylene. This mixture was degassed by being stirred while the pressure was reduced. To this mixture was added 24 mg (41 μmol) of bis(dibenzylideneacetone)palladium(0), and the mixture was stirred under a nitrogen stream at 150° C. for 29 hours.

After the stirring, water and ethanol were added to the mixture, and irradiation with ultrasonic waves was performed; then, the mixture was subjected to suction filtration, the filtrate was concentrated, and a solid was collected. The obtained solid was purified by silica gel column chromatography (developing solvent: toluene:hexane=3:7), so that a solid was obtained. Furthermore, the obtained solid was recrystallized with toluene twice, so that 1.5 g of a yellow solid was obtained in a yield of 74%.

By a train sublimation method, 1.1 g of the yellow solid was sublimated and purified. The heating was performed at 385° C. under the conditions where the pressure was 2.5× $10^{-2}$ Pa and the flow rate of argon was 0 mL/min. After the sublimation purification, 0.91 g of a yellow solid was obtained at a collection rate of 85%.

[$^1$H NMR]

FIG. 23A and FIG. 23B show the $^1$H NMR spectra of a dichloromethane solution of the obtained yellow solid. In addition, numerical data is shown below. This indicated that tBuFrA2Dfbf-02 was obtained in this synthesis example.

$^1$H NMR ($CD_2Cl_2$, 300 MHz): δ=1.35 (s, 18H), 7.14-7.19 (m, 8H), 7.29-7.44 (m, 12H), 7.45-7.53 (m, 2H), 7.83-7.92 (m, 6H), 8.00 (d, $J_1$=0.9 Hz, 2H), 8.04 (d, $J_1$=0.6 Hz, 2H).

Example 2

In this example, the structures, fabrication methods, and characteristics of a light-emitting device 1 to a light-emitting device 3 of embodiments of the present invention are described with reference to FIG. 24, FIG. 25 to FIG. 31, and FIG. 45 to FIG. 50.

Figure 24:
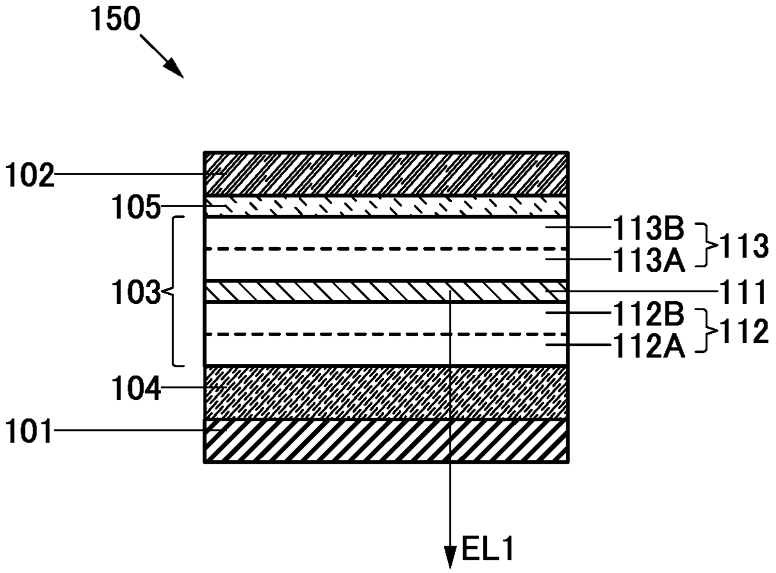
FIG. 24 is a diagram illustrating a structure of a light-emitting device of an example.

FIG. 24 is a cross-sectional view illustrating the structure of the fabricated light-emitting devices.

Figure 25:
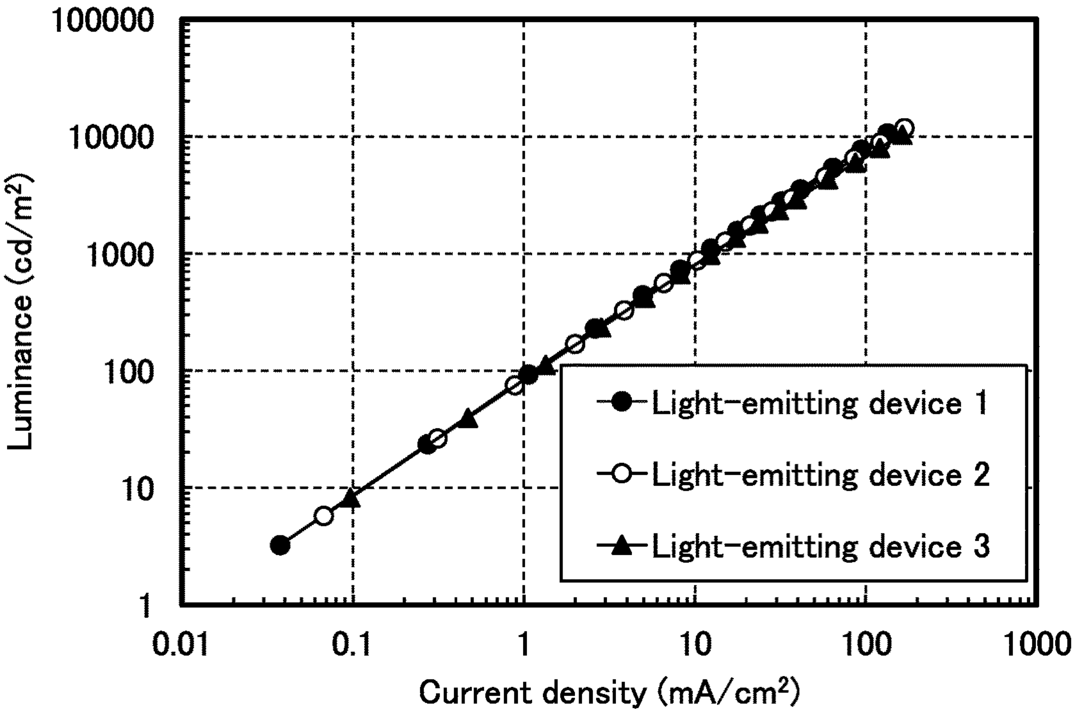
FIG. 25 is a diagram illustrating current density-luminance characteristics of light-emitting devices of an example.

FIG. 25 is a diagram illustrating the current density-luminance characteristics of the light-emitting device 1 to the light-emitting device 3.

Figure 26:
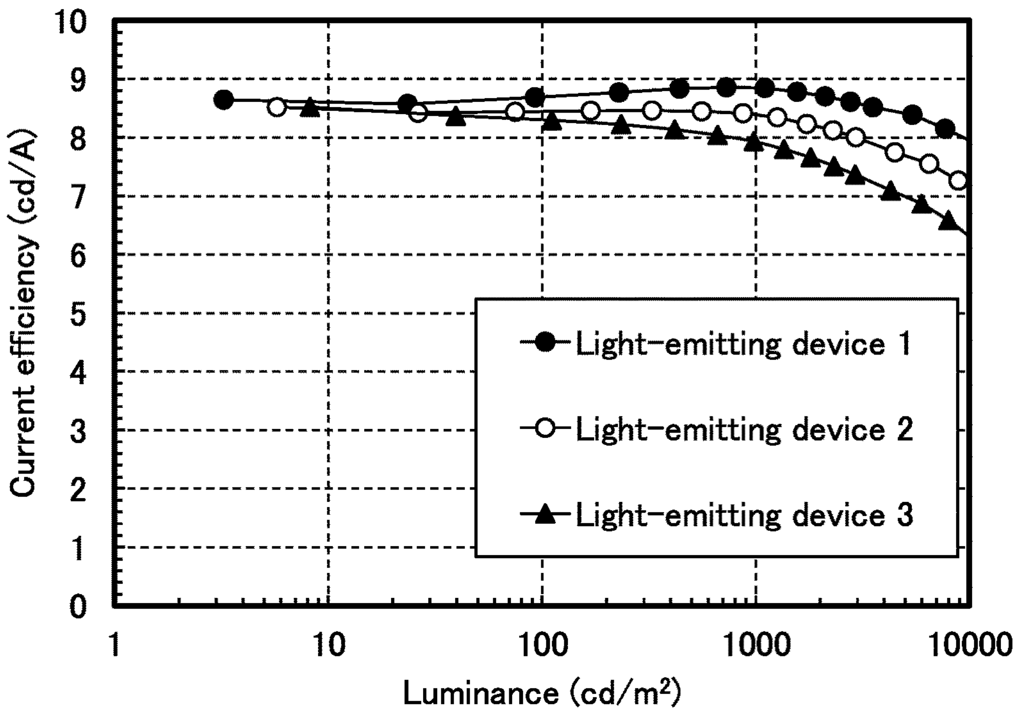
FIG. 26 is a diagram illustrating luminance-current efficiency characteristics of light-emitting devices of an example.

FIG. 26 is a diagram illustrating the luminance-current efficiency characteristics of the light-emitting device 1 to the light-emitting device 3.

Figure 27:
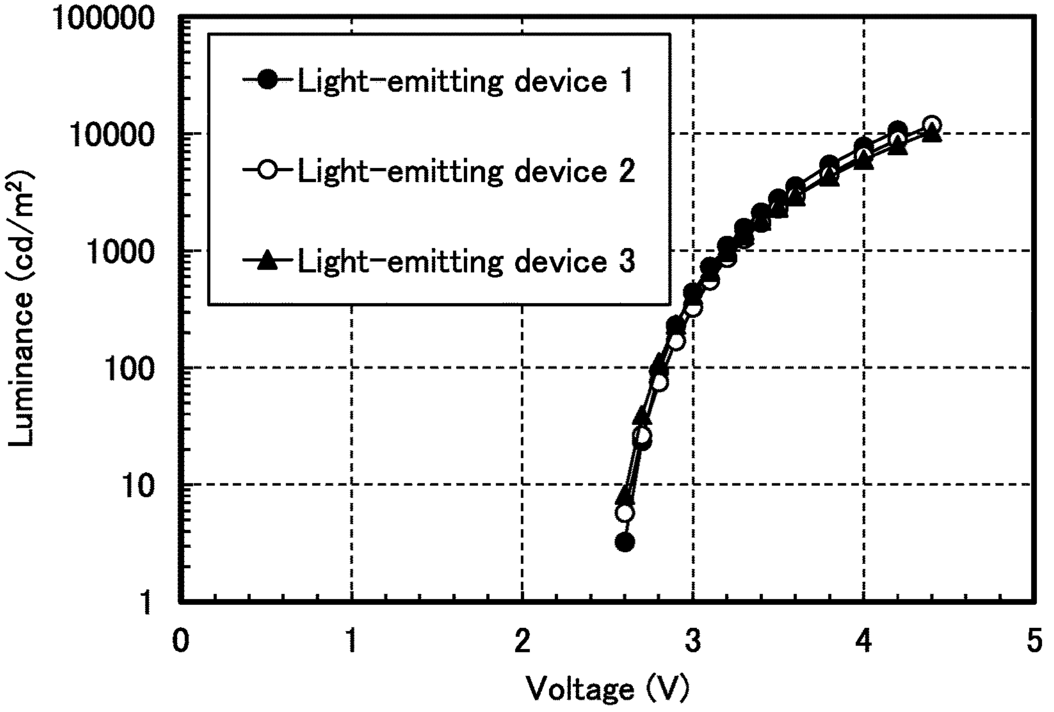
FIG. 27 is a diagram illustrating voltage-luminance characteristics of light-emitting devices of an example.

FIG. 27 is a diagram illustrating the voltage-luminance characteristics of the light-emitting device 1 to the light-emitting device 3.

Figure 28:
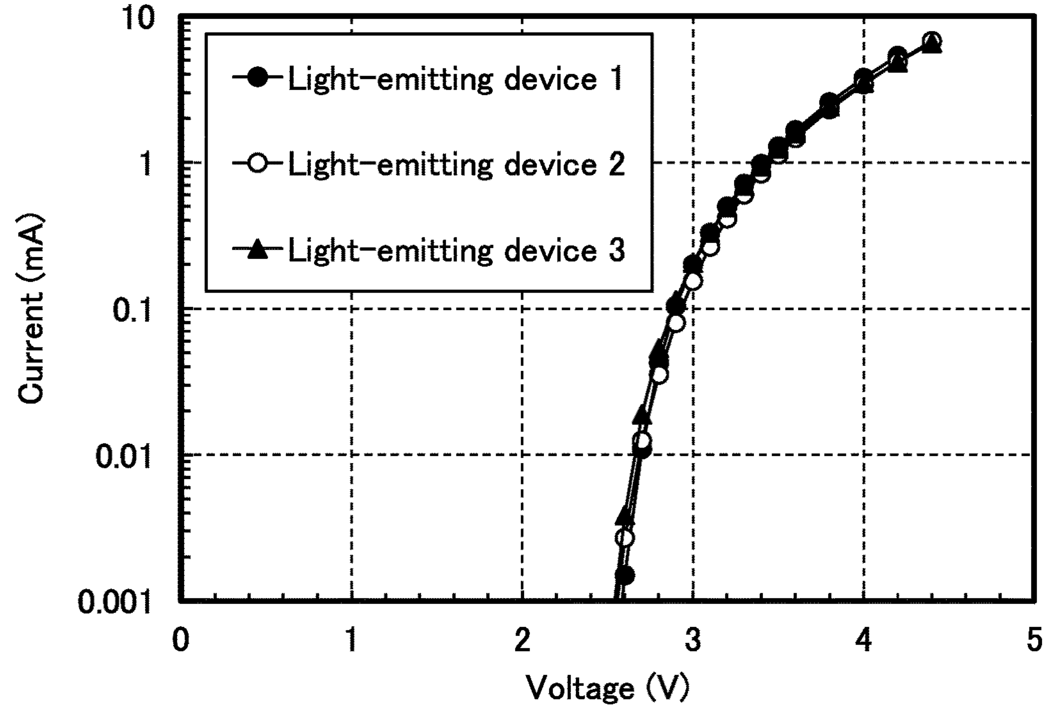
FIG. 28 is a diagram illustrating voltage-current characteristics of light-emitting devices of an example.

FIG. 28 is a diagram illustrating the voltage-current characteristics of the light-emitting device 1 to the light-emitting device 3.

Figure 29:
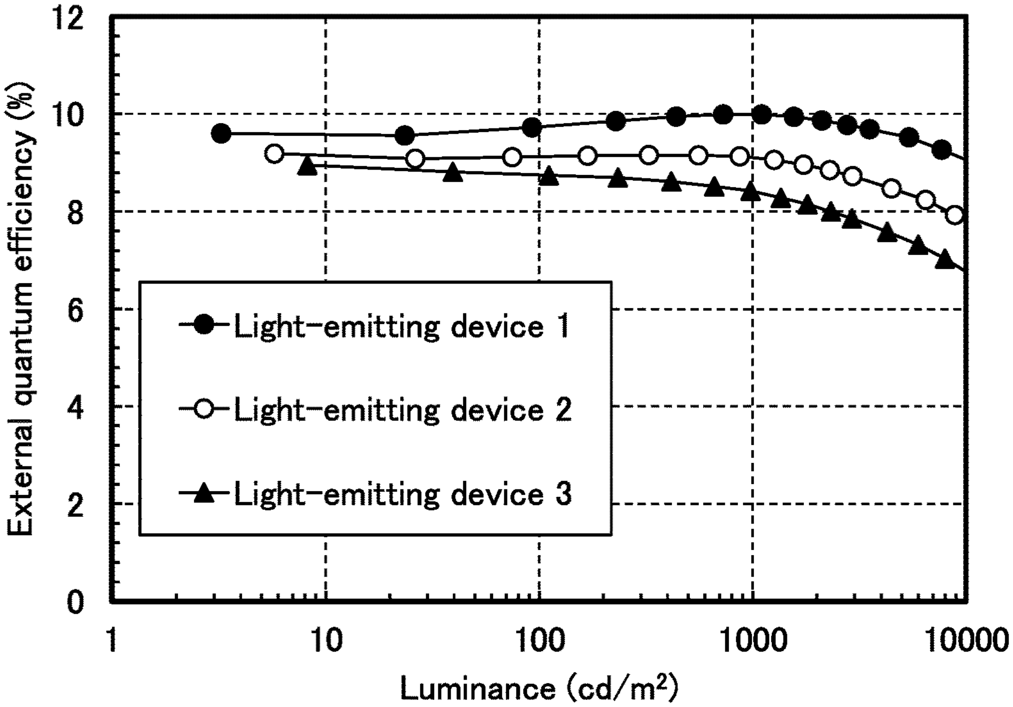
FIG. 29 is a diagram illustrating luminance-external quantum efficiency characteristics of light-emitting devices of an example.

FIG. 29 is a diagram illustrating the luminance-external quantum efficiency characteristics of the light-emitting device 1 to the light-emitting device 3. Note that the external quantum efficiency was calculated from an emission spectrum and luminance in frontal observation assuming that the light distribution characteristics of the light-emitting device are of a Lambertian type.

Figure 30:
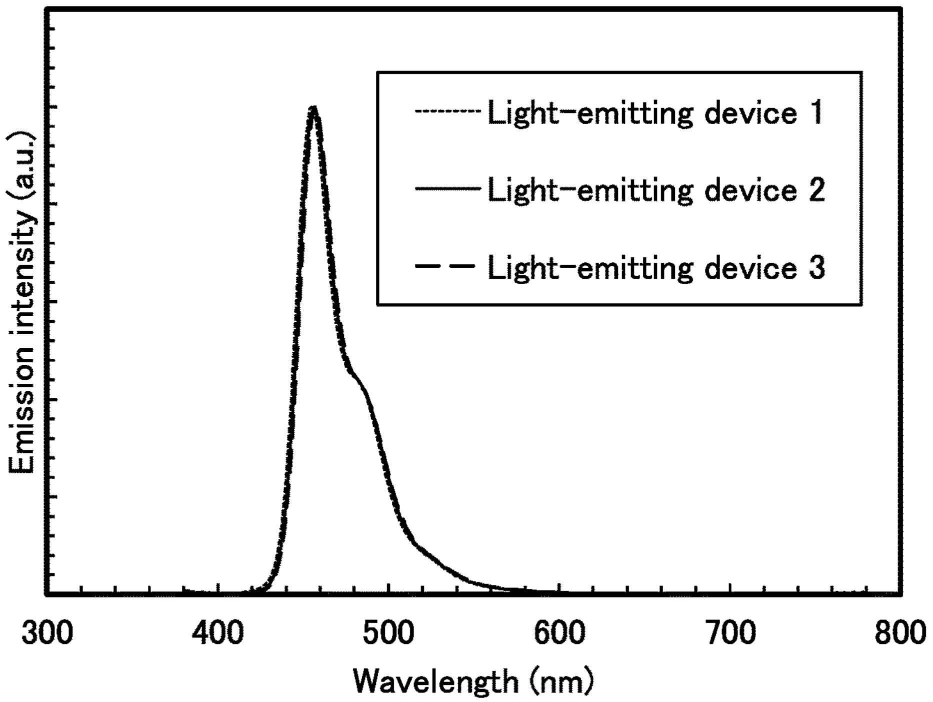
FIG. 30 is a diagram illustrating emission spectra of light-emitting devices of an example.

FIG. 30 is a diagram illustrating emission spectra of the light-emitting device 1 to the light-emitting element 3 emitting light at a luminance of 1000 cd/$m^2$.

Figure 31:
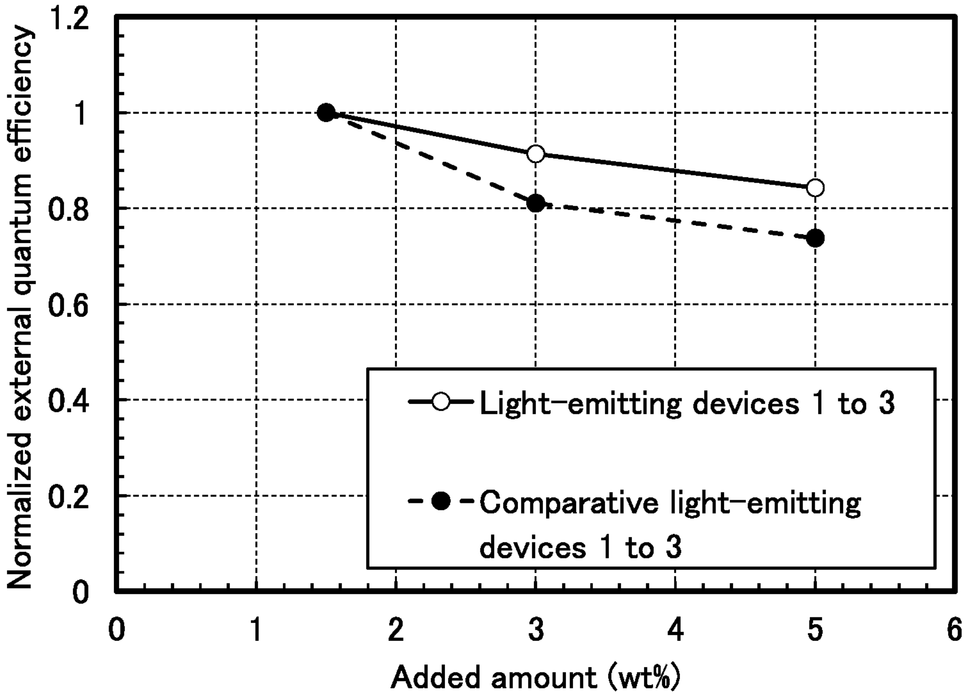
FIG. 31 is a diagram illustrating characteristics of light-emitting devices of an example.

FIG. 31 is a diagram illustrating the difference in external quantum efficiency when the light-emitting device 1 to the light-emitting device 3 emitted light at a luminance of 1000 cd/m$^2$. Specifically, with the external quantum efficiency of the light-emitting device in which the light-emitting material EM was added at 1.5 wt % being 1, the external quantum efficiency of the light-emitting device in which the light-emitting material EM was added at 3 wt % and the external quantum efficiency of the light-emitting device in which the light-emitting material EM was added at 5 wt % are compared in the diagram.

Figure 45:
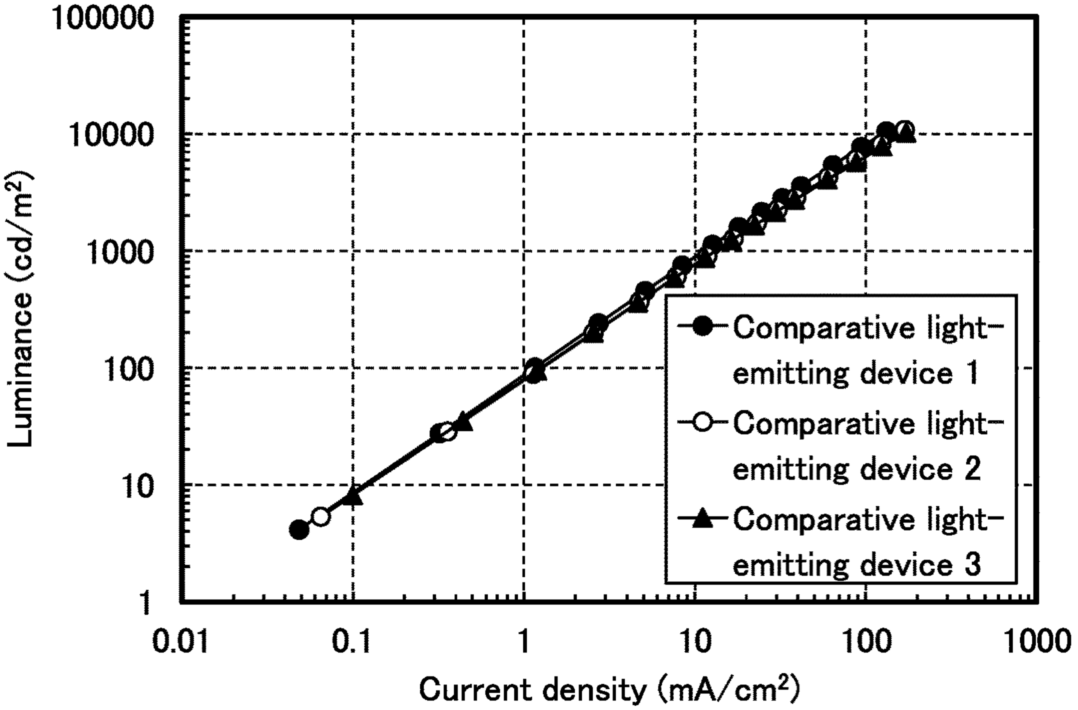
FIG. 45 is a diagram illustrating current density-luminance characteristics of light-emitting devices of an example.

FIG. 45 is a diagram illustrating the current density-luminance characteristics of a comparative light-emitting device 1 to a comparative light-emitting device 3.

Figure 46:
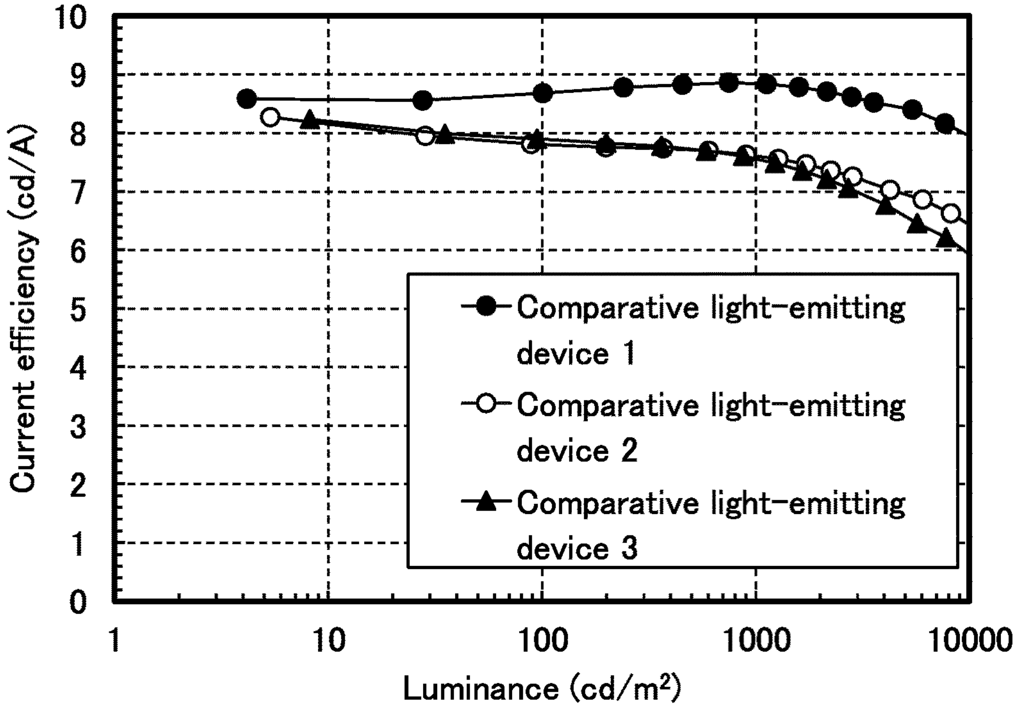
FIG. 46 is a diagram illustrating luminance-current efficiency characteristics of light-emitting devices of an example.

FIG. 46 is a diagram illustrating the luminance-current efficiency characteristics of the comparative light-emitting device 1 to the comparative light-emitting device 3.

Figure 47:
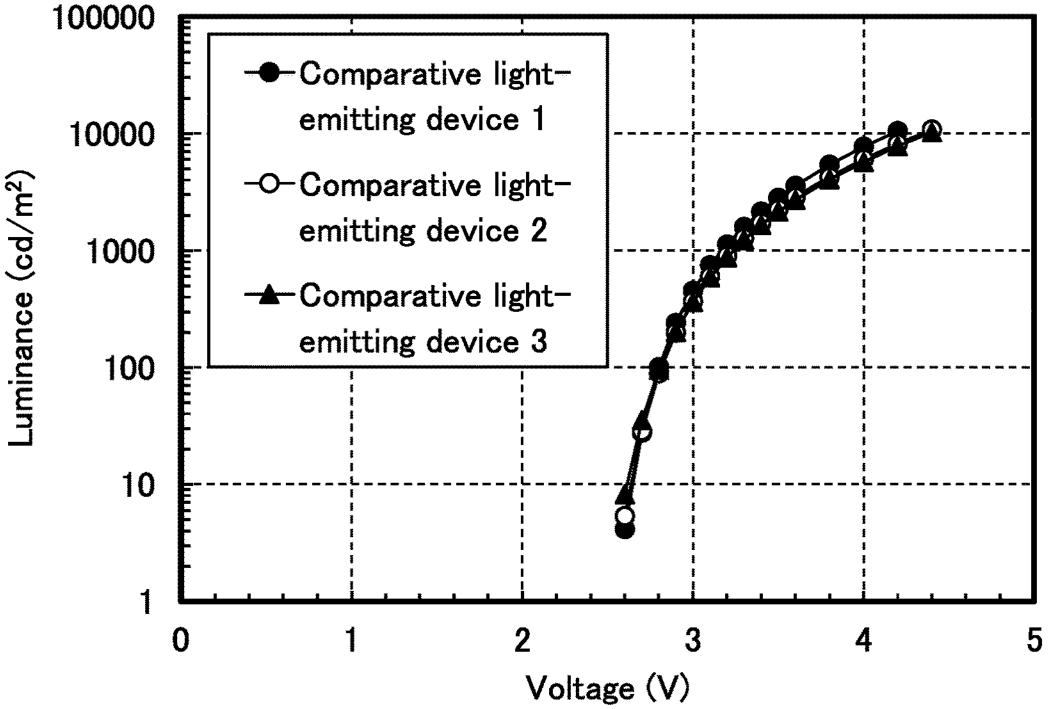
FIG. 47 is a diagram illustrating voltage-luminance characteristics of light-emitting devices of an example.

FIG. 47 is a diagram illustrating the voltage-luminance characteristics of the comparative light-emitting device 1 to the comparative light-emitting device 3.

Figure 48:
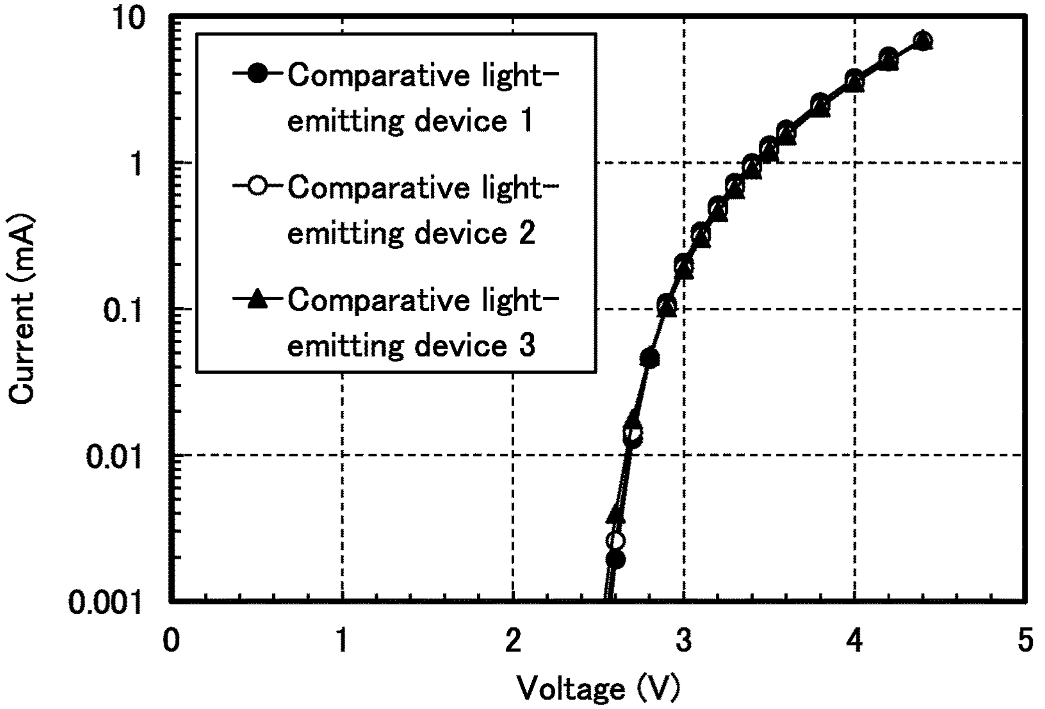
FIG. 48 is a diagram illustrating voltage-current characteristics of light-emitting devices of an example.

FIG. 48 is a diagram illustrating the voltage-current characteristics of the comparative light-emitting device 1 to the comparative light-emitting device 3.

Figure 49:
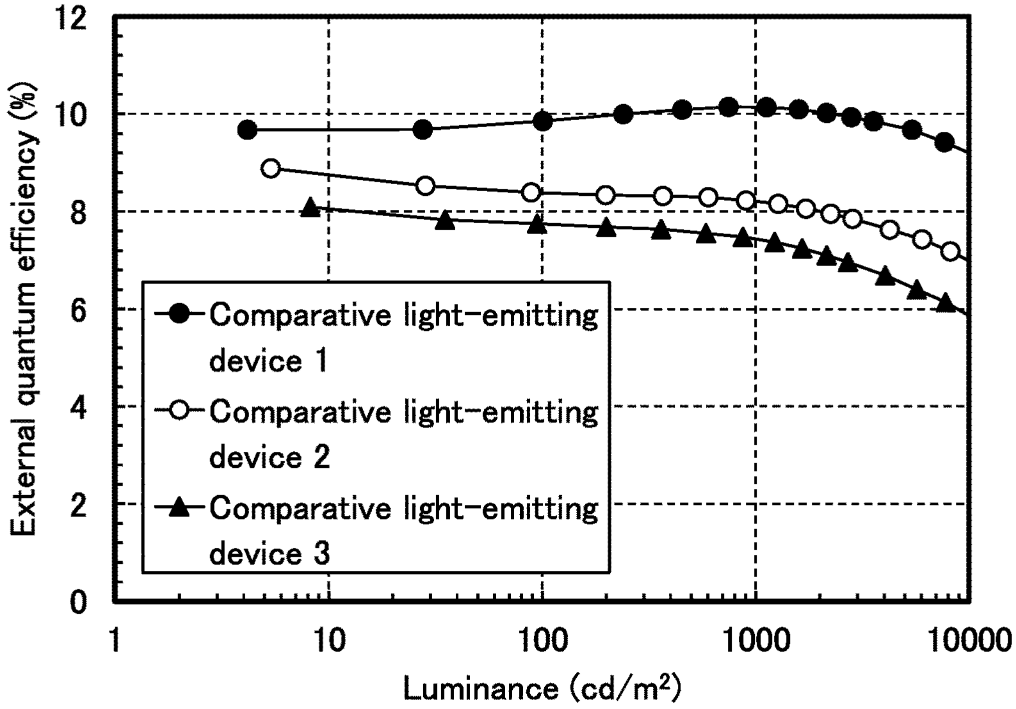
FIG. 49 is a diagram illustrating luminance-external quantum efficiency characteristics of light-emitting devices of an example.

FIG. 49 is a diagram illustrating the luminance-external quantum efficiency characteristics of the comparative light-emitting device 1 to the comparative light-emitting device 3. Note that the external quantum efficiency was calculated from an emission spectrum and luminance in frontal observation assuming that the light distribution characteristics of the light-emitting device are of a Lambertian type.

Figure 50:
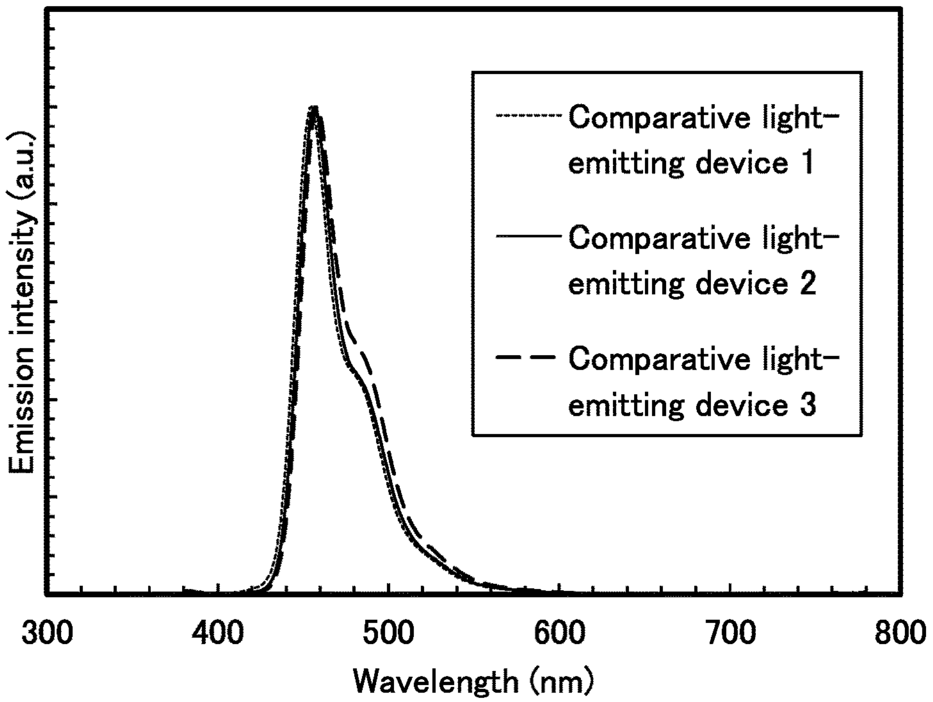
FIG. 50 is a diagram illustrating emission spectra of light-emitting devices of an example.

FIG. 50 is a diagram illustrating emission spectra of the comparative light-emitting device 1 to the comparative light-emitting element 3 emitting light at a luminance of 1000 cd/m$^2$.

<Light-Emitting Device 1 to Light-Emitting Device 3>

The fabricated light-emitting device 1 to light-emitting device 3, which are described in this example, have a structure similar to that of the light-emitting device 150 (see FIG. 24). The light-emitting device 150 includes the electrode 101, the electrode 102, the unit 103, and the layer 104, and the electrode 102 includes a region overlapping with the electrode 101. The light-emitting device 150 includes the layer 105.

The unit 103 includes a region positioned between the electrode 101 and the electrode 102, and the unit 103 includes the layer 111, the layer 112, and the layer 113.

The layer 112 includes a region positioned between the electrode 101 and the layer 111, and the layer 113 includes a region positioned between the layer 111 and the electrode 102.

The layer 111 contains the light-emitting material EM. Note that tBuFrA2Dfbf-02 was used as the light-emitting material EM in the light-emitting device 1 to the light-emitting device 3.

The layer 104 contains the material AM having an acceptor property and the material HT1. The material HT1 has the first HOMO level HOMO1, and the first HOMO level HOMO1 is higher than or equal to −5.7 eV and lower than or equal to −5.4 eV. Note that oFBiSF was used as the material HT1 in the light-emitting device 1 to the light-emitting device 3. The HOMO level of oFBiSF was −5.5 eV in cyclic voltammetry (CV) measurement.

The layer 113 contains the material OMC, and the material OMC is an organometallic complex of an alkali metal or an organometallic complex of an alkaline earth metal. Note that Liq was used as the material OMC in the light-emitting device 1 to the light-emitting device 3.

The layer 112 includes the region 112A and the region 112B. The region 112B includes a region positioned between the layer 111 and the region 112A, and the region 112B contains the material HT2. The material HT2 has the second HOMO level HOMO2, and the second HOMO level HOMO2 differs by −0.2 eV to 0 eV inclusive from the first HOMO level HOMO1. Note that BBABnf was used as the material HT2 in the light-emitting device 1 to the light-emitting device 3. The HOMO level of BBABnf was −5.56 eV in cyclic voltammetry (CV) measurement.

<<Structure of Light-Emitting Device 1 to Light-Emitting Device 3>>

Table 1 shows the structure of each of the light-emitting device 1 to the light-emitting device 3. The structural formulae of the materials used in the light-emitting devices and the comparative light-emitting devices described in this example are shown below.

TABLE 1

| Component | Reference numeral | Material | Composition ratio | Thickness/nm |
|---|---|---|---|---|
| Electrode | 102 | Al | | 200 |
| Layer | 105 | Liq | | 1 |
| Region | 113B | mPn-mDMePyPTzn:Liq | 1:1 | 15 |
| Region | 113A | 6BP-4Cz2PPm | | 10 |
| Layer | 111 | cgDBCzPA: tBuFrA2Dfbf-02 | 1:X | 25 |
| Region | 112B | BBABnf | | 10 |
| Region | 112A | oFBiSF | | 20 |
| Layer | 104 | oFBiSF:OCHD-001 | 1:0.1 | 10 |
| Electrode | 101 | ITSO | | 70 |

[Chemical Formula 50]

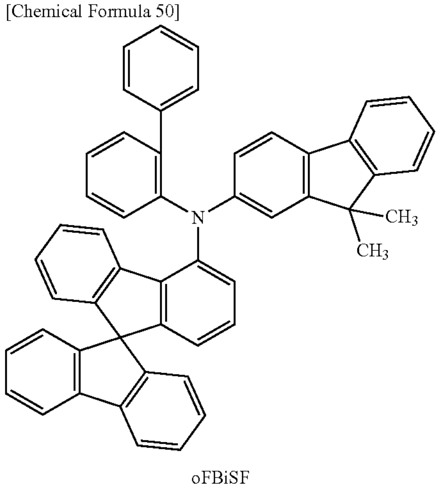

oFBiSF

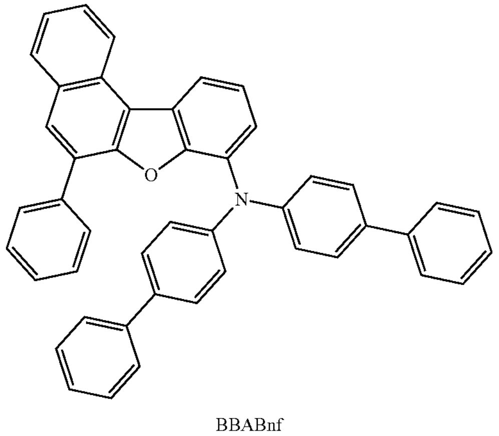

BBABnf

-continued

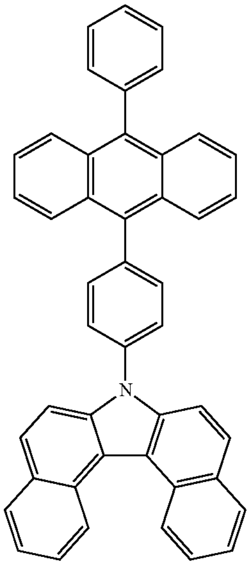

cgDBCzPA

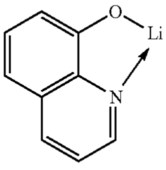

Liq

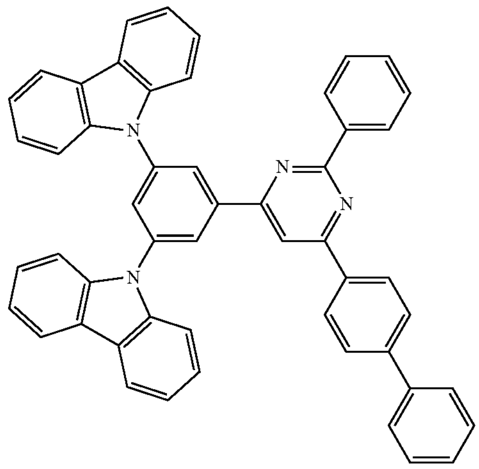

6BP-4Cz2PPm

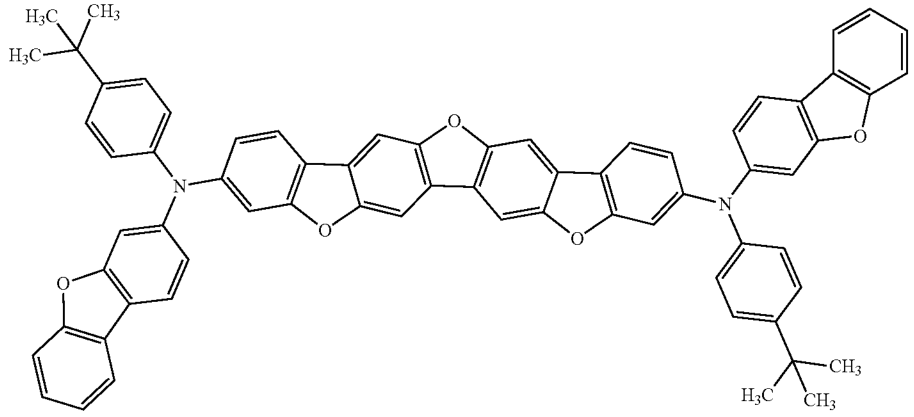

tBuFrA2Dfbf-02

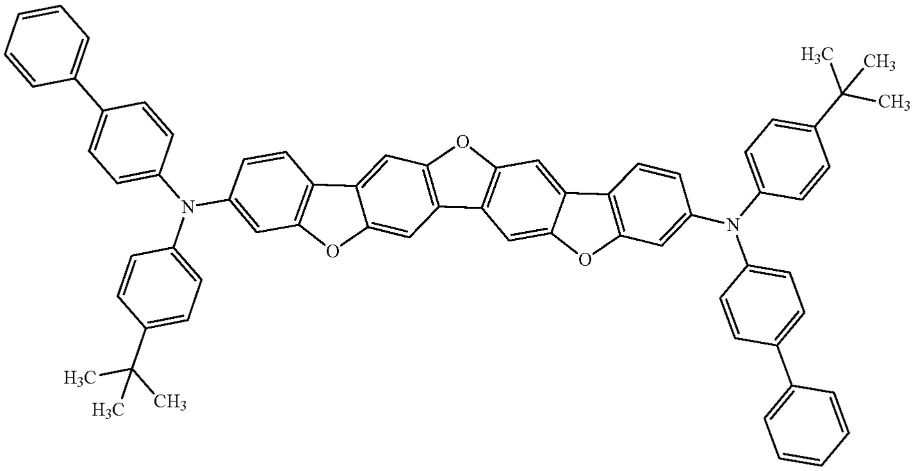

tBuBPA2Dfbf

<<Fabrication Method of Light-Emitting Device 1 to Light-Emitting Device 3>>

The light-emitting device 1 to the light-emitting device 3 described in this example were fabricated using a method including the following steps.

[First Step]

In the first step, the electrode 101 was formed. Specifically, the electrode 101 was formed by a sputtering method using indium oxide-tin oxide containing silicon or silicon oxide (ITSO) as a target.

The electrode 101 contains ITSO and has a thickness of 70 nm and an area of 4 $mm^2$ (2 mm×2 mm).

Next, a base material over which the electrode 101 was formed was washed with water, baked at 200° C. for one hour, and then subjected to UV ozone treatment for 370 seconds. Then, the substrate was transferred into a vacuum evaporation apparatus where the pressure was reduced to approximately $10^{-4}$ Pa, and vacuum baking was performed at 170° C. for 30 minutes in a heating chamber of the vacuum evaporation apparatus. Then, the substrate was cooled down for approximately 30 minutes.

[Second Step]

In the second step, the layer 104 was formed over the electrode 101. Specifically, materials were deposited by co-evaporation using a resistance-heating method.

Note that the layer 104 contains oFBiSF and an electron accepter material (abbreviation: OCHD-001) at oFBiSF: OCHD-001=1:0.1 (weight ratio), and has a thickness of 10 nm. Note that OCHD-001 has an acceptor property.

[Third Step]

In the third step, the region 112A was formed over the layer 104. Specifically, a material was deposited by evaporation using a resistance-heating method.

The region 112A contains oFBiSF and has a thickness of 20 nm.

[Fourth Step]

In the fourth step, the region 112B was formed over the region 112A. Specifically, a material was deposited by evaporation using a resistance-heating method.

The region 112B contains BBABnf and has a thickness of 10 nm.

[Fifth Step]

In the fifth step, the layer 111 was formed over the region 112B. Specifically, materials were deposited by co-evaporation using a resistance-heating method.

Note that the layer 111 contains cgDBCzPA and tBuFrA2Dfbf-02 and has a thickness of 25 nm.

Specifically, the layer 111 in the light-emitting device 1 contains tBuFrA2Dfbf-02 at cgDBCzPA:tBuFrA2Dfbf-02=1:0.015 (weight ratio), the layer 111 in the light-emitting device 2 contains tBuFrA2Dfbf-02 at cgDBCzPA: tBuFrA2Dfbf-02=1:0.03 (weight ratio), and the layer 111 in the light-emitting device 3 contains tBuFrA2Dfbf-02 at cgDBCzPA:tBuFrA2Dfbf-02=1:0.05 (weight ratio).

[Sixth Step]

In the sixth step, the region 113A was formed over the layer 111. Specifically, a material was deposited by evaporation using a resistance-heating method.

The region 113A contains 4-[3,5-bis(9H-carbazol-9-yl) phenyl]-2-phenyl-6-(1,1'-biphenyl-4-yl)pyrimidine (abbreviation: 6BP-4Cz2PPm) and has a thickness of 10 nm.

[Seventh Step]

In the seventh step, the region 113B was formed over the region 113A. Specifically, materials were deposited by co-evaporation using a resistance-heating method.

The region 113B contains 2-[3-(2,6-dimethyl-3-pyridinyl)-5-(9-phenanthrenyl)phenyl]-4,6-diphenyl-1,3,5-triazine (abbreviation: mPn-mDMePyPTzn) and Liq at mPn-mDMePyPTzn:Liq=1:1 (weight ratio) and has a thickness of 15 nm.

[Eighth Step]

In the eighth step, the layer 105 was formed over the region 113B. Specifically, a material was deposited by evaporation using a resistance-heating method.

Note that the layer 105 contains Liq and has a thickness of 1 nm.

[Ninth Step]

In the ninth step, the electrode 102 was formed over the layer 105. Specifically, a material was deposited by evaporation using a resistance-heating method.

The electrode 102 contains Al and has a thickness of 200 nm.

<<Operation Characteristics of Light-Emitting Device 1 to Light-Emitting Device 3>>

When supplied with electric power, the light-emitting device 1 to the light-emitting device 3 emitted the light EL1 (see FIG. 24). The operation characteristics of the light-emitting device 1 to the light-emitting device 3 were measured (see FIG. 25 to FIG. 30). Note that the measurement was performed at room temperature.

Table 2 shows main initial characteristics of the light-emitting device 1 to the light-emitting device 3 emitting light at a luminance of approximately 1000 cd/$m^2$ (initial characteristics of other light-emitting devices are also shown in Table 2, and their structures will be described later).

TABLE 2

| | Voltage (V) | Current (mA) | Current density (mA/cm2) | Chromaticity x | Chromaticity y | Current efficiency (cd/A) | External quantum efficiency (%) |
|---|---|---|---|---|---|---|---|
| Light-emitting device 1 | 3.2 | 0.50 | 12.5 | 0.14 | 0.10 | 8.8 | 10.0 |
| Light-emitting device 2 | 3.2 | 0.41 | 10.3 | 0.14 | 0.10 | 8.4 | 9.1 |
| Light-emitting device 3 | 3.2 | 0.49 | 12.3 | 0.14 | 0.11 | 7.9 | 8.4 |
| Light-emitting device 4 | 4.4 | 0.41 | 10.1 | 0.14 | 0.10 | 10.5 | 11.5 |
| Light-emitting device 5 | 4.4 | 0.47 | 11.7 | 0.14 | 0.08 | 8.1 | 10.6 |
| Light-emitting device 6 | 3.7 | 0.26 | 6.6 | 0.14 | 0.10 | 12.6 | 14.0 |
| Comparative light-emitting device 1 | 3.2 | 0.51 | 12.7 | 0.14 | 0.10 | 8.8 | 10.1 |
| Comparative light-emitting device 2 | 3.2 | 0.47 | 11.8 | 0.14 | 0.11 | 7.6 | 8.2 |
| Comparative light-emitting device 3 | 3.2 | 0.46 | 11.5 | 0.14 | 0.12 | 7.6 | 7.5 |
| Comparative light-emitting device 4 | 4.4 | 0.37 | 9.4 | 0.14 | 0.11 | 10.5 | 10.9 |

The light-emitting device 1 to the light-emitting device 3 were found to have favorable characteristics. For example, each light-emitting device was found to have favorable chromaticity and high external quantum efficiency higher than or equal to 8.4%. In addition, the external quantum efficiency of the light-emitting device 1 to the light-emitting device 3 was found to less change with respect to the added amount of the light-emitting material EM than that of the comparative light-emitting device 1 to the comparative light-emitting device 3. For example, with the external quantum efficiency of the comparative light-emitting device 1 at a luminance of around 1000 cd/$m^2$ being 1, the external quantum efficiency of the comparative light-emitting device 3 decreased to 0.74. By contrast, as for the light-emitting device 1 to the light-emitting device 3, the external quantum efficiency of the light-emitting device 3 was inhibited from decreasing to lower than 0.84, with the external quantum efficiency of the light-emitting device 1 being 1 (see FIG. 31). In this manner, the light-emitting devices had the characteristics unlikely to be affected by a change in production facility. Alternatively, the light-emitting devices had the characteristics unlikely to be affected by a slight difference in the concentration of the added light-emitting material EM. As a result, novel light-emitting devices that are highly convenient, useful, or reliable were successfully provided.

Reference Example 1

Table 3 shows the structure of each of the comparative light-emitting device 1 to the comparative light-emitting device 3.

In each of the fabricated comparative light-emitting device 1 to comparative light-emitting device 3, which are described in this example, the layer 111 contains tBuBPA2Dfbf instead of tBuFrA2Dfbf-02.

TABLE 3

| Component | Reference numeral | Material | Composition ratio | Thickness/nm |
|---|---|---|---|---|
| Electrode | 102 | Al | | 200 |
| Layer | 105 | Liq | | 1 |
| Region | 113B | mPn-mDMePyPTzn:Liq | 1:1 | 15 |
| Region | 113A | 6BP-4Cz2PPm | | 10 |
| Layer | 111 | cgDBCzPA:tBuBP A2Dfbf | 1:X | 25 |
| Region | 112B | BBABnf | | 10 |
| Region | 112A | oFBiSF | | 20 |
| Layer | 104 | oFBiSF:OCHD-001 | 1:0.1 | 10 |
| Electrode | 101 | ITSO | | 70 |

<<Fabrication Method of Comparative Light-Emitting Device 1 to Comparative Light-Emitting Device 3>>

The comparative light-emitting device 1 to the comparative light-emitting device 3 were fabricated using a method including the following steps.

Note that the fabrication method of the comparative light-emitting device 1 to the comparative light-emitting device 3 is different from the fabrication method of the light-emitting device 1 to the light-emitting device 3 in that, in the step of forming the layer 111, tBuBPA2Dfbf is deposited by co-evaporation for the layer 111 instead of tBuFrA2Dfbf-02. Different portions are described in detail here, and the above description is referred to for portions formed using a similar method.

[Fifth Step]

In the fifth step, the layer 111 was formed over the region 112B. Specifically, materials were deposited by co-evaporation using a resistance-heating method.

Note that the layer 111 contains cgDBCzPA and tBuBPA2Dfbf and has a thickness of 25 nm. Specifically, the layer 111 in the comparative light-emitting device 1 contains tBuBPA2Dfbf at cgDBCzPA:tBuBPA2Dfbf=1:0.015 (weight ratio), the layer 111 in the comparative light-emitting device 2 contains tBuBPA2Dfbf at cgDBCzPA:tBuBPA2Dfbf=1:0.03 (weight ratio), and the layer 111 in the comparative light-emitting device 3 contains tBuBPA2Dfbf at cgDBCzPA:tBuBPA2Dfbf=1:0.05 (weight ratio).

<<Operation Characteristics of Comparative Light-Emitting Device 1 to Comparative Light-Emitting Device 3>>

The operation characteristics of the comparative light-emitting device 1 to the comparative light-emitting device 3 were measured. Note that the measurement was performed at room temperature.

Table 2 shows main initial characteristics of the comparative light-emitting device 1 to the comparative light-emitting device 3.

<Method for Calculating HOMO Level and LUMO Level of Material>

The HOMO levels and the LUMO levels of the materials were calculated on the basis of cyclic voltammetry (CV) measurement. The calculation method is shown below.

An electrochemical analyzer (model number: ALS model 600A or 600C, manufactured by BAS Inc.) was used as a measurement apparatus. To prepare a solution for the CV measurement, dehydrated dimethylformamide (DMF) (manufactured by Sigma-Aldrich Inc., 99.8%, catalog No. 22705-6) was used as a solvent, tetra-n-butylammonium perchlorate ($n\text{-}Bu_4NClO_4$) (manufactured by Tokyo Chemical Industry Co., Ltd., catalog No. T0836) as a supporting electrolyte was dissolved at a concentration of 100 mmol/L, and the object to be measured was dissolved at a concentration of 2 mmol/L.

A platinum electrode (PTE platinum electrode, manufactured by BAS Inc.) was used as a working electrode, another platinum electrode (Pt counter electrode for VC-3 (5 cm), manufactured by BAS Inc.) was used as an auxiliary electrode, and an $Ag/Ag^+$ electrode (RE7 reference electrode for non-aqueous solvent, manufactured by BAS Inc.) was used as a reference electrode. Note that the measurement was performed at room temperature (20 to 25° C.).

The scan speed in the CV measurement was fixed to 0.1 V/sec, and an oxidation potential Ea [V] and a reduction potential Ec [V] with respect to the reference electrode were measured. Ea was an intermediate potential of an oxidation-reduction wave, and Ec was an intermediate potential of a reduction-oxidation wave. Here, since the potential energy of the reference electrode used in this example with respect to the vacuum level is known to be −4.94 [eV], the HOMO level and the LUMO level can be calculated by the following formulae: HOMO level [eV]=−4.94−Ea and LUMO level [eV]−4.94−Ec.

Example 3

In this example, the structure, fabrication method, and characteristics of a light-emitting device 4 of one embodiment of the present invention are described with reference to FIG. 24 and FIG. 32 to FIG. 38.

Figure 32:
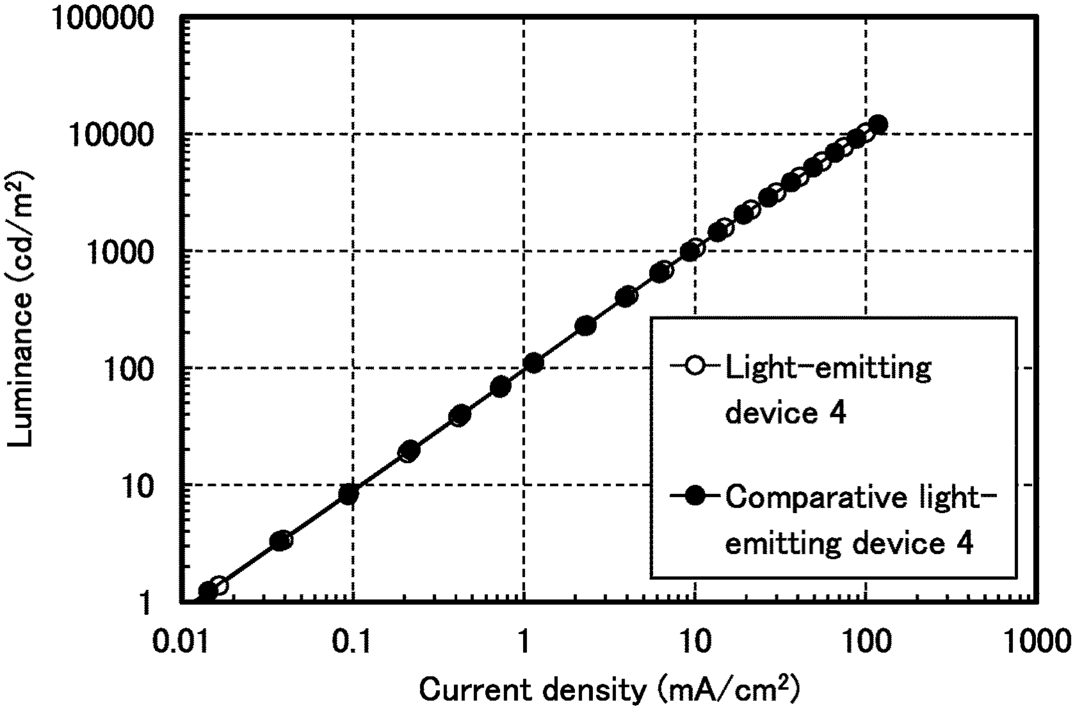
FIG. 32 is a diagram illustrating current density-luminance characteristics of light-emitting devices of an example.

FIG. 32 is a diagram illustrating the current density-luminance characteristics of the light-emitting device 4.

Figure 33:
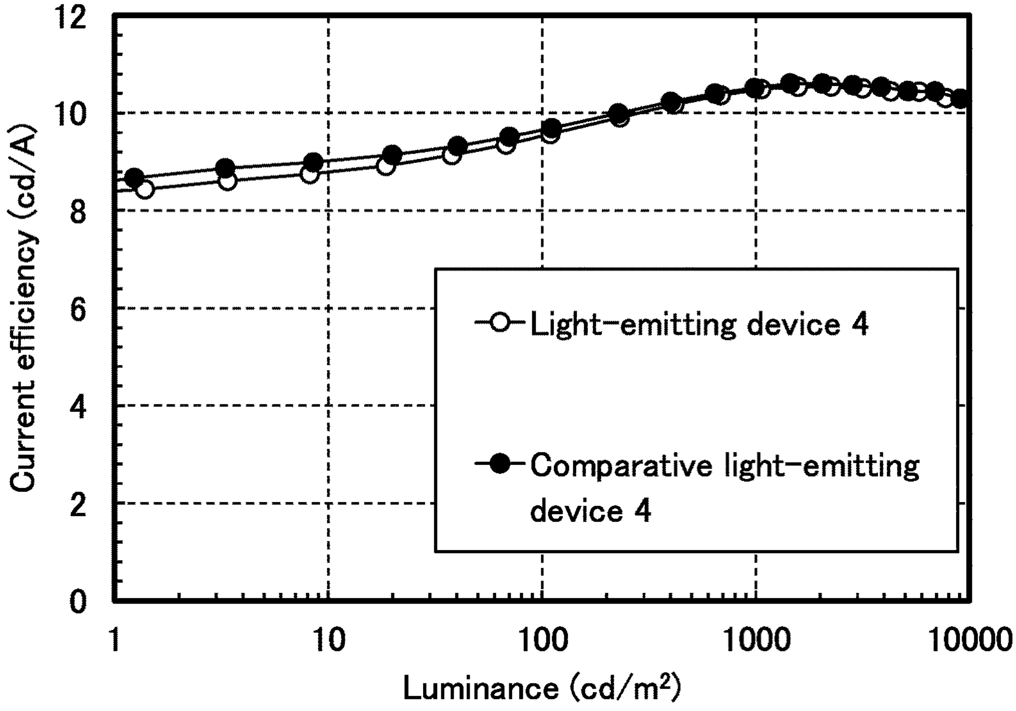
FIG. 33 is a diagram illustrating luminance-current efficiency characteristics of light-emitting devices of an example.

FIG. 33 is a diagram illustrating the luminance-current efficiency characteristics of the light-emitting device 4.

Figure 34:
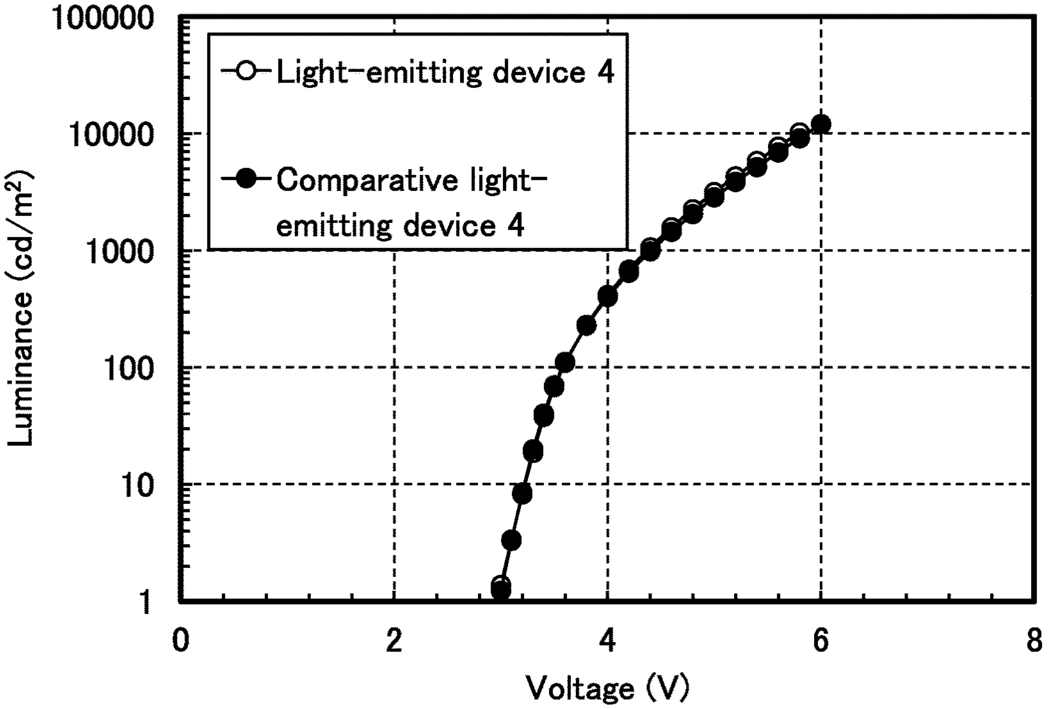
FIG. 34 is a diagram illustrating voltage-luminance characteristics of light-emitting devices of an example.

FIG. 34 is a diagram illustrating the voltage-luminance characteristics of the light-emitting device 4.

Figure 35:
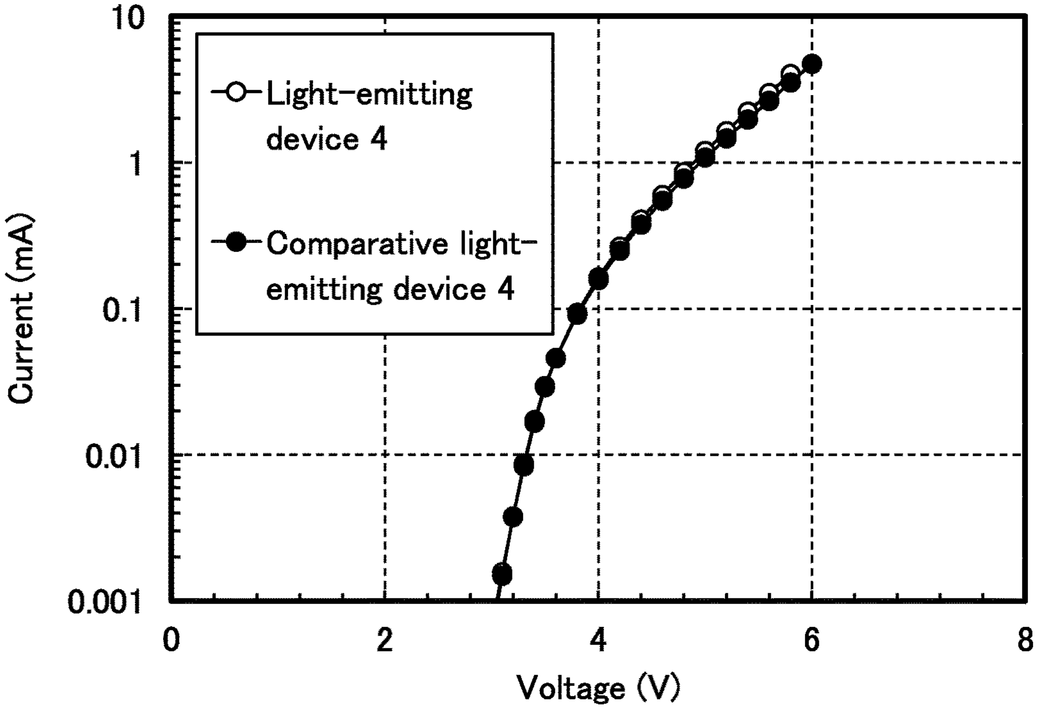
FIG. 35 is a diagram illustrating voltage-current characteristics of light-emitting devices of an example.

FIG. 35 is a diagram illustrating the voltage-current characteristics of the light-emitting device 4.

Figure 36:
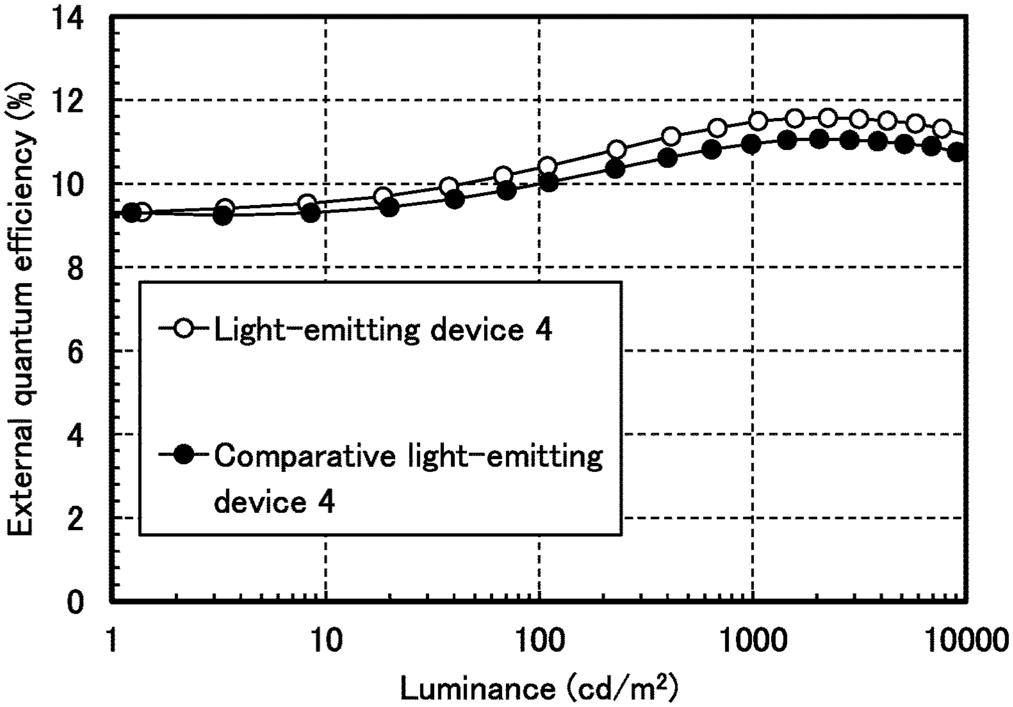
FIG. 36 is a diagram illustrating luminance-external quantum efficiency characteristics of light-emitting devices of an example.

FIG. 36 is a diagram illustrating the luminance-external quantum efficiency characteristics of the light-emitting device 4. Note that the external quantum efficiency was calculated from an emission spectrum and luminance in frontal observation assuming that the light distribution characteristics of the light-emitting device are of a Lambertian type.

Figure 37:
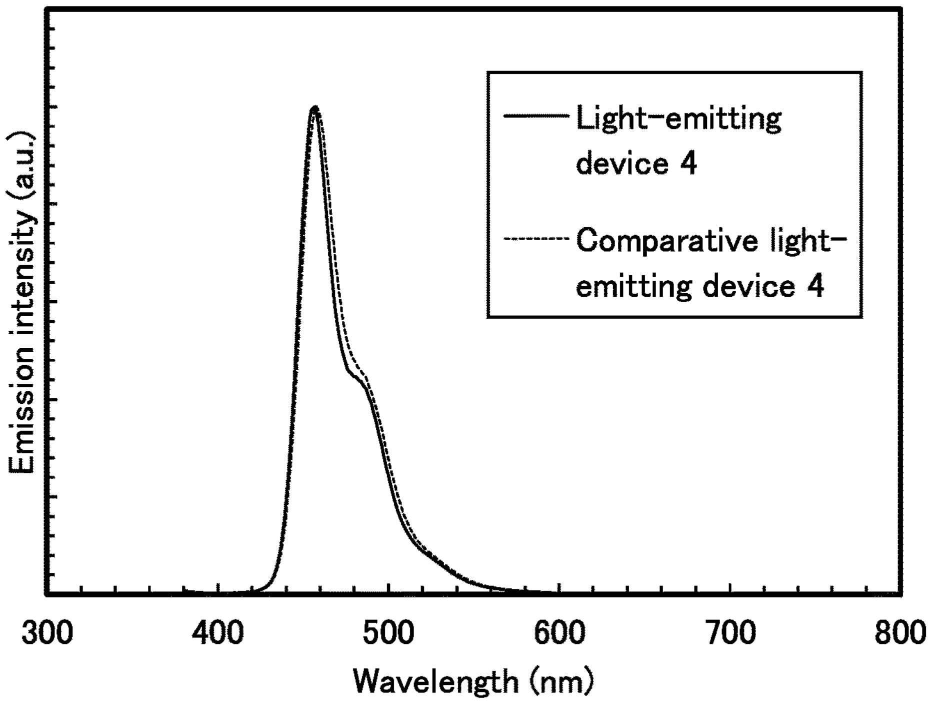
FIG. 37 is a diagram illustrating emission spectra of light-emitting devices of an example.

FIG. 37 is a diagram illustrating an emission spectrum of the light-emitting device 4 emitting light at a luminance of 1000 $cd/m^2$.

Figure 38:
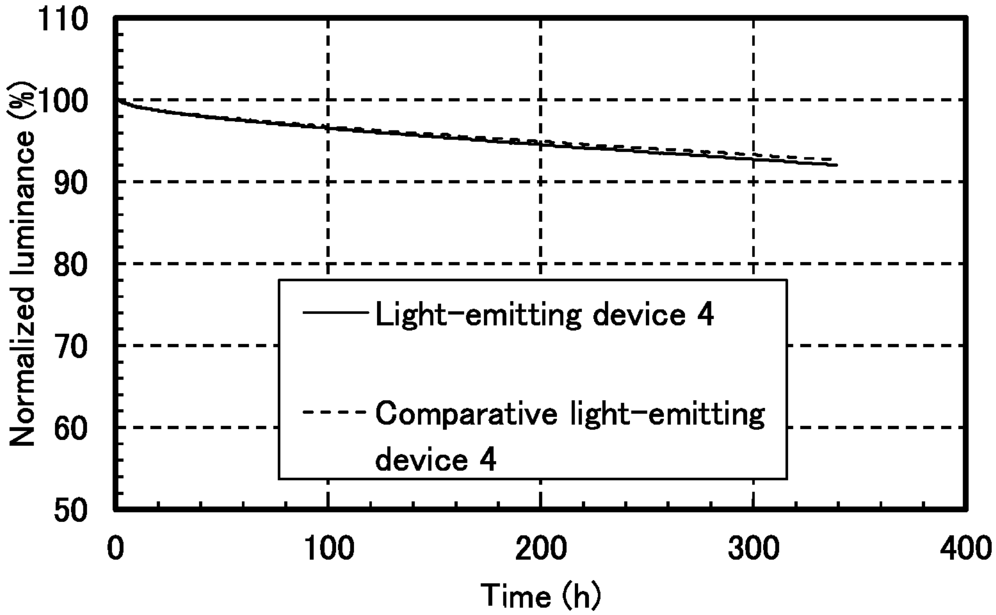
FIG. 38 is a diagram illustrating a time-dependent change in normalized luminance of light-emitting devices of an example.

FIG. 38 is a diagram illustrating a time-dependent change in normalized luminance of the light-emitting device 4 emitting light at a constant current density of 50 $mA/cm^2$. Note that this diagram also shows a time-dependent change in normalized luminance of a comparative light-emitting device emitting light at a constant current density of 50 $mA/cm^2$.

<Light-Emitting Device 4>

The fabricated light-emitting device 4, which is described in this example, has a structure similar to that of the light-emitting device 150 (see FIG. 24).

The light-emitting device 150 includes the electrode 101, the electrode 102, the unit 103, and the layer 104, and the electrode 102 includes a region overlapping with the electrode 101. The light-emitting device 150 includes the layer 105.

The unit 103 includes a region positioned between the electrode 101 and the electrode 102, and the unit 103 includes the layer 111, the layer 112, and the layer 113.

The layer 112 includes a region positioned between the electrode 101 and the layer 111, and the layer 113 includes a region positioned between the layer 111 and the electrode 102.

The layer 111 contains the light-emitting material EM. Note that PCA2Dfbf-02 was used as the light-emitting material EM in the light-emitting device 4.

<<Structure of Light-Emitting Device 4>>

Table 4 shows the structure of the light-emitting device 4. The structural formulae of the materials used in the light-emitting device 4 and a comparative light-emitting device 4 described in this example are shown below.

TABLE 4

| Component | Reference numeral | Material | Composition ratio | Thickness/nm |
|---|---|---|---|---|
| Electrode | 102 | Al | | 150 |
| Layer | 105 | LiF | | 1 |
| Region | 113B | NBPhen | | 10 |
| Region | 113A | 2mDBTBPDBq-II | | 15 |
| Layer | 111 | αN-βNP Anth:PCA2Dfbf-02 | 1:0.015 | 25 |
| Region | 112B | PCzN2 | | 10 |
| Region | 112A | BBABnf | | 20 |
| Layer | 104 | BBABnf:OCHD-001 | 1:0.1 | 10 |
| Electrode | 101 | ITSO | | 70 |

[Chemical Formula 51]

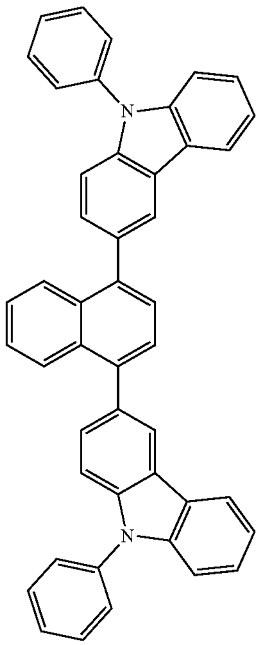

PCzN2

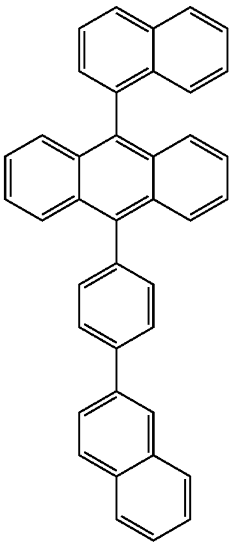

α N-β NPAnth

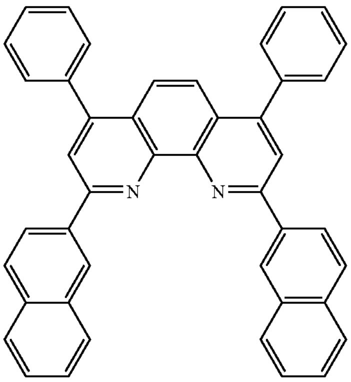

NBPhen

-continued

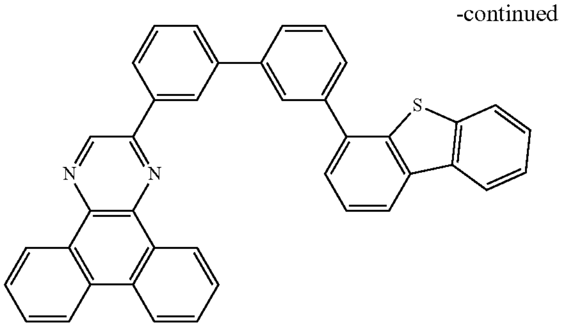

2mDBTBPDBq-II

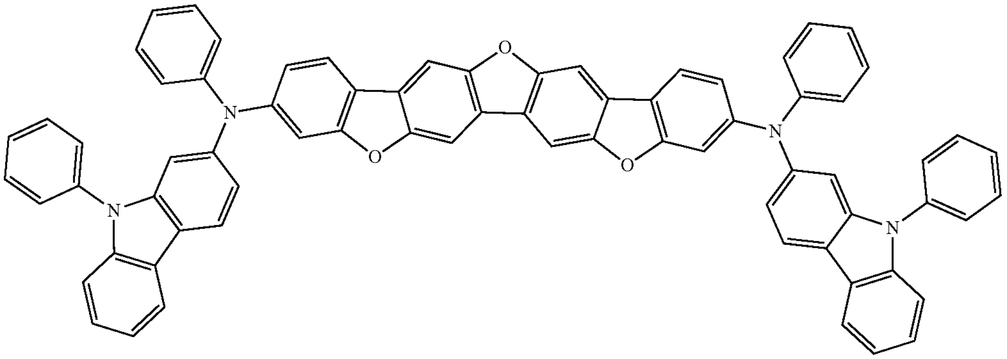

PCA2Dfbf-02

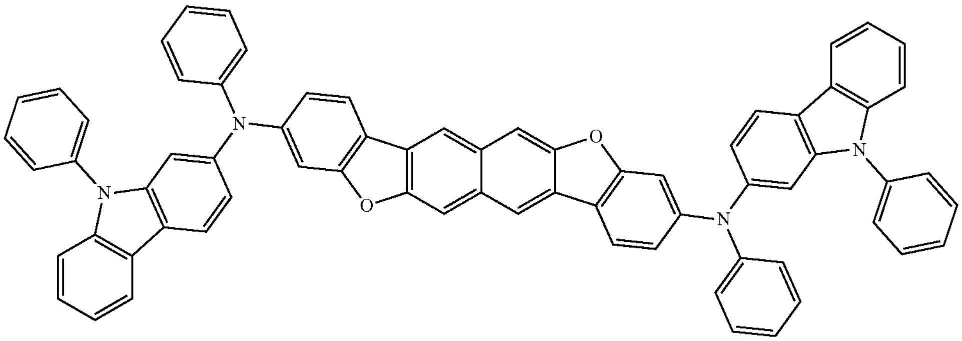

3,10PCA2Nbf(IV)-02

<<Fabrication Method of Light-Emitting Device 4>>

The light-emitting device 4 described in this example was fabricated using a method including the following steps.

[First Step]

In the first step, the electrode 101 was formed. Specifically, the electrode 101 was formed by a sputtering method using indium oxide-tin oxide containing silicon or silicon oxide (ITSO) as a target.

The electrode 101 contains ITSO and has a thickness of 70 nm and an area of 4 $mm^2$ (2 mm×2 mm).

Next, a base material over which the electrode 101 was formed was washed with water, baked at 200° C. for one hour, and then subjected to UV ozone treatment for 370 seconds. Then, the substrate was transferred into a vacuum evaporation apparatus where the pressure was reduced to approximately $10^{-4}$ Pa, and vacuum baking was performed at 170° C. for 30 minutes in a heating chamber of the vacuum evaporation apparatus. Then, the substrate was cooled down for approximately 30 minutes.

[Second Step]

In the second step, the layer 104 was formed over the electrode 101. Specifically, materials were deposited by co-evaporation using a resistance-heating method.

The layer 104 contains BBABnf and OCHD-001 at BBABnf:OCHD-001=1:0.1 (weight ratio), and has a thickness of 10 nm.

[Third Step]

In the third step, the region 112A was formed over the layer 104. Specifically, a material was deposited by evaporation using a resistance-heating method.

The region 112A contains BBABnf and has a thickness of 20 nm.

[Fourth Step]

In the fourth step, the region 112B was formed over the region 112A. Specifically, a material was deposited by evaporation using a resistance-heating method.

Note that the region 112B contains 3,3'-(naphthalene-1,4-diyl)bis(9-phenyl-9H-carbazole) (abbreviation: PCzN2) and has a thickness of 10 nm.

[Fifth Step]

In the fifth step, the layer 111 was formed over the region 112B. Specifically, materials were deposited by co-evaporation using a resistance-heating method.

Note that the layer 111 contains α,N-βNPAnth and PCA2Dfbf-02 at αN-βNPAnth:PCA2Dfbf-02=1:0.015 (weight ratio) and has a thickness of 25 nm.

[Sixth Step]

In the sixth step, the region 113A was formed over the layer 111. Specifically, a material was deposited by evaporation using a resistance-heating method.

Note that the region 113A contains 2mDBTBPDBq-II and has a thickness of 15 nm.

[Seventh Step]

In the seventh step, the region 113B was formed over the region 113A. Specifically, a material was deposited by evaporation using a resistance-heating method.

Note that the region 113B contains NBPhen and has a thickness of 10 nm.

[Eighth Step]

In the eighth step, the layer 105 was formed over the region 113B. Specifically, a material was deposited by evaporation using a resistance-heating method.

Note that the layer 105 contains LiF and has a thickness of 1 nm.

[Ninth Step]

In the ninth step, the electrode 102 was formed over the layer 105. Specifically, a material was deposited by evaporation using a resistance-heating method.

The electrode 102 contains Al and has a thickness of 150 nm.

<<Operation Characteristics of Light-Emitting Device 4>>

When supplied with electric power, the light-emitting device 4 emitted the light EL1 (see FIG. 24). The operation characteristics of the light-emitting device 4 were measured (see FIG. 32 to FIG. 38). Note that the measurement was performed at room temperature.

Table 2 shows main initial characteristics of the light-emitting device 4 emitting light at a luminance of approximately 1000 cd/m$^2$.

The light-emitting device 4 was found to have favorable characteristics. For example, the light-emitting device 4 was found to have favorable chromaticity and a high external quantum efficiency of 11.5%. The external quantum efficiency of the light-emitting device 4 was found to be higher than that of the comparative light-emitting device 4, which was 10.9%. The emission spectrum of the light-emitting device 4 was found to have a smaller half width than that of the comparative light-emitting device 4 (see FIG. 37). As a result, a novel light-emitting device that is highly convenient, useful, or reliable was successfully provided.

Reference Example 2

Table 5 shows the structure of the comparative light-emitting device 4.

The layer 111 of the fabricated comparative light-emitting device 4, which is described in this example, contains 3,10PCA2Nbf(IV)-02 instead of PCA2Dfbf-02.

TABLE 5

| Component | Reference numeral | Material | Composition ratio | Thickness/nm |
|---|---|---|---|---|
| Electrode | 102 | Al | | 150 |
| Layer | 105 | LiF | | 1 |
| Region | 113B | NBPhen | | 10 |
| Region | 113A | 2mDBTBPDBq-II | | 15 |
| Layer | 111 | αN-βNP Anth: 3,10PCA2Nbf(IV)-02 | 1:0.015 | 25 |
| Region | 112B | PCzN2 | | 10 |
| Region | 112A | BBABnf | | 20 |
| Layer | 104 | BBABnf:OCHD-001 | 1:0.1 | 10 |
| Electrode | 101 | ITSO | | 70 |

<<Fabrication Method of Comparative Light-Emitting Device 4>>

The comparative light-emitting element 4 was fabricated using a method including the following steps.

Note that the fabrication method of the comparative light-emitting device 4 is different from the fabrication method of the light-emitting device 4 in the step of forming the layer 111. Specifically, a difference from the fabrication method of the light-emitting device 4 is that 3,10PCA2Nbf(IV)-02 is deposited by co-evaporation instead of PCA2Dfbf-02 such that the ratio of 3,10PCA2Nbf(IV)-02 to αN-βNPAnth was 0.015 (weight ratio). Different portions are described in detail here, and the above description is referred to for portions formed using a similar method.

[Fifth Step]

In the fifth step, the layer 111 was formed over the region 112B. Specifically, materials were deposited by co-evaporation using a resistance-heating method.

Note that the layer 111 contains α,N-βNPAnth and 3,10PCA2Nbf(IV)-02 at αN-βNPAnth:3,10PCA2Nbf(IV)-02=1:0.015 (weight ratio) and has a thickness of 25 nm.

<<Operation Characteristics of Comparative Light-Emitting Device 4>>

The operation characteristics of the comparative light-emitting device 4 were measured. Note that the measurement was performed at room temperature.

Table 2 shows main initial characteristics of the comparative light-emitting device 4.

Example 4

In this example, the structure, fabrication method, and characteristics of a light-emitting device 5 of one embodiment of the present invention are described with reference to FIG. 24 and FIG. 39 to FIG. 44.

Figure 39:
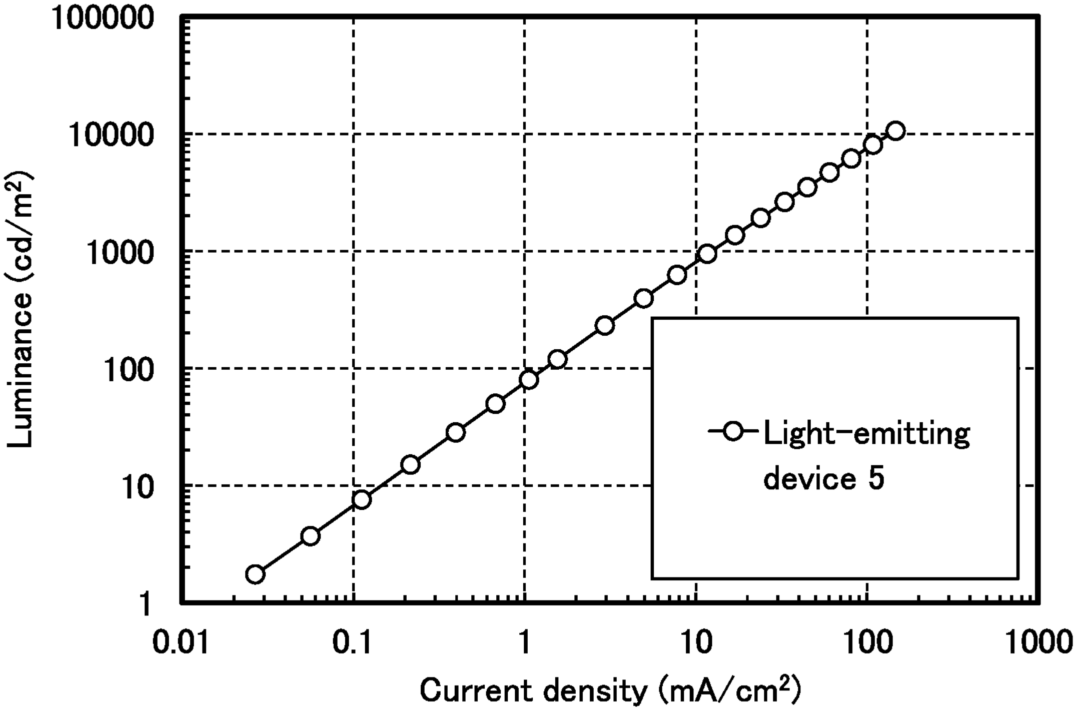
FIG. 39 is a diagram illustrating current density-luminance characteristics of a light-emitting device of an example.

FIG. 39 is a diagram illustrating the current density-luminance characteristics of the light-emitting device 5.

Figure 40:
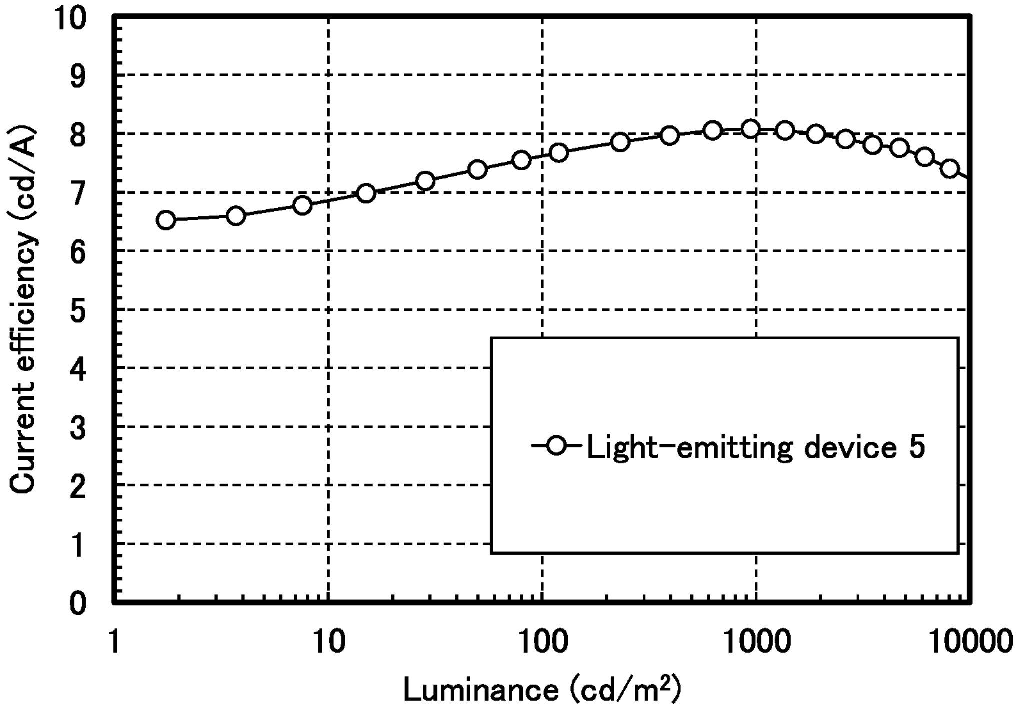
FIG. 40 is a diagram illustrating luminance-current efficiency characteristics of a light-emitting device of an example.

FIG. 40 is a diagram illustrating the luminance-current efficiency characteristics of the light-emitting device 5.

Figure 41:
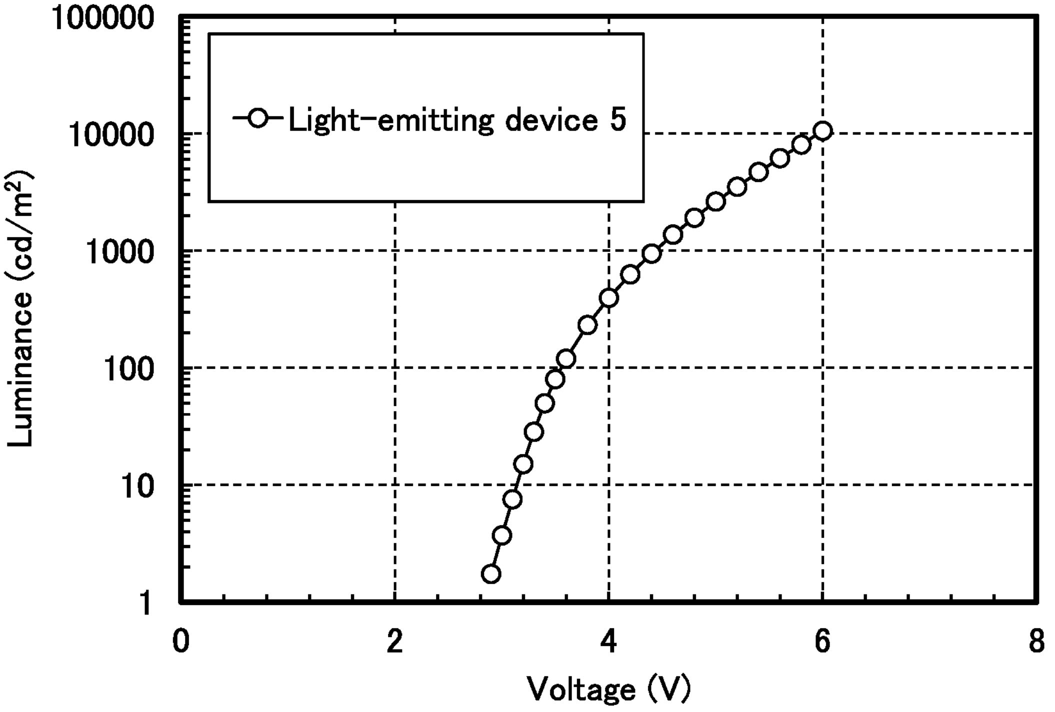
FIG. 41 is a diagram illustrating voltage-luminance characteristics of a light-emitting device of an example.

FIG. 41 is a diagram illustrating the voltage-luminance characteristics of the light-emitting device 5.

Figure 42:
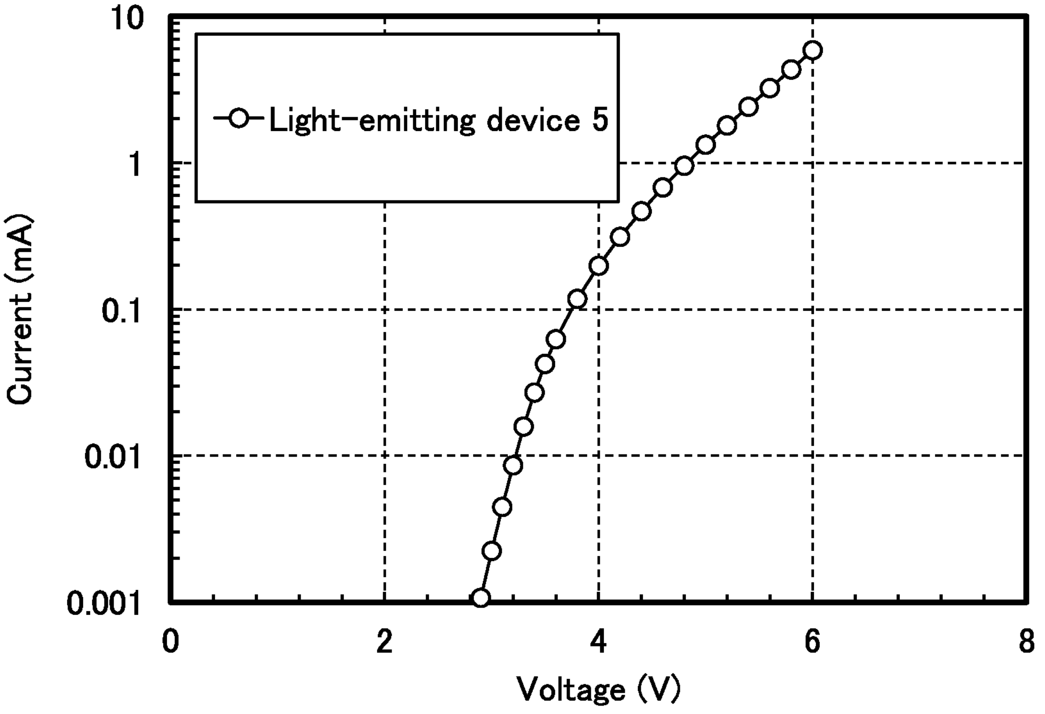
FIG. 42 is a diagram illustrating voltage-current characteristics of a light-emitting device of an example.

FIG. 42 is a diagram illustrating the voltage-current characteristics of the light-emitting device 5.

Figure 43:
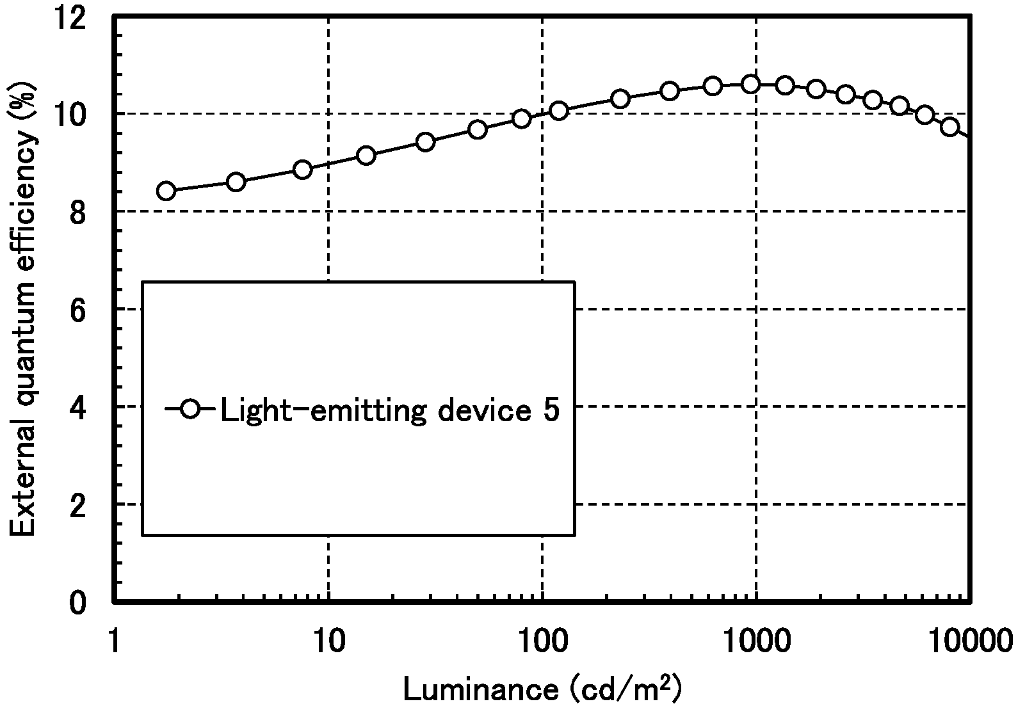
FIG. 43 is a diagram illustrating luminance-external quantum efficiency characteristics of a light-emitting device of an example.

FIG. 43 is a diagram illustrating the luminance-external quantum efficiency characteristics of the light-emitting device 5. Note that the external quantum efficiency was calculated from an emission spectrum and luminance in frontal observation assuming that the light distribution characteristics of the light-emitting device are of a Lambertian type.

Figure 44:
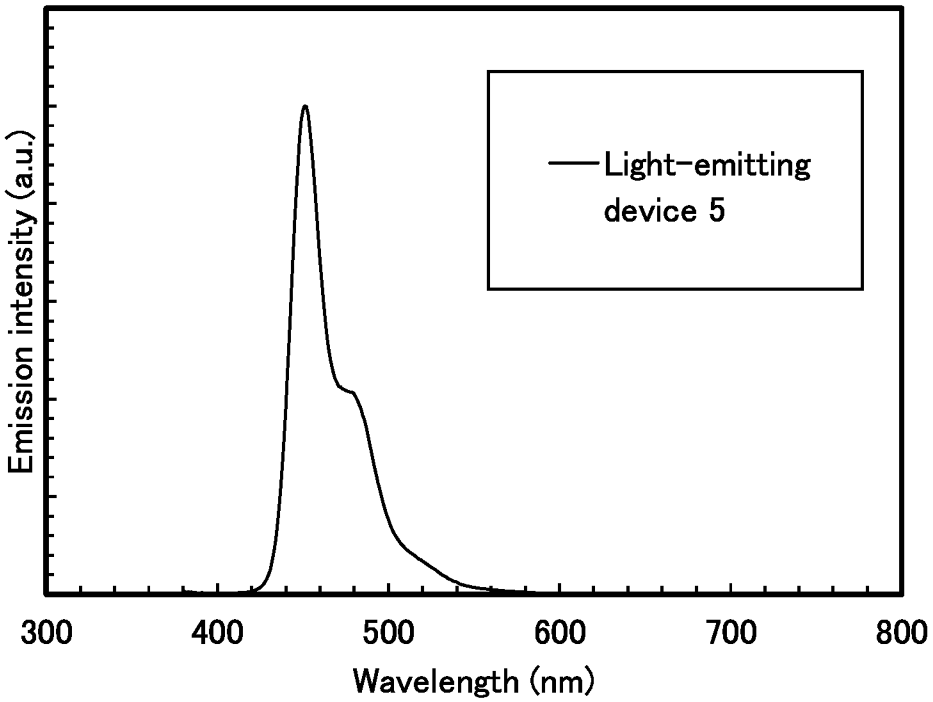
FIG. 44 is a diagram illustrating an emission spectrum of a light-emitting device of an example.

FIG. 44 is a diagram illustrating an emission spectrum of the light-emitting device 5 emitting light at a luminance of 1000 cd/m$^2$.

<Light-Emitting Device 5>

The fabricated light-emitting device 5, which is described in this example, has a structure similar to that of the light-emitting device 150 (see FIG. 24). The light-emitting device 5 is different from the light-emitting device 4 in that not PCA2Dfbf-02 but FrA2Dfbf-02 was used as the light-emitting material EM. Different portions are described in detail here, and the above description is referred to for portions that have similar structures.

The layer 111 contains the light-emitting material EM. Note that FrA2Dfbf-02 was used as the light-emitting material EM in the light-emitting device 5.

<<Structure of Light-Emitting Device 5>>

Table 6 shows the structure of the light-emitting device 5.

TABLE 6

| Component | Reference numeral | Material | Composition ratio | Thickness/nm |
|---|---|---|---|---|
| Electrode | 102 | Al | | 150 |
| Layer | 105 | LiF | | 1 |
| Region | 113B | NBPhen | | 10 |
| Region | 113A | 2mDBTBPDBq-II | | 15 |
| Layer | 111 | αN-βNP Anth:FrA2Dfbf-02 | 1:0.015 | 25 |
| Region | 112B | PCzN2 | | 10 |
| Region | 112A | BBABnf | | 20 |
| Layer | 104 | BBABnf:OCHD-001 | 1:0.1 | 10 |
| Electrode | 101 | ITSO | | 70 |

<<Fabrication Method of Light-Emitting Device 5>>

The light-emitting device 5 described in this example was fabricated using a method including the following steps.

Note that the fabrication method of the light-emitting device 5 is different from the fabrication method of the light-emitting device 4 in the step of forming the layer 111. Specifically, a difference from the fabrication method of the light-emitting device 4 is that FrA2Dfbf-02 is deposited by co-evaporation instead of PCA2Dfbf-02 such that the ratio of FrA2Dfbf-02 to αN-βNPAnth was 0.015 (weight ratio). Different portions are described in detail here, and the above description is referred to for portions formed using a similar method.

[Fifth Step]

In the fifth step, the layer 111 was formed over the region 112B. Specifically, materials were deposited by co-evaporation using a resistance-heating method.

Note that the layer 111 contains αN-βNPAnth and FrA2Dfbf-02 at αN-βNPAnth:FrA2Dfbf-02=1:0.015 (weight ratio) and has a thickness of 25 nm.

<<Operation Characteristics of Light-Emitting Device 5>>

When supplied with electric power, the light-emitting device 5 emitted the light EL1 (see FIG. 24). The operation characteristics of the light-emitting device 5 were measured (see FIG. 39 to FIG. 44). Note that the measurement was performed at room temperature.

Table 2 shows main initial characteristics of the light-emitting device 5 emitting light at a luminance of approximately 1000 $cd/m^2$.

The light-emitting device 5 was found to have favorable characteristics. As a result, a novel light-emitting device that is highly convenient, useful, or reliable was successfully provided.

Example 5

Synthesis Example 4

In this example, the physical properties of the organic compound of one embodiment of the present invention and a method for synthesizing the organic compound will be described with reference to FIG. 51 to FIG. 53. Specifically, the characteristics and synthesis method of N,N-bis[9-(3,5-di-tert-butylphenyl)-9H-carbazol-2-yl]-N,N-diphenyldibenzo[b,b']furo[2,3-f;5,4-f]bisbenzofuran-3,10-diamine (abbreviation: mmtBuPCA2Dfbf-02) represented by Structural Formula (111) in Embodiment 1 are described. The structural formula of mmtBuPCA2Dfbf-02 is shown below.

[Chemical Formula 52]

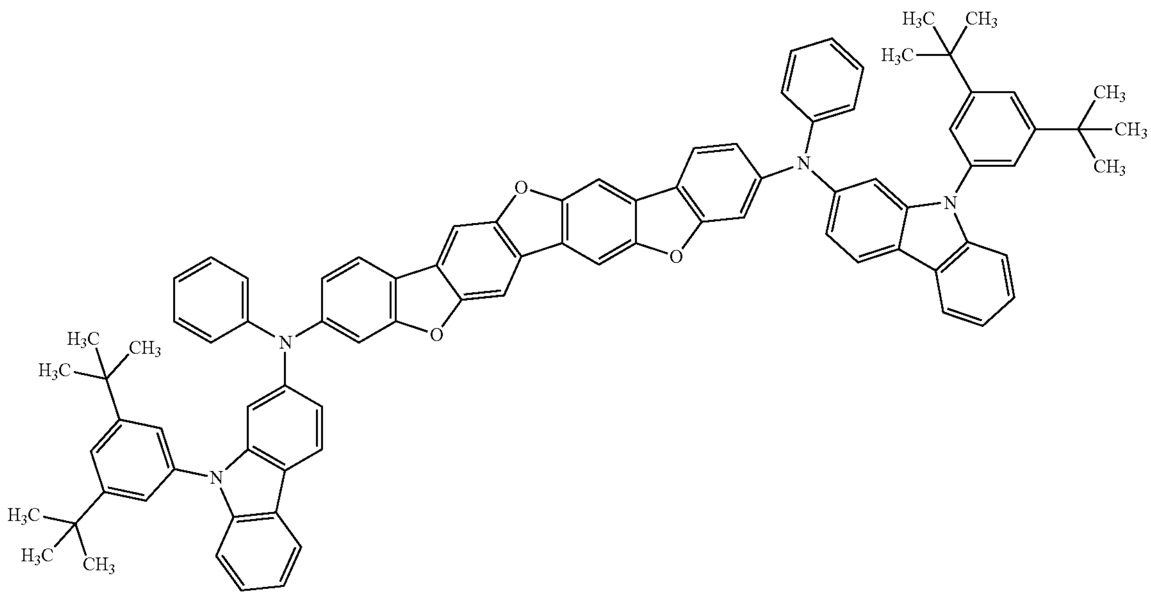

PCA2Dfbf-02

Figure 51:
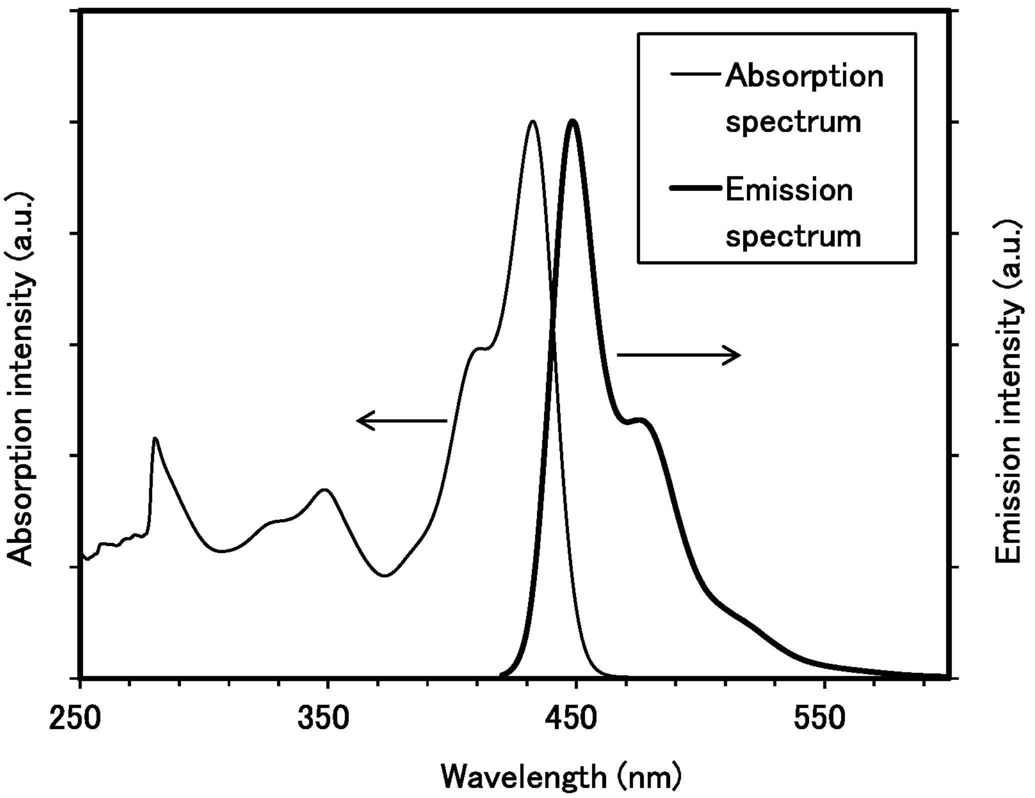
FIG. 51 is a diagram showing an absorption spectrum and an emission spectrum of mmtBuPCA2Dfbf-02 in a toluene solution.

FIG. 51 is a diagram illustrating an absorption spectrum and an emission spectrum of a toluene solution containing mmtBuPCA2Dfbf-02.

Figure 52:
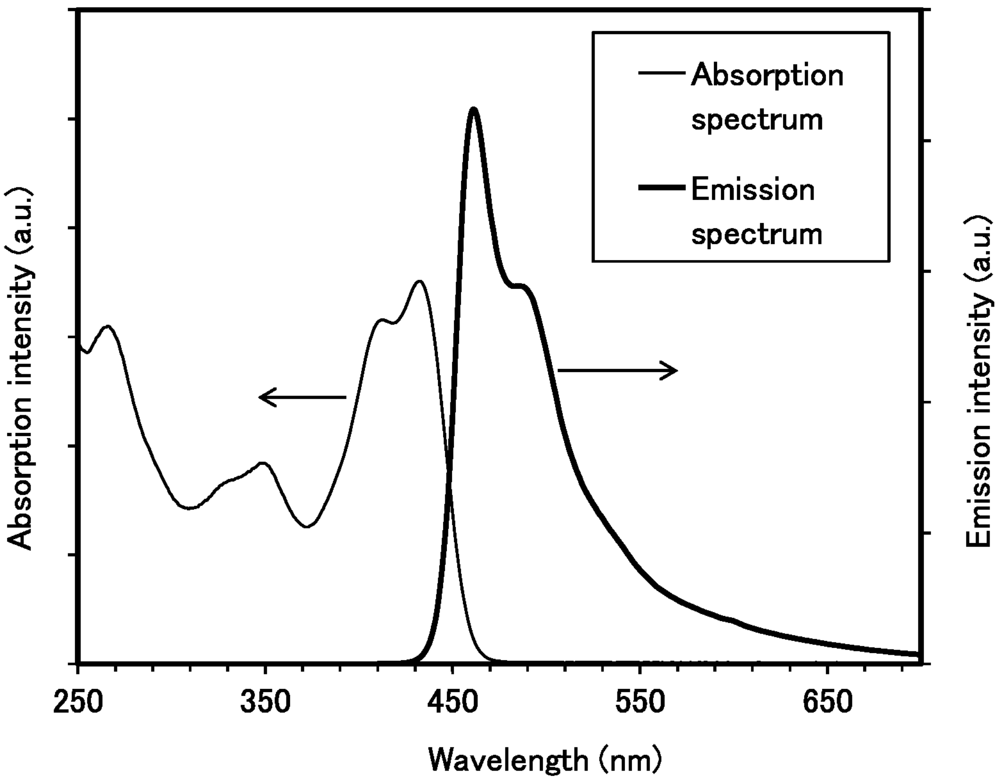
FIG. 52 is a diagram showing an absorption spectrum and an emission spectrum of mmtBuPCA2Dfbf-02 in a thin film state.

FIG. 52 is a diagram illustrating an absorption spectrum and an emission spectrum of mmtBuPCA2Dfbf-02 in a solid thin film form.

Figure 53A:
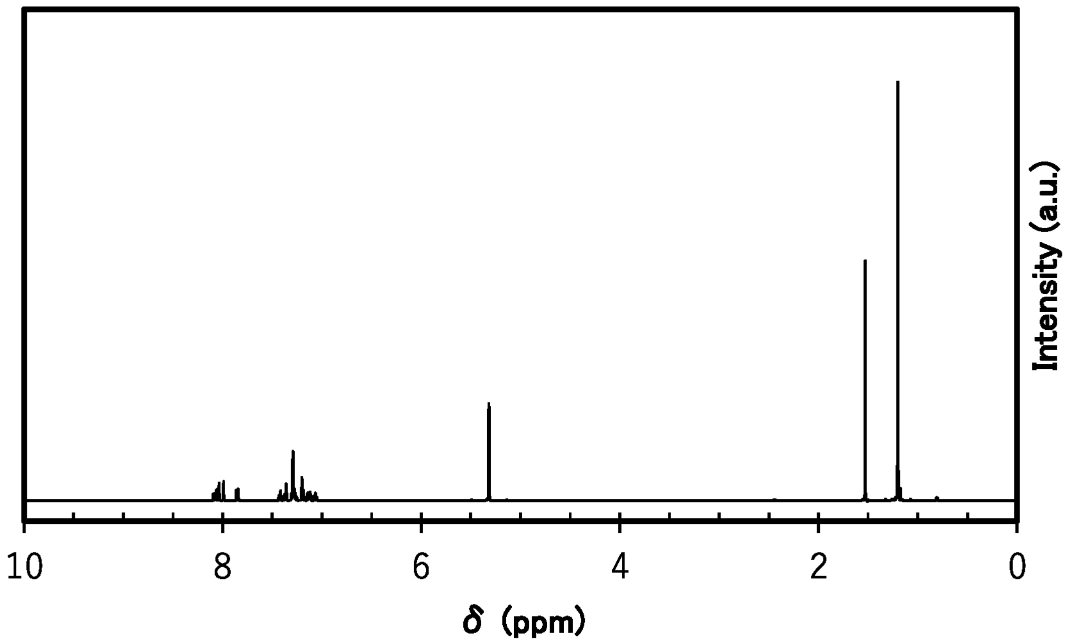
FIG. 53A and FIG. 53B are diagrams showing $^1$H NMR spectra of mmtBuPCA2Dfbf-02.
Figure 53B:
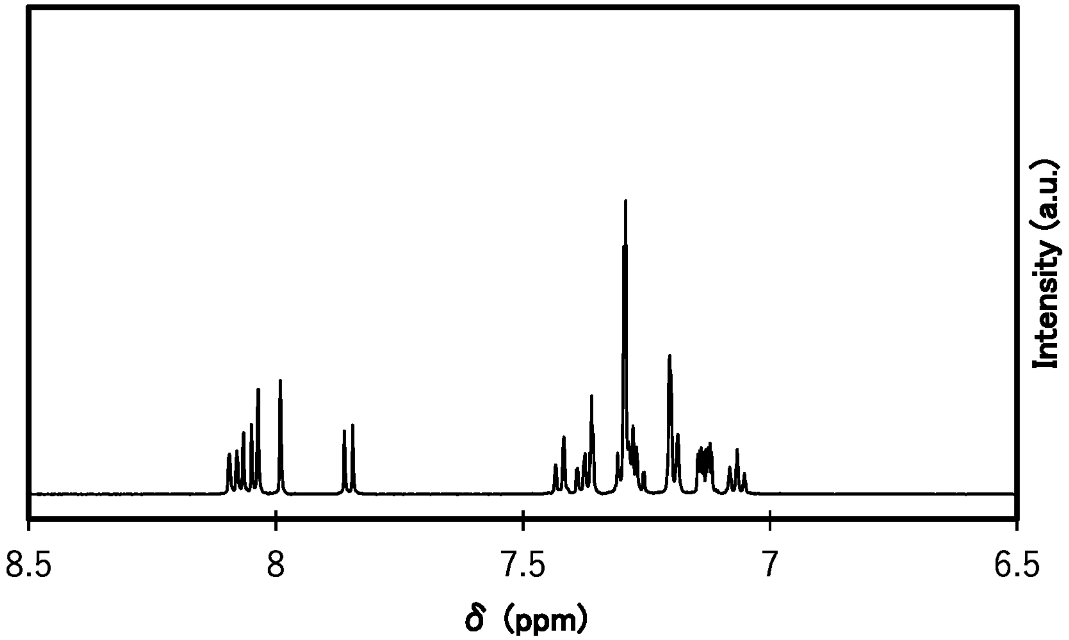

FIG. 53A and FIG. 53B are diagrams illustrating $^1$H NMR spectra of mmtBuPCA2Dfbf-02.

<Measurement Apparatus and Method for Manufacturing Measurement Sample>

The absorption spectrum of the toluene solution was measured with an ultraviolet and visible spectrophotometer (V550, manufactured by JASCO Corporation), and the absorption spectrum derived from toluene was subtracted.

For the absorption spectrum of the sample in the solid thin film form, a spectrophotometer (U4100 Spectrophotometer, manufactured by Hitachi High-Technologies Corporation) was used.

The emission spectra were measured using a fluorescence spectrophotometer (FP-8600, manufactured by JASCO Corporation), and the quantum yield was measured using an absolute PL quantum yields measurement system (Quantaurus-QY, manufactured by Hamamatsu Photonics K.K.).

Note that the solid sample in the thin film form was formed over a quartz substrate by a vacuum evaporation method.

<Physical Properties>

The absorption spectrum of the toluene solution containing mmtBuPCA2Dfbf-02 had peaks at 432 nm, 410 nm, 349 nm, 327 nm, and 280 nm (see FIG. 51). The emission spectrum thereof had peaks at 448 nm and 475 nm. Note that light with a wavelength of 410 nm was used as excitation light. The quantum yield in the toluene solution was 92%.

The absorption spectrum of the solid thin film of mmtBuPCA2Dfbf-02 had peaks at 433 nm, 415 nm, 350 nm, 330 nm, and 295 nm (see FIG. 52). The emission spectrum thereof had peaks at 463 nm, 490 nm, and 540 nm. Note that light with a wavelength of 400 nm was used as excitation light.

It was thus found that mmtBuPCA2Dfbf-02 emits blue light. Moreover, mmtBuPCA2Dfbf-02 was found to be usable as a light-emitting material or a host material for a fluorescent material in the visible region. Furthermore, mmtBuPCA2Dfbf-02 was found to have an extremely high quantum yield and to be suitable as a light-emitting material.

<Synthesis Method>

A method for synthesizing mmtBuPCA2Dfbf-02 is described. Synthesis Scheme (SC5) is shown below.

[Chemical Formula 53]

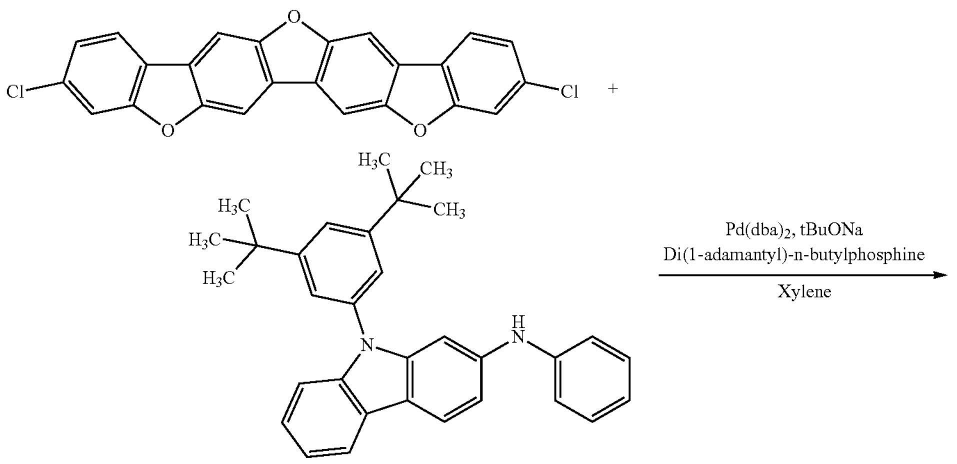

-continued

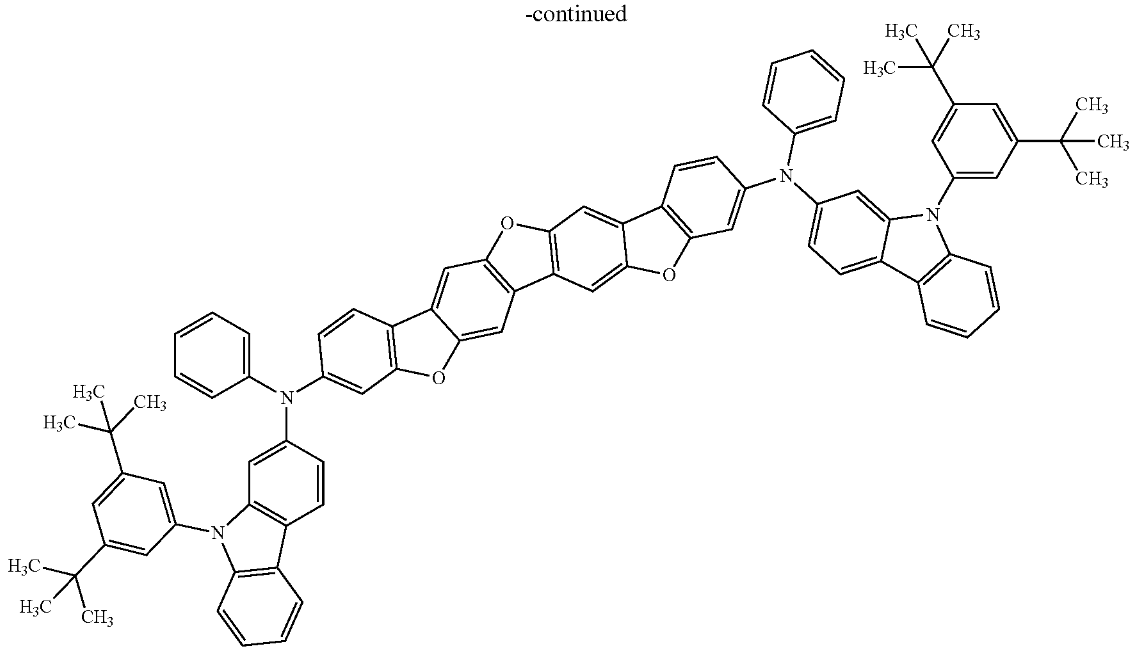

(SC5)

Into a 200-mL three-necked flask were put 0.84 g (2.0 mmol) of 3,10-dichlorodibenzo[b,b']furo[2,3-f;5,4-f]bisbenzofuran, 2.3 g (5.1 mmol) of N-phenyl-9-(3,5-di-tert-butylphenyl)-9H-carbazol-2-amine, 72 mg (0.20 mmol) of di(1-adamantyl)-n-butylphosphine, and 1.2 g (12 mmol) of sodium tert-butoxide. To this mixture was added 20 mL of xylene. This mixture was degassed by being stirred while the pressure was reduced. To this mixture was added 23 mg (40 μmol) of bis(dibenzylideneacetone)palladium(0), and the mixture was stirred under a nitrogen stream at 150° C. for 21 hours.

After the stirring, toluene was added to this mixture, which was then subjected to suction filtration through Celite, alumina, and Florisil, and the filtrate was concentrated to give a solid.

The obtained solid was purified by silica gel column chromatography (developing solvent: toluene:hexane=1:3 and then toluene:hexane=3:7), so that a solid was obtained. Furthermore, the obtained solid was reprecipitated with toluene/ethanol, so that 1.9 g of a yellow solid was obtained in a yield of 77%.

By a train sublimation method, 1.2 g of the yellow solid was sublimated and purified. The heating was performed at 385° C. under the conditions where the pressure was $2.9\times10^{-2}$ Pa and the flow rate of argon was 0 mL/min.

After the sublimation purification, 1.0 g of a yellow solid was obtained at a collection rate of 86%.

[$^1$H NMR]

FIG. 53A and FIG. 53B show the $^1$H NMR spectra of a dichloromethane solution of the obtained yellow solid. In addition, numerical data is shown below. This indicated that mmtBuPCA2Dfbf-02 was obtained in this synthesis example.

$^1$H NMR ($CD_2Cl_2$, 500 MHz): δ=1.20 (s, 36H), 7.07 (t, $J_1$=7.5 Hz, 2H), 7.12-7.43 (m, 28H), 7.85 (d, $J_1$=8.5 Hz, 2H), 7.99 (s, 2H), 8.04 (s, 2H), 8.06 (d, $J_1$=8.0 Hz, 2H), 8.09 (d, $J_1$=7.5 Hz, 2H).

Example 6

In this example, a light-emitting device 6 of one embodiment of the present invention is described with reference to FIG. 54 to FIG. 60.

Figure 54:
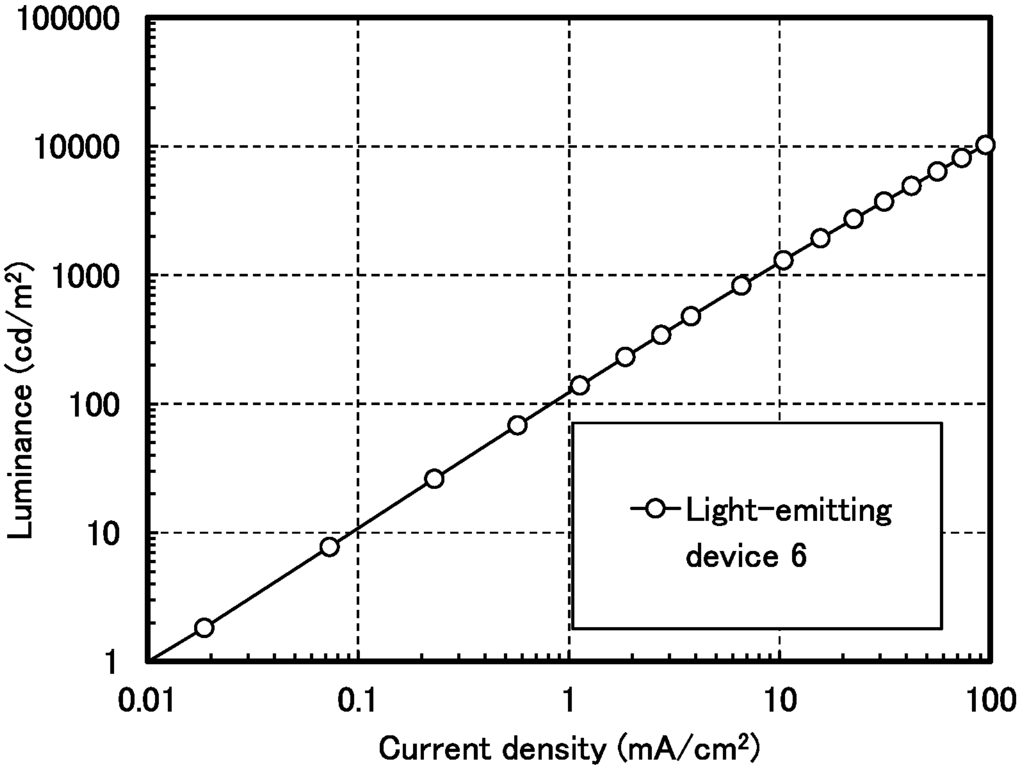
FIG. 54 is a diagram illustrating current density-luminance characteristics of a light-emitting device of an example.

FIG. 54 is a diagram illustrating the current density-luminance characteristics of the light-emitting device 6.

Figure 55:
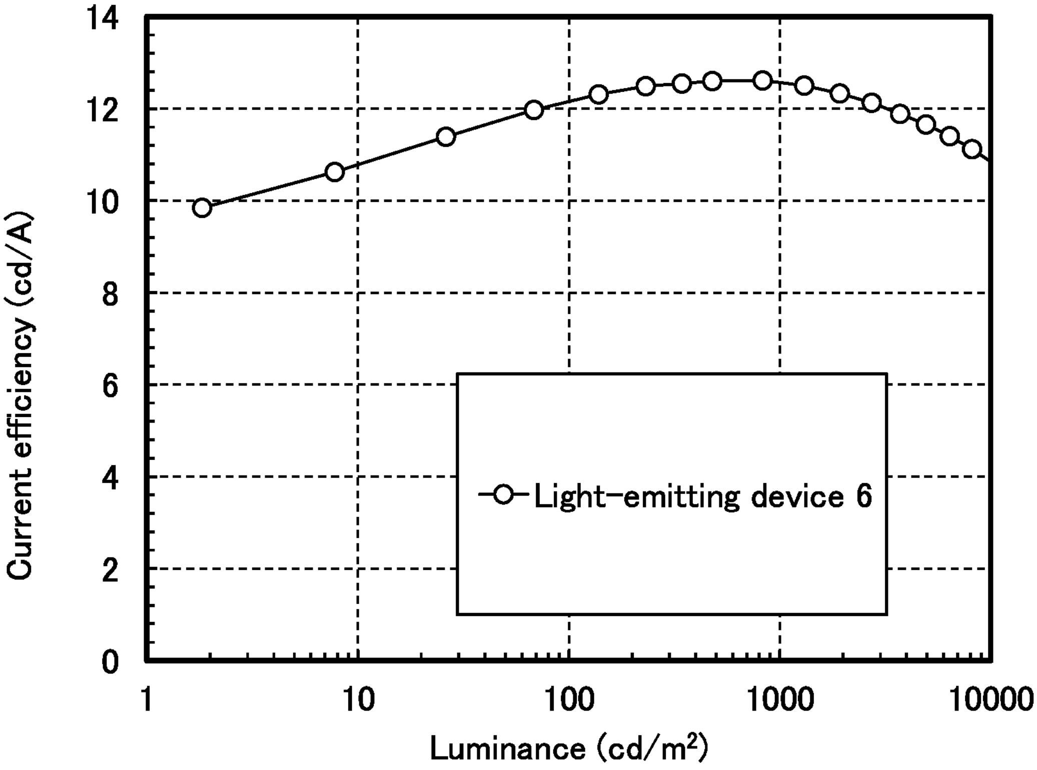
FIG. 55 is a diagram illustrating luminance-current efficiency characteristics of a light-emitting device of an example.

FIG. 55 is a diagram illustrating the luminance-current efficiency characteristics of the light-emitting device 6.

Figure 56:
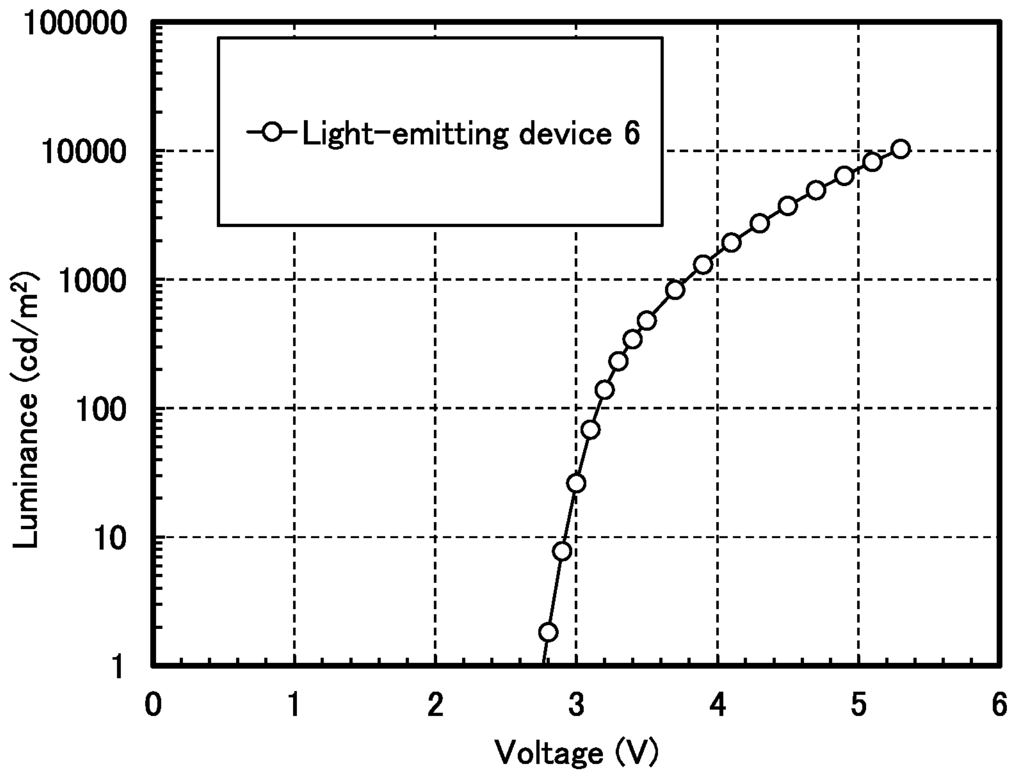
FIG. 56 is a diagram illustrating voltage-luminance characteristics of a light-emitting device of an example.

FIG. 56 is a diagram illustrating the voltage-luminance characteristics of the light-emitting device 6.

Figure 57:
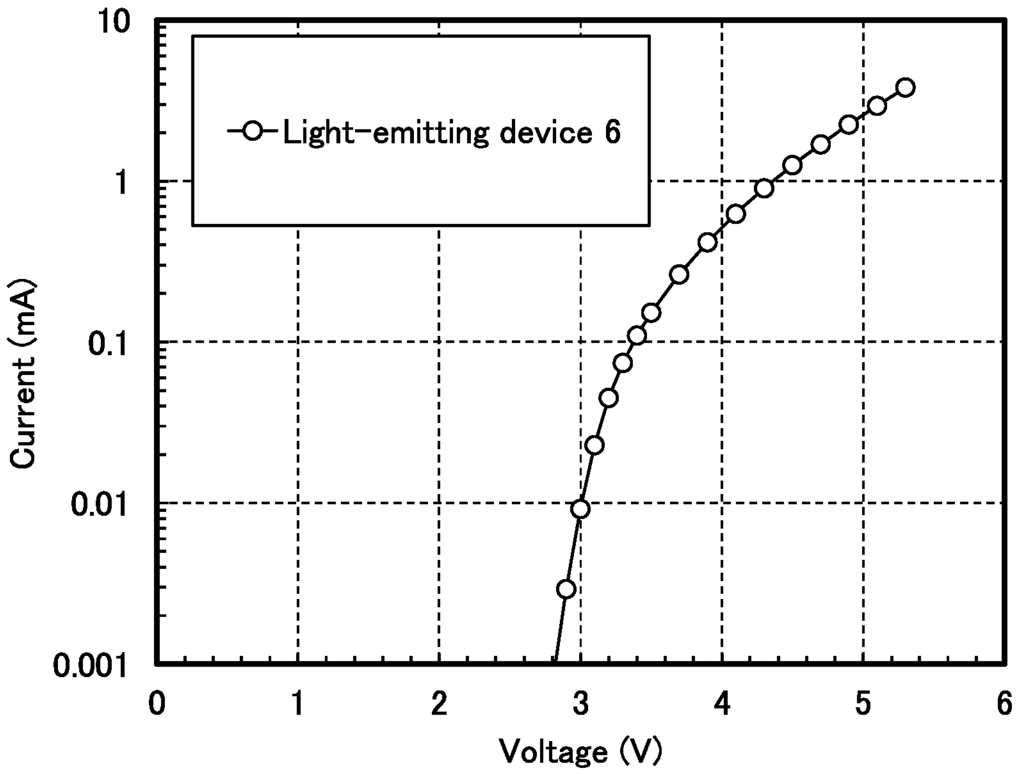
FIG. 57 is a diagram illustrating voltage-current characteristics of a light-emitting device of an example.

FIG. 57 is a diagram illustrating the voltage-current characteristics of the light-emitting device 6.

Figure 58:
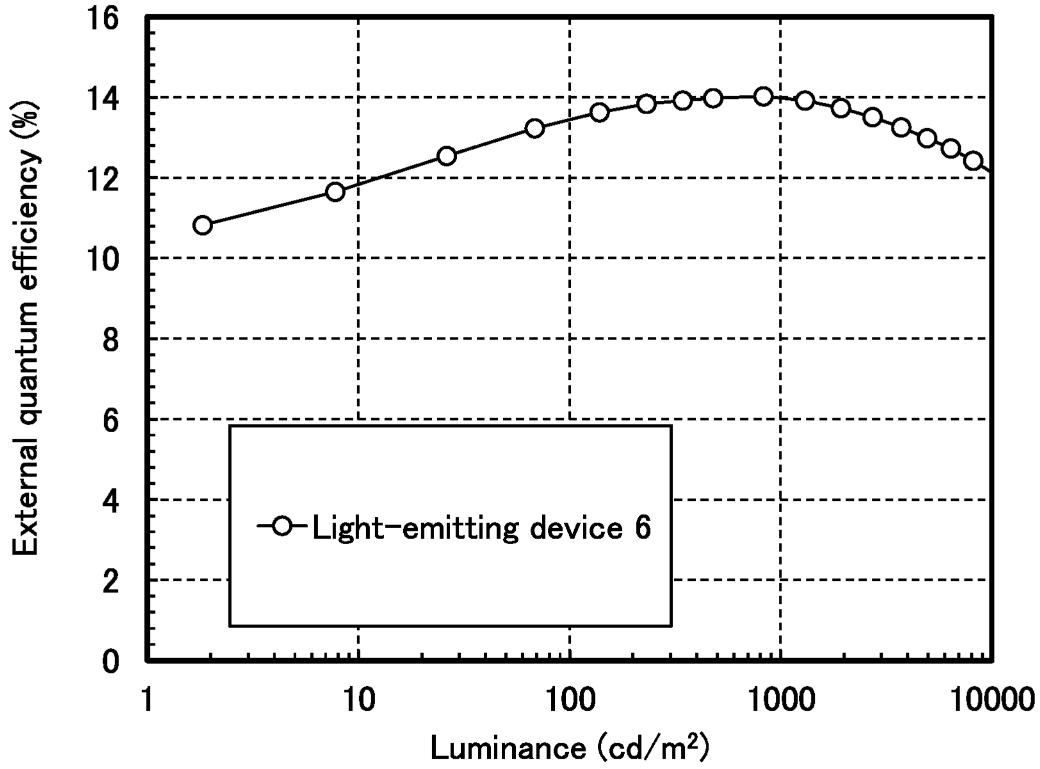
FIG. 58 is a diagram illustrating luminance-external quantum efficiency characteristics of a light-emitting device of an example.

FIG. 58 is a diagram illustrating the luminance-external quantum efficiency characteristics of the light-emitting device 6. Note that the external quantum efficiency was calculated from an emission spectrum and luminance in frontal observation assuming that the light distribution characteristics of the light-emitting device are of a Lambertian type.

Figure 59:
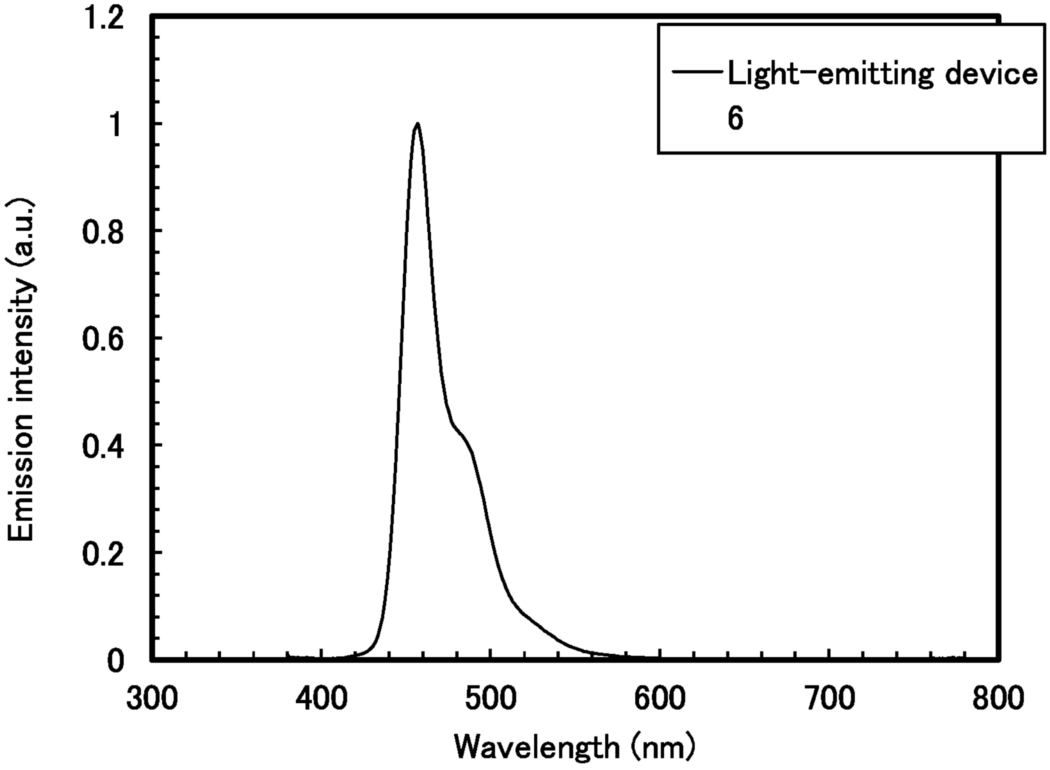
FIG. 59 is a diagram illustrating an emission spectrum of a light-emitting device of an example.

FIG. 59 is a diagram illustrating an emission spectrum of the light-emitting device 6 emitting light at a luminance of 1000 cd/$m^2$.

Figure 60:
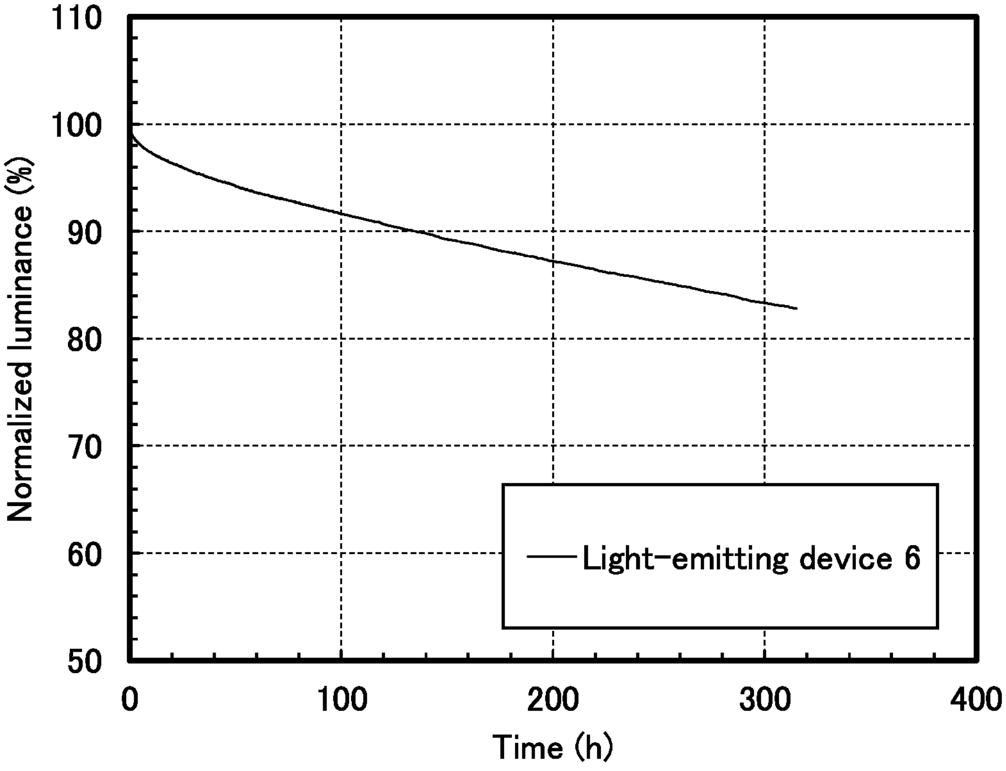
FIG. 60 is a diagram illustrating a time-dependent change in normalized luminance of a light-emitting device of an example.

FIG. 60 is a diagram illustrating a time-dependent change in normalized luminance of the light-emitting device 6 emitting light at a constant current density of 50 mA/$cm^2$.

<Light-Emitting Device 6>

The fabricated light-emitting device 6, which is described in this example, has a structure similar to that of the light-emitting device 150 (see FIG. 24). The light-emitting device 150 includes the electrode 101, the electrode 102, the unit 103, and the layer 104, and the electrode 102 includes a region overlapping with the electrode 101. The light-emitting device 150 includes the layer 105.

The unit 103 includes a region positioned between the electrode 101 and the electrode 102, and the unit 103 includes the layer 111, the layer 112, and the layer 113.

The layer 112 includes a region positioned between the electrode 101 and the layer 111, and the layer 113 includes a region positioned between the layer 111 and the electrode 102.

The layer 111 contains the light-emitting material EM. Note that mmtBuPCA2Dfbf-02 was used as the light-emitting material EM in the light-emitting device 6.

The layer 104 contains the material AM having an acceptor property and the material HT1. The material HT1 has the first HOMO level HOMO1, and the first HOMO level HOMO1 is higher than or equal to −5.7 eV and lower than or equal to −5.4 eV. Note that BBABnf was used as the material HT1 in the light-emitting device 6. The HOMO level of BBABnf was −5.56 eV in cyclic voltammetry (CV) measurement.

The layer 113 contains the material OMC, and the material OMC is an organometallic complex of an alkali metal or an organometallic complex of an alkaline earth metal. Note that Liq was used as the material OMC in the light-emitting device 6.

The layer 112 includes the region 112A and the region 112B. The region 112B includes a region positioned between the layer 111 and the region 112A, and the region 112B contains the material HT2. The material HT2 has the second HOMO level HOMO2, and the second HOMO level HOMO2 differs by −0.2 eV to 0 eV inclusive from the first HOMO level HOMO1. Note that PCzN2 was used as the material HT2 in the light-emitting device 6. The HOMO level of PCzN2 was −5.71 eV in cyclic voltammetry (CV) measurement.

<<Structure of Light-Emitting Device 6>>

Table 7 shows the structure of the light-emitting device 6. The structural formulae of the materials used in the light-emitting device described in this example are shown below.

TABLE 7

| Component | Reference numeral | Material | Composition ratio | Thickness/ nm |
|---|---|---|---|---|
| Electrode | 102 | Al | | 150 |
| Layer | 105 | Liq | | 1 |
| Region | 113B | mPn-mDMePyPTzn:Liq | 1:1 | 15 |
| Region | 113A | mFBPTzn | | 10 |
| Layer | 111 | αN-βNP Anth:mmtBuPCA2Dfbf-02 | 1:0.015 | 25 |
| Region | 112B | PCzN2 | | 10 |
| Region | 112A | BBABnf | | 20 |
| Layer | 104 | BBABnf:OCHD-001 | 1:0.1 | 10 |
| Electrode | 101 | ITSO | | 70 |

[Chemical Formula 54]

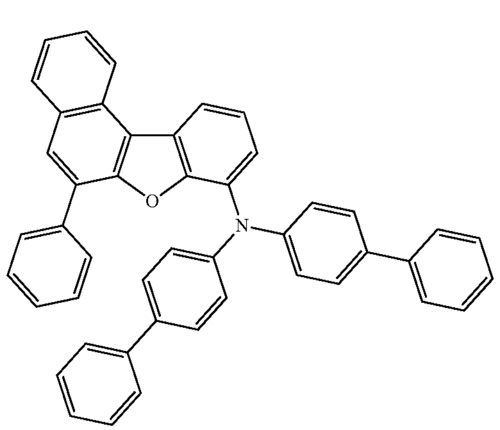

BBABnf

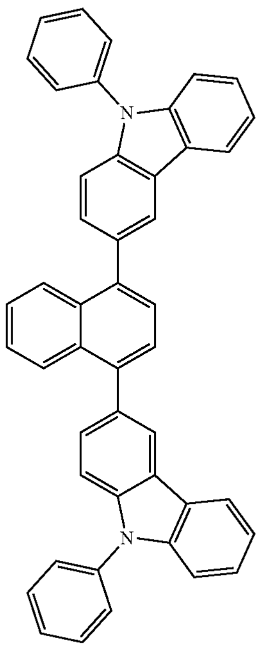

PCzN2

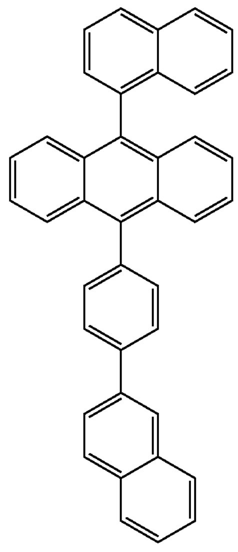

α N-β NPAnth

-continued

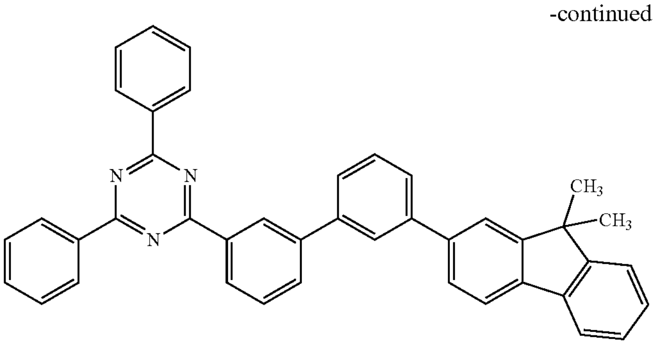

mFBPTzn

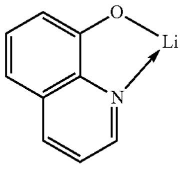

Liq

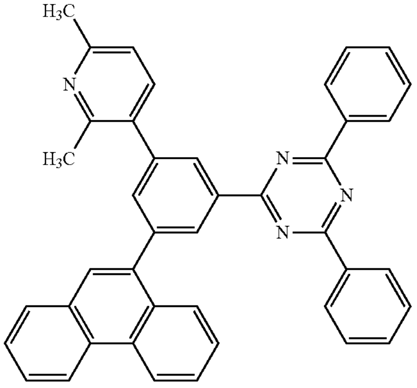

mPn-mDMePyPTzn

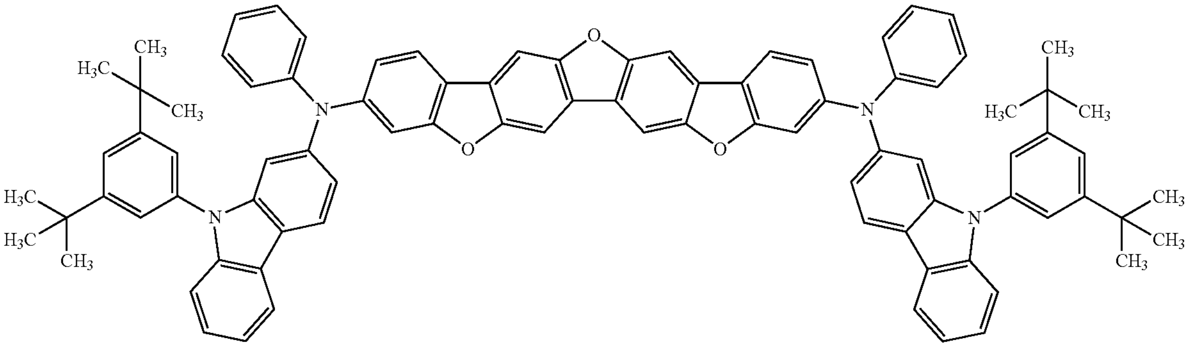

mmtBuPCA2Dfbf-02

<<Fabrication Method of Light-Emitting Device 6>>

The light-emitting device 6 described in this example was fabricated using a method including the following steps.

[First Step]

In the first step, the electrode 101 was formed. Specifically, the electrode 101 was formed by a sputtering method using indium oxide-tin oxide containing silicon or silicon oxide (abbreviation: ITSO) as a target.

The electrode 101 contains ITSO and has a thickness of 70 nm and an area of 4 $mm^2$ (2 mm×2 mm).

Next, a base material over which the electrode 101 was formed was washed with water, baked at 200° C. for one hour, and then subjected to UV ozone treatment for 370 seconds. Then, the substrate was transferred into a vacuum evaporation apparatus where the pressure was reduced to approximately $10^{-4}$ Pa, and vacuum baking was performed at 170° C. for 30 minutes in a heating chamber of the vacuum evaporation apparatus. Then, the substrate was cooled down for approximately 30 minutes.

[Second Step]

In the second step, the layer 104 was formed over the electrode 101. Specifically, materials were deposited by co-evaporation using a resistance-heating method.

Note that the layer 104 contains BBABnf and an electron accepter material (abbreviation: OCHD-001) at BBABnf: OCHD-001=1:0.1 (weight ratio), and has a thickness of 10 nm. Note that OCHD-001 has an acceptor property.

[Third Step]

In the third step, the region 112A was formed over the layer 104. Specifically, a material was deposited by evaporation using a resistance-heating method.

The region 112A contains BBABnf and has a thickness of 20 nm.

[Fourth Step]

In the fourth step, the region 112B was formed over the region 112A. Specifically, a material was deposited by evaporation using a resistance-heating method.

Note that the region 112B contains 3,3'-(naphthalene-1,4-diyl)bis(9-phenyl-9H-carbazole) (abbreviation: PCzN2) and has a thickness of 10 nm.

[Fifth Step]

In the fifth step, the layer 111 was formed over the region 112B. Specifically, materials were deposited by co-evaporation using a resistance-heating method.

Note that the layer 111 contains αN-βNPAnth and mmtBuPCA2Dfbf-02 at αN-βNPAnth:mmtBuPCA2Dfbf-02=1:0.015 (weight ratio) and has a thickness of 25 nm.

[Sixth Step]

In the sixth step, the region 113A was formed over the layer 111. Specifically, a material was deposited by evaporation using a resistance-heating method.

Note that the region 113A contains 2-[3'-(9,9-dimethyl-9H-fluoren-2-yl)-1,1'-biphenyl-3-yl]-4,6-diphenyl-1,3,5-triazine (abbreviation: mFBPTzn) and has a thickness of 10 nm.

[Seventh Step]

In the seventh step, the region 113B was formed over the region 113A. Specifically, materials were deposited by co-evaporation using a resistance-heating method.

The region 113B contains 2-[3-(2,6-dimethylpyridin-3-yl)-5-(9-phenanthryl)phenyl]-4,6-diphenyl-1,3,5-triazine (abbreviation: mPn-mDMePyPTzn) and Liq at mPn-mDMePyPTzn:Liq=1:1 (weight ratio) and has a thickness of 15 nm.

[Eighth Step]

In the eighth step, the layer 105 was formed over the region 113B. Specifically, a material was deposited by evaporation using a resistance-heating method.

Note that the layer 105 contains Liq and has a thickness of 1 nm.

[Ninth Step]

In the ninth step, the electrode 102 was formed over the layer 105. Specifically, a material was deposited by evaporation using a resistance-heating method.

The electrode 102 contains Al and has a thickness of 150 nm.

<<Operation Characteristics of Light-Emitting Device 6>>

When supplied with electric power, the light-emitting device 6 emitted the light EL1 (see FIG. 24). The operation characteristics of the light-emitting device 6 were measured at room temperature (see FIG. 54 to FIG. 60). The luminance, CIE chromaticity, and emission spectrum were measured using a spectroradiometer (SR-UL1R, manufactured by TOPCON TECHNOHOUSE CORPORATION).

Table 2 shows main initial characteristics of the fabricated light-emitting device emitting light at a luminance of approximately 1000 cd/$m^2$.

The light-emitting device 6 was found to have favorable characteristics. For example, the light-emitting device 6 showed high external quantum efficiency exceeding 14% in blue chromaticity. Also in a constant current driving test at 50 mA/$cm^2$, the 10% decay time was approximately 130 hours, which means a long lifetime. As a result, a novel light-emitting device that is highly convenient, useful, or reliable was successfully provided.

REFERENCE NUMERALS

101: electrode, 102: electrode, 103: unit, 103PD: unit, 104: layer, 105: layer, 106: intermediate layer, 106A: layer, 106B: layer, 111: layer, 112: layer, 112A: region, 112B: region, 113: layer, 113A: region, 113B: region, 150: light-emitting device, 150PD: photoelectric conversion device, 400: substrate, 401: electrode, 403: EL layer, 404: electrode, 405: sealant, 406: sealant, 407: sealing substrate, 412: pad, 420: IC chip, 601: source line driver circuit, 602: pixel portion, 603: gate line driver circuit, 604: sealing substrate, 605: sealant, 607: space, 608: wiring, 610: element substrate, 611: switching FET, 612: current control FET, 613: electrode, 614: insulator, 616: EL layer, 617: electrode, 618: light-emitting device, 623: FET, 700: light-emitting panel, 951: substrate, 952: electrode, 953: insulating layer, 954: partition layer, 955: EL layer, 956: electrode, 1001: substrate, 1002: base insulating film, 1003: gate insulating film, 1006: gate electrode, 1007: gate electrode, 1008: gate electrode, 1020: interlayer insulating film, 1021: interlayer insulating film, 1022: electrode, 1024B: electrode, 1024G: electrode, 1024R: electrode, 1024W: electrode, 1025: partition, 1028: EL layer, 1029: electrode, 1031: sealing substrate, 1032: sealant, 1033: base material, 1034B: coloring layer, 1034G: coloring layer, 1034R: coloring layer, 1035: black matrix, 1036: overcoat layer, 1037: interlayer insulating film, 1040: pixel portion, 1041: driver circuit portion, 1042: peripheral portion, 2001: housing, 2002: light source, 2100: robot, 2101: illuminance sensor, 2102: microphone, 2103: upper camera, 2104: speaker, 2105: display, 2106: lower camera, 2107: obstacle sensor, 2108: moving mechanism, 2110: arithmetic device, 3001: lighting device, 5000: housing, 5001: display portion, 5002: display portion, 5003: speaker, 5004: LED lamp, 5005: operation key, 5006: connection terminal, 5007: sensor, 5008: microphone, 5012: support, 5013: earphone, 5100: cleaning robot, 5101: display, 5102: camera, 5103: brush, 5104: operation button, 5120: dust, 5140: portable electronic device, 5200: display region, 5201: display region, 5202: display region, 5203: display region, 7101: housing, 7103: display portion, 7105: stand, 7107: display portion, 7109: operation key, 7110: remote controller, 7201: main body, 7202: housing, 7203: display portion, 7204: keyboard, 7205: external connection port, 7206: pointing device, 7210: display portion, 7401: housing, 7402: display portion, 7403: operation button, 7404: external connection port, 7405: speaker, 7406: microphone, 9310: portable information terminal, 9311: display panel, 9313: hinge, 9315: housing

The invention claimed is:

1. An organic compound represented by General Formula (G1):

(G1)

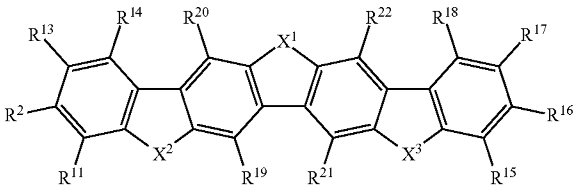

(R0)

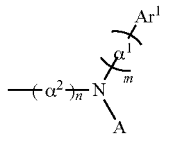

wherein:

$X^1$ to $X^3$ each independently represents oxygen or sulfur;

one or two of $R^{11}$ to $R^{22}$ each independently represents an amino group or an aryl group comprising an amino group, represented by General Formula (R0), and the others of $R^{11}$ to $R^{22}$ each independently represents any of hydrogen, an alkyl group having 1 to 6 carbon atoms, an alicyclic hydrocarbon group having 3 to 6 carbon atoms, and a substituted or unsubstituted aromatic hydrocarbon group having 6 to 13 carbon atoms;

when two of $R^{11}$ to $R^{22}$ each represents the amino group or the aryl group comprising the amino group represented by General Formula (R0), two of $R^{11}$ to $R^{22}$ each independently represents the amino group or the aryl group comprising the amino group represented by General Formula (R0);

$\alpha 1$ and $\alpha^2$ each independently represents a substituted or unsubstituted divalent aromatic hydrocarbon group having 6 to 25 carbon atoms;

A represents a substituted or unsubstituted heteroaryl group;

$Ar^1$ represents any of a substituted or unsubstituted aromatic hydrocarbon group having 6 to 25 carbon atoms and a substituted or unsubstituted heteroaryl group having 5 to 25 carbon atoms; and m and n each independently represents an integer of 0 or 1.

2. The organic compound according to claim 1, wherein $R^{12}$ and $R^{16}$ each independently represents the amino group or the aryl group comprising the amino group, represented by General Formula (R0).

3. The organic compound according to claim 1, wherein A comprises a five-membered ring, and wherein the five-membered ring comprises a heteroatom.

4. The organic compound according to claim 1, wherein A represents a heteroaryl group comprising any of a carbazole skeleton, a dibenzofuran skeleton, and a dibenzothiophene skeleton, and wherein $Ar^1$ represents any one of a phenyl group, a biphenyl group, a naphthyl group, a phenanthryl group, a fluorenyl group, and a substituent comprising any of a carbazole skeleton, a dibenzofuran skeleton, and a dibenzothiophene skeleton.

5. The organic compound according to claim 1, wherein the amino group or the aryl group comprising the amino group is represented by General Formula (R1):

(R1)

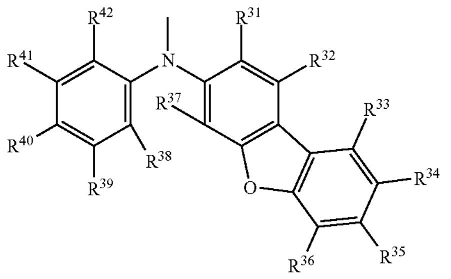

and wherein $R^{31}$ to $R^{42}$ each independently represents any of hydrogen, an alkyl group having 1 to 6 carbon atoms, an alicyclic hydrocarbon group having 3 to 6 carbon atoms, and a substituted or unsubstituted aromatic hydrocarbon group having 6 to 13 carbon atoms.

6. The organic compound according to claim 1, wherein the amino group or the aryl group comprising the amino group is represented by General Formula (R2):

(R2)

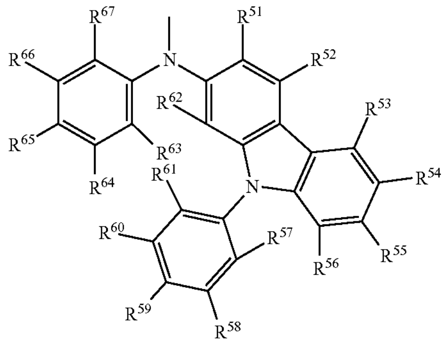

and wherein $R^{51}$ to $R^{67}$ each independently represents any of hydrogen, an alkyl group having 1 to 6 carbon atoms, an alicyclic hydrocarbon group having 3 to 6 carbon atoms, and a substituted or unsubstituted aromatic hydrocarbon group having 6 to 13 carbon atoms.

7. A light-emitting device comprising:

a first electrode;

a second electrode; and a unit, wherein the second electrode comprises a region overlapping with the first electrode, wherein the unit comprises a region positioned between the first electrode and the second electrode, and wherein the unit comprises the organic compound according to claim 1.

8. A light-emitting apparatus comprising:

the light-emitting device according to claim 7; and a transistor or a substrate.

9. A display device comprising:

the light-emitting device according to claim 7; and a transistor or a substrate.

10. A lighting device comprising:

the light-emitting apparatus according to claim 8; and a housing.

11. An electronic device comprising:

the display device according to claim 9; and a sensor, an operation button, a speaker, or a microphone.

* * * * *